US007666840B2

(12) United States Patent
Watkins et al.

(10) Patent No.: US 7,666,840 B2

(45) Date of Patent: Feb. 23, 2010

(54) α-CONOTOXIN PEPTIDES

(75) Inventors: Maren Watkins, Salt Lake City, UT (US); Baldomero M. Olivera, Salt Lake City, UT (US); David R. Hillyard, Salt Lake City, UT (US); J. Michael McIntosh, Salt Lake City, UT (US); Robert M. Jones, Salt Lake City, UT (US)

(73) Assignees: The University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 107 days.

(21) Appl. No.: 11/869,480

(22) Filed: Oct. 9, 2007

(65) Prior Publication Data

US 2008/0081901 A1 Apr. 3, 2008

Related U.S. Application Data

(62) Division of application No. 10/895,372, filed on Jul. 21, 2004, now Pat. No. 7,279,549, which is a division of application No. 09/493,795, filed on Jan. 28, 2000, now Pat. No. 6,797,808.

(60) Provisional application No. 60/118,381, filed on Jan. 29, 1999.

(51) Int. Cl.

| | |
|---|---|
| ***A61K 38/10*** | (2006.01) |
| ***A61K 38/17*** | (2006.01) |
| ***C07K 7/08*** | (2006.01) |
| ***C07K 14/435*** | (2006.01) |

(52) U.S. Cl. .......................... 514/13; 514/12; 530/326; 530/324; 530/857

(58) Field of Classification Search .................. 514/13, 514/12; 530/326, 324, 857

See application file for complete search history.

(56) References Cited

U.S. PATENT DOCUMENTS

| | | | |
|---|---|---|---|
| 4,447,356 | A | 5/1984 | Olivera et al. |
| 5,231,011 | A | 7/1993 | Hillyard et al. |
| 5,432,155 | A | 7/1995 | Olivera et al. |
| 5,514,774 | A | 5/1996 | Olivera et al. |
| 5,595,972 | A | 1/1997 | Olivera et al. |
| 5,670,622 | A | 9/1997 | Shon et al. |
| 5,672,682 | A | 9/1997 | Terlau et al. |
| 5,719,264 | A | 2/1998 | Shon et al. |
| 5,739,276 | A | 4/1998 | Shon et al. |
| 5,866,682 | A | 2/1999 | McIntosh et al. |
| 5,889,147 | A | 3/1999 | Cruz et al. |
| 5,969,096 | A | 10/1999 | Shon et al. |

FOREIGN PATENT DOCUMENTS

| | | | |
|---|---|---|---|
| WO | 9511256 | A1 | 4/1995 |
| WO | 9824462 | A1 | 6/1998 |

OTHER PUBLICATIONS

Result 9, search in the Uniprot database on Jul. 24, 2009, alignment of instant SEQ ID No. 300 with the polypeptide of Lu et al., "Conopeptides from Conus striatus and Conus textile by cDNA cloning," Peptides 20:1139-1144, 1999.*

Cartier, GE et al., "A New Alpha-Conotoxin Which Targets alpha3beta2 Nicotinic Acetylcholine Receptors," Journal of Biological Chemistry, The American Society for Biochemistry and Molecular Biology, Inc., vol. 271, No. 13, Mar. 29, 1996, pp. 7522-7528, XP-002170539.

Codignola, Agnese et al., "Alpha-Conotoxin Imperialis I Inhibits Nicotine-Evoked Hormone Release and Cell Proliferation in Human Neuroendocrine Carcinoma Cells," Neuroscience Letters, vol. 206, No. 1, 1996, pp. 53-56, XP-002290023.

McIntosh, J.M. et al. (1999). *Ann Rev Biochem* 68:59-88.

* cited by examiner

*Primary Examiner*—Karen Cochrane Carlson

*Assistant Examiner*—Rosanne Kosson

(74) *Attorney, Agent, or Firm*—Rothwell, Figg, Ernst & Manbeck P.C.

(57) ABSTRACT

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

5 Claims, No Drawings

α-CONOTOXIN PEPTIDES

CROSS-REFERENCE TO RELATED APPLICATION

The present application is a division of U.S. patent application Ser. No. 10/895,372 filed 21 Jul. 2004, now U.S. Pat. No. 7,279,549, which in turn is a division of U.S. patent application Ser. No. 09/493,795 filed 28 Jan. 2000, now U.S. Pat. No. 6,797,808. U.S. patent application Ser. No. 09/493,795 is related to and claims priority under 35 U.S.C. § 119(e) to U.S. provisional patent application Ser. No. 60/118,381, filed 29 Jan. 1999. Each application is incorporated herein by reference.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The predatory cone snails (*Conus*) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these peptides are a large genus of venomous gastropods comprising approximately 500 species. All cone snail species are predators that inject venom to capture prey, and the spectrum of animals that the genus as a whole can envenomate is broad. A wide variety of hunting strategies are used; however, every *Conus* species uses fundamentally the same basic pattern of envenomation.

Several peptides isolated from *Conus* venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conotoxins have been isolated from *Conus geographus* and *Conus tulipa* (Mena et al., 1990; Haack et al., 1990).

The α-conotoxins are small peptides highly specific for neuromuscular junction nicotinic acetylcholine receptors (Gray et al., 1981; Marshall and Harvey, 1990; Blount et al., 1992; Jacobsen et al., 1997) or highly specific for neuronal nicotinic acetylcholine receptors (Fainzilber et al., 1994; Johnson et al., 1995; Cartier et al., 1996; Luo et al., 1998). The α-conotoxins with specificity for neuromuscular junction nicotinic acetylcholine receptors are used as neuromuscular blocking agents for use in conjunction with surgery, as disclosed in U.S. patent application Ser. No. 09/488,799, filed 21 Jan. 2000, incorporated by reference herein. Additional α-conotoxins and uses for them have been described in U.S. Pat. Nos. 4,447,356 (Olivera et al., 1984); 5,432,155; 5,514,774, each incorporated herein by reference.

Additional uses for α-conotoxins are described in U.S. Ser. No. 09/219,446, filed 22 Dec. 1998, incorporated herein by reference. In this application, α-conotoxins with specificity for neuronal nicotinic acetylcholine receptors are used for treating disorders regulated at neuronal nicotinic acetylcholine receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma.

It is desired to provide additional α-conotoxin peptides having uses as described herein.

SUMMARY OF THE INVENTION

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

More specifically, the present invention is directed to α-conotoxin peptides having the general formula I:

$Xaa_1$-$Xaa_2$-$Xaa_3$-$Xaa_4$-$Xaa_5$-Cys-Cys-$Xaa_6$-$Xaa_7$-$Xaa_8$-$Xaa_9$-Cys-$Xaa_{10}$-$Xaa_{11}$-$Xaa_{12}$-Cys-$Xaa_{13}$ (SEQ ID NO1:), wherein $Xaa_1$ is des-$Xaa_1$, Ile, Leu or Val; $Xaa_2$ is des-$Xaa_2$, Ala or Gly; $Xaa_3$ is des-$Xaa_3$, Gly, Trp (D or L), neo-Trp, halo-Trp or any unnatural aromatic amino acid; $Xaa_4$ is des-$Xaa_4$, Asp, Phe, Gly, Ala, Glu, γ-carboxy-Glu (Gla) or any unnatural aromatic amino acid; $Xaa_5$ is Glu, Gla, Asp, Ala, Thr, Ser, Gly, Ile, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_6$ is Ser, Thr, Arg, ornithine, homoarginine, Lys, N-methyl-Lys, N,N-dimethyl-Lys, N,N,N-trimethyl-Lys or any unnatural basic amino acid; $Xaa_7$ is Asp, Glu, Gla, Arg, ornithine, homoarginine, Lys, N-methyl-Lys, N,N-dimethyl-Lys, N,N,N-trimethyl-Lys or any unnatural basic amino acid; $Xaa_8$ is Ser, Thr, Asn, Ala, Gly, Arg, Lys, ornithine, homoarginine, N-methyl-Lys, N,N-dimethyl-Lys, N,N,N-trimethyl-Lys, any unnatural basic amino acid, His, halo-His, Pro or hydroxy-Pro; $Xaa_9$ is Thr, Ser, Ala, Asp, Asn, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_{10}$ is Gly, Ser, Thr, Ala, Asn, Arg, ornithine, homoarginine, Lys, N-methyl-Lys, N,N-dimethyl-Lys, N,N,N-trimethyl-Lys or any unnatural basic amino acid; $Xaa_{11}$ is Gln, Leu, His, halo-His, Trp (D or L), halo-Trp, neo-Trp, Tyr, nor-Tyr, mono-halo-Tyr, di-halo-Tyr, O-sulpho-Tyr, O-phospho-Tyr, nitro-Tyr, Arg, ornithine, homoarginine, Lys, N-methyl-Lys, N,N-dimethyl-Lys, N,N,N-trimethyl-Lys, any unnatural basic amino acid or any unnatural aromatic amino acid; $Xaa_{12}$ is Asn, His, halo-His, Ile, Leu, Val, Gln, Arg, ornithine, homoarginine, Lys, N-methyl-Lys, N,N-dimethyl-Lys, N,N,N-trimethyl-Lys or any unnatural basic amino acid; $Xaa_{13}$ is des-$Xaa_{13}$, Val, Ile, Leu, Arg, ornithine, homoarginine, Lys, N-methyl-Lys, N,N-dimethyl-Lys, N,N,N-trimethyl-Lys or any unnatural basic amino acid. The C-terminus may contain a free carboxyl group or an amide group. The halo is chlorine, bromine or iodine, preferably iodine for Tyr and His and preferably bromine for Trp. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to α-conotoxin peptides having the general formula II:

$Xaa_1$-$Xaa_2$-$Xaa_3$-$Xaa_4$-Cys-Cys-$Xaa_5$-$Xaa_6$-$Xaa_7$-$Xaa_8$-Cys-$Xaa_9$-$Xaa_{10}$-$Xaa_{11}$-$Xaa_{12}$-$Xaa_{13}$-$Xaa_{14}$-Cys-$Xaa_{15}$-$Xaa_{16}$-$Xaa_{17}$ (SEQ ID NO:2), wherein $Xaa_1$ is des-$Xaa_1$, Asp, Glu or γ-carboxy-Glu (Gla); $Xaa_2$ is des-$Xaa_2$, Gln, Ala, Asp, Glu, Gla; $Xaa_3$ is des-$Xaa_3$, Gly, Ala, Asp, Glu, Gla, Pro or hydroxy-Pro; $Xaa_4$ is des-$Xaa_4$, Gly, Glu, Gla, Gln, Asp, Asn, Pro or hydroxy-Pro; $Xaa_5$ is Ser, Thr, Gly, Glu, Gla, Asn, Trp (D or L), neo-Trp, halo-Trp, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_6$ is Asp, Asn, His, halo-His, Thr, Ser, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_7$ is Pro or hydroxy-Pro; $Xaa_8$ is Ala, Ser, Thr, Asp, Val, Ile, Pro, hydroxy-Pro, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_9$ is Gly, Ile, Leu, Val, Ala, Thr, Ser, Pro, hydroxy-Pro, Phe, Trp (D or L), neo-Trp, halo-Trp, Arg, ornithine, homoarginine, Lys, N-methyl-Lys, N,N-dimethyl-Lys, N,N,N-trimethyl-Lys, any unnatural basic amino acid or any unnatural aromatic amino acid; $Xaa_{10}$ is Ala, Asn, Phe, Pro, hydroxy-Pro, Glu, Gla, Gln, His, halo-His, Val, Ser, Thr, Arg, ornithine, homoarginine, Lys, N-methyl-Lys, N,N-dimethyl-Lys, N,N,N-trimethyl-Lys or any unnatural basic amino acid; $Xaa_{11}$ is Thr, Ser, His, halo-His, Leu, Ile, Val, Asn, Met, Pro, hydroxy-Pro, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{12}$ is Asn, Pro, hydroxy-Pro, Gln, Ser, Thr, Arg, ornithine, homoarginine, Lys, N-methyl-Lys, N,N-dimethyl-Lys N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{13}$ is des-$Xaa_{13}$, Gly, Thr, Ser, Pro, hydroxy-Pro, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{14}$ is des-$Xaa_{14}$, Ile, Val, Asp, Leu, Phe, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; and $Xaa_{15}$ is des-$Xaa_{15}$, Gly, Ala, Met, Ser, Thr, Trp (D or L), neo-Trp, halo-Trp, any unnatural aromatic amino acid, Arg, ornithine, homoarginine, Lys, N-methyl-Lys, N,N-dimethyl-Lys, N,N,N-trimethyl-Lys or any unnatural basic amino acid; $Xaa_{16}$ is des-$Xaa_{16}$, Trp (D or L), neo-Trp, halo-Trp, any unnatural aromatic amino acid, Arg, ornithine, homoarginine, Lys, N-methyl-Lys, N,N-dimethyl-Lys, N,N,N-trimethyl-Lys or any unnatural basic amino acid; $Xaa_{17}$ is des-$Xaa_{17}$, Arg, ornithine, homoarginine, Lys, N-methyl-Lys, N,N-dimethyl-Lys, N,N,N-trimethyl-Lys or any unnatural basic amino acid. The C-terminus may contain a free carboxyl group or an amide group. The halo is preferably bromine, chlorine or iodine, more preferably iodine for His or Tyr and bromine for Trp. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to α-conotoxin peptides having the general formula III:

$Xaa_1$-$Xaa_2$-$Xaa_3$-$Xaa_4$-$Xaa_5$-Cys-Cys-$Xaa_6$-$Xaa_7$-$Xaa_8$-$Xaa_9$-Cys-$Xaa_{10}$-$Xaa_{11}$-$Xaa_{12}$-$Xaa_{13}$-$Xaa_{14}$-$Xaa_{15}$-$Xaa_{16}$-Cys-$Xaa_{17}$-$Xaa_{18}$-$Xaa_{19}$-$Xaa_{20}$-$Xaa_{21}$-$Xaa_{22}$-$Xaa_{23}$-$Xaa_{24}$ (SEQ ID NO:3), wherein $Xaa_1$ is des-$Xaa_1$, Ser or Thr; $Xaa_2$ is des-$Xaa_2$, Asp, Glu, γ-carboxy-Glu (Gla), Asn, Ser or Thr; $Xaa_3$ is des-$Xaa_3$, Ala, Gly, Asn, Ser, Thr, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_4$ is des-$Xaa_4$, Ala, Val, Leu, Ile, Gly, Glu, Gla, Gln, Asp, Asn, Phe, Pro, hydroxy-Pro or any unnatural aromatic amino acid; $Xaa_5$ is des-$Xaa_5$, Thr, Ser, Asp, Glu, Gla, Gln, Gly, Val, Asp, Asn, Ala, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_6$ is Thr, Ser, Asp, Asn, Met, Val, Ala, Gly, Leu, Ile, Phe, any unnatural aromatic amino acid, Pro, hydroxy-Pro, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_7$ is Ile, Leu, Val, Ser, Thr, Gln, Asn, Asp, Arg, His, halo-His, Phe, any unnatural aromatic amino acid, homoarginine, ornithine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_8$ is Pro, hydroxy-Pro, Ser, Thr, Ile, Asp, Leu, Val, Gly, Ala, Phe, any unnatural aromatic amino acid, Arg, ornithine, homoarginine, Lys, N-methyl-Lys, N,N-dimethyl-Lys, N,N,N-trimethyl-Lys or any unnatural basic amino acid; $Xaa_9$ is Val, Ala, Gly, Ile, Leu, Asp, Ser, Thr, Pro, hydroxy-Pro, Arg, ornithine, homoarginine, Lys, N-methyl-Lys, N,N-dimethyl-Lys, N,N,N-trimethyl-Lys or any unnatural basic amino acid; $Xaa_{10}$ is His, halo-His, Arg, homoarginine, ornithine, Lys, N-methyl-Lys, N,N-dimethyl-Lys, N,N,N-trimethyl-Lys, any unnatural basic amino acid, Asn, Ala, Ser, Thr, Phe, Ile, Leu, Gly, Trp (D or L), neo-Trp, halo-Trp, any unnatural aromatic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{11}$ is Leu, Gln, Val, Ile, Gly, Met, Ala, Lys, N-methyl-Lys, N,N-dimethyl-Lys, N,N,N-trimethyl-Lys, Ser, Thr, Arg, homoarginine, ornithine, any unnatural basic amino acid, Asn, Glu, Gla, Gln, Phe, Trp (D or L), neo-Trp, halo-Trp or any unnatural aromatic amino acid; $Xaa_{12}$ is Glu, Gla, Gln, Asn, Asp, Pro, hydroxy-Pro, Ser, Gly, Thr, Lys, N-methyl-Lys, N,N-dimethyl-Lys, N,N,N-trimethyl-Lys, Arg, homoarginine, ornithine, any unnatural basic amino acid, Phe, His, halo-His, any unnatural aromatic amino acid, Leu, Met, Gly, Ala, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{13}$ is His, halo-His, Asn, Thr, Ser, Ile, Val, Leu, Phe, any unnatural aromatic amino acid, Arg, homoarginine, ornithine, Lys, N-methyl-Lys, N,N-dimethyl-Lys, N,N,N-trimethyl-Lys, any unnatural basic amino acid, Tyr, nor-Try, mono-halo-Tyr, di-halo-Tyr, O-sulpho-Tyr, O-phospho-Tyr, nitro-Tyr or any unnatural hydroxy containing amino acid; $Xaa_{14}$ is Ser, Thr, Ala, Gln, Pro, hydroxy-Pro, Gly, Ile, Leu, Arg, ornithine, homoarginine, Lys, N-methyl-Lys, N,N-dimethyl-Lys, N,N,N-trimethyl-Lys or any unnatural basic amino acid; $Xaa_{15}$ is Asn, Glu, Gla, Asp, Gly, His, halo-His, Ala, Leu, Gln, Arg, ornithine, homoarginine, Lys, N-methyl-Lys, N,N-dimethyl-Lys, N,N,N-trimethyl-Lys, any unnatural basic amino acid, Tyr, nor-Tyr, mono-halo-Tyr, di-halo-Tyr, O-sulpho-Tyr, O-phospho-Tyr, nitro-Tyr or any unnatural hydroxy containing amino acid; $Xaa_{16}$ is Met, Ile, Thr, Ser, Val, Leu, Pro, hydroxy-Pro, Phe, any unnatural aromatic amino acid, Tyr, nor-Tyr, mono-halo-Tyr, di-halo-Tyr, O-sulpho-Tyr, O-phospho-Tyr, nitro-Tyr, any unnatural hydroxy containing amino acid, Glu, Gla, Ala, His, halo-His, Arg, ornithine, homoarginine, Lys, N-methyl-Lys, N,N-dimethyl-Lys, N,N,N-trimethyl-Lys or any unnatural basic amino acid; $Xaa_{17}$ is des-$Xaa_{17}$, Gly, Asp, Asn, Ala, Ile, Leu, Ser, Thr, His, halo-His, Arg, ornithine, homoarginine, Lys, N-methyl-Lys, N,N-dimethyl-Lys, N,N,N-trimethyl-Lys or any unnatural basic amino acid; $Xaa_{18}$ is des-$Xaa_{18}$, Gly, Glu, Gla, Gln, Trp (D or L), neo, halo-Trp, any unnatural aromatic amino acid, Arg, ornithine, homoarginine, Lys, N-methyl-Lys, N,N-dimethyl-lys, N,N,N-trimethyl-Lys or any unnatural basic amino acid; $Xaa_{19}$ is des-$Xaa_{19}$, Ser, Thr, Val, Ile, Ala, Arg, ornithine, homoarginine, Lys, N-methyl-Lys, N,N-dimethyl-Lys, N,N,N-trimethyl-Lys or any unnatural basic amino acid; $Xaa_{20}$ is des-$Xaa_{20}$, Val, Asp, His, halo-His, Arg, ornithine, homoarginine, Lys, N-methyl-Lys, N,N-dimethyl-Lys, N,N,N-trimethyl-Lys or any unnatural basic amino acid; $Xaa_{21}$ is des-$Xaa_{21}$, Asn, Pro or hydroxy-Pro; $Xaa_{22}$ is des-$Xaa_{22}$, Arg, ornithine, homoarginine, Lys, N-methyl-Lys, N,N-dimethyl-Lys, N,N,N-trimethyl-Lys or any unnatural basic amino acid; $Xaa_{23}$ is des-$Xaa_{23}$, Ser or Thr; $Xaa_{24}$ is des-$Xaa_{24}$, Leu, Ile or Val; with the proviso that (a) $Xaa_5$ is not Gly, when $Xaa_1$ is des-$Xaa_1$, $Xaa_2$ is des-$Xaa_2$, $Xaa_3$ is des-$Xaa_3$, $Xaa_4$ is des-$Xaa_4$, $Xaa_6$ is Ser, $Xaa_7$ is His, $Xaa_8$ is Pro, $Xaa_9$ is Ala, $Xaa_{10}$ is Ser, $Xaa_{11}$ is Val, $Xaa_{12}$ is Asn, $Xaa_{13}$ is Asn, $Xaa_{14}$ is Pro, $Xaa_{15}$ is Asp, $Xaa_{16}$ is Ile, $Xaa_{17}$ is des-$Xaa_{17}$, $Xaa_{18}$ is des-$Xaa_{18}$, $Xaa_{19}$ is des-$Xaa_{19}$, $Xaa_{20}$ is des-$Xaa_{20}$, $Xaa_{21}$ is des-$Xaa_{21}$, $Xaa_{22}$ is des-$Xaa_{22}$, $Xaa_{23}$ is des-$Xaa_{23}$, and $Xaa_{24}$ is des-$Xaa_{24}$. The C-terminus may contain a free carboxyl group or an amide group. The halo is preferably bromine, chlorine or iodine, more preferably iodine for His and Tyr and bromine for Trp. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

The present invention is also directed to novel specific α-conotoxin peptides of general formula I having the formulas:

(SEQ ID NO:4)
Asp-$Xaa_1$-Cys-Cys-Ser-Asp-Ser-Arg-Cys-Gly-$Xaa_2$-Asn-Cys-Leu;

(SEQ ID NO:5)
Ala-Cys-Cys-Ser-Asp-Arg-Arg-Cys-Arg-$Xaa_3$-Arg-Cys;

(SEQ ID NO:6)
Phe-Thr-Cys-Cys-Arg-Arg-Gly-Thr-Cys-Ser-Gln-His-Cys;

-continued (SEQ ID NO:7)
Asp-$Xaa_4$-Cys-Cys-Arg-Arg-His-Ala-Cys-Thr-Leu-Ile-Cys;

(SEQ ID NO:8)
Asp-$Xaa_4$-Cys-Cys-Arg-$Xaa_5$-$Xaa_5$-Cys-Thr-Leu-Ile-Cys;

(SEQ ID NO:9)
Gly-Cys-Cys-Ser-Asp-$Xaa_5$-Arg-Cys-Arg-$Xaa_4$-Arg-Cys-Arg;

(SEQ ID NO:10)
Gly-Gly-Cys-Cys-Ser-Asp-$Xaa_5$-Arg-Cys-Ala-$Xaa_3$-Arg-Cys;

(SEQ ID NO:11)
Ile-Ala-$Xaa_3$-Asp-Ile-Cys-Cys-Ser-$Xaa_1$-$Xaa_5$-Asp-Cys-Asn-His-$Xaa_2$-Cys-Val;
and (SEQ ID NO:12)
Gly-Cys-Cys-Ser-Asp-$Xaa_5$-Arg-Cys-$Xaa_2$-His-Gln-Cys, wherein $Xaa_1$ is Glu or γ-carboxy-Glu (Gla); $Xaa_2$ is Lys, N-methyl-Lys, N,N-dimethyl-Lys or N,N,N-trimethyl-Lys; $Xaa_3$ is Trp (D or L), halo-Trp or neo-Trp; $Xaa_4$ is Tyr, nor-Tyr, mono-halo-Tyr, di-halo-Tyr, O-sulpho-Tyr, O-phospho-Tyr or nitro-Tyr; and $Xaa_5$ is Pro or hydroxy-Pro; and the C-terminus contains a carboxyl or amide group. The halo is preferably bromine, chlorine or iodine, more preferably iodine for Tyr and bromine for Trp. In addition, the His residues may be substituted with halo-His; the Arg residues may be substituted by Lys, ornithine, homoarginine, N-methyl-Lys, N,N-dimethyl-Lys, N,N,N-trimethyl-Lys or any unnatural basic amino acid; the Lys residues may be substituted by Arg, ornithine, homoarginine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe and Trp residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to the following α-conotoxin peptides of general formula I:

Im1.1: SEQ ID NO:4, wherein $Xaa_1$ is Glu and $Xaa_2$ is Lys;

Im1.2: SEQ ID NO:5, wherein $Xaa_3$ is Trp;

Rg1.2: SEQ ID NO:6;

Rg1.6: SEQ ID NO:7, wherein $Xaa_4$ is Tyr;

Rg1.6A: SEQ ID NO:8, wherein $Xaa_4$ is Tyr and $Xaa_5$ is Pro;

Rg1.7: SEQ ID NO:9, wherein $Xaa_4$ is Tyr and $Xaa_5$ is Pro;

Rg1.9: SEQ ID NO:10, wherein $Xaa_3$ is Trp and $Xaa_5$ is Pro;

Rg1.10: SEQ ID NO:11, wherein $Xaa_1$ is Glu, $Xaa_2$ is Lys, $Xaa_3$ is Trp and $Xaa_5$ is Pro; and Rg1.11: SEQ ID NO:12, wherein $Xaa_2$ is Lys and $Xaa_5$ is Pro.

The C-terminus of Im1.1, Rg1.7 an Rg1.10 preferably contains a free carboxyl group. The C-terminus of Im1.2, Rg1.2, Rg1.6, Rg1.6A, Rg1.9 and Rg1.11 preferably contains an amide group.

The present invention is further directed to novel specific α-conotoxin peptides of general formula II having the formulas:

(SEQ ID NO:13)
Cys-Cys-Ser-Asp-$Xaa_5$-Ala-Cys-$Xaa_2$-Gln-Thr-$Xaa_5$-Gly-Cys-Arg;

(SEQ ID NO:14)
Cys-Cys-$Xaa_1$-Asn-$Xaa_5$-Ala-Cys-Arg-His-Thr-Gln-Gly-Cys;

(SEQ ID NO:15)
Gly-Cys-Cys-$Xaa_3$-His-$Xaa_5$-Ala-Cys-Gly-Arg-His-$Xaa_4$-Cys;

(SEQ ID NO:16)
Ala-$Xaa_5$-Cys-Cys-Asn-Asn-$Xaa_5$-Ala-Cys-Val-$Xaa_2$-His-Arg-Cys;

(SEQ ID NO:17)
Ala-$Xaa_5$-Gly-Cys-Cys-Asn-Asn-$Xaa_5$-Ala-Cys-Val-$Xaa_2$-His-Arg-Cys;

(SEQ ID NO:18)
$Xaa_5$-$Xaa_5$-Cys-Cys-Asn-Asn-$Xaa_5$-Ala-Cys-Val-$Xaa_2$-His-Arg-Cys;

(SEQ ID NO:19)
Asp-$Xaa_1$-Asn-Cys-Cys-$Xaa_3$-Asn-$Xaa_5$-Ser-Cys-$Xaa_5$-Arg-$Xaa_5$-Arg-Cys-Thr;

(SEQ ID NO:20)
Gly-Cys-Cys-Ser-Thr-$Xaa_5$-$Xaa_5$-Cys-Ala-Val-Leu-$Xaa_4$-Cys;

(SEQ ID NO:21)
Gly-Cys-Cys-Gly-Asn-$Xaa_5$-Asp-Cys-Thr-Ser-His-Ser-Cys;

(SEQ ID NO:42)
Gly-Cys-Cys-Ser-Asn-$Xaa_5$-$Xaa_5$-Cys-Ala-His-Asn-Asn-$Xaa_5$-Asp-Cys-Arg;

(SEQ ID NO:154)
Gly-Cys-Cys-$Xaa_4$-Asn-$Xaa_5$-Val-Cys-$Xaa_2$-$Xaa_2$-$Xaa_4$-$Xaa_4$-Cys-$Xaa_3$-$Xaa_2$;

(SEQ ID NO:155)
$Xaa_6$-$Xaa_1$-$Xaa_5$-Gly-Cys-Cys-Arg-His-$Xaa_5$-Ala-Cys-Gly-$Xaa_2$-Asn-Arg-Cys;

(SEQ ID NO:156)
Cys-Cys-Ala-Asp-$Xaa_5$-Asp-Cys-Arg-Phe-Arg-$Xaa_5$-Gly-Cys;

-continued (SEQ ID NO:157)
Gly-Cys-Cys-$Xaa_4$-Asn-$Xaa_5$-Ser-Cys-$Xaa_3$-$Xaa_5$-$Xaa_2$-Thr-$Xaa_4$-Cys-Ser-$Xaa_3$-$Xaa_2$;

(SEQ ID NO:158)
Cys-Cys-Ser-Asn-$Xaa_5$-Thr-Cys-$Xaa_2$-$Xaa_1$-Thr-$Xaa_4$-Gly-Cys;

(SEQ ID NO:159)
Cys-Cys-Ala-Asn-$Xaa_5$-Ile-Cys-$Xaa_2$-Asn-Thr-$Xaa_5$-Gly-Cys;

(SEQ ID NO:160)
Cys-Cys-Asn-Asn-$Xaa_5$-Thr-Cys-$Xaa_2$-$Xaa_1$-Thr-$Xaa_4$-Gly-Cys;

(SEQ ID NO:161)
Cys-Cys-Ser-Asn-$Xaa_5$-Val-Cys-$Xaa_2$-$Xaa_1$-Thr-$Xaa_4$-Gly-Cys;

(SEQ ID NO:162)
Gly-Gly-Cys-Cys-Ser-$Xaa_4$-$Xaa_5$-$Xaa_5$-Cys-Ile-Ala-Ser-Asn-$Xaa_5$-$Xaa_2$-Cys-Gly;

(SEQ ID NO:163)
Gly-Cys-Cys-Ser-His-$Xaa_5$-Val-Cys-Ser-Ala-Met-Ser-$Xaa_5$-Ile-Cys;

(SEQ ID NO:164)
Gly-Cys-Cys-$Xaa_2$-Asn-$Xaa_5$-$Xaa_4$-Cys-Gly-Ala-Ser-$Xaa_2$-Thr-$Xaa_4$-Cys;

(SEQ ID NO:165)
Gly-Cys-Cys-Ser-$Xaa_4$-$Xaa_5$-$Xaa_5$-Cys-Phe-Ala-Thr-Asn-$Xaa_5$-Asp-Cys;

(SEQ ID NO:166)
Gly-Gly-Cys-Cys-Ser-$Xaa_4$-$Xaa_5$-$Xaa_5$-Cys-Ile-Ala-Asn-Asn-$Xaa_5$-Leu-Cys-Ala;

(SEQ ID NO:167)
Gly-Gly-Cys-Cys-Ser-$Xaa_4$-$Xaa_5$-$Xaa_5$-Cys-Ile-Ala-Asn-Asn-$Xaa_5$-Phe-Cys-Ala;

(SEQ ID NO:168)
Asp-Cys-Cys-Ser-Asn-$Xaa_5$-$Xaa_5$-Cys-Ser-Gln-Asn-Asn-$Xaa_5$-Asp-Cys-Met;
and (SEQ ID NO:169)
Asp-Cys-Cys-Ser-Asn-$Xaa_5$-$Xaa_5$-Cys-Ala-His-Asn-Asn-$Xaa_5$-Asp-Cys-Arg, wherein $Xaa_1$ is Glu or γ-carboxy-Glu (Gla); $Xaa_2$ is Lys, N-methyl-Lys, N,N-dimethyl-Lys or N,N,N-trimethyl-Lys; $Xaa_3$ is Trp (D or L), halo-Trp or neo-Trp; $Xaa_4$ is Tyr, nor-Tyr, mono-halo-Tyr, di-halo-Tyr, O-sulpho-Tyr, O-phospho-Tyr or nitro-Tyr; and $Xaa_5$ is Pro or hydroxy-Pro; and the C-terminus contains a carboxyl or amide group. The halo is preferably bromine, chlorine or iodine, more preferably iodine for Tyr and bromine for Trp. In addition, the His residues may be substituted with halo-His; the Arg residues may be substituted by Lys, ornithine, homoarginine, N-methyl-Lys, N,N-dimethyl-Lys, N,N,N-trimethyl-Lys or any unnatural basic amino acid; the Lys residues may be substituted by Arg, ornithine, homoarginine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe and Trp residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to the following α-conotoxin peptides of general formula II:

Sn1.1: SEQ ID NO:13, wherein $Xaa_2$ is Lys and $Xaa_5$ is Pro;
Sn1.2: SEQ ID NO:14, wherein $Xaa_1$ is Glu and $Xaa_5$ is Pro;
Sl1.3: SEQ ID NO:15, wherein $Xaa_3$ is Trp, $Xaa_4$ is Tyr and $Xaa_5$ is Pro;
A1.2: SEQ ID NO:16, wherein $Xaa_2$ is Lys and $Xaa_5$ is Pro;
Bu1.1: SEQ ID NO:17, wherein $Xaa_2$ is Lys and $Xaa_5$ is Pro;
Bu1.2: SEQ ID NO:18, wherein $Xaa_2$ is Lys and $Xaa_5$ is Pro;
Bu1.3: SEQ ID NO:19, wherein $Xaa_1$ is Glu, $Xaa_3$ is Trp and $Xaa_5$ is Pro;
Bu1.4: SEQ ID NO:20, wherein $Xaa_4$ is Tyr and $Xaa_5$ is Pro;
Cr1.3: SEQ ID NO:21, wherein $Xaa_5$ is Pro;
Di1.1: SEQ ID NO:42 wherein $Xaa_5$ is Pro;
Ms1.7: SEQ ID NO:154, wherein $Xaa_2$ is Lys, $Xaa_3$ is Trp, $Xaa_4$ is Tyr and $Xaa_5$ is Pro;
P1.7: SEQ ID NO:155, wherein $Xaa_1$ is Glu, $Xaa_2$ is Lys, $Xaa_5$ is Pro and $Xaa_6$ is Gln;
Ms1.2: SEQ ID NO:156, wherein $Xaa_5$ is Pro;
Ms1.3: SEQ ID NO:157, wherein $Xaa_2$ is Lys, $Xaa_3$ is Trp, $Xaa_4$ is Tyr and $Xaa_5$ is Pro;
Ms1.4: SEQ ID NO:158, wherein $Xaa_1$ is Glu, $Xaa_2$ is Lys, $Xaa_4$ is Tyr and $Xaa_5$ is Pro;
Ms1.5: SEQ ID NO:159, wherein $Xaa_2$ is Lys and $Xaa_5$ is Pro;
Ms1.8: SEQ ID NO:160, wherein $Xaa_1$ is Glu, $Xaa_2$ is Lys, $Xaa_4$ is Tyr and $Xaa_5$ is Pro;
Ms1.9: SEQ ID NO:161, wherein $Xaa_1$ is Glu, $Xaa_2$ is Lys, $Xaa_4$ is Tyr and $Xaa_5$ is Pro;
Bt1.7: SEQ ID NO:162, wherein $Xaa_2$ is Lys, $Xaa_4$ is Tyr and $Xaa_5$ is Pro;
Lv1.5: SEQ ID NO:163, wherein $Xaa_5$ is Pro;
Ms1.10: SEQ ID NO:164, wherein $Xaa_2$ is Lys, $Xaa_4$ is Tyr and $Xaa_5$ is Pro;
Om1.1: SEQ ID NO:165, wherein $Xaa_4$ is Tyr and $Xaa_5$ is Pro;
R1.6: SEQ ID NO:166, wherein $Xaa_4$ is Tyr and $Xaa_5$ is Pro;
R1.7: SEQ ID NO:167, wherein $Xaa_4$ is Tyr and $Xaa_5$ is Pro;
Vr1.1: SEQ ID NO:168, wherein $Xaa_5$ is Pro; and
Vr1.2: SEQ ID NO:169, wherein $Xaa_5$ is Pro.

The C-terminus preferably contains a carboxyl group for the peptides 5 n1.1, 5 n1.2, Cr1.3, Di1.1, Ms1.2, Ms1.4, Ms1.5, Ms1.8, Ms1.9, Vr1.1 and Vr1.2. The C-terminus of the other peptides preferably contains an amide group.

The present invention is also directed to novel specific α-conotoxin peptides of general formula III having the formulas:

(SEQ ID NO:22)
Gly-Cys-Cys-Ser-Asn-$Xaa_5$-Val-Cys-His-Leu-$Xaa_1$-His-Ser-Asn-Met-Cys;

(SEQ ID NO:23)
Gly-Cys-Cys-Ser-Asn-$Xaa_5$-Val-Cys-Arg-Gln-Asn-Asn-Ala-$Xaa_1$-$Xaa_4$-Cys-Arg;

(SEQ ID NO:24)
$Xaa_5$-Gln-Cys-Cys-Ser-His-$Xaa_5$-Ala-Cys-Asn-Val-Asp-His-$Xaa_5$-$Xaa_1$-Ile-Cys-Arg;

(SEQ ID NO:25)
$Xaa_5$-$Xaa_1$-Cys-Cys-Ser-His-$Xaa_5$-Ala-Cys-Asn-Val-Asp-His-$Xaa_5$-$Xaa_1$-Ile-Cys-Arg;

(SEQ ID NO:26)
$Xaa_5$-Gln-Cys-Cys-Ser-His-$Xaa_5$-Ala-Cys-Asn-Val-Asp-His-$Xaa_5$-$Xaa_1$-Ile-Cys-Asp;

(SEQ ID NO:27)
$Xaa_5$-Arg-Cys-Cys-Ser-His-$Xaa_5$-Ala-Cys-Asn-Val-Asp-His-$Xaa_5$-$Xaa_1$-Ile-Cys-Arg;

(SEQ ID NO:28)
$Xaa_5$-Gln-Cys-Cys-Ser-His-$Xaa_5$-Ala-Cys-Asn-Val-Asp-His-$Xaa_5$-Gly-Ile-Cys-Arg;

(SEQ ID NO:29)
$Xaa_5$-Gln-Cys-Cys-Ser-His-$Xaa_5$-Ala-Cys-Asn-Val-Asp-His-$Xaa_5$-$Xaa_1$-Thr-Cys-Arg;

(SEQ ID NO:30)
$Xaa_5$-Gln-Cys-Cys-Ser-His-$Xaa_5$-Ala-Cys-Asn-Val-Asp-His-$Xaa_5$-$Xaa_1$-Val-Cys-Arg;

(SEQ ID NO:31)
$Xaa_5$-Gln-Cys-Cys-Ser-His-$Xaa_5$-Ala-Cys-Asn-Ile-Asp-His-$Xaa_5$-$Xaa_1$-Ile-Cys-Arg;

(SEQ ID NO:32)
$Xaa_5$-Gln-Cys-Cys-Ser-His-$Xaa_5$-Ala-Cys-Asn-Val-Asp-His-$Xaa_5$-$Xaa_1$-Ile-Cys-Arg-Arg-Arg-Arg;

(SEQ ID NO:33)
Gly-Gly-Cys-Cys-Ser-His-$Xaa_5$-Ala-Cys-Ala-Val-Asn-His-$Xaa_5$-$Xaa_1$-Leu-Cys;

(SEQ ID NO:34)
Gly-Cys-Cys-Ser-His-$Xaa_5$-Ala-Cys-Ser-Val-Asn-His-$Xaa_5$-$Xaa_1$-Leu-Cys;

(SEQ ID NO:35)
Gly-Cys-Cys-Ser-His-$Xaa_5$-Ala-Cys-Asn-Val-Asp-His-$Xaa_5$-$Xaa_1$-Ile-Cys;

(SEQ ID NO:36)
Gly-Cys-Cys-Ser-His-$Xaa_5$-Ala-Cys-Ser-Gly-$Xaa_2$-Thr-Gln-$Xaa_1$-$Xaa_5$-Cys-Arg-$Xaa_1$-Ser;

-continued (SEQ ID NO:37)
$Xaa_5$-Cys-Cys-Ser-His-$Xaa_5$-Ala-Cys-Ser-Gly-Asn-Asn-$Xaa_5$-$Xaa_1$-Phe-Cys-Arg-Gln;

(SEQ ID NO:38)
Gly-Cys-Cys-Ser-His-$Xaa_5$-Ala-Cys-Ser-Gly-Asn-Asn-$Xaa_5$-$Xaa_1$-Phe-Cys-Arg-Gln;

(SEQ ID NO:39)
Gly-Cys-Cys-Ser-His-$Xaa_5$-$Xaa_5$-Cys-Ala-Met-Asn-Asn-$Xaa_5$-Asp-$Xaa_4$-Cys;

(SEQ ID NO:40)
Gly-Cys-Cys-Ser-His-$Xaa_5$-$Xaa_5$-Cys-Phe-Leu-Asn-Asn-$Xaa_5$-Asp-$Xaa_4$-Cys;

(SEQ ID NO:41)
Gly-Cys-Cys-Ser-Asn-$Xaa_5$-$Xaa_5$-Cys-Ile-Ala-$Xaa_2$-Asn-$Xaa_5$-His-Met-Cys-Gly;

(SEQ ID NO:43)
Gly-Cys-Cys-Ser-Asn-$Xaa_5$-Ala-Cys-Ala-Gly-Asn-Asn-$Xaa_5$-His-Val-Cys-Arg-Gln;

(SEQ ID NO:44)
Gly-Cys-Cys-Ser-Arg-$Xaa_5$-Ala-Cys-Ile-Ala-Asn-Asn-$Xaa_5$-Asp-Leu-Cys;

(SEQ ID NO:45)
Gly-Cys-Cys-Ser-Asn-$Xaa_5$-Val-Cys-His-Val-$Xaa_1$-His-$Xaa_5$-$Xaa_1$-Leu-Cys-Arg-Arg-Arg-Arg;

(SEQ ID NO:46)
Gly-Gly-Cys-Cys-Ser-Phe-$Xaa_5$-Ala-Cys-Arg-$Xaa_2$-$Xaa_5$-Arg-$Xaa_5$-$Xaa_1$-Met-Cys-Gly;

(SEQ ID NO:47)
$Xaa_5$-$Xaa_1$-Cys-Cys-Ser-Asp-$Xaa_5$-Arg-Cys-Asn-Ser-Ser-His-$Xaa_5$-$Xaa_1$-Leu-Cys-Gly;

(SEQ ID NO:48)
$Xaa_5$-Gln-Cys-Cys-Ser-Asp-$Xaa_5$-Arg-Cys-Asn-Val-Gly-His-$Xaa_5$-$Xaa_1$-Leu-Cys-Gly;

(SEQ ID NO:49)
$Xaa_6$-Val-Cys-Cys-Ser-Asp-$Xaa_5$-Arg-Cys-Asn-Val-Gly-His-$Xaa_5$-$Xaa_1$-Ile-Cys-Gly;

(SEQ ID NO:50)
Gly-Cys-Cys-Ser-Arg-$Xaa_5$-$Xaa_5$-Cys-Ile-Ala-Asn-Asn-$Xaa_5$-Asp-Leu-Cys;

(SEQ ID NO:51)
$Xaa_5$-Gln-Cys-Cys-Ser-His-Leu-Ala-Cys-Asn-Val-Asp-His-$Xaa_5$-$Xaa_1$-Ile-Cys-Arg;

(SEQ ID NO:52)
Gly-Cys-Cys-Ser-$Xaa_4$-Phe-Asp-Cys-Arg-Met-Met-Phe-$Xaa_5$-$Xaa_1$-Met-Cys-Gly-$Xaa_3$-Arg;

(SEQ ID NO:53)
Gly-Gly-Cys-Cys-Ser-Phe-Ala-Ala-Cys-Arg-$Xaa_2$-$Xaa_4$-Arg-$Xaa_5$-$Xaa_1$-Met-Cys-Gly;

-continued (SEQ ID NO:54)
Gly-Gly-Cys-Cys-Phe-His-$Xaa_5$-Val-Cys-$Xaa_4$-Ile-Asn-Leu-Leu-$Xaa_1$-Met-Cys-Arg-Gln-Arg;

(SEQ ID NO:55)
Ser-Ala-Thr-Cys-Cys-Asn-$Xaa_4$-$Xaa_5$-$Xaa_5$-Cys-$Xaa_4$-$Xaa_1$-Thr-$Xaa_4$-$Xaa_5$-$Xaa_1$-Ser-Cys-Leu;

(SEQ ID NO:56)
Ala-Cys-Cys-Ala-$Xaa_4$-$Xaa_5$-$Xaa_5$-Cys-Phe-$Xaa_1$-Ala-$Xaa_4$-$Xaa_5$-$Xaa_1$-Arg-Cys-Leu;

(SEQ ID NO:57)
Asn-Ala-$Xaa_1$-Cys-Cys-$Xaa_4$-$Xaa_4$-$Xaa_5$-$Xaa_5$-Cys-$Xaa_4$-$Xaa_1$-Ala-$Xaa_4$-$Xaa_5$-$Xaa_1$-Ile-Cys-Leu;

(SEQ ID NO:170)
$Xaa_1$-Cys-Cys-Thr-Asn-$Xaa_5$-Val-Cys-His-Ala-$Xaa_1$-His-Gln-$Xaa_1$-Leu-Cys-Ala-Arg-Arg-Arg;

(SEQ ID NO:171)
Gly-Cys-Cys-Ser-Asn-$Xaa_5$-Val-Cys-His-Leu-$Xaa_1$-His-Ser-Asn-Leu-Cys;

(SEQ ID NO:172)
$Xaa_1$-Cys-Cys-Thr-Asn-$Xaa_5$-Val-Cys-His-Val-$Xaa_1$-His-Gln-$Xaa_1$-Leu-Cys-Ala-Arg-Arg-Arg;

(SEQ ID NO:173)
$Xaa_6$-$Xaa_1$-Cys-Cys-Ser-$Xaa_4$-$Xaa_5$-Ala-Cys-Asn-Leu-Asp-His-$Xaa_5$-$Xaa_1$-Leu-Cys;

(SEQ ID NO:174)
$Xaa_5$-$Xaa_1$-Cys-Cys-Ser-Asp-$Xaa_5$-Arg-Cys-Asn-Ser-Thr-His-$Xaa_5$-$Xaa_1$-Leu-Cys-Gly;

(SEQ ID NO:175)
Leu-Asn-Cys-Cys-Met-Ile-$Xaa_5$-$Xaa_5$-Cys-$Xaa_3$-$Xaa_2$-$Xaa_2$-$Xaa_4$-Gly-Asp-Arg-Cys-Ser-$Xaa_1$-Val-Arg;

(SEQ ID NO:176)
Ala-Phe-Gly-Cys-Cys-Asp-Leu-Ile-$Xaa_5$-Cys-Leu-$Xaa_1$-Arg-$Xaa_4$-Gly-Asn-Arg-Cys-Asn-$Xaa_1$-Val-His;

(SEQ ID NO:177)
Leu-Gly-Cys-Cys-Asn-Val-Thr-$Xaa_5$-Cys-$Xaa_3$-$Xaa_1$-$Xaa_2$-$Xaa_4$-Gly-Asp-$Xaa_2$-Cys-Asn-$Xaa_1$-Val-Arg;

(SEQ ID NO:178)
Asp-$Xaa_1$-Cys-Cys-Ser-Asn-$Xaa_5$-Ala-Cys-Arg-Val-Asn-Asn-$Xaa_5$-His-Val-Cys-Arg-Arg-Arg;

(SEQ ID NO:179)
Leu-Asn-Cys-Cys-Ser-Ile-$Xaa_5$-Gly-Cys-$Xaa_3$-Asn-$Xaa_1$-$Xaa_4$-$Xaa_2$-Asp-Arg-Cys-Ser-$Xaa_2$-Val-Arg;

(SEQ ID NO:180)
Gly-Gly-Cys-Cys-Ser-His-$Xaa_5$-Val-Cys-$Xaa_4$-Phe-Asn-Asn-$Xaa_5$-Gln-Met-Cys-Arg;

(SEQ ID NO:181)
Gly-Gly-Cys-Cys-Ser-His-$Xaa_5$-Val-Cys-Asn-Leu-Asn-Asn-$Xaa_5$-Gln-Met-Cys-Arg;

-continued (SEQ ID NO:182)
Gly-Cys-Cys-Ser-His-$Xaa_5$-$Xaa_5$-Cys-$Xaa_4$-Ala-Asn-Asn-Gln-Ala-$Xaa_4$-Cys-Asn;

(SEQ ID NO:183)
Gly-Gly-Cys-Cys-Ser-His-$Xaa_5$-Ala-Cys-Ser-Val-Thr-His-$Xaa_5$-$Xaa_1$-Leu-Cys;

(SEQ ID NO:184)
Gly-Gly-Cys-Cys-Ser-$Xaa_4$-$Xaa_5$-Ala-Cys-Ser-Val-$Xaa_1$-His-Gln-Asp-Leu-Cys-Asp;

(SEQ ID NO:185)
Val-Ser-Cys-Cys-Val-Val-Arg-$Xaa_5$-Cys-$Xaa_3$-Ile-Arg-$Xaa_4$-Gln-$Xaa_1$-$Xaa_1$-Cys-Leu-$Xaa_1$-Ala-Asp-$Xaa_5$-Arg-Thr-Leu;

(SEQ ID NO:186)
$Xaa_6$-Asn-Cys-Cys-Ser-Ile-$Xaa_5$-Gly-Cys-$Xaa_3$-$Xaa_1$-$Xaa_2$-$Xaa_4$-Gly-Asp-$Xaa_2$-Cys-Ser-$Xaa_1$-Val-Arg;

(SEQ ID NO:187)
Gly-Cys-Cys-Ser-Asn-$Xaa_5$-Val-Cys-His-Leu-$Xaa_1$-His-$Xaa_5$-Asn-Ala-Cys;

(SEQ ID NO:188)
Gly-Cys-Cys-Ser-Asn-$Xaa_5$-Ile-Cys-$Xaa_4$-Phe-Asn-Asn-$Xaa_5$-Arg-Ile-Cys-Arg;

(SEQ ID NO:189)
$Xaa_1$-Cys-Cys-Ser-Gln-$Xaa_5$-$Xaa_5$-Cys-Arg-$Xaa_3$-$Xaa_2$-His-$Xaa_5$-$Xaa_1$-Leu-Cys-Ser;

(SEQ ID NO:190)
Gly-Cys-Cys-Ser-His-$Xaa_5$-Ala-Cys-Ala-Gly-Asn-Asn-Gln-His-Ile-Cys;

(SEQ ID NO:191)
Gly-Cys-Cys-Ala-Val-$Xaa_5$-Ser-Cys-Arg-Leu-Arg-Asn-$Xaa_5$-Asp-Leu-Cys-Gly-Gly;

(SEQ ID NO:192)
Gly-Cys-Cys-Ser-His-$Xaa_5$-Ala-Cys-Asn-Val-Asn-Asn-$Xaa_5$-His-Ile-Cys;

(SEQ ID NO:193)
Thr-$Xaa_5$-$Xaa_1$-$Xaa_1$-Cys-Cys-$Xaa_5$-Asn-$Xaa_5$-$Xaa_5$-Cys-Phe-Ala-Thr-Asn-Ser-Asp-Ile-Cys-Gly;

(SEQ ID NO:194)
Asp-Ala-Cys-Cys-Ser-Asp-$Xaa_5$-Arg-Cys-Ser-Gly-$Xaa_2$-His-Gln-Asp-Leu-Cys;

(SEQ ID NO:195)
$Xaa_1$-Asp-Cys-Cys-Ser-Asp-$Xaa_5$-Arg-Cys-Ser-Val-Gly-His-Gln-Asp-Leu-Cys;

(SEQ ID NO:196)
Gly-Cys-Cys-Ser-His-$Xaa_5$-Ala-Cys-Ala-Gly-Ser-Asn-Ala-His-Ile-Cys;

-continued (SEQ ID NO:197)
$Xaa_1$-Asp-Cys-Cys-Ser-Asp-$Xaa_5$-Arg-Cys-Ser-Val-Gly-His-Gln-Asp-Met-Cys;

(SEQ ID NO:198)
Gly-Cys-Cys-Ser-His-$Xaa_5$-Ala-Cys-Ala-Gly-Asn-Asn-$Xaa_5$-His-Ile-Cys;

(SEQ ID NO:199)
Gly-Cys-Cys-Gly-Asn-$Xaa_5$-Ser-Cys-Ser-Ile-His-Ile-$Xaa_5$-$Xaa_4$-Val-Cys-Asn;

(SEQ ID NO:200)
Thr-Asp-Ser-$Xaa_1$-$Xaa_1$-Cys-Cys-Leu-Asp-Ser-Arg-Cys-Ala-Gly-Gln-His-Gln-Asp-Leu-Cys-Gly;

(SEQ ID NO:201)
Gly-Cys-Cys-Ser-Asn-$Xaa_5$-$Xaa_5$-Cys-$Xaa_4$-Ala-Asn-Asn-Gln-Ala-$Xaa_4$-Cys-Asn;

(SEQ ID NO:202)
Gly-Cys-Cys-Ser-His-$Xaa_5$-Ala-Cys-Ser-Val-Asn-Asn-$Xaa_5$-Asp-Ile-Cys;

(SEQ ID NO:203)
Gly-$Xaa_2$-Cys-Cys-Ile-Asn-Asp-Ala-Cys-Arg-Ser-$Xaa_2$-His-$Xaa_5$-Gln-$Xaa_4$-Cys-Ser;

(SEQ ID NO:204)
Gly-Cys-Cys-$Xaa_4$-Asn-Ile-Ala-Cys-Arg-Ile-Asn-Asn-$Xaa_5$-Arg-$Xaa_4$-Cys-Arg;

(SEQ ID NO:205)
Gly-Cys-Cys-Ser-His-$Xaa_5$-Val-Cys-Arg-Phe-Asn-$Xaa_4$-$Xaa_5$-$Xaa_2$-$Xaa_4$-Cys-Gly;

(SEQ ID NO:206)
Asp-$Xaa_1$-Cys-Cys-Ala-Ser-$Xaa_5$-$Xaa_5$-Cys-Arg-Leu-Asn-Asn-$Xaa_5$-$Xaa_4$-Val-Cys-His;

(SEQ ID NO:207)
Gly-Cys-Cys-Ser-Asn-$Xaa_5$-Val-Cys-$Xaa_3$-Gln-Asn-Asn-Ala-$Xaa_1$-$Xaa_4$-Cys-Arg-$Xaa_1$-Ser;

(SEQ ID NO:208)
Gly-Cys-Cys-Ser-His-$Xaa_5$-$Xaa_5$-Cys-Ala-Gln-Asn-Asn-Gln-Asp-$Xaa_4$-Cys;

(SEQ ID NO:209)
Gly-Cys-Cys-Ser-His-$Xaa_5$-Ala-Cys-Ser-Gly-Asn-Asn-Arg-$Xaa_1$-$Xaa_4$-Cys-Arg-$Xaa_1$-Ser;

(SEQ ID NO:210)
Asp-$Xaa_5$-Cys-Cys-Ser-$Xaa_4$-$Xaa_5$-Asp-Cys-Gly-Ala-Asn-His-$Xaa_5$-$Xaa_1$-Ile-Cys-Gly;

(SEQ ID NO:211)
$Xaa_1$-Cys-Cys-Ser-Gln-$Xaa_5$-$Xaa_5$-Cys-Arg-$Xaa_3$-$Xaa_2$-His-$Xaa_5$-$Xaa_1$-Leu-Cys-Ser;

(SEQ ID NO:212)
Gly-Cys-Cys-Ser-His-$Xaa_5$-Ala-Cys-Ala-Gly-Asn-Asn-$Xaa_5$-His-Ile-Cys;

-continued (SEQ ID NO:213)
Gly-Cys-Cys-Ser-Asp-$Xaa_5$-Ser-Cys-Asn-Val-Asn-Asn-$Xaa_5$-Asp-$Xaa_4$-Cys;

(SEQ ID NO:214)
$Xaa_1$-$Xaa_1$-Cys-Cys-Ser-Asp-$Xaa_5$-Arg-Cys-Ser-Val-Gly-His-Gln-Asp-Met-Cys-Arg;

(SEQ ID NO:215)
Gly-Gly-Cys-Cys-Ser-Asn-$Xaa_5$-Ala-Cys-Leu-Val-Asn-His-Leu-$Xaa_1$-Met-Cys;

(SEQ ID NO:216)
Arg-Asp-$Xaa_5$-Cys-Cys-Phe-Asn-$Xaa_5$-Ala-Cys-Asn-Val-Asn-Asn-$Xaa_5$-Gln-Ile-Cys;

(SEQ ID NO:217)
Cys-Cys-Ser-Asp-$Xaa_5$-Ser-Cys-$Xaa_3$-Arg-Leu-His-Ser-Leu-Ala-Cys-Thr-Gly-Ile-Val-Asn-Arg;

(SEQ ID NO:218)
Cys-Cys-Thr-Asn-$Xaa_5$-Ala-Cys-Leu-Val-Asn-Asn-Ile-Arg-Phe-Cys-Gly;

(SEQ ID NO:219)
Asp-$Xaa_1$-Cys-Cys-Ser-Asp-$Xaa_5$-Arg-Cys-His-Gly-Asn-Asn-Arg-Asp-His-Cys-Ala;

(SEQ ID NO:220)
Asp-Cys-Cys-Ser-His-$Xaa_5$-Leu-Cys-Arg-Leu-Phe-Val-$Xaa_5$-Gly-Leu-Cys-Ile;

(SEQ ID NO:221)
Gly-Cys-Cys-Ser-His-$Xaa_5$-Val-Cys-$Xaa_2$-Val-Arg-$Xaa_4$-$Xaa_5$-Asp-Leu-Cys-Arg;

(SEQ ID NO:222)
Gly-Cys-Cys-Ser-His-$Xaa_5$-Ala-Cys-Asn-Val-Asn-Asn-$Xaa_5$-His-Ile-Cys;

(SEQ ID NO:223)
Gly-Cys-Cys-Ser-His-$Xaa_5$-Val-Cys-$Xaa_2$-Val-Arg-$Xaa_4$-Ser-Asp-Met-Cys;

(SEQ ID NO:224)
Gly-Gly-Cys-Cys-Ser-His-$Xaa_5$-Ala-Cys-$Xaa_2$-Val-His-Phe-$Xaa_5$-His-Ser-Cys;

(SEQ ID NO:225)
Val-Cys-Cys-Ser-Asn-$Xaa_5$-Val-Cys-His-Val-Asp-His-$Xaa_5$-$Xaa_1$-Leu-Cys-Arg-Arg-Arg-Arg;

(SEQ ID NO:226)
Gly-Cys-Cys-Ser-His-$Xaa_5$-Val-Cys-Asn-Leu-Ser-Asn-$Xaa_5$-Gln-Ile-Cys-Arg;

(SEQ ID NO:227)
$Xaa_6$-$Xaa_1$-Cys-Cys-Ser-His-$Xaa_5$-Ala-Cys-Asn-Val-Asp-His-$Xaa_5$-$Xaa_1$-Ile-Cys-Arg;

(SEQ ID NO:228)
Gly-Cys-Cys-Ser-Asn-$Xaa_5$-Ala-Cys-Leu-Val-Asn-His-Ile-Arg-Phe-Cys-Gly;

-continued (SEQ ID NO:229)
Asp-Cys-Cys-Asp-Asp-$Xaa_5$-Ala-Cys-Thr-Val-Asn-Asn-$Xaa_5$-Gly-Leu-Cys-Thr;
and (SEQ ID NO:230)
Gly-Cys-Cys-Ser-Asn-$Xaa_5$-$Xaa_5$-Cys-Ile-Ala-$Xaa_2$-Asn-$Xaa_5$-His-Met-Cys-Gly-Gly-Arg-Arg, wherein $Xaa_1$ is Glu or γ-carboxy-Glu (Gla); $Xaa_2$ is Lys, N-methyl-Lys, N,N-dimethyl-Lys or N,N,N-trimethyl-Lys; $Xaa_3$ is Trp (D or L), halo-Trp or neo-Trp; $Xaa_4$ is Tyr, nor-Tyr, mono-halo-Tyr, di-halo-Tyr, O-sulpho-Tyr, O-phospho-Tyr or nitro-Tyr; and $Xaa_5$ is Pro or hydroxy-Pro; $Xaa_6$ is Gln or pyro-Glu; and the C-terminus contains a carboxyl or amide group. The halo is preferably bromine, chlorine or iodine, more preferably iodine for Tyr and bromine for Trp. In addition, the His residues may be substituted with halo-His; the Arg residues may be substituted by Lys, ornithine, homoarginine, N-methyl-Lys, N,N-dimethyl-Lys, N,N,N-trimethyl-Lys or any unnatural basic amino acid; the Lys residues may be substituted by Arg, ornithine, homoarginine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe and Trp residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to the following α-conotoxin peptides of general formula III:

SmI: SEQ ID NO:22, wherein $Xaa_1$ is Glu and $Xaa_5$ is Pro;

OB-29: SEQ ID NO:23, wherein $Xaa_1$ is Glu, $Xaa_3$ is Tyr and $Xaa_5$ is Pro;

Tx1.1: SEQ ID NO:24, wherein $Xaa_1$ is Glu and $Xaa_5$ is Pro;

R1.1A: SEQ ID NO:25, wherein $Xaa_1$ is Glu and $Xaa_5$ is Pro;

R1.1B: SEQ ID NO:26, wherein $Xaa_1$ is Glu and $Xaa_5$ is Pro;

Om-9: SEQ ID NO:27, wherein $Xaa_1$ is Glu and $Xaa_5$ is Pro;

Om-10: SEQ ID NO:28, wherein $Xaa_5$ is Pro;

Om-21: SEQ ID NO:29, wherein $Xaa_1$ is Glu and $Xaa_5$ is Pro;

Om-25: SEQ ID NO:30, wherein $Xaa_1$ is Glu and $Xaa_5$ is Pro;

Om-27: SEQ ID NO:31, wherein $Xaa_1$ is Glu and $Xaa_5$ is Pro;

Om-28: SEQ ID NO:32, wherein $Xaa_1$ is Glu and $Xaa_5$ is Pro;

Bt1.2: SEQ ID NO:33, wherein $Xaa_1$ is Glu and $Xaa_5$ is Pro;

Bt1.4: SEQ ID NO:34, wherein $Xaa_1$ is Glu and $Xaa_5$ is Pro;

Da1.1: SEQ ID NO:35, wherein $Xaa_1$ is Glu and $Xaa_5$ is Pro; OB-20: SEQ ID NO:36, wherein $Xaa_1$ is Glu, $Xaa_2$ is Lys and $Xaa_5$ is Pro;

TI: SEQ ID NO:37, wherein $Xaa_1$ is Glu and $Xaa_5$ is Pro;
TIB: SEQ ID NO:38, wherein $Xaa_1$ is Glu and $Xaa_5$ is Pro;
Pn1.1: SEQ ID NO:39, wherein $Xaa_5$ is Pro;
Pn1.2: SEQ ID NO:40, wherein $Xaa_1$ is Glu and $Xaa_5$ is Pro;
T1: SEQ ID NO:41, wherein $Xaa_2$ is Lys and $Xaa_5$ is Pro;
TIA: SEQ ID NO:43, wherein $Xaa_5$ is Pro;
Da1.2: SEQ ID NO:44, wherein $Xaa_5$ is Pro;
Cr1.2: SEQ ID NO:45, wherein $Xaa_1$ is Glu and $Xaa_5$ is Pro;
SI1.2: SEQ ID NO:46, wherein $Xaa_1$ is Glu, $Xaa_2$ is Lys and $Xaa_5$ is Pro;
Tx1.3: SEQ ID NO:47, wherein $Xaa_1$ is Glu and $Xaa_5$ is Pro;
Da1.3: SEQ ID NO:48, wherein $Xaa_1$ is Glu and $Xaa_5$ is Pro;
Da1.4: SEQ ID NO:49, wherein $Xaa_1$ is Glu, $Xaa_5$ is Pro and $Xaa_6$ is Gln;
Tx1.2: SEQ ID NO:50, wherein $Xaa_5$ is Pro;
Om-35: SEQ ID NO:51, wherein $Xaa_1$ is Glu and $Xaa_5$ is Pro;
Sl1.1: SEQ ID NO:52, wherein $Xaa_1$ is Glu, $Xaa_3$ is Trp, $Xaa_4$ is Tyr and $Xaa_5$ is Pro;
Sl1.6: SEQ ID NO:53, wherein $Xaa_1$ is Glu, $Xaa_2$ is Lys, $Xaa_4$ is Tyr and $Xaa_5$ is Pro;
Sl1.7: SEQ ID NO:54, wherein $Xaa_1$ is Glu $Xaa_4$ is Tyr and $Xaa_5$ is Pro;
Bt1.1: SEQ ID NO:55, wherein $Xaa_1$ is Glu $Xaa_4$ is Tyr and $Xaa_5$ is Pro;
Bt:1.3: SEQ ID NO:56, wherein $Xaa_1$ is Glu $Xaa_4$ is Tyr and $Xaa_5$ is Pro;
Bt1.5: SEQ ID NO:57, wherein $Xaa_1$ is Glu $Xaa_4$ is Tyr and $Xaa_5$ is Pro;
A1.4: SEQ ID NO:170, wherein $Xaa_1$ is Glu and $Xaa_5$ is Pro;
A1.5: SEQ ID NO:171, wherein $Xaa_1$ is Glu and $Xaa_5$ is Pro;
A1.6: SEQ ID NO:172, wherein $Xaa_1$ is Glu and $Xaa_5$ is Pro;
Af1.1: SEQ ID NO:173, wherein $Xaa_1$ is Glu $Xaa_4$ is Tyr, $Xaa_5$ is Pro and $Xaa_6$ is Gln;
Af1.2: SEQ ID NO:174, wherein $Xaa_1$ is Glu and $Xaa_5$ is Pro;
Ar1.2: SEQ ID NO:175, wherein $Xaa_1$ is Glu, $Xaa_2$ is Lys, $Xaa_3$ is Trp, $Xaa_4$ is Try and $Xaa_5$ is Pro;
Ar1.3: SEQ ID NO:176, wherein $Xaa_1$ is Glu, $Xaa_4$ is Tyr and $Xaa_5$ is Pro;
Ar1.4: SEQ ID NO:177, wherein $Xaa_1$ is Glu, $Xaa_2$ is Lys, $Xaa_3$ is Trp, $Xaa_4$ is Try and $Xaa_5$ is Pro;
Ar1.5: SEQ ID NO:178, wherein $Xaa_1$ is Glu and $Xaa_5$ is Pro;
Ar1.6: SEQ ID NO:179, wherein $Xaa_1$ is Glu, $Xaa_2$ is Lys, $Xaa_3$ is Trp, $Xaa_4$ is Try and $Xaa_5$ is Pro;
Ay1.2: SEQ ID NO:180, wherein $Xaa_4$ is Tyr and $Xaa_5$ is Pro;
Ay1.3: SEQ ID NO:181, wherein $Xaa_5$ is Pro;
Bn1.4: SEQ ID NO:182, wherein $Xaa_4$ is Tyr and $Xaa_5$ is Pro;
Bt1.8: SEQ ID NO:183, wherein $Xaa_1$ is Glu and $Xaa_5$ is Pro;
Bt1.9: SEQ ID NO:184, wherein $Xaa_1$ is Glu, $Xaa_4$ is Tyr and $Xaa_5$ is Pro;
Ca1.3: SEQ ID NO:185, wherein $Xaa_1$ is Glu, $Xaa_3$ is Trp, $Xaa_4$ is Try and $Xaa_5$ is Pro;
Ca1.4: SEQ ID NO:186, wherein $Xaa_1$ is Glu, $Xaa_2$ is Lys, $Xaa_3$ is Trp, $Xaa_4$ is Try, $Xaa_5$ is Pro and $Xaa_6$ is Gln;
C1.2: SEQ ID NO:187, wherein $Xaa_1$ is Glu and $Xaa_5$ is Pro;
C1.3: SEQ ID NO:188, wherein $Xaa_4$ is Tyr and $Xaa_5$ is Pro;
Ep1.2: SEQ ID NO:189, wherein $Xaa_1$ is Glu, $Xaa_2$ is Lys, $Xaa_3$ is Trp and $Xaa_5$ is Pro;
G1.1: SEQ ID NO:190, wherein $Xaa_5$ is Pro;
G1.3: SEQ ID NO:191, wherein $Xaa_5$ is Pro;
Im1.3: SEQ ID NO:192, wherein $Xaa_5$ is Pro;
Lv1.2: SEQ ID NO:193, wherein $Xaa_1$ is Glu and $Xaa_5$ is Pro;
Lv1.3: SEQ ID NO:194, wherein $Xaa_2$ is Lys and $Xaa_5$ is Pro;
Lv1.4: SEQ ID NO:195, wherein $Xaa_1$ is Glu and $Xaa_5$ is Pro;
Lv1.6: SEQ ID NO:196, wherein $Xaa_5$ is Pro;
Lv1.7: SEQ ID NO:197, wherein $Xaa_1$ is Glu and $Xaa_5$ is Pro;
Lv1.8: SEQ ID NO:198, wherein $Xaa_5$ is Pro;
Lv1.9: SEQ ID NO:199, wherein $Xaa_4$ is Tyr and $Xaa_5$ is Pro;
Lv1.10: SEQ ID NO:200, wherein $Xaa_1$ is Glu;
Mr1.3: SEQ ID NO:201, wherein $Xaa_4$ is Tyr and $Xaa_5$ is Pro;
Mr1.4: SEQ ID NO:202, wherein $Xaa_5$ is Pro;
Ms 1.1: SEQ ID NO:203, wherein $Xaa_2$ is Lys, $Xaa_4$ is Tyr and $Xaa_5$ is Pro;
Ms1.6: SEQ ID NO:204, wherein $Xaa_4$ is Tyr and $Xaa_5$ is Pro;
O1.1: SEQ ID NO:205, wherein $Xaa_2$ is Lys, $Xaa_4$ is Tyr and $Xaa_5$ is Pro;
O1.2: SEQ ID NO:206, wherein $Xaa_1$ is Glu, $Xaa_4$ is Tyr and $Xaa_5$ is Pro;
O1.4: SEQ ID NO:207, wherein $Xaa_1$ is Glu, $Xaa_3$ is Trp, $Xaa_4$ is Tyr and $Xaa_5$ is Pro;
O1.7: SEQ ID NO:208, wherein $Xaa_4$ is Tyr and $Xaa_5$ is Pro;
O1.8: SEQ ID NO:209, wherein $Xaa_1$ is Glu, $Xaa_4$ is Tyr and $Xaa_5$ is Pro;
Om1.2: SEQ ID NO:210, wherein $Xaa_1$ is Glu, $Xaa_4$ is Tyr and $Xaa_5$ is Pro;
Om1.3: SEQ ID NO:211, wherein $Xaa_1$ is Glu, $Xaa_2$ is Lys, $Xaa_3$ is Trp and $Xaa_5$ is Pro;
Om1.4: SEQ ID NO:212, wherein $Xaa_5$ is Pro;
Om1.5: SEQ ID NO:213, wherein $Xaa_4$ is Tyr and $Xaa_5$ is Pro;
Om1.6: SEQ ID NO:214, wherein $Xaa_1$ is Glu and $Xaa_5$ is Pro;
P1.4: SEQ ID NO:215, wherein $Xaa_1$ is Glu and $Xaa_5$ is Pro;
P1.5: SEQ ID NO:216, wherein $Xaa_5$ is Pro;
P1.6: SEQ ID NO:217, wherein $Xaa_3$ is Trp and $Xaa_5$ is Pro;
P1.8: SEQ ID NO:218, wherein $Xaa_5$ is Pro;
Rg1.1: SEQ ID NO:219, wherein $Xaa_1$ is Glu and $Xaa_5$ is Pro;
Rg1.3: SEQ ID NO:220, wherein $Xaa_5$ is Pro;
Rg1.4: SEQ ID NO:221, wherein $Xaa_2$ is Lys, $Xaa_4$ is Tyr and $Xaa_5$ is Pro;
Rg1.5: SEQ ID NO:222, wherein $Xaa_5$ is Pro;
Rg1.8: SEQ ID NO:223, wherein $Xaa_2$ is Lys, $Xaa_4$ is Tyr and $Xaa_5$ is Pro;
Sm1.4: SEQ ID NO:224, wherein $Xaa_2$ is Lys and $Xaa_5$ is Pro;
Sm1.5: SEQ ID NO:225, wherein $Xaa_1$ is Glu and $Xaa_5$ is Pro;
S1.5: SEQ ID NO:226, wherein $Xaa_5$ is Pro;

Tx1.5: SEQ ID NO:227, wherein $Xaa_1$ is Glu, $Xaa_5$ is Pro and $Xaa_6$ is Gln;

T1.1: SEQ ID NO:228, wherein $Xaa_5$ is Pro;

Vr1.3: SEQ ID NO:229, wherein $Xaa_5$ is Pro; and

Tb: SEQ ID NO:230, wherein $Xaa_2$ is Lys and $Xaa_5$ is Pro.

The C-terminus preferably contains a carboxyl group for the peptides OB-29, Tx1.1, R1.1A, R1.1B, Om-9, Om-10, Om-21, Om-25, Om-27, Om-28, Cr1.2, Om-35, Bt1.1, Bt1.3, Bt1.5, A1.4, A1.6, Ar1.2, Ar1.3, Ar1.4, Ar1.5, Ar1.6, Ca1.3, Ca1.4, Ep1.2, Lv1.9, 01.2, Om1.3, Om1.6, P1.6, Rg1.1, Rg1.3, Rg1.4, Sm1.5, Tx1.5 and Vr1.3. The C-terminus of the other peptides preferably contains an amide group.

The present invention is also directed to the novel specific α-conotoxin peptides having the formulas:

(SEQ ID NO:231)
Cys-Cys-Thr-Ile-$Xaa_5$-Ser-Cys-$Xaa_4$-$Xaa_1$-$Xaa_2$-$Xaa_2$-

$Xaa_2$-Ile-$Xaa_2$-Ala-Cys-Val-Phe and (SEQ ID NO:232)
Gly-Cys-Cys-Gly-Asn-$Xaa_5$-Ala-Cys-Ser-Gly-Ser-Ser- $Xaa_2$-Asp-Ala-$Xaa_5$-Ser-Cys, wherein $Xaa_1$ is Glu or γ-carboxy-Glu (Gla); $Xaa_2$ is Lys, N-methyl-Lys, N,N-dimethyl-Lys or N,N,N-trimethyl-Lys; $Xaa_4$ is Tyr, nor-Tyr, mono-halo-Tyr, di-halo-Tyr, O-sulpho-Tyr, O-phospho-Tyr or nitro-Tyr; and $Xaa_5$ is Pro or hydroxy-Pro; and the C-terminus contains a carboxyl or amide group. The halo is preferably bromine, chlorine or iodine, more preferably iodine for Tyr. In addition, the His residues may be substituted with halo-His; the Arg residues may be substituted by Lys, ornithine, homoarginine, N-methyl-Lys, N,N-dimethyl-Lys, N,N,N-trimethyl-Lys or any unnatural basic amino acid; the Lys residues may be substituted by Arg, ornithine, homoarginine, N-methyl-Lys, N,N-dimethyl-Lys, N,N,N-trimethyl-Lys or any unnatural basic amino acid; the Tyr residues may be substituted with any unnatural hydroxy containing amino acid; the Ser residues may be substituted with Thr; the Thr residues may be substituted with Ser; and the Phe residues may be substituted with any unnatural aromatic amino acid. The Cys residues may be in D or L configuration and may optionally be substituted with homocysteine (D or L). The Tyr residues may be substituted with the 3-hydroxyl or 2-hydroxyl isomers and corresponding O-sulpho- and O-phospho-derivatives. The acidic amino acid residues may be substituted with any synthetic acidic bioisoteric amino acid surrogate, e.g., tetrazolyl derivatives of Gly and Ala.

More specifically, the present invention is directed to the following α-conotoxin peptides:

G1.2: SEQ ID NO:231, wherein $Xaa_1$ is Glu, $Xaa_2$ is Lys, $Xaa_4$ is Tyr and $Xaa_5$ is Pro; and Rg1.12: SEQ ID NO:232, wherein $Xaa_2$ is Lys and $Xaa_5$ is Pro.

The C-terminus of G1.2 preferably contains a carboxyl group, and the C-terminus of Rg1.12 preferably contains an amide group.

Examples of unnatural aromatic amino acid include, but are not limited to, such as nitro-Phe, 4-substituted-Phe wherein the substituent is $C_1$-$C_3$ alkyl, carboxyl, hydroxymethyl, sulphomethyl, halo, phenyl, —CHO, —CN, —$SO_3H$ and —NHAc. Examples of unnatural hydroxy containing amino acid, include, but are not limited to, such as 4-hydroxymethyl-Phe, 4-hydroxyphenyl-Gly, 2,6-dimethyl-Tyr and 5-amino-Tyr. Examples of unnatural basic amino acids include, but are not limited to, N-1-(2-pyrazolinyl)-Arg, 2-(4-piperinyl)-Gly, 2-(4-piperinyl)-Ala, 2-[3-(2S)pyrrolininyl)-Gly and 2-[3-(2S)pyrrolininyl)-Ala. These and other unnatural basic amino acids, unnatural hydroxy containing amino acids or unnatural aromatic amino acids are described in Building Block Index, Version 3.0 (1999 Catalog, pages 4-47 for hydroxy containing amino acids and aromatic amino acids and pages 66-87 for basic amino acids; see also website "amino-acids.com"), incorporated herein by reference, by and available from RSP Amino Acid Analogues, Inc., Worcester, Mass.

Optionally, in the peptides of general formulas I, II and III and the specific peptides described above, the Asn residues may be modified to contain an N-glycan and the Ser and Thr residues may be modified to contain an O-glycan. In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The glycan may also include similar polyhydroxy groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1−.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420,797, filed 19 Oct. 1999 (now U.S. Pat. No. 6,369,193) and in PCT Application No. PCT/US99/24380, filed 19 Oct. 1999, both incorporated herein by reference. A preferred glycan is Gal(β1→3)GalNAc(α1→).

Optionally, in the peptides of general formulas I and II and the specific peptides described above, pairs of Cys residues may be replaced pairwise with Ser/(Glu or Asp) or Lys/(Glu or Asp) combinations. Sequential coupling by known methods (Barnay et al., 2000; Hruby et al., 1994; Bitan et al., 1997) allows replacement of native Cys bridges with lactam bridges.

The present invention is further directed to propeptides and nucleic acid sequences encoding the propeptides or peptides as described in further detail herein.

DETAILED DESCRIPTION OF THE INVENTION

The invention relates to relatively short peptides (termed α-conotoxins herein), about 10-30 residues in length, which are naturally available in minute amounts in the venom of the cone snails or analogous to the naturally available peptides, and which preferably include two disulfide bonds.

The present invention, in another aspect, relates to a pharmaceutical composition comprising an effective amount of an α-conotoxin peptide. Such a pharmaceutical composition has the capability of acting as antagonists for nicotinic acetylcholine receptors. In one aspect, the α-conotoxins with specificity for neuromuscular junction nicotinic acetylcholine receptors are used as neuromuscular blocking agents for use in conjunction with surgery, as disclosed in U.S. patent application Ser. No. 09/488,799, filed 21 Jan. 2000, incorporated by reference herein. In a second aspect, additional α-conotoxins and uses for them have been described in U.S. Pat. Nos. 4,447,356 (Olivera et al., 1984); 5,432,155; 5,514,774, each incorporated herein by reference.

In a third aspect additional uses for α-conotoxins are described in U.S. Ser. No. 09/219,446, filed 22 Dec. 1998, incorporated herein by reference. In this application, α-conotoxins with specificity for neuronal nicotinic acetylcholine receptors are used for treating disorders regulated at neuronal nicotinic acetylcholine receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma.

The α-conotoxin peptides described herein are sufficiently small to be chemically synthesized. General chemical syntheses for preparing the foregoing α-conotoxin peptides are described hereinafter. Various ones of the α-conotoxin peptides can also be obtained by isolation and purification from specific *Conus* species using the technique described in U.S. Pat. No. 4,447,356 (Olivera et al., 1984), the disclosure of which is incorporated herein by reference.

Although the α-conotoxin peptides of the present invention can be obtained by purification from cone snails, because the amounts of α-conotoxin peptides obtainable from individual snails are very small, the desired substantially pure α-conotoxin peptides are best practically obtained in commercially valuable amounts by chemical synthesis using solid-phase strategy. For example, the yield from a single cone snail may be about 10 micrograms or less of α-conotoxin peptide. By "substantially pure" is meant that the peptide is present in the substantial absence of other biological molecules of the same type; it is preferably present in an amount of at least about 85% purity and preferably at least about 95% purity. Chemical synthesis of biologically active α-conotoxin peptides depends of course upon correct determination of the amino acid sequence.

The α-conotoxin peptides can also be produced by recombinant DNA techniques well known in the art. Such techniques are described by Sambrook et al. (1989). The peptides produced in this manner are isolated, reduced if necessary, and oxidized to form the correct disulfide bonds.

One method of forming disulfide bonds in the conotoxin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF): $CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptide-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodimide in N-methylpyrrolidinone (NMP) or by 2-(1H-benzotriazole-1-yl)-1,1,3,3-tetramethyluronium hexafluorophosphate (HBTU) and diethyliso-propylethylamine (DIEA). The FMOC protecting group is removed by treatment with a 20% solution of piperidine in dimethylformamide (DMF). Resins are subsequently washed with DMF (twice), followed by methanol and NMP.

Pharmaceutical compositions containing a compound of the present invention or its pharmaceutically acceptable salts as the active ingredient can be prepared according to conventional pharmaceutical compounding techniques. See, for example, *Remington's Pharmaceutical Sciences,* 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*. Typically the conopeptides of the present invention exhibit their effect at a dosage range from about 0.001 mg/kg to about 250 mg/kg, preferably from about 0.05 mg/kg to about 100 mg/kg of the active ingredient, more preferably from a bout 0.1 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

EXAMPLES

The present invention is described by reference to the following Examples, which are offered by way of illustration and are not intended to limit the invention in any manner. Standard techniques well known in the art or the techniques specifically described below were utilized.

Example 1

Isolation of α-Conotoxins

Crude venom was extracted from venom ducts (Cruz et al., 1976), and the components were purified as previously described (Cartier et al., 1996a). The crude extract from venom ducts was purified by reverse phase liquid chromatography (RPLC) using a Vydac $C_{18}$ semi-preparative column (10×250 mm) and elution with a linear gradient of acetonitrile in 0.1% TFA. Further purification of bioactive peaks was done on a Vydac CIS analytical column (4.6×220 mm) eluted with a gradient of acetonitrile in 0.1% TFA. The effluents were monitored at 220 nm. Peaks were collected, and aliquots were assayed for activity. Activity was monitored by assessing block of α3β4 nAChRs expressed in *Xenopus* oocytes.

The amino acid sequence of the purified peptides were determined by standard methods. The purified peptides were reduced and alkylated prior to sequencing by automated Edman degradation on an Applied Biosystems 477A Protein Sequencer with a 120A Analyzer (DNA/Peptide Facility, University of Utah) (Martinez et al., 1995; Shon et al., 1994).

In accordance with this method, peptides MII, AuIA, AuIB, AuIC, MAR-1, MAR-2, TI, OB-29, EpI, S1.1, Bn1.1, Bn1.2, Ca1.1, Ca1.2, Cn1.1, Cn1.2 and S1.3 were obtained.

Example 2

Synthesis of Conopeptides

The synthesis of conopeptides, either the mature toxins or the precursor peptides, was separately performed using conventional protection chemistry as described by Cartier et al. (1996). Briefly, the linear chains were built on Rink amide resin by Fmoc procedures with 2-(1H-benzotriol-1-yl)-1,1,3, 3,-tetramethyluronium tetrafluoroborated coupling using an ABI model 430A peptide synthesizer with amino acid derivatives purchased from Bachem (Torrance Calif.). Orthogonal protection was used on cysteines: $Cys^3$ and $Cys^{16}$ were protected as the stable Cys(S-acetamidomethyl), while $Cys^2$ and $Cys^8$ were protected as the acid-labile Cys(S-trityl). After removal of the terminal Fmoc protecting group and cleavage of the peptides from the resins, the released peptides were precipitated by filtering the reaction mixture into −10° C. methyl t-butyl ether, which removed the protecting groups except on $Cys^3$ and $Cys^{16}$. The peptides were dissolved in 0.1% TFA and 60% acetonitrile and purified by RPLC on a Vydac $C_{18}$ preparative column (22×250 mm) and eluted at a flow rate of 20 mL/min with a gradient of acetonitrile in 0.1% TFA.

The disulfide bridges in the three conopeptides were formed as described in Cartier et al. (1996). Briefly, the disulfide bridges between $Cys^2$ and $Cys^8$ were formed by air oxidation which was judged to be complete by analytical RPLC. The monocyclic peptides were purified by RPLC on a Vydac $C_{18}$ preparative column (22×250 mm) and eluted with a gradient of acetonitrile in 0.1% TFA. Removal of S-acetamidomethyl groups and closure of the disulfide bridge between $Cys^3$ and $Cys^{16}$ was carried out simultaneously be iodine oxidation. The cyclic peptides were purified by RPLC on a Vydac $C_{18}$ preparative column (22×250 mm) and eluted with a gradient of acetonitrile in 0.1% TFA.

Example 3

Isolation of DNA Encoding α-Conotoxins

DNA coding for α-conotoxins was isolated and cloned in accordance with conventional techniques using general procedures well known in the art, such as described in Olivera et al. (1996). Alternatively, cDNA libraries was prepared from *Conus* venom duct using conventional techniques. DNA from single clones was amplified by conventional techniques using primers which correspond approximately to the M13 universal priming site and the M13 reverse universal priming site. Clones having a size of approximately 300 nucleotides were sequenced and screened for similarity in sequence to known α-conotoxins. The DNA sequences and encoded propeptide or peptide sequences are set forth in Tables 1-134.

TABLE 1

| DNA Sequence (SEQ ID NO:58) and Protein Sequence (SEQ ID NO:59) of MII |
|---|
| atg ttc acc gtg ttt ctg ttg gtt gtc ttg gca acc |
| Met Phe Thr Val Phe Leu Leu Val Val Leu Ala Thr |
| act gtc gtt tcc ttc cct tca gat cgt gca tct gat |
| Thr Val Val Ser Phe Pro Ser Asp Arg Ala Ser Asp |
| ggc agg aat gcc gca gcc aac gac aaa gcg tct gac |
| Gly Arg Asn Ala Ala Ala Asn Asp Lys Ala Ser Asp |
| gtg atc acg ctg gcc ctc aag gga tgc tgt tcc aac |
| Val Ile Thr Leu Ala Leu Lys Gly Cys Cys Ser Asn |
| cct gtc tgt cac ttg gag cat tca aac ctt tgt ggt |
| Pro Val Cys His Leu Glu His Ser Asn Leu Cys Gly |
| aga aga cgc tgatgctcca ggaccctctg aaccacgacg |
| Arg Arg Arg |
| ttcgagca |

TABLE 2

| DNA Sequence (SEQ ID NO:60) and Protein Sequence (SEQ ID NO:61) of AuIA |
|---|
| atg ttc acc gtg ttt ctg ttg gtt gtc ttg gca acc |
| Met Phe Thr Val Phe Leu Leu Val Val Leu Ala Thr |
| acc gtc gtt tcc ttc act tca gat cgt gca tat gat |
| Thr Val Val Ser Phe Thr Ser Asp Arg Ala Ser Asp |
| ggc agg aag gac gca gag tat ggc ctg atc gct ctg |
| Gly Arg Lys Asp Ala Ala Ser Gly Leu Ile Ala Leu |
| acc atc aag gga tgc tgt tat tat cat ccc tgt ttc |
| Thr Ile Lys Gly Cys Cys Ser Tyr Pro Pro Cys Phe |
| gag act aat tca gac tat tgt ggt tgacgacgct |
| Ala Thr Asn Ser Asp Tyr Cys Gly |
| gatgctccag gaccctctga accacgacgt |

TABLE 3

| DNA Sequence (SEQ ID NO:62) and Protein Sequence (SEQ ID NO:63) of AuIB |
|---|
| atg ttc acc gtg ttt ctg ttg gtc gtc ttg gca acc |
| Met Phe Thr Val Phe Leu Leu Val Val Leu Ala Thr |
| acc gtc gtt tcc ttc act tca gat cgt gca tat gat |
| Thr Val Val Ser Phe Thr Ser Asp Arg Ala Ser Asp |
| ggc agg aag gac gca gag tat ggc ctg att gct ctg |
| Gly Arg Lys Asp Ala Ala Ser Gly Leu Ile Ala Leu |
| acc atg aag gga tgc tgt tat tat cat ccc tgt ttc |
| Thr Met Lys Gly Cys Cys Ser Tyr Pro Pro Cys Phe |
| gag act aat cca gac tgt ggt cga cga agc tgatgctcca |
| Ala Thr Asn Pro Asp Cys Gly Arg Arg Arg |
| ggaccctctg aaccacgacg t |

TABLE 4

| DNA Sequence (SEQ ID NO:64) and Protein Sequence (SEQ ID NO:65) of Tx1.3 |
|---|
| atg ttc acc gtg ttt ctg ttg gtt gtc ttg gca acc |
| Met Phe Thr Val Phe Leu Leu Val Val Leu Ala Thr |
| acc gtc gtt tcc ttc tat tca ggt cgt agt aca ttt |
| Thr Val Val Ser Phe Ser Ser Gly Arg Ser Thr Phe |
| cgt ggc agg aat gcc gca gcc aaa gcg tct ggc ctg |
| Arg Gly Arg Asn Ala Ala Ala Lys Ala Ser Gly Leu |
| gtc agt ctg act gac agg aga cca gaa tgc tgt agt |
| Val Ser Leu Thr Asp Arg Arg Pro Glu Cys Cys Ser |
| gat cct cgc tgt aac tcg agt cat cca gaa ctt tgt |
| Asp Pro Arg Cys Asn Ser Ser His Pro Glu Leu Cys |
| ggt gga aga cgc tgatgctcca ggaccctctg aaccacgacg t |
| Gly Gly Arg Arg |

TABLE 5

| DNA Sequence (SEQ ID NO:66) and Protein Sequence (SEQ ID NO:67) of Tx1.2 |
|---|
| atg ttc acc gtg ttt ctg ttg gtt gtc ttg gca acc |
| Met Phe Thr Val Phe Leu Leu Val Val Leu Ala Thr |
| gcc gtc gtt tcc ttc act tca gat cgt gca tct gat |
| Ala Val Val Ser Phe Thr Ser Asp Arg Ala Ser Asp |
| gac ggg aaa gcc gct gcg tct gac ctg atc act ctg |
| Asp Gly Lys Ala Ala Ala Ser Asp Leu Ile Thr Leu |
| acc atc aag gga tgc tgt tct cgt cct ccc tgt atc |
| Thr Ile Lys Gly Cys Cys Ser Arg Pro Pro Cys Ile |
| gcg aat aat cca gac ttg tgt ggt tgacgacgct |
| Ala Asn Asn Pro Asp Leu Cys Gly |
| gatgctccag aacggtctga accacgacgt tcgagcaatg |
| ttcaccgtgt ttctgttggt tgtctt |

TABLE 6

DNA Sequence (SEQ ID NO:68) and Protein Sequence (SEQ ID NO:69) of Tx1.1

```
atg ttc acc gtg ttt ctg ttg gtt gtc ttg gca acc
Met Phe Thr Val Phe Leu Leu Val Val Leu Ala Thr

acc gtc gtt tcc ttc act tca ggt cgt agt aca ttt
Thr Val Val Ser Phe Thr Ser Gly Arg Ser Thr Phe

cgt ggc agg aat gcc gca gcc aaa gcg tct ggc ctg
Arg Gly Arg Asn Ala Ala Ala Lys Ala Ser Gly Leu

gtc agt ctg act gac agg aga cca caa tgc tgt tct
Val Ser Leu Thr Asp Arg Arg Pro Gln Cys Cys Ser

cat cct gcc tgt aac gta gat cat cca gaa att tgt
His Pro Ala Cys Asn Val Asp His Pro Glu Ile Cys

cgt tgaagacgct gatgctccag gaccctctga accacgacgt
Arg
```

TABLE 7

DNA Sequence (SEQ ID NO:70) and Protein Sequence (SEQ ID NO:71) of R1.1A

```
atg ttc acc gtg ttt ctg ttg gtt gtc ttg gca acc
Met Phe Thr Val Phe Leu Leu Val Val Leu Ala Thr

acc gtc gtt tcc ttc act tca ggt cgt cgt aca ttt
Thr Val Val Ser Phe Thr Ser Gly Arg Arg Thr Phe

cat ggc agg aat gcc gca gcc aaa gcg tct ggc ctg
His Gly Arg Asn Ala Ala Ala Lys Ala Ser Gly Leu

gtc agt ctg act gac agg aga cca gaa tgc tgt tct
Val Ser Leu Thr Asp Arg Arg Pro Glu Cys Cys Ser

cat cct gcc tgt aac gta gat cat cca gaa att tgt
His Pro Ala Cys Asn Val Asp His Pro Glu Ile Cys

cgt tgaagacgct gatgctccag gaccctctga accacgacgt
Arg
```

TABLE 8

DNA Sequence (SEQ ID NO:72) and Protein Sequence (SEQ ID NO:73) of R1.1B

```
atg ttc acc gtg ttt ctg ttg gtt gtc ttg gca acc
Met Phe Thr Val Phe Leu Leu Val Val Leu Ala Thr

acc gtc gtt tcc ttc act tca ggt cgt agt aca ttt
Thr Val Val Ser Phe Thr Ser Gly Arg Ser Thr Phe

cgt ggc agg aat gcc gca gcc aaa gcg tct ggc ctg
Arg Gly Arg Asn Ala Ala Ala Lys Ala Ser Gly Leu

gtc agt ctg act gac agg aga cca caa tgc tgt tct
Val Ser Leu Thr Asp Arg Arg Pro Gln Cys Cys Ser

cat cct gcc tgt aac gta gat cat cca gaa att tgc
His Pro Ala Cys Asn Val Asp His Pro Glu Ile Cys

gat tgaagacgct gatgctccag gaccctctga accacgacgt
Asp
```

TABLE 9

DNA Sequence (SEQ ID NO:74) and Protein Sequence (SEQ ID NO:75) of S1.1

```
atg ttc act gtg ttt ctg ttg gtt gtc ttg gca atc
Met Phe Thr Val Phe Leu Leu Val Val Leu Ala Ile

act gtc gtt tcc ttc cat tta gat cgt gaa tat gat
Thr Val Val Ser Phe Pro Leu Asp Arg Glu Ser Asp

ggc gag aat gcc gaa gcc agc acc cac gat cat gag
Gly Ala Asn Ala Glu Ala Arg Thr His Asp His Glu

aag cac gca ctg gac cgg aat gga tgc tgt agg aat
Lys His Ala Leu Asp Arg Asn Gly Cys Cys Arg Asn

cat gcc tgt gag agc cac aga tgt ggt tgacgacgct
Pro Ala Cys Glu Ser His Arg Cys Gly

gatgctccag gaccctctga accacgacgt tcgagca
```

TABLE 10

DNA Sequence (SEQ ID NO:76) and Protein Sequence (SEQ ID NO:77) of Bn1.1

```
atg ttc acc atg ttt ctg ttg gtt gtc ttg gca acc
Met Phe Thr Met Phe Leu Leu Val Val Leu Ala Thr

act gtc gtt tcc ttc gct tca gat cgt gca tct gat
Thr Val Val Ser Phe Ala Ser Asp Arg Ala Ser Asp

ggc agg aat gcc gca gcc aag gac aaa gcg tct gac
Gly Arg Asn Ala Ala Ala Lys Asp Lys Ala Ser Asp

ctg gtc gct ctg acc gtc aag gga tgc tgt tct cat
Leu Val Ala Leu Thr Val Lys Gly Cys Cys Ser His

cct gcc tgt agc gtg aat aat cca gac att tgt ggt
Pro Ala Cys Ser Val Asn Asn Pro Asp Ile Cys Gly

tgaagacgct gatgctccag gaccctctga accacgacgt

tcgagca
```

TABLE 11

DNA Sequence (SEQ ID NO:78) and Protein Sequence (SEQ ID NO:79) of Bn1.2

```
aaa gaa tgc tgt act cat act gcc tgt cac gtg agt
Lys Glu Cys Cys Thr His Pro Ala Cys His Val Ser

cat cca gaa ctc tgt ggt tgaaaagcga cgtgacgctc
His Pro Glu Leu Cys Gly

caggaccctc tgaaccacga cgttcgagca
```

TABLE 12

DNA Sequence (SEQ ID NO:80) and Protein Sequence (SEQ ID NO:81) of Bn1.3

```
atg ttc acc gtg ttt ctg ttg gtt gtc ttg gca act
Met Phe Thr Val Phe Leu Leu Val Val Leu Ala Thr

gct gtt ctt cca gtc act tta gat cgt gca tct gat
Ala Val Leu Pro Val Thr Leu Asp Arg Ala Ser Asp

gga agg aat gca gca gcc aac gcc aaa acg cct cgc
Gly Arg Asn Ala Ala Ala Asn Ala Lys Thr Pro Arg

ctg atc gcg cca ttc atc agg gat tat tgc tgt cat
```

TABLE 12-continued

| DNA Sequence (SEQ ID NO:80) and Protein Sequence (SEQ ID NO:81) of Bn1.3 |
|---|
| Leu Ile Ala Pro Phe Ile Arg Asp Tyr Cys Cys His |
| aga ggt ccc tgt atg gta tgg tgt ggt tgaagccgct<br>Arg Gly Pro Cys Met Val Trp Cys Gly |
| gctgctccag gaccctctga accac |

TABLE 13

| DNA Sequence (SEQ ID NO:82) and Protein Sequence (SEQ ID NO:83) of Ca1.1 |
|---|
| atg ttc acc gtg ttt ctg ttg gtt gtc ttg gca acc<br>Met Phe Thr Val Phe Leu Leu Val Val Leu Ala Thr |
| act gtg gtt tcc ttc act tca gat cgt gct tct gat<br>Thr Val Val Ser Phe Thr Ser Asp Arg Ala Ser Asp |
| ggc agg aat gcc gca gcc aac gcg ttt gac ctg atc<br>Gly Arg Asn Ala Ala Ala Asn Ala Phe Asp Leu Ile |
| gct ctg atc gcc agg caa aat tgc tgt agc att ccc<br>Ala Leu Ile Ala Arg Gln Asn Cys Cys Ser Ile Pro |
| agc tgt tgg gag aaa tat aaa tgt agt taa<br>Ser Cys Trp Glu Lys Tyr Lys Cys Ser |

TABLE 14

| DNA Sequence (SEQ ID NO:84) and Protein Sequence (SEQ ID NO:85) of Ca1.2 |
|---|
| atg ttc acc gtg ttt ctg ttg gtt gtc ttg gca acc<br>Met Phe Thr Val Phe Leu Leu Val Val Leu Ala Thr |
| act gtg gtt tcc ttc act tca gat cgt gcg tct gaa<br>Thr Val Val Ser Phe Thr Ser Asp Arg Ala Ser Glu |
| ggc agg aat gct gca gcc aag gac aaa gcg tct gac<br>Gly Arg Asn Ala Ala Ala Lys Asp Lys Ala Ser Asp |
| ctg gtg gct ctg aca gtc agg gga tgc tgt gcc att<br>Leu Val Ala Leu Thr Val Arg Gly Cys Cys Ala Ile |
| cgt gaa tgt cgc ttg cag aat gca gcg tat tgt ggt<br>Arg Glu Cys Arg Leu Gln Asn Ala Ala Tyr Cys Gly |
| gga ata tac tgatgctcca ggaccctctg aaccacgacg<br>Gly Ile Tyr |

TABLE 15

| DNA Sequence (SEQ ID NO:86) and Protein Sequence (SEQ ID NO:87) of TIB |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc cct tca gat att gca act gag<br>Thr Val Val Ser Phe Pro Ser Asp Ile Ala Thr Glu |
| ggc agg aat gcc gca gcc aaa gcg ttt gac ctg ata<br>Gly Arg Asn Ala Ala Ala Lys Ala Phe Asp Leu Ile |
| tct tcg atc gtc aag aaa gga tgc tgt tcc cat cct<br>Ser Ser Ile Val Lys Lys Gly Cys Cys Ser His Pro |

TABLE 15-continued

| DNA Sequence (SEQ ID NO:86) and Protein Sequence (SEQ ID NO:87) of TIB |
|---|
| gcc tgt tcg ggg aat aat cca gaa ttt tgt cgt caa<br>Ala Cys Ser Gly Asn Asn Pro Glu Phe Cys Arg Gln |
| ggt cgc tgatgctcca ggaccctctg aaccacgacg t |

TABLE 16

| DNA Sequence (SEQ ID NO:88) and Protein Sequence (SEQ ID NO:89) of TIA |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc cct tca gat ata gca act gag<br>Thr Val Val Ser Phe Pro Ser Asp Ile Ala Thr Glu |
| ggc agg aat gcc gca gcc aaa gcg ttt gac ctg ata<br>Gly Arg Asn Ala Ala Ala Lys Ala Phe Asp Leu Ile |
| tct tcg atc gtc agg aaa gga tgc tgt tcc aat ccc<br>Ser Ser Ile Val Arg Lys Gly Cys Cys Ser Asn Pro |
| gcc tgt gcg ggg aat aat cca cat gtt tgt cgt caa<br>Ala Cys Ala Gly Asn Asn Pro His Val Cys Arg Gln |
| ggt cgc tgatgctcca ggaccctctg aaccacgacg t<br>Gly Arg |

TABLE 17

| DNA Sequence (SEQ ID NO:90) and Protein Sequence (SEQ ID NO:91) of S11.1 |
|---|
| atg ttc acc gtg ttt ctg ttg gtt gtc ttg gca acc<br>Met Phe Thr Val Phe Leu Leu Val Val Leu Ala Thr |
| acc gtc gtt tcc ttc aat tca gat cgt gat cca gca<br>Thr Val Val Ser Phe Asn Ser Asp Arg Asp Pro Ala |
| tta ggt ggc agg aat gct gca gcc aaa gcg tct gac<br>Leu Gly Gly Arg Asn Ala Ala Ala Lys Ala Ser Asp |
| aag atc gct tcg acc ctc aag aga aga gga tgc tgt<br>Lys Ile Ala Ser Thr Leu Lys Arg Arg Gly Cys Cys |
| tcg tat ttt gac tgt aga atg atg ttt cca gaa atg<br>Ser Tyr Phe Asp Cys Arg Met Met Phe Pro Glu Met |
| tgt ggt tgg cga ggc tgatgctcca ggaccctctg<br>Cys Gly Trp Arg Gly |
| aaccacgacg t |

TABLE 18

| DNA Sequence (SEQ ID NO:92) and Protein Sequence (SEQ ID NO:93) of S11.2 |
|---|
| atg ttc acc gtg ttt ctg ttg gtt gtc ttg gca acc<br>Met Phe Thr Val Phe Leu Leu Val Val Leu Ala Thr |
| acc gtc gtt tcc ttc aat tca gat cgt gat cca gca<br>Thr Val Val Ser Phe Asn Ser Asp Arg Asp Pro Ala |
| tta ggt ggc agg aat gct gca gcc ata gcg tct gac<br>Leu Gly Gly Arg Asn Ala Ala Ala Ile Ala Ser Asp |

TABLE 18-continued

| DNA Sequence (SEQ ID NO:92) and Protein Sequence (SEQ ID NO:93) of S11.2 |
|---|
| aag atc gct tcg acc ctc agg aga gga gga tgc tgt<br>Lys Ile Ala Ser Thr Leu Arg Arg Gly Gly Cys Cys |
| tct ttt cct gcc tgt aga aag tat cgt cca gaa atg<br>Ser Phe Pro Ala Cys Arg Lys Tyr Arg Pro Glu Met |
| tgt ggt gga cga cgc tgatgctcca ggaccctctg<br>Cys Gly Gly Arg Arg |
| aaccacgacg t |

TABLE 19

| DNA Sequence (SEQ ID NO:94) and Protein Sequence (SEQ ID NO:95) of S11.3 |
|---|
| atg ttc acc gtg ttt ctg ttg gtt gtc ttg gca acc<br>Met Phe Thr Val Phe Leu Leu Val Val Leu Ala Thr |
| acc gtc gtt tcc ttc act tca gat cat gaa tat gat<br>Thr Val Val Ser Phe Thr Ser Asp His Glu Ser Asp |
| agc ggt gat gcc caa acc atc caa gaa gtg ttt gag<br>Arg Gly Asp Ala Gln Thr Ile Gln Glu Val Phe Glu |
| atg ttc gct ctg gac agc gat gga tgc tgt tgg cat<br>Met Phe Ala Leu Asp Ser Asp Gly Cys Cys Trp His |
| cct gct tgt ggc aga cac tat tgt ggt cga aga cgc<br>Pro Ala Cys Gly Arg His Tyr Cys Gly Arg Arg Arg |
| tgatgctcca ggaccctctg aaccacgacg t |

TABLE 20

| DNA Sequence (SEQ ID NO:96) and Protein Sequence (SEQ ID NO:97) of S11.6 |
|---|
| atg ttc acc gtg ttt ctg ttg gtt gtc ttg gca acc<br>Met Phe Thr Val Phe Leu Leu Val Val Leu Ala Thr |
| acc gtc gtt tcc ttc aat tca gat cgt gat cca gca<br>Thr Val Val Ser Phe Asn Ser Asp Arg Asp Pro Ala |
| tta ggt ggc agg aat gct gca gcc ata gcg tct gac<br>Leu Gly Gly Arg Asn Ala Ala Ala Ile Ala Ser Asp |
| aag atc gct tcg acc ctc agg aga gga gga tgc tgt<br>Lys Ile Ala Ser Thr Leu Arg Arg Gly Gly Cys Cys |
| tct ttt gct gcc tgt aga aag tat cgt cca gaa atg<br>Ser Phe Ala Ala Cys Arg Lys Tyr Arg Pro Glu Met |
| tgt ggt gga cga cgc tgatgct<br>Cys Gly Gly Arg Arg |

TABLE 21

| DNA Sequence (SEQ ID NO:98) and Protein Sequence (SEQ ID NO:99) of S11.7 |
|---|
| atg ttc acc gtg ttt ctg ttg gtt ctc ttg gca acc<br>Met Phe Thr Val Phe Leu Leu Val Leu Leu Ala Thr |
| acc gtc gtt tcc ttc aat tca gat cgt gca tta ggt<br>Thr Val Val Ser Phe Asn Ser Asp Arg Ala Leu Gly |

TABLE 21-continued

| DNA Sequence (SEQ ID NO:98) and Protein Sequence (SEQ ID NO:99) of S11.7 |
|---|
| ggc agg aat gct gca gcc aaa gcg tct gac aag atc<br>Gly Arg Asn Ala Ala Ala Lys Ala Ser Asp Lys Ile |
| ctt tcg aac ctc agg aga gga gga tgc tgt ttt cat<br>Leu Ser Asn Leu Arg Arg Gly Gly Cys Cys Phe His |
| cct gtc tgt tac atc aat ctt cta gaa atg tgt cgt<br>Pro Val Cys Tyr Ile Asn Leu Leu Glu Met Cys Arg |
| caa cga ggc tgatcgtcca ggaccctctg aaccacgacg t<br>Gln Arg Gly |

TABLE 22

| DNA Sequence (SEQ ID NO:100) and Protein Sequence (SEQ ID NO:101) of Cn1.1 |
|---|
| atg ttc acc gtg ttt ctg ttg gtt gtc ttg aca acc<br>Met Phe Thr Val Phe Leu Leu Val Val Leu Thr Thr |
| act gtc gtt tcc ttc cct tca gat agt gca tct gat<br>Thr Val Val Ser Phe Pro Ser Asp Ser Ala Ser Asp |
| gtc agg gat gac gaa gcc aaa gac gaa agg tct gac<br>Val Arg Asp Asp Glu Ala Lys Asp Glu Arg Ser Asp |
| atg tac aaa tcg aaa cgg aat gga cgc tgt tgc cat<br>Met Tyr Lys Ser Lys Arg Asn Gly Arg Cys Cys His |
| cct gcc tgt ggc aaa cac ttt agt tgt gga cgc<br>Pro Ala Cys Gly Lys His Phe Ser Cys Gly Arg |
| tgatgctcca ggaccctctg aaccacgacg t |

TABLE 23

| DNA Sequence (SEQ ID NO:102) and Protein Sequence (SEQ ID NO:103) of SmI |
|---|
| atg ttc acc gtg ttt ctg ttg gtt gtc ttg gca acc<br>Met Phe Thr Val Phe Leu Leu Val Val Leu Ala Thr |
| act gtc gtt tcc tcc cct tca gat cgt gca tct gat<br>Thr Val Val Ser Ser Pro Ser Asp Arg Ala Ser Asp |
| ggc agg aat gcc gca gcc aac gag aaa gcg tct gac<br>Gly Arg Asn Ala Ala Ala Asn Glu Lys Ala Ser Asp |
| gtg atc gcg ctg gcc ctc aag gga tgc tgt tcc aac<br>Val Ile Ala Leu Ala Leu Lys Gly Cys Cys Ser Asn |
| cct gtc tgt cac ctg gag cat tca aac atg tgt ggt<br>Pro Val Cys His Leu Glu His Ser Asn Met Cys Gly |
| aga aga cgc tgatgctcca ggaccctctg aaccacgacg<br>Arg Arg Arg |

TABLE 24

| DNA Sequence (SEQ ID NO:104) and Protein Sequence (SEQ ID NO:105) of Bt1.1 |
|---|
| atg ttc tcc gtg ttt ctg ttg gtt gtc ttg gca acc<br>Met Phe Ser Val Phe Leu Leu Val Val Leu Ala Thr |
| act gtc gtt tcc tcc act tca ggt ggt gca tct ggt<br>Thr Val Val Ser Ser Thr Ser Gly Gly Ala Ser Gly |

TABLE 24-continued

| DNA Sequence (SEQ ID NO:104) and Protein Sequence (SEQ ID NO:105) of Bt1.1 |
|---|
| ggc agg aag gct gca gcc aaa gcg tct aac cgg atc<br>Gly Arg Lys Ala Ala Ala Lys Ala Ser Asn Arg Ile |
| gct ctg acc gtc agg agt gca aca tgc tgt aat tat<br>Ala Leu Thr Val Arg Ser Ala Thr Cys Cys Asn Tyr |
| cct ccc tgt tac gag act tat cca gaa agt tgt ctg<br>Pro Pro Cys Tyr Glu Thr Tyr Pro Glu Ser Cys Leu |
| taacgtgaat catccagagc tttgtggctg aagacactga |
| tgctccagga ccctctgaac cacgacgt |

TABLE 25

| DNA Sequence (SEQ ID NO:106) and Protein Sequence (SEQ ID NO:107) of Bt1.2 |
|---|
| atg ttc acc gtg ttt ctg ttg gtt gtc ttg gca acc<br>Met Phe Thr Val Phe Leu Leu Val Val Leu Ala Thr |
| act gtg gtt tcc ttc act tca ggt cgt gca ttt cgt<br>Thr Val Val Ser Phe Thr Ser Gly Arg Ala Phe Arg |
| ggc agg aat cgc gca gcc gac gac aaa agg tct gac<br>Gly Arg Asn Arg Ala Ala Asp Asp Lys Arg Ser Asp |
| ctg gcc gct ctg agc gtc agg gga gga tgc tgt tcc<br>Leu Ala Ala Leu Ser Val Arg Gly Gly Cys Cys Ser |
| cat cct gcc tgt gcg gtg aat cat cca gag ctt tgt<br>His Pro Ala Cys Ala Val Asn His Pro Glu Leu Cys |
| ggc tgaagacgct gatgccccag gaccctctga accacgacgt<br>Gly |

TABLE 26

| DNA Sequence (SEQ ID NO:108) and Protein Sequence (SEQ ID NO:109) of Bt1.3 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc act tca ggt cgt gca tct ggt<br>Thr Val Val Ser Phe Thr Ser Gly Arg Ala Ser Gly |
| ggc agg aat gct gca gcc aaa gcg tct aac cgg atc<br>Gly Arg Asn Ala Ala Ala Lys Ala Ser Asn Arg Ile |
| gct atg gcc atc agc agt gga gca tgc tgt gca tat<br>Ala Met Ala Ile Ser Ser Gly Ala Cys Cys Ala Tyr |
| cct ccc tgt ttc gag gct tat cca gaa aga tgt ctg<br>Pro Pro Cys Phe Glu Ala Tyr Pro Glu Arg Cys Leu |
| taacgtgaat catccagacc tttgtggctg aagacgctga |
| tgccccagga ccctctgaac cacgacgt |

TABLE 27

| DNA Sequence (SEQ ID NO:110) and Protein Sequence (SEQ ID NO:111) of Bt1.4 |
|---|
| atg ttc acc gtg ttt ctg ttg gtt gtc ttg gca acc<br>Met Phe Thr Val Phe Leu Leu Val Val Leu Ala Thr |

TABLE 27-continued

| DNA Sequence (SEQ ID NO:110) and Protein Sequence (SEQ ID NO:111) of Bt1.4 |
|---|
| act gtc gtt tcc ttc act tca gat cgt gca ttt cgt<br>Thr Val Val Ser Phe Thr Ser Asp Arg Ala Phe Arg |
| ggc agg aat tcc gca gcc aac gac aaa agg tct gac<br>Gly Arg Asn Ser Ala Ala Asn Asp Lys Arg Ser Asp |
| ctg gcc gct ctg agc gtc agg aga gga tgc tgc tcc<br>Leu Ala Ala Leu Ser Val Arg Arg Gly Cys Cys Ser |
| cat ccc gcc tgt agc gtg aat cat cca gag ctt tgt<br>His Pro Ala Cys Ser Val Asn His Pro Glu Leu Cys |
| ggt aga aga cgc tgatgcccca ggaccctctg aaccacgacg t<br>Gly Arg Arg Arg |

TABLE 28

| DNA Sequence (SEQ ID NO:112) and Protein Sequence (SEQ ID NO:113) of Bt1.5 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc act tca ggt cgt gca tct ggt<br>Thr Val Val Ser Phe Thr Ser Gly Arg Ala Ser Gly |
| ggc agg aat gct gca gcc aaa gcg tct aac cgg atc<br>Gly Arg Asn Ala Ala Ala Lys Ala Ser Asn Arg Ile |
| gct ctg atc gtc agg aat gca gaa tgc tgt tat tat<br>Ala Leu Ile Val Arg Asn Ala Glu Cys Cys Tyr Tyr |
| cct ccc tgt tac gag gct tat cca gaa att tgt ctg<br>Pro Pro Cys Tyr Glu Ala Tyr Pro Glu Ile Cys Leu |
| taacgtgaat catccagacc tttgtggctg aagaccctga |
| tgctccagga ccctctgaac cacgacgt |

TABLE 29

| DNA Sequence (SEQ ID NO:114) and Protein Sequence (SEQ ID NO:115) of Pn1.1 |
|---|
| atg ttc acc gtg ttt ctg ttg gtt gtc ttg gca acc<br>Met Phe Thr Val Phe Leu Leu Val Val Leu Ala Thr |
| acc gtc att tcc ttc act tca gat cgt gca tat gat<br>Thr Val Ile Ser Phe Thr Ser Asp Arg Ala Ser Asp |
| ggc ggg aat gcc gca gcg tct gac ctg atc gct ctg<br>Gly Gly Asn Ala Ala Ala Ser Asp Leu Ile Ala Leu |
| acc atc aag gga tgc tgt tct cat cct ccc tgt gcc<br>Thr Ile Lys Gly Cys Cys Ser His Pro Pro Cys Ala |
| atg aat aat cca gac tat tgt ggt tgacgacgct<br>Met Asn Asn Pro Asp Tyr Cys Gly |
| gatgctccag gaccctctga accacgacg |

TABLE 30

| DNA Sequence (SEQ ID NO:116) and Protein Sequence (SEQ ID NO:117) of Pn1.2 |
|---|
| atg ttc acc gtg ttt ctg ttg gtt gtc ttg gca acc<br>Met Phe Thr Val Phe Leu Leu Val Val Leu Ala Thr |

TABLE 30-continued

| DNA Sequence (SEQ ID NO:116) and Protein Sequence (SEQ ID NO:117) of Pn1.2 |
|---|
| acc gtc gtt tcc ttc act tca gat cgt gca tct gat<br>Thr Val Val Ser Phe Thr Ser Asp Arg Ala Ser Asp |
| ggc ggg aat gcc gca atg tct gac ctg atc gct ctg<br>Gly Gly Asn Ala Ala Met Ser Asp Leu Ile Ala Leu |
| acc atc aag gga tgc tgt tct cat cct ccc tgt ttc<br>Thr Ile Lys Gly Cys Cys Ser His Pro Pro Cys Phe |
| ctg aat aat cca gac tat tgt ggt tgacgacgct<br>Leu Asn Asn Pro Asp Tyr Cys Gly |
| gatgctccag gaccctctga accacgacg |

TABLE 31

| DNA Sequence (SEQ ID NO:118) and Protein Sequence (SEQ ID NO:119) of Sm1.3 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc cct tca gat cgt gaa tct gat<br>Thr Val Val Ser Phe Pro Ser Asp Arg Glu Ser Asp |
| ggc gcg aat gac gaa gcc cgc acc gac gag cct gag<br>Gly Ala Asn Asp Glu Ala Arg Thr Asp Glu Pro Glu |
| gag cac gga ccg gac agg aat gga tgc tgt agg aat<br>Glu His Gly Pro Asp Arg Asn Gly Cys Cys Arg Asn |
| cct gcc tgt gag agc cac aga tgt ggt tgacgacgct<br>Pro Ala Cys Glu Ser His Arg Cys Gly |
| gatgctccag gaccctctga accacgacg |

TABLE 32

| DNA Sequence (SEQ ID NO:120) and Protein Sequence (SEQ ID NO:121) of Cr1.2 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc cct tca gat cgt gca tct gat<br>Thr Val Val Ser Phe Pro Ser Asp Arg Ala Ser Asp |
| ggc agg aat gcc gca gcc agc gac aga gcg tct gac<br>Gly Arg Asn Ala Ala Ala Ser Asp Arg Ala Ser Asp |
| gcg gcc cac cag gga tgc tgt tcc aac cct gtc tgt<br>Ala Ala His Gln Gly Cys Cys Ser Asn Pro Val Cys |
| cac gtg gaa cat cca gaa ctt tgt cgt aga aga cgc<br>His Val Glu His Pro Glu Leu Cys Arg Arg Arg Arg |
| tgatgctcca ggaccctctg aaccacgacg |

TABLE 33

| DNA Sequence (SEQ ID NO:122) and Protein Sequence (SEQ ID NO:123) of Cr1.3 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc cct tca aat cgt gaa tct gat<br>Thr Val Val Ser Phe Pro Ser Asn Arg Glu Ser Asp |

TABLE 33-continued

| DNA Sequence (SEQ ID NO:122) and Protein Sequence (SEQ ID NO:123) of Cr1.3 |
|---|
| ggc gcg aat gcc gaa gtc cgc acc gac gag cct gag<br>Gly Ala Asn Ala Glu Val Arg Thr Asp Glu Pro Glu |
| gag cac gac gaa ctg ggc ggg aat gga tgc tgt ggg<br>Glu His Asp Glu Leu Gly Gly Asn Gly Cys Cys Gly |
| aat cct gac tgt acg agc cac agt tgt gat tgacgacgct<br>Asn Pro Asp Cys Thr Ser His Ser Cys Asp |
| gatgctccag gaccctctga accacgacg |

TABLE 34

| DNA Sequence (SEQ ID NO:124) and Protein Sequence (SEQ ID NO:125) of EpI |
|---|
| atg ttc acc gtg ttt ctg ttg gtt gtc ttg gca acc<br>Met Phe Thr Val Phe Leu Leu Val Val Leu Ala Thr |
| acc gtc gtt tcc ttc act tca gat cgt gca tct gat<br>Thr Val Val Ser Phe Thr Ser Asp Arg Ala Ser Asp |
| agc agg aag gac gca gcg tct ggc ctg atc gct ctg<br>Ser Arg Lys Asp Ala Ala Ser Gly Leu Ile Ala Leu |
| acc atc aag gga tgc tgt tct gat cct cgc tgt aac<br>Thr Ile Lys Gly Cys Cys Ser Asp Pro Arg Cys Asn |
| atg aat aat cca gac tat tgt ggt tgacgacgct<br>Met Asn Asn Pro Asp Tyr Cys Gly |
| gatgctccag gaccctctga accacgacg |

TABLE 35

| DNA Sequence (SEQ ID NO:126) and Protein Sequence (SEQ ID NO:127) of Sn1.1 |
|---|
| atg tcc acc gtg ttt ctg ttg gtt gtc ctc gca acc<br>Met Ser Thr Val Phe Leu Leu Val Val Leu Ala Thr |
| acc gtc gtt tcc ttc act gta gat cgt gca tat gat<br>Thr Val Val Ser Phe Thr Val Asp Arg Ala Ser Asp |
| ggc agg gat gtc gca atc gac gac aga ttg gtg tat<br>Gly Arg Asp Val Ala Ile Asp Asp Arg Leu Val Ser |
| ctc cat cag atc gcc cat gct gac tgt tgt tcc gat<br>Leu Pro Gln Ile Ala His Ala Asp Cys Cys Ser Asp |
| cat gcc tgc aag cag acg ccc ggt tgt cgt taaagacgct<br>Pro Ala Cys Lys Gln Thr Pro Gly Cys Arg |
| gctgctccag gaccctctga accacgacg |

TABLE 36

| DNA Sequence (SEQ ID NO:128) and Protein Sequence (SEQ ID NO:129) of Sn1.2 |
|---|
| atg ttc acc gtg ttt ctg ttg gtt gtc ttg gca acc<br>Met Phe Thr Val Phe Leu Leu Val Val Leu Ala Thr |
| acc gtc gct tcc ttc att atc gat gat cca tct gat<br>Thr Val Ala Ser Phe Ile Ile Asp Asp Pro Ser Asp |
| ggc agg aat att gca gtc gac gac aga ggg ctt ttc<br>Gly Arg Asn Ile Ala Val Asp Asp Arg Gly Leu Phe |

TABLE 36-continued

| DNA Sequence (SEQ ID NO:128) and Protein Sequence (SEQ ID NO:129) of Sn1.2 |
|---|
| tct acg ctc ttc cat gct gat tgc tgt gaa aat cct<br>Ser Thr Leu Phe His Ala Asp Cys Cys Glu Asn Pro |
| gcc tgt aga cac acg cag ggt tgt tgatctttgt<br>Ala Cys Arg His Thr Gln Gly Cys |
| tcttcaaaga cactgctggc ccaggaccct ctgaaccacg acg |

TABLE 37

| DNA Sequence (SEQ ID NO:130) and Protein Sequence (SEQ ID NO:131) of Da1.1 |
|---|
| atg ttc acc gtg ttt ctg ttg gtt gtc ttg gca acc<br>Met Phe Thr Val Phe Leu Leu Val Val Leu Ala Thr |
| acc gtc gtt tcc ttc act tca gat cgt gca ttt cgt<br>Thr Val Val Ser Phe Thr Ser Asp Arg Ala Phe Arg |
| ggc agg aat gcc gca gcc aaa gag tct ggc ctg gtc<br>Gly Arg Asn Ala Ala Ala Lys Glu Ser Gly Leu Val |
| ggt ctg acc gac aag acg cga gga tgc tgt tct cat<br>Gly Leu Thr Asp Lys Thr Arg Gly Cys Cys Ser His |
| cct gcc tgt aac gta gat cat cca gaa att tgt ggt<br>Pro Ala Cys Asn Val Asp His Pro Glu Ile Cys Gly |
| tgaagacgct gatgctccag gaccctctga accacgacgt |

TABLE 38

| DNA Sequence (SEQ ID NO:132) and Protein Sequence (SEQ ID NO:133) of Da1.2 |
|---|
| atg ttc acc gtg ttt ctg ttg gtt gtc ttg gca acc<br>Met Phe Thr Val Phe Leu Leu Val Val Leu Ala Thr |
| acc gtc gtt tcc ttc act tca gat ggt gca tat gat<br>Thr Val Val Ser Phe Thr Ser Asp Gly Ala Ser Asp |
| gac agg aaa gcc gct gcg tct gac ctg atc act ctg<br>Asp Arg Lys Ala Ala Ala Ser Asp Leu Ile Thr Leu |
| acc atc aag gga tgc tgt tct cgt cct ccc tgt atc<br>Thr Ile Lys Gly Cys Cys Ser Arg Pro Pro Cys Ile |
| gcg aat aat cca gac ttg tgt ggt cga cga cgc<br>Ala Asn Asn Pro Asp Leu Cys Gly Arg Arg Arg |
| tgatgctcca ggaccctctg |

TABLE 39

| DNA Sequence (SEQ ID NO:134) and Protein Sequence (SEQ ID NO:135) of Da1.3 |
|---|
| atg ttc acc gtg ttt ctg ttg gtt gtc ttg gca acc<br>Met Phe Thr Val Phe Leu Leu Val Val Leu Ala Thr |
| act gtc gtt tcc tcc act tca ggt cgt cgt gca ttt<br>Thr Val Val Ser Ser Thr Ser Gly Arg Arg Ala Phe |
| cat ggc agg aat gcc gca gcc aaa gcg tct gga ctg<br>His Gly Arg Asn Ala Ala Ala Lys Ala Ser Gly Leu |
| gtc ggt ctg act gac agg aga cca caa tgc tgt agt<br>Val Gly Leu Thr Asp Arg Arg Pro Gln Cys Cys Ser |

TABLE 39-continued

| DNA Sequence (SEQ ID NO:134) and Protein Sequence (SEQ ID NO:135) of Da1.3 |
|---|
| gat cct cgc tgt aac gta ggt cat cca gaa ctt tgt<br>Asp Pro Arg Cys Asn Val Gly His Pro Glu Leu Cys |
| ggt gga aga cgc tgatgctcca ggaccctctg aaccacaacg t<br>Gly Gly Arg Arg |

TABLE 40

| DNA Sequence (SEQ ID NO:136) and Protein Sequence (SEQ ID NO:137) of Da1.4 |
|---|
| atg ttc acc gtg ttt ctg ttg gtt gtc ttg gca acc<br>Met Phe Thr Val Phe Leu Leu Val Val Leu Ala Thr |
| act gtc gtt tcc tcc act tca ggt cgt gca ttt cat<br>Thr Val Val Ser Ser Thr Ser Gly Arg Ala Phe His |
| ggc agg aat gcc gca gcc aaa gcg tct ggc ctg gtc<br>Gly Arg Asn Ala Ala Ala Lys Ala Ser Gly Leu Val |
| ggt ctg acc gac aag agg caa gta tgc tgt agt gat<br>Gly Leu Thr Asp Lys Arg Gln Val Cys Cys Ser Asp |
| cct cgc tgt aac gta ggt cat cca gaa att tgt ggt<br>Pro Arg Cys Asn Val Gly His Pro Glu Ile Cys Gly |
| gga aga cgc tgatgctcca ggaccctctg aaccacgacg t<br>Gly Arg Arg |

TABLE 41

| DNA Sequence (SEQ ID NO:138) and Protein Sequence (SEQ ID NO:139) of A1.2 |
|---|
| atg ttc acc gtg ttt ctg ttg gtt gtc ttg aca acc<br>Met Phe Thr Val Phe Leu Leu Val Val Leu Thr Thr |
| act gtc gtt tcc ttc cct tca gat agt gca tct ggt<br>Thr Val Val Ser Phe Pro Ser Asp Ser Ala Ser Gly |
| ggc agg gat gac gag gcc aaa gac gaa agg tct gac<br>Gly Arg Asp Asp Glu Ala Lys Asp Glu Arg Ser Asp |
| atg tac gaa ttg aaa cgg aat gga cgc tgt tgc cat<br>Met Tyr Glu Leu Lys Arg Asn Gly Arg Cys Cys His |
| cct gcc tgt ggt ggc aaa tac gtt aaa tgt gga cgc<br>Pro Ala Cys Gly Gly Lys Tyr Val Lys Cys Gly Arg |
| tgatgctcca ggaccctctc gaaccacg |

TABLE 42

| DNA Sequence (SEQ ID NO:140) and Protein Sequence (SEQ ID NO:141) of Bu1.1 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc tct aca gat gat gaa tct gat<br>Thr Val Val Ser Phe Ser Thr Asp Asp Glu Ser Asp |
| ggc tcg aat gaa gaa ccc agc gcc gac cag act gcc<br>Gly Ser Asn Glu Glu Pro Ser Ala Asp Gln Thr Ala |
| agg tcc tca atg aac agg gcg cct gga tgc tgt aac<br>Arg Ser Ser Met Asn Arg Ala Pro Gly Cys Cys Asn |

TABLE 42-continued

| DNA Sequence (SEQ ID NO:140) and Protein Sequence (SEQ ID NO:141) of Bu1.1 |
|---|
| aat cct gcc tgt gtg aag cac aga tgt gga tgacgctgat<br>Asn Pro Ala Cys Val Lys His Arg Cys Gly |
| gctccaggac cctctgaacc acgacgt |

TABLE 43

| DNA Sequence (SEQ ID NO:142) and Protein Sequence (SEQ ID NO:143) of Bu1.2 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc tct aca gat gat gaa tct gat<br>Thr Val Val Ser Phe Ser Thr Asp Asp Glu Ser Asp |
| ggc tcg aat gaa gaa ccc agc gcc gac cag gct gcc<br>Gly Ser Asn Glu Glu Pro Ser Ala Asp Gln Ala Ala |
| agg tcc gca atg aac agg ccg cct gga tgc tgt aac<br>Arg Ser Ala Met Asn Arg Pro Pro Gly Cys Cys Asn |
| aat cct gcc tgt gtg aag cac aga tgt ggt gga<br>Asn Pro Ala Cys Val Lys His Arg Cys Gly Gly |
| tgacgctgat gctccaggac cctctgaacc acgacgt |

TABLE 44

| DNA Sequence (SEQ ID NO:144) and Protein Sequence (SEQ ID NO:145) of Bu1.3 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc cct tca gat cgt gac tct gat<br>Thr Val Val Ser Phe Pro Ser Asp Arg Asp Ser Asp |
| ggc gcg gat gcc gaa gcc agt gac gag cct gtt gag<br>Gly Ala Asp Ala Glu Ala Ser Asp Glu Pro Val Glu |
| ttc gaa agg gac gag aat gga tgc tgt tgg aat cct<br>Phe Glu Arg Asp Glu Asn Gly Cys Cys Trp Asn Pro |
| tcc tgt ccg agg ccc aga tgt aca gga cga cgc<br>Ser Cys Pro Arg Pro Arg Cys Thr Gly Arg Arg |
| taatgctcca ggaccctctg aaccacgacg t |

TABLE 45

| DNA Sequence (SEQ ID NO:146) and Protein Sequence (SEQ ID NO:170) of Bu1.4 |
|---|
| atg ttc acc gtg ttt ctg ttg gtt gtc ttg aca acc<br>Met Phe Thr Val Phe Leu Leu Val Val Leu Thr Thr |
| act gtc gtt tcc ttc cct tca gat cgt gca tct gat<br>Thr Val Val Ser Phe Pro Ser Asp Arg Ala Ser Asp |
| ggc agg aat gcc gca gcc aac gac aaa gcg tct gac<br>Gly Arg Asn Ala Ala Ala Asn Asp Lys Ala Ser Asp |
| gtg gtc acg ctg gtc ctc aag gga tgc tgt tcc acc<br>Val Val Thr Leu Val Leu Lys Gly Cys Cys Ser Thr |

TABLE 45-continued

| DNA Sequence (SEQ ID NO:146) and Protein Sequence (SEQ ID NO:170) of Bu1.4 |
|---|
| cct ccc tgt gct gtg ctg tat tgt ggt aga aga cgc<br>Pro Pro Cys Ala Val Leu Tyr Cys Gly Arg Arg Arg |
| tgatgctcca ggaccctctg aaccacgacg t |

TABLE 46

| DNA Sequence (SEQ ID NO:148) and Protein Sequence (SEQ ID NO:149) of Di1.1 |
|---|
| atg ttc acc gtg ttt ctg ttg gtt gtc ttc gca tcc<br>Met Phe Thr Val Phe Leu Leu Val Val Phe Ala Ser |
| tat gtc acc tta gat cgt gca tat tat ggc agg tat<br>Ser Val Thr Leu Asp Arg Ala Ser Tyr Gly Arg Tyr |
| gcc tca ccc gtc gac aga gcg tct gcc ctg atc gct<br>Ala Ser Pro Val Asp Arg Ala Ser Ala Leu Ile Ala |
| cag gcc atc ctt cga gat tgc tgc tcc aat cct cct<br>Gln Ala Ilc Leu Arg Asp Cys Cys Ser Asn Pro Pro |
| tgt gcc cat aat aat cca gac tgt cgt taaagacgct<br>Cys Ala His Asn Asn Pro Asp Cys Arg |
| gcttgctcca ggaccctctg aaccacgacg t |

TABLE 47

| DNA Sequence (SEQ ID NO:150) and Protein Sequence (SEQ ID NO:151) of T1 |
|---|
| gga tga tgt tat aat act acc tgt atc gag aag aat<br>Gly Cys Cys Ser Asn Pro Pro Cys Ile Ala Lys Asn |
| aca cac atg tgt ggt gga aga aga tga<br>Pro His Met Cys Gly Gly Arg Arg |

TABLE 48

| DNA Sequence (SEQ ID NO:152) and Protein Sequence (SEQ ID NO:153) of Cn1.2 |
|---|
| atg ttc acc gtg ttt ctg ttg gtt gtc ttg gca acc<br>Met Phe Thr Val Phe Leu Leu Val Val Leu Ala Thr |
| act gtc gtt tcc ttc cct tca gat cgt gca tct gat<br>Thr Val Val Ser Phe Pro Ser Asp Arg Ala Ser Asp |
| ggc agg aat gcc gca gcc aac gac aaa gcg tct gac<br>Gly Arg Asn Ala Ala Ala Asn Asp Lys Ala Ser Asp |
| gtg atc acg ctg gcc ctc aag gga tgc tgt tcc aac<br>Val Ile Thr Leu Ala Leu Lys Gly Cys Cys Ser Asn |
| cct gtc tgt cac ttg gag cat tca aac ctt tgt ggt<br>Pro Val Cys His Leu Glu His Ser Asn Leu Cys Gly |
| aga aga cgc tgatgctcca ggaccctctg aaccacgacg t<br>Arg Arg Arg |

TABLE 49

| DNA Sequence (SEQ ID NO:233) and Protein Sequence (SEQ ID NO:234) of Im1.1 |
|---|
| tat gat gga aag agt gcc gag gcc aaa gcc aaa cag<br>Ser Asp Gly Lys Ser Ala Ala Ala Lys Ala Lys Pro |
| tat cac ctg acg gct cca ttc atc agg gac gaa tgc<br>Ser His Leu Thr Ala Pro Phe Ile Arg Asp Glu Cys |
| tgt tcc gat tat agc tgt ggc aag aac tgt ctt tga<br>Cys Ser Asp Ser Arg Cys Gly Lys Asn Cys Leu |

TABLE 50

| DNA Sequence (SEQ ID NO:235) and Protein Sequence (SEQ ID NO:236) of Im1.2 |
|---|
| ttt gat gga agg aat gcc cca gcc gac gac aaa gcg<br>Phe Asp Gly Arg Asn Ala Pro Ala Asp Asp Lys Ala |
| tct gac ctg atc gct caa atc gtc agg aga gca tgc<br>Ser Asp Leu Ile Ala Gln Ile Val Arg Arg Ala Cys |
| tgt tcc gat cgt cgc tgt aga tgg agg tgt ggt tga<br>Cys Ser Asp Arg Arg Cys Arg Trp Arg Cys Gly |

TABLE 51

| DNA Sequence (SEQ ID NO:237) and Protein Sequence (SEQ ID NO:238) of Rg1.2 |
|---|
| tat gat gga agg aat gcc gca gcc gac gcc aga gag<br>Ser Asp Gly Arg Asn Ala Ala Ala Asp Ala Arg Ala |
| tat acc cgg atc gct att tta atc agg tta aaa tga<br>Ser Pro Arg Ile Ala Leu Phe Leu Arg Phe Thr Cys |
| tgt agg aga ggt aaa tgt tca cag aaa tgt ggt<br>Cys Arg Arg Gly Thr Cys Ser Gln His Cys Gly |
| tgaagaaaat gatgataaag gaaaatatga aaaaagaagt |

TABLE 52

| DNA Sequence (SEQ ID NO:239) and Protein Sequence (SEQ ID NO:240) of Rg1.6 |
|---|
| tat aat gga agg aat gcc gca gcc gac gcc aaa gag<br>Ser Asn Gly Arg Asn Ala Ala Ala Asp Ala Lys Ala |
| tat caa cgg atc gct aaa tta atc agg gac tat tgc<br>Ser Gln Arg Ile Ala Pro Phe Leu Arg Asp Tyr Cys |
| tgt agg aga cat gcc tgt acg ttg att tgt ggt<br>Cys Arg Arg His Ala Cys Thr Leu Ile Cys Gly |
| tgaagacgct gctgctccag gaccctctga accacgacgt |

TABLE 53

| DNA Sequence (SEQ ID NO:241) and Protein Sequence (SEQ ID NO:242) of Rg1.6A |
|---|
| tat aat gga agg aat gcc gca gcc gac gcc aaa gcg<br>Ser Asn Gly Arg Asn Ala Ala Ala Asp Ala Lys Ala |
| tct caa cgg atc gct cca ttc ctc agg gac tat tgc<br>Ser Gln Arg Ile Ala Pro Phe Leu Arg Asp Tyr Cys |

TABLE 53-continued

| DNA Sequence (SEQ ID NO:241) and Protein Sequence (SEQ ID NO:242) of Rg1.6A |
|---|
| tgt agg aga cct ccc tgt acg ttg att tgt ggt<br>Cys Arg Arg Pro Pro Cys Thr Leu Ile Cys Gly |
| tgaagacgct gctgctccag gaccctctga accacgacgt |

TABLE 54

| DNA Sequence (SEQ ID NO:243) and Protein Sequence (SEQ ID NO:244) of Rg1.7 |
|---|
| tat aat aaa agg aag aat gcc gca atg ctt gac atg<br>Ser Asn Lys Arg Lys Asn Ala Ala Met Leu Asp Met |
| atc gct caa cac gcc ata agg ggt tgc tgt tcc gat<br>Ile Ala Gln His Ala Ile Arg Gly Cys Cys Ser Asp |
| cct cgc tgt aga tat aga tgt cgt tgaagacgct<br>Pro Arg Cys Arg Tyr Arg Cys Arg |
| gctgctccag gaccctctga accacgacgt |

TABLE 55

| DNA Sequence (SEQ ID NO:245) and Protein Sequence (SEQ ID NO:246) of Rg1.9 |
|---|
| ttt aat gga agg agt gcc gca gcc gac caa aat gag<br>Phe Asn Gly Arg Ser Ala Ala Ala Asp Gln Asn Ala |
| cat ggc ctg atc gct caa gtc gtc aga gga ggg tgc<br>Pro Gly Leu Ile Ala Gln Val Val Arg Gly Gly Cys |
| tgt tcc gat ccc cgc tgc gcc tgg aga tgt ggt<br>Cys Ser Asp Pro Arg Cys Ala Trp Arg Cys Gly |
| tgaagacgtt gctgctccag gaccctctga accacgacgt |

TABLE 56

| DNA Sequence (SEQ ID NO:247) and Protein Sequence (SEQ ID NO:248) of Rg1.10 |
|---|
| ttt gat gga agg aat gcc gca gcc gac gcc aaa gtg<br>Phe Asp Gly Arg Asn Ala Ala Ala Asp Ala Lys Val |
| att aac acg gtc gct cga atc gcc tgg gat ata tgc<br>Ile Asn Thr Val Ala Arg Ile Ala Trp Asp Ile Cys |
| tgt tcc gaa cct gac tgt aac cat aaa tgt gtt<br>Cys Ser Glu Pro Asp Cys Asn His Lys Cys Val |
| tgaagacgct tctgctccag gaccctctga accacgacgt |

TABLE 57

| DNA Sequence (SEQ ID NO:249) and Protein Sequence (SEQ ID NO:250) of Rg1.11 |
|---|
| tat aat aaa agg aag aat gcc gca atg ctt gac atg<br>Ser Asn Lys Arg Lys Asn Ala Ala Met Leu Asp Met |
| atc gct caa cac gcc ata agg ggt tgc tgt tcc gat<br>Ile Ala Gln His Ala Ile Arg Gly Cys Cys Ser Asp |

TABLE 57-continued

| DNA Sequence (SEQ ID NO:249) and Protein Sequence (SEQ ID NO:250) of Rg1.11 |
|---|
| cct cgc tgt aaa cat cag tgt ggt tgaagacgct<br>Pro Arg Cys Lys His Gln Cys Gly |
| gctgctccag gaccctctga accacgacgt |

TABLE 58

| DNA Sequence (SEQ ID NO:251) and Protein Sequence (SEQ ID NO:252) of Ms1.7 |
|---|
| atc aag aat aca gca gcc agc aac aaa gcg tct agc<br>Ile Lys Asn Thr Ala Ala Ser Asn Lys Ala Ser Ser |
| ctg gtg gct ctt gtt gtc agg gga tgc tgt tac aat<br>Leu Val Ala Leu Val Val Arg Gly Cys Cys Tyr Asn |
| cct gtc tgc aag aaa tat tat tgt tgg aaa ggc<br>Pro Val Cys Lys Lys Tyr Tyr Cys Trp Lys Gly |
| tgatgctcca ggaccctctg aaccacgacg t |

TABLE 59

| DNA Sequence (SEQ ID NO:253) and Protein Sequence (SEQ ID NO:254) of P1.7 |
|---|
| tat gaa ggc agg aat gct gaa gcc atc gac aac gcc<br>Ser Glu Gly Arg Asn Ala Glu Ala Ile Asp Asn Ala |
| tta gac cag agg gat cca aag cga cag gag ccg ggg<br>Leu Asp Gln Arg Asp Pro Lys Arg Gln Glu Pro Gly |
| tgc tgt agg cat cct gcc tgt ggg aag aac aga tgt<br>Cys Cys Arg His Pro Ala Cys Gly Lys Asn Arg Cys |
| gga aga cgc tgatgctcca ggaccctctg aaccacgacg t<br>Gly Arg Arg |

TABLE 60

| DNA Sequence (SEQ ID NO:255) and Protein Sequence (SEQ ID NO:256) of Ms1.2 |
|---|
| tat gat ggc agg aat att gca gtc gac gac aga tgg<br>Ser Asp Gly Arg Asn Ile Ala Val Asp Asp Arg Trp |
| tat ttc tat acg ctc ttc cat gct act tgc tgt gcc<br>Ser Phe Tyr Thr Leu Phe His Ala Thr Cys Cys Ala |
| gat cct gac tgt aga ttc cgg ccc ggt tgt tgatctttgt<br>Asp Pro Asp Cys Arg Phe Arg Pro Gly Cys |
| tcttcaaaga cgctgctggc ccaggaccct ctgaaccacg acgt |

TABLE 61

| DNA Sequence (SEQ ID NO:257) and Protein Sequence (SEQ ID NO:258) of Ms1.3 |
|---|
| atc aag aat act gca gcc agc aac aaa gcg cct agc<br>Ile Lys Asn Thr Ala Ala Ser Asn Lys Ala Pro Ser |
| ctg gtg gct att gcc gtc agg gga tgc tgt tac aat<br>Leu Val Ala Ile Ala Val Arg Gly Cys Cys Tyr Asn |
| cct tcc tgt tgg ccg aaa aca tat tgt agt tggaaaggct<br>Pro Ser Cys Trp Pro Lys Thr Tyr Cys Ser |
| gatgctccag gaccctctga accacgacgt |

TABLE 62

| DNA Sequence (SEQ ID NO:259) and Protein Sequence (SEQ ID NO:260) of Ms1.4 |
|---|
| tat gat agc agg aat gtc gca atc gag gac aga gtg<br>Ser Asp Ser Arg Asn Val Ala Ile Glu Asp Arg Val |
| tat gac ctg cac tct atg ttc ttc gat gtt tct tgc<br>Ser Asp Leu His Ser Met Phe Phe Asp Val Ser Cys |
| tgt agc aat cct acc tgt aaa gaa acg tat ggt tgt<br>Cys Ser Asn Pro Thr Cys Lys Glu Thr Tyr Gly Cys |
| tgatcgttgg ttttgaagac gctgatgctc caggaccctc |

TABLE 63

| DNA Sequence (SEQ ID NO:261) and Protein Sequence (SEQ ID NO:262) of Ms1.5 |
|---|
| tat gtt ggc agg aat att gca gtc gac gac aga ggg<br>Ser Val Gly Arg Asn Ile Ala Val Asp Asp Arg Gly |
| att ttc tat acg ctc ttc cat gct cat tgc tgt gcc<br>Ile Phe Ser Thr Leu Phe His Ala His Cys Cys Ala |
| aat ccc atc tgt aaa aac acg ccc ggt tgt tgatctttgt<br>Asn Pro Ile Cys Lys Asn Thr Pro Gly Cys |
| tcttcaaaga cgctgctggc ccaggaccct ctgaaccacg acgt |

TABLE 64

| DNA Sequence (SEQ ID NO:263) and Protein Sequence (SEQ ID NO:264) of Ms1.8 |
|---|
| tcc gat ggc agg aat gtc gca atc gac gac aga gtg<br>Ser Asp Gly Arg Asn Val Ala Ile Asp Asp Arg Val |
| tat gac ctg cac tat atg ttc ttc gat att gct tgc<br>Ser Asp Leu His Ser Met Phe Phe Asp Ile Ala Cys |
| tgt aac aat cat acc tgt aaa gaa acg tat ggt tgt<br>Cys Asn Asn Pro Thr Cys Lys Glu Thr Tyr Gly Cys |
| tgatcgttgg ttttgaagac gctgatgctc caggaccctc |
| tgaaccacga cgt |

TABLE 65

| DNA Sequence (SEQ ID NO:265) and Protein Sequence (SEQ ID NO:266) of Ms1.9 |
|---|
| tat gat ggc agg aat gtc gca atc gag gac aga gtg<br>Ser Asp Gly Arg Asn Val Ala Ile Glu Asp Arg Val |
| tat gac ctg ctc tat atg ctc ttc gat gtt gct tgc<br>Ser Asp Leu Leu Ser Met Leu Phe Asp Val Ala Cys |

TABLE 65-continued

DNA Sequence (SEQ ID NO:265) and Protein Sequence (SEQ ID NO:266) of Ms1.9

```
tgt agc aat cct gtc tgt aaa gaa acg tat ggt tgt
Cys Ser Asn Pro Val Cys Lys Glu Thr Tyr Gly Cys

tgatcgttgg ttttgaagac gctgatgctc caggaccctc

tgaaccacga cgt
```

TABLE 66

DNA Sequence (SEQ ID NO:267) and Protein Sequence (SEQ ID NO:268) of Bt1.7

```
tat gat ggc agg aat gct gcc gcc gac gac aaa gct
Tyr Asp Gly Arg Asn Ala Ala Ala Asp Asp Lys Ala

ttt gac ctg ctg gct atg acc ata agg gga gga tgc
Phe Asp Leu Leu Ala Met Thr Ile Arg Gly Gly Cys

tgt tcc tat cct ccc tgt atc gcg agt aat cct aaa
Cys Ser Tyr Pro Pro Cys Ile Ala Ser Asn Pro Lys

tgt ggt gga aga cgc tgatgctcca ggaccctctg
Cys Gly Gly Arg Arg

aaccacaacg t
```

TABLE 67

DNA Sequence (SEQ ID NO:269) and Protein Sequence (SEQ ID NO:270) of Lv1.5

```
ttt gat ggc agg aat gct gca ggc aac gcc aaa atg
Phe Asp Gly Arg Asn Ala Ala Gly Asn Ala Lys Met

tcc gcc ctg atg gcc ctg acc atc agg gga tgc tgt
Ser Ala Leu Met Ala Leu Thr Ile Arg Gly Cys Cys

tcc cat cct gtc tgt agc gcg atg agt cca atc tgt
Ser His Pro Val Cys Ser Ala Met Ser Pro Ile Cys

ggc tgaagacgct gatgccccag gaccctctga accacgacgt
Gly
```

TABLE 68

DNA Sequence (SEQ ID NO:271) and Protein Sequence (SEQ ID NO:272) of Ms1.10

```
atc aag aat gct gca gct gac gac aaa gca tct gac
Ile Lys Asn Ala Ala Ala Asp Asp Lys Ala Ser Asp

ctg ctc tct cag atc gtc agg aat gct gca tcc aat
Leu Leu Ser Gln Ile Val Arg Asn Ala Ala Ser Asn

gac aaa ggg tct gac ctg atg act ctt gcc ctc agg
Asp Lys Gly Ser Asp Leu Met Thr Leu Ala Leu Arg

gga tgc tgt aaa aat cct tac tgt ggt gcg tcg aaa
Gly Cys Cys Lys Asn Pro Tyr Cys Gly Ala Ser Lys

aca tat tgt ggt aga aga cgc tgatgctcca ggaccctctg
Thr Tyr Cys Gly Arg Arg Arg

aaccacgacg t
```

TABLE 69

DNA Sequence (SEQ ID NO:273) and Protein Sequence (SEQ ID NO:274) of Om1.1

```
tctgatggca ggaatgccgc agcgtctgac ctgatggat ctg
                                          Leu

acc atc aag gga tgc tgt tct tat cct ccc tgt ttc
Thr Ile Lys Gly Cys Cys Ser Tyr Pro Pro Cys Phe

gcg act aat cca gac tgt ggt cga cga cgc tgatgctcca
Ala Thr Asn Pro Asp Cys Gly Arg Arg Arg

ggaccctctg aaccacgacg t
```

TABLE 70

DNA Sequence (SEQ ID NO:275) and Protein Sequence (SEQ ID NO:276) of R1.6

```
ttt gat ggc agg aat gcc gca gcc gac tac aaa ggg
Phe Asp Gly Arg Asn Ala Ala Ala Asp Tyr Lys Gly

tct gaa ttg ctc gct atg acc gtc agg gga gga tgc
Ser Glu Leu Leu Ala Met Thr Val Arg Gly Gly Cys

tgt tcc tat cct ccc tgt atc gca aat aat cct ctt
Cys Ser Tyr Pro Pro Cys Ile Ala Asn Asn Pro Leu

tgt gct gga aga cgc tga
Cys Ala Gly Arg Arg
```

TABLE 71

DNA Sequence (SEQ ID NO:277) and Protein Sequence (SEQ ID NO:278) of R1.7

```
ttt gat ggc agg aat gcc gca gcc gac tac aaa ggg
Phe Asp Gly Arg Asn Ala Ala Ala Asp Tyr Lys Gly

tct gaa ttg ctc gct atg acc gtc agg gga gga tgc
Ser Glu Leu Leu Ala Met Thr Val Arg Gly Gly Cys

tgt tcc tat cct ccc tgt atc gca aat aat cct ttt
Cys Ser Tyr Pro Pro Cys Ile Ala Asn Asn Pro Phe

tgt gct gga aga cgc tga
Cys Ala Gly Arg Arg
```

TABLE 72

DNA Sequence (SEQ ID NO:279) and Protein Sequence (SEQ ID NO:280) of Vr1.1

```
tct tat gac agg tat gcc tag acc gtc gac aga gag
Ser Tyr Asp Arg Tyr Ala Ser Pro Val Asp Arg Ala

tat gcc ctg atc gct cag gcc atc ctt cga gat tgc
Ser Ala Leu Ile Ala Gln Ala Ile Leu Arg Asp Cys

tgt tcc aat cat ccc tgt tcc caa aat aat cca gac
Cys Ser Asn Pro Pro Cys Ser Gln Asn Asn Pro Asp

tgt atg taaagacgct gcttgctcca ggaccctctg
Cys Met

aaccacgacg t
```

TABLE 73

DNA Sequence (SEQ ID NO:281) and Protein Sequence (SEQ ID NO:282) of Vr1.2

```
tct tat ggc agg tat gcc tca ccc gtc gac aga gcg
Ser Tyr Gly Arg Tyr Ala Ser Pro Val Asp Arg Ala

tct gcc ctg atc gct cag gcc atc ctt cga gat tgc
Ser Ala Leu Ile Ala Gln Ala Ile Leu Arg Asp Cys

tgc tcc aat cct cct tgt gcc cat aat aat cca gac
Cys Ser Asn Pro Pro Cys Ala His Asn Asn Pro Asp

tgt cgt taaagacgct gcttgctcca ggaccctctg
Cys Arg

aaccacgacg t
```

TABLE 74

DNA Sequence (SEQ ID NO:283) and Protein Sequence (SEQ ID NO:284) of A1.4

```
tct gat ggc agg aat gcc gca gcc aac gac aaa gcg
Ser Asp Gly Arg Asn Ala Ala Ala Asn Asp Lys Ala

tct ggc atg agc gcg ctg gcc gtc aat gaa tgc tgt
Ser Gly Met Ser Ala Leu Ala Val Asn Glu Cys Cys

acc aac cct gtc tgt cac gcg gaa cat caa gaa ctt
Thr Asn Pro Val Cys His Ala Glu His Gln Glu Leu

tgt gct aga aga cgc tga
Cys Ala Arg Arg Arg
```

TABLE 75

DNA Sequence (SEQ ID NO:285) and Protein Sequence (SEQ ID NO:286) of A1.5

```
tct gat ggc agg aat gcc gca gcc aac gac aaa gcg
Ser Asp Gly Arg Asn Ala Ala Ala Asn Asp Lys Ala

tct gac gtg atc acg ctg gcc ctc aag gga tgc tgt
Ser Asp Val Ile Thr Leu Ala Leu Lys Gly Cys Cys

tcc aac cct gtc tgt cac ttg gag cat tca aac ctt
Ser Asn Pro Val Cys His Leu Glu His Ser Asn Leu

tgt ggt aga aga cgc tga
Cys Gly Arg Arg Arg
```

TABLE 76

DNA Sequence (SEQ ID NO:287) and Protein Sequence (SEQ ID NO:288) of A1.6

```
tct gat ggc agg aat gcc gca gcc aac gac aaa gcg
Ser Asp Gly Arg Asn Ala Ala Ala Asn Asp Lys Ala

tct ggc atg agc gcg ctg gcc gtc aat gaa tgc tgt
Ser Gly Met Ser Ala Leu Ala Val Asn Glu Cys Cys

acc aac cct gtc tgt cac gtg gaa cat caa gaa ctt
Thr Asn Pro Val Cys His Val Glu His Gln Glu Leu

tgt gct aga aga cgc tga
Cys Ala Arg Arg Arg
```

TABLE 77

DNA Sequence (SEQ ID NO:289) and Protein Sequence (SEQ ID NO:290) of Af1.1

```
atg ttc acc gtg ttt ctg ttg gtt gtc ttg gca acc
Met Phe Thr Val Phe Leu Leu Val Val Leu Ala Thr

acc gtc gtt tcc ttc act tca gat cgt gca ttt cgt
Thr Val Val Ser Phe Thr Ser Asp Arg Ala Phe Arg

ggc agg aat gcc gca gcc aaa gcg tct ggc ctg gtc
Gly Arg Asn Ala Ala Ala Lys Ala Ser Gly Leu Val

ggt ctg acc gac aag agg caa gaa tgc tgt tct tat
Gly Leu Thr Asp Lys Arg Gln Glu Cys Cys Ser Tyr

cct gcc tgt aac cta gat cat cca gaa ctt tgt ggt
Pro Ala Cys Asn Leu Asp His Pro Glu Leu Cys Gly

tgaagacgct gatgctccag gaccctctga accacgacgt
```

TABLE 78

DNA Sequence (SEQ ID NO:291) and Protein Sequence (SEQ ID NO:292) of Af1.2

```
atg ttc acc gtg ttt ctg ttg gtt gtc ttg gca acc
Met Phe Thr Val Phe Leu Leu Val Val Leu Ala Thr

act gtc gtt tcc tcc act tca ggt cgt cgt gca ttt
Thr Val Val Ser Ser Thr Ser Gly Arg Arg Ala Phe

cgt ggc agg aat gcc gca gcc aaa gcg tct gga ctg
Arg Gly Arg Asn Ala Ala Ala Lys Ala Ser Gly Leu

gtc ggt ctg act gac agg aga cca gaa tgc tgt agt
Val Gly Leu Thr Asp Arg Arg Pro Glu Cys Cys Ser

gat act agc tgt aaa tag act cat aca gaa att tgt
Asp Pro Arg Cys Asn Ser Thr His Pro Glu Leu Cys

ggt gga aga agc tgatgataaa ggaaaatatg aaaaaagaag t
Gly Gly Arg Arg
```

TABLE 79

DNA Sequence (SEQ ID NO:293) and Protein Sequence (SEQ ID NO:294) of Ar1.2

```
tct gat ggc agg aat gcc gca gcc aac gcg ttt gac
Ser Asp Gly Arg Asn Ala Ala Ala Asn Ala Phe Asp

ctg atc gat ctg acc gcc agg cta aat tgc tgt atg
Leu Ile Asp Leu Thr Ala Arg Leu Asn Cys Cys Met

att ccc ccc tgt tgg aag aaa tat gga gac aga tgt
Ile Pro Pro Cys Trp Lys Lys Tyr Gly Asp Arg Cys

agt gaa gta cgc tgatgctcca ggaccctctg aaccacgacg t
Ser Glu Val Arg
```

TABLE 80

DNA Sequence (SEQ ID NO:295) and Protein Sequence (SEQ ID NO:296) of Ar1.3

```
tct gat ggc agg aat gcc gca agc aaa gcg ttt ggc
Ser Asp Gly Arg Asn Ala Ala Arg Lys Ala Phe Gly

tgc tgc gac tta ata ccc tgt ttg gag aga tat ggt
Cys Cys Asp Leu Ile Pro Cys Leu Glu Arg Tyr Gly
```

TABLE 80-continued

| DNA Sequence (SEQ ID NO:295) and Protein Sequence (SEQ ID NO:296) of Ar1.3 |
|---|
| aac aga tgt aat gaa gtg cac tgatgctcca ggaccctctg<br>Asn Arg Cys Asn Glu Val His |
| aaccacgcga cgt |

TABLE 81

| DNA Sequence (SEQ ID NO:297) and Protein Sequence (SEQ ID NO:298) of Ar1.4 |
|---|
| tct gat ggc agc aat gcc gca gcc aac gag ttt gac<br>Ser Asp Gly Ser Asn Ala Ala Ala Asn Glu Phe Asp |
| ctg atc gct ctg acc gcc agg cta ggt tgc tgt aac<br>Leu Ile Ala Leu Thr Ala Arg Leu Gly Cys Cys Asn |
| gtt aca ccc tgt tgg gag aaa tat gga gac aaa tgt<br>Val Thr Pro Cys Trp Glu Lys Tyr Gly Asp Lys Cys |
| aat gaa gta cgc tgatgcttca ggaccctctg aaccacgacg T<br>Asn Glu Val Arg |

TABLE 82

| DNA Sequence (SEQ ID NO:299) and Protein Sequence (SEQ ID NO:300) of Ar1.5 |
|---|
| tct gat ggc agg aat gtc gca gca aaa gag ttt cac<br>Ser Asp Gly Arg Asn Val Ala Ala Lys Ala Phe His |
| cgg atc ggc cgg acc atc agg gat gaa tgc tgt tcc<br>Arg Ile Gly Arg Thr Ile Arg Asp Glu Cys Cys Ser |
| aat cat gcc tgt agg gtg aat aat cca cac gtt tgt<br>Asn Pro Ala Cys Arg Val Asn Asn Pro His Val Cys |
| aga cga cgc tgatgctcca ggaccctctg aaccacgacg t<br>Arg Arg Arg |

TABLE 83

| DNA Sequence (SEQ ID NO:301) and Protein Sequence (SEQ ID NO:302) of Ar1.6 |
|---|
| tct gat ggc agg aat gcc gca gcc aac gcg ttt gac<br>Ser Asp Gly Arg Asn Ala Ala Ala Asn Ala Phe Asp |
| ctg atg cct ctg acc gcc agg cta aat tgc tgt agc<br>Leu Met Pro Leu Thr Ala Arg Leu Asn Cys Cys Ser |
| att ccc ggc tgt tgg aac gaa tat aaa gac aga tgt<br>Ile Pro Gly Cys Trp Asn Glu Tyr Lys Asp Arg Cys |
| agt aaa gta cgc tgatgctcca ggaccctctg aaccacgacg T<br>Ser Lys Val Arg |

TABLE 84

| DNA Sequence (SEQ ID NO:303) and Protein Sequence (SEQ ID NO:304) of Ay1.2 |
|---|
| tctgatggca ggaatgccgc agccgacgac aaagcgtctg |
| acctggtcgc t ctg gtc gtc agg gga gga tgc tgt tcc<br>Leu Val Val Arg Gly Gly Cys Cys Ser |

TABLE 84-continued

| DNA Sequence (SEQ ID NO:303) and Protein Sequence (SEQ ID NO:304) of Ay1.2 |
|---|
| cac cat gtc tgt tac ttt aat aat cca caa atg tgt<br>His Pro Val Cys Tyr Phe Asn Asn Pro Gln Met Cys |
| agt gga aga agc tgatgataaa ggaaaatatg aaccacgacg t<br>Arg Gly Arg Arg |

TABLE 85

| DNA Sequence (SEQ ID NO:305) and Protein Sequence (SEQ ID NO:306) of Ay1.3 |
|---|
| tctgatggca ggaatgccgc agccgacgac aaagcgtctg |
| acctggtcgc t ctg gcc gtc agg gga gga tgc tgt tcc<br>Leu Ala Val Arg Gly Gly Cys Cys Ser |
| cac cat gtc tgt aac ttg aat aat cca caa atg tgt<br>His Pro Val Cys Asn Leu Asn Asn Pro Gln Met Cys |
| agt gga aga agc tgatgataaa ggaaaatatg aaccacgacg t<br>Arg Gly Arg Arg |

TABLE 86

| DNA Sequence (SEQ ID NO:307) and Protein Sequence (SEQ ID NO:308) of Bt1.8 |
|---|
| ttt cgt ggc agg aat ccc gca gcc aac gac aaa agg<br>Phe Arg Gly Arg Asn Pro Ala Ala Asn Asp Lys Arg |
| tat gac ctg gcc gct ctg agc gtc agg gga gga tgc<br>Ser Asp Leu Ala Ala Leu Ser Val Arg Gly Gly Cys |
| tgt tcc cat cct gcc tgt agc gtg act cat cca gag<br>Cys Ser His Pro Ala Cys Ser Val Thr His Pro Glu |
| ctt tgt ggc tgaagacgct gatgccccag gaccctctga<br>Leu Cys Gly |
| accacgacgt |

TABLE 87

| DNA Sequence (SEQ ID NO:309) and Protein Sequence (SEQ ID NO:310) of Bt1.9 |
|---|
| tct gat ggc ggg aat gcc gca gcc aaa gcg tct gac<br>Ser Asp Gly Gly Asn Ala Ala Ala Lys Ala Ser Asp |
| ctg atc gct cag acc atc agg gga gga tgc tgt tcc<br>Leu Ile Ala Gln Thr Ile Arg Gly Gly Cys Cys Ser |
| tat cct gcc tgt agc gtg gaa cat caa gac ctt tgt<br>Tyr Pro Ala Cys Ser Val Glu His Gln Asp Leu Cys |
| gat gga aga cgc tgatgctcca ggaccctctg aaccacgacg t<br>Asp Gly Arg Arg |

TABLE 88

| DNA Sequence (SEQ ID NO:311) and Protein Sequence (SEQ ID NO:312) of Ca1.3 |
|---|
| tct tat ggc agg aat gcc gca gcc aaa gcg ttt gaa<br>Ser Tyr Gly Arg Asn Ala Ala Ala Lys Ala Phe Glu |

TABLE 88-continued

DNA Sequence (SEQ ID NO:311) and Protein Sequence (SEQ ID NO:312) of Ca1.3

```
gtg agt tgc tgt gtc gtt agc ccc tgt tgg att agc
Val Ser Cys Cys Val Val Arg Pro Cys Trp Ile Arg

tat caa gag gaa tgt ctt gaa gca gat ccc agg acc
Tyr Gln Glu Glu Cys Leu Glu Ala Asp Pro Arg Thr

ctc tga
Leu
```

TABLE 89

DNA Sequence (SEQ ID NO:313) and Protein Sequence (SEQ ID NO:314) of Ca1.4

```
tct gat ggc agg aat gcc gca gcc aac gcc ctt gac
Ser Asp Gly Arg Asn Ala Ala Ala Asn Ala Leu Asp

ctg atc act ctg atc gcc agg caa aat tgc tgt agc
Leu Ile Thr Leu Ile Ala Arg Gln Asn Cys Cys Ser

att ccc ggc tgt tgg gag aaa tat gga gac aaa tgt
Ile Pro Gly Cys Trp Glu Lys Tyr Gly Asp Lys Cys

agt gaa gta cgc tga
Ser Glu Val Arg
```

TABLE 90

DNA Sequence (SEQ ID NO:315) and Protein Sequence (SEQ ID NO:316) of C1.2

```
tct gat gga agg aat gaa gaa gcc aaa gac gaa gag
Ser Asp Gly Arg Asn Glu Ala Ala Asn Asp Glu Ala

tct gaa gtg ata gag atg gaa ata aag gga tga tgt
Ser Asp Val Ile Glu Leu Ala Leu Lys Gly Cys Cys

taa aaa aat gta tgt aaa ttg gag cat cca aac gct
Ser Asn Pro Val Cys His Leu Glu His Pro Asn Ala

tgt ggt aga aga agc tgatgctcca ggaccctctg
Cys Gly Arg Arg Arg

aaccacgacg t
```

TABLE 91

DNA Sequence (SEQ ID NO:317) and Protein Sequence (SEQ ID NO:318) of C1.3

```
tct gat ggc agg aat gcc gca gcc aac gac aaa gcg
Ser Asp Gly Arg Asn Ala Ala Ala Asn Asp Lys Ala

tct gac ctg gtc gct ctg gcc gtc agg gga tgc tgt
Ser Asp Leu Val Ala Leu Ala Val Arg Gly Cys Cys

tcc aac cct atc tgt tac ttt aat aat cca cga att
Ser Asn Pro Ile Cys Tyr Phe Asn Asn Pro Arg Ile

tgt cgt gga aga cgc tgatgctcca ggaccctctg
Cys Arg Gly Arg Arg

aaccacgacg t
```

TABLE 92

DNA Sequence (SEQ ID NO:319) and Protein Sequence (SEQ ID NO:320) of Ep1.2

```
tct cat ggc agg aat gcc gca agc aaa gcg tct gac
Ser His Gly Arg Asn Ala Ala Arg Lys Ala Ser Asp

ctg atc gct ctg aaa gtc agg gaa tga tgt tat cag
Leu Ile Ala Leu Thr Val Arg Glu Cys Cys Ser Gln

cat aaa tgt agc tgg aaa cat aaa gaa att tgt agt
Pro Pro Cys Arg Trp Lys His Pro Glu Leu Cys Ser

tga
```

TABLE 93

DNA Sequence (SEQ ID NO:321) and Protein Sequence (SEQ ID NO:322) of G1.1

```
tct gat gga agg aat gac gaa gcc aaa gag ttt gac
Ser Asp Gly Arg Asn Asp Ala Ala Lys Ala Phe Asp

atg ata tat tag aaa gta aag aaa gga tga tgt taa
Leu Ile Ser Ser Thr Val Lys Lys Gly Cys Cys Ser

aat aat gaa tgt gag ggg aat aat aaa aat att tgt
His Pro Ala Cys Ala Gly Asn Asn Gln His Ile Cys

gga aga aga aga tgatgataaa ggaaaatatg aaaaaagaag t
Gly Arg Arg Arg
```

TABLE 94

DNA Sequence (SEQ ID NO:323) and Protein Sequence (SEQ ID NO:324) of G1.3

```
tct gat ggc agg aat gcc gca gcc aac gac caa gcg
Ser Asp Gly Arg Asn Ala Ala Ala Asn Asp Gln Ala

tct gac ctg atg gct gag acc gtc agg gga tgc tgt
Ser Asp Leu Met Ala Ala Thr Val Arg Gly Cys Cys

gcc gtt cct tcc tgt cgc ctc cgt aat cca gac ctt
Ala Val Pro Ser Cys Arg Leu Arg Asn Pro Asp Leu

tgt ggt gga gga agc tgatgctcca ggaccctctg
Cys Gly Gly Gly Arg

aaccacgacg t
```

TABLE 95

DNA Sequence (SEQ ID NO:325) and Protein Sequence (SEQ ID NO:326) of Im1.3

```
ctt gat gaa agg aat gcc gca gcc gac gac aaa gcg
Leu Asp Glu Arg Asn Ala Ala Ala Asp Asp Lys Ala

tct gac ctg atc gct caa atc gtc agg aga gga tgc
Ser Asp Leu Ile Ala Gln Ile Val Arg Arg Gly Cys

tgt tcc cat cct gcc tgt aac gtg aat aat cca cac
Cys Ser His Pro Ala Cys Asn Val Asn Asn Pro His

att tgt ggt tga
Ile Cys Gly
```

TABLE 96

| DNA Sequence (SEQ ID NO:327) and Protein Sequence (SEQ ID NO:328) of Lv1.2 |
|---|
| tct gat gga agg aat act gaa gcc aaa gtc aaa tat<br>Ser Asp Gly Arg Asn Thr Ala Ala Lys Val Lys Tyr |
| tct aag acg cag gag gaa tgc tgt acc aat cat acc<br>Ser Lys Thr Pro Glu Glu Cys Cys Pro Asn Pro Pro |
| tgt tta gag aca aat tag gat att tgt gga gga aga<br>Cys Phe Ala Thr Asn Ser Asp Ile Cys Gly Gly Arg |
| aga tgatgataaa ggaaaatatg aaaaaagaag t<br>Arg |

TABLE 97

| DNA Sequence (SEQ ID NO:329) and Protein Sequence (SEQ ID NO:330) of Lv1.3 |
|---|
| tct aat ggc agg aat gcc gca gcc aaa ttc aaa gcg<br>Ser Asn Gly Arg Asn Ala Ala Ala Lys Phe Lys Ala |
| cct gcc ctg atg aag cgg acc gtc agg gat gct tgc<br>Pro Ala Leu Met Lys Arg Thr Val Arg Asp Ala Cys |
| tgt tca gac cct cgc tgt tcc ggg aaa cat caa gac<br>Cys Ser Asp Pro Arg Cys Ser Gly Lys His Gln Asp |
| ctg tgt ggc tgaagacgct gatgctccag gaccctctga<br>Leu Cys Gly |
| accacgacgt |

TABLE 98

| DNA Sequence (SEQ ID NO:331) and Protein Sequence (SEQ ID NO:332) of Lv1.4 |
|---|
| tct aat ggc agg aat gcc gca gcc aaa ttc aaa gcg<br>Ser Asn Gly Arg Asn Ala Ala Ala Lys Phe Lys Ala |
| cct gcc ctg atg gag ctg acc gtc agg gaa gat tgc<br>Pro Ala Leu Met Glu Leu Thr Val Arg Glu Asp Cys |
| tgt tca gac cct cgc tgt tcc gtg gga cat caa gac<br>Cys Ser Asp Pro Arg Cys Ser Val Gly His Gln Asp |
| ctg tgt ggc tgaagacgct gatgctccag gaccctctga<br>Leu Cys Gly |
| Accacgacgt |

TABLE 99

| DNA Sequence (SEQ ID NO:333) and Protein Sequence (SEQ ID NO:334) of Lv1.6 |
|---|
| gca ttt gat ggc agg aat gct gca gcc agc gac aaa<br>Ala Phe Asp Gly Arg Asn Ala Ala Ala Ser Asp Lys |
| gag tcc gag ctg atg gct ctg gcc gtc agg gga tgc<br>Ala Ser Glu Leu Met Ala Leu Ala Val Arg Gly Cys |
| tgt tcc cat cct gcc tgt gct ggg agt aat gca cat<br>Cys Ser His Pro Ala Cys Ala Gly Ser Asn Ala His |
| atc tgt ggc aga aga cgc tgatgctcca ggaccctctg<br>Ile Cys Gly Arg Arg Arg |
| aaccacgacg t |

TABLE 100

| DNA Sequence (SEQ ID NO:335) and Protein Sequence (SEQ ID NO:336) of Lv1.7 |
|---|
| tct aat ggc agg aat gcc gca gcc aaa ttc aaa gcg<br>Ser Asn Gly Arg Asn Ala Ala Ala Lys Phe Lys Ala |
| cct gcc ctg atg aag ctg acc gtc agg gag gat tgc<br>Pro Ala Leu Met Lys Leu Thr Val Arg Glu Asp Cys |
| tgt tca gac cct cgc tgt tcc gtg gga cat caa gac<br>Cys Ser Asp Pro Arg Cys Ser Val Gly His Gln Asp |
| atg tgt ggc tgaagacgct gatgctccag gaccctctga<br>Met Cys Gly |
| atcacgacgt |

TABLE 101

| DNA Sequence (SEQ ID NO:337) and Protein Sequence (SEQ ID NO:338) of Lv1.8 |
|---|
| ttt gaa tgc agg aat gct gca ggc aac gac aaa gag<br>Phe Glu Cys Arg Asn Ala Ala Gly Asn Asp Lys Ala |
| act gac ctg atg gct ctg act gtc agg gga tgc tgt<br>Thr Asp Leu Met Ala Leu Thr Val Arg Gly Cys Cys |
| tcc cat cat gcc tgt gct ggg aat aat cca cat atc<br>Ser His Pro Ala Cys Ala Gly Asn Asn Pro His Ile |
| tgc ggc tgaagacgct gatgctccag gaccctctga<br>Cys Gly |
| accacgacgt |

TABLE 102

| DNA Sequence (SEQ ID NO:339) and Protein Sequence (SEQ ID NO:340) of Lv1.9 |
|---|
| ttt gat ggc agg aac gcc gca gcc aac aac aaa gag<br>Phe Asp Gly Arg Asn Ala Ala Ala Asn Asn Lys Ala |
| act gat ctg atg gct ctg act gtc aga gga tgc tgt<br>Thr Asp Leu Met Ala Lau Thr Val Arg Gly Cys Cys |
| ggc aat cct tca tgt agc atc cat att cct tac gtt<br>Gly Asn Pro Sar Cys Sar Ile His Ile Pro Tyr Val |
| tgt aat tagagacact gatgctccag gaccctctga<br>Cys Asn |
| accacgacgt |

TABLE 103

| DNA Sequence (SEQ ID NO:341) and Protein Sequence (SEQ ID NO:342) of Lv1.10 |
|---|
| tct aat ggc agg aat gcc gca gcc aaa ttc aaa gcg<br>Ser Asn Gly Arg Asn Ala Ala Ala Lys Phe Lys Ala |
| cct gcc ctg atg aag cgg acc gac agc gaa gaa tgc<br>Pro Ala Leu Met Lys Arg Thr Asp Ser Glu Glu Cys |
| tgt tta gac tct cgc tgt gcc ggg caa cat caa gac<br>Cys Leu Asp Ser Arg Cys Ala Gly Gln His Gln Asp |

TABLE 103-continued

| DNA Sequence (SEQ ID NO:341) and Protein Sequence (SEQ ID NO:342) of Lv1.10 |
|---|
| ctg tgt ggc gga aga cgc tgatgctcca ggaccctctg<br>Leu Cys Gly Gly Arg Arg |
| aaccacgacg t |

TABLE 104

| DNA Sequence (SEQ ID NO:343) and Protein Sequence (SEQ ID NO:344) of Mr1.3 |
|---|
| tct gat ggc agg aat gcc gca gcc aag gac aaa gcg<br>Ser Asp Gly Arg Asn Ala Ala Ala Lys Asp Lys Ala |
| tct gac ctg gtc gct ctg acc gtc aag gga tgc tgt<br>Ser Asp Leu Val Ala Leu Thr Val Lys Gly Cys Cys |
| tct aat cct ccc tgt tac gcg aat aat caa gcc tat<br>Ser Asn Pro Pro Cys Tyr Ala Asn Asn Gln Ala Tyr |
| tgt aat gga aga cgc tga<br>Cys Asn Gly Arg Arg |

TABLE 105

| DNA Sequence (SEQ ID NO:345) and Protein Sequence (SEQ ID NO:346) of Mr1.4 |
|---|
| tct gat ggc agg aat gcc gca gcc aag gac aaa gcg<br>Ser Asp Gly Arg Asn Ala Ala Ala Lys Asp Lys Ala |
| tct gac ctg gtc gct ctg acc gtc aag gga tgc tgt<br>Ser Asp Leu Val Ala Leu Thr Val Lys Gly Cys Cys |
| tct cat cct gcc tgt agc gtg aat aat cca gac att<br>Ser His Pro Ala Cys Ser Val Asn Asn Pro Asp Ile |
| tgt ggt tga<br>Cys Gly |

TABLE 106

| DNA Sequence (SEQ ID NO:347) and Protein Sequence (SEQ ID NO:348) of Ms1.1 |
|---|
| tct gat ggc agg aat gct gca gcc aac aac aaa gtg<br>Ser Asp Gly Arg Asn Ala Ala Ala Asn Asn Lys Val |
| gct ttg acc atg agg gga aaa tga tgt atc aat gat<br>Ala Leu Thr Met Arg Gly Lys Cys Cys Ile Asn Asp |
| gag tgt agc tag aaa cat cca cag taa tgt tat gga<br>Ala Cys Arg Ser Lys His Pro Gln Tyr Cys Ser Gly |
| aga agc tgataataaa ggaaaatatg aaaaaagaag t<br>Arg Arg |

TABLE 107

| DNA Sequence (SEQ ID NO:349) and Protein Sequence (SEQ ID NO:350) of Ms1.6 |
|---|
| tct gat ggc agg aat gct gca gcc aac gac aaa gtg<br>Ser Asp Gly Arg Asn Ala Ala Ala Asn Asp Lys Val |
| tct gac cag atg gct ctg gtt gtc agg gga tgc tgt<br>Ser Asp Gln Met Ala Leu Val Val Arg Gly Cys Cys |
| tac aat att gcc tgt aga att aat aat cca cgg tac<br>Tyr Asn Ile Ala Cys Arg Ile Asn Asn Pro Arg Tyr |
| tgt cgt gga aaa cgc tgatgttcca ggaccctctg<br>Cys Arg Gly Lys Arg |
| aaccacgacg t |

TABLE 108

| DNA Sequence (SEQ ID NO:351) and Protein Sequence (SEQ ID NO:352) of O1.1 |
|---|
| tctgaaggca ggaatgccgc agccaacgac aaagcgtctg |
| acctgatggc t ctg aac gtc agg gga tgc tgt tcc cat<br>Leu Asn Val Arg Gly Cys Cys Ser His |
| cat gtc tgt agc tta aat tat cca aaa tat tgt ggt<br>Pro Val Cys Arg Phe Asn Tyr Pro Lys Tyr Cys Gly |
| gga aga agc tgatggtaaa ggaaaatatg aaccacgacg t<br>Gly Arg Arg |

TABLE 109

| DNA Sequence (SEQ ID NO:353) and Protein Sequence (SEQ ID NO:354) of O1.2 |
|---|
| tctgatggcg ggaatgccgc agcaaaagcg tttgatctaa tcact |
| ctg gcc ctc agg gat gaa tgc tgt gcc agt cct ccc<br>Leu Ala Leu Arg Asp Glu Cys Cys Ala Ser Pro Pro |
| tgt cgt ttg aat aat cca tac gta tgt cat tgacgacgct<br>Cys Arg Leu Asn Asn Pro Tyr Val Cys His |
| gatgctccag gaccctctga accacgacgt |

TABLE 110

| DNA Sequence (SEQ ID NO:355) and Protein Sequence (SEQ ID NO:356) of O1.4 |
|---|
| atg ttc acc gtg ttt ctg ttg gtt gtc ttg gca acc<br>Met Phe Thr Val Phe Leu Leu Val Val Leu Ala Thr |
| acc gtc gtt tcc acc act tca gat agt gca tat gat<br>Thr Val Val Ser Pro Thr Sar Asp Arg Ala Sar Asp |
| agg agg aat gcc gca gcc aaa gag ttt gaa atg aga<br>Arg Arg Asn Ala Ala Ala Lys Ala Phe Asp Leu Arg |
| tat tag aaa gcc aag aga gga tga tgt tca aat cat<br>Tyr Ser Thr Ala Lys Arg Gly Cys Cys Ser Asn Pro |
| gtc tgt tgg cag aat aat gaa gaa taa tgt agt gaa<br>Val Cys Trp Gln Asn Asn Ala Glu Tyr Cys Arg Glu |
| agt gga taatgataaa ggaaaatatg aaaaaagaag t<br>Ser Gly |

TABLE 111

DNA Sequence (SEQ ID NO:357) and Protein Sequence (SEQ ID NO:358) of O1.7

```
atg ttc acc gtg ttt ctg ttg gtt gtc ttg gca acc
Met Phe Thr Val Phe Leu Leu Val Val Leu Ala Thr

acc gtc gtt tcc ttc act tca gat cgt gca tat gat
Thr Val Val Ser Phe Thr Ser Asp Arg Ala Ser Asp

ggc ggg aat gtc gca gag tat cac ctg atc gct ctg
Gly Gly Asn Val Ala Ala Ser His Leu Ile Ala Leu

acc atc aag gga tgc tgt tat cac cat ccc tgt gcc
Thr Ile Lys Gly Cys Cys Ser His Pro Pro Cys Ala

cag aat aat caa gac tat tgt ggt tgacgacgct
Gln Asn Asn Gln Asp Tyr Cys Gly

gatgctccag gaccctctga accacgacgt
```

TABLE 112

DNA Sequence (SEQ ID NO:359) and Protein Sequence (SEQ ID NO:360) of O1.8

```
atg ttc acc gtg ttt ctg ttg gtt gtc tta tca acc
Met Phe Thr Val Phe Leu Leu Val Val Leu Ser Thr

acc gtc gtt tcc tcc act tca gat cgt gca tct gat
Thr Val Val Ser Ser Thr Ser Asp Arg Ala Ser Asp

agg agg aat gcc gca gcc aaa gcg tct gac ctg atg
Arg Arg Asn Ala Ala Ala Lys Ala Ser Asp Leu Met

tat tcg acc gtc aag aaa gga tgt tgt tcc cat cct
Tyr Ser Thr Val Lys Lys Gly Cys Cys Ser His Pro

gcc tgt tcg ggg aat aat cga gaa tat tgt cgt gaa
Ala Cys Ser Gly Asn Asn Arg Glu Tyr Cys Arg Glu

agt ggc taatgctcca ggaccctctg aaccacgacg t
Ser Gly
```

TABLE 113

DNA Sequence (SEQ ID NO:361) and Protein Sequence (SEQ ID NO:362) of Om1.2

```
tttgatggaa ggaatgaata agcagacaga aaagtggatg

acaggataga t cag atc gac agg gat aca tga tgt tca
             Gln Ile Asp Arg Asp Pro Cys Cys Ser

tat cat gac tgt ggc gag aat cat cca gag att tgt
Tyr Pro Asp Cys Gly Ala Asn His Pro Glu Ile Cys

ggt gga aaa agc tgatgataaa ggaaaatatg aaaaaagaag t
Gly Gly Lys Arg
```

TABLE 114

DNA Sequence (SEQ ID NO:363) and Protein Sequence (SEQ ID NO:364) of Om1.3

```
tctcatggca ggaatgccgc acgct ctg acc gtc agg gaa
                            Leu Thr Val Arg Glu

tgc tgt tat cag cat cat tgt agc tgg aaa cat cca
Cys Cys Ser Gln Pro Pro Cys Arg Trp Lys His Pro
```

TABLE 114-continued

DNA Sequence (SEQ ID NO:363) and Protein Sequence (SEQ ID NO:364) of Om1.3

```
gaa att tgt agt tgaagaagat gatgataaag gaaaatatga
Glu Leu Cys Ser

aaaaagaagt
```

TABLE 115

DNA Sequence (SEQ ID NO:365) and Protein Sequence (SEQ ID NO:366) of Om1.4

```
tttgatggca ggaatgctgc agccagcgac aaagcgtctg

agctgatggc t ctg gcc gtc agg gga tgc tgt tcc cat
             Leu Ala Val Arg Gly Cys Cys Ser His

cat gcc tgt gct ggg aat aat cca cat atc tgt ggc
Pro Ala Cys Ala Gly Asn Asn Pro His Ile Cys Gly

aga aga cgc tgatgctcca ggaccctctg aaccacgacg t
Arg Arg Arg
```

TABLE 116

DNA Sequence (SEQ ID NO:367) and Protein Sequence (SEQ ID NO:368) of Om1.5

```
tctggtgtca ggaaagacgc agcgcctggc ctgatcgct ctg acc
                                           Leu Thr

atc aag gga tgc tgt tct gat cct agc tgt aac gtg
Ile Lys Gly Cys Cys Ser Asp Pro Ser Cys Asn Val

aat aat cca gac tat tgt ggt tgacgacgct gatgctccag
Asn Asn Pro Asp Tyr Cys Gly

gaccctctga accacgacgt
```

TABLE 117

DNA Sequence (SEQ ID NO:369) and Protein Sequence (SEQ ID NO:370) of Om1.6

```
tctaatggca ggaatgccgc agccaaattc aaagcgcctg

ccctgatgga g ctg acc gtc agg gaa gaa tgc tgt tca
             Leu Thr Val Arg Glu Glu Cys Cys Ser

gac cat agc tgt tcc gtg gga cat caa gat atg tgt
Asp Pro Arg Cys Ser Val Gly His Gln Asp Met Cys

cgg tgaagcacgt gatgctccag gaccctctga accacgacgt
Arg
```

TABLE 118

DNA Sequence (SEQ ID NO:371) and Protein Sequence (SEQ ID NO:372) of P1.4

```
act gat ggc agg aat gct gca gcc ata gcg ctt gac
Thr Asp Gly Arg Asn Ala Ala Ala Ile Ala Leu Asp

ctg atc gct ccg gcc gtc agg gga gga tgc tgt tcc
Leu Ile Ala Pro Ala Val Arg Gly Gly Cys Cys Ser

aat cct gcc tgt tta gtg aat cat cta gaa atg tgt
Asn Pro Ala Cys Leu Val Asn His Leu Glu Met Cys
```

TABLE 118-continued

| DNA Sequence (SEQ ID NO:371) and Protein Sequence (SEQ ID NO:372) of P1.4 |
|---|
| ggt aaa aga cgc tgatgcccca ggaccctctg aaccacgacg t<br>Gly Lys Arg Arg |

TABLE 119

| DNA Sequence (SEQ ID NO:373) and Protein Sequence (SEQ ID NO:374) of P1.5 |
|---|
| tct gat ggc agg gat gcc gca gcc aac gac aaa gcg<br>Ser Asp Gly Arg Asp Ala Ala Ala Asn Asp Lys Ala |
| tct gac ctg atc gct ctg acc gcc agg aga gat cca<br>Ser Asp Leu Ile Ala Leu Thr Ala Arg Arg Asp Pro |
| tgc tgt ttc aat cct gcc tgt aac gtg aat aat cca<br>Cys Cys Phe Asn Pro Ala Cys Asn Val Asn Asn Pro |
| cag att tgt ggt tgaagacgct gatgctccag gaccctctga<br>Gln Ile Cys Gly |
| accacgacgt |

TABLE 120

| DNA Sequence (SEQ ID NO:375) and Protein Sequence (SEQ ID NO:376) of P1.6 |
|---|
| tct gat ggc agg gat gct gag aaa aca ggc ttt gac<br>Ser Asp Gly Arg Asp Ala Glu Lys Thr Gly Phe Asp |
| acg acc att gtg ccg gaa gac tgc tgt tcg gat cct<br>Thr Thr Ile Val Pro Glu Asp Cys Cys Ser Asp Pro |
| tcc tgt tgg agg ctg cat agt tta gct tgt act gga<br>Ser Cys Trp Arg Leu His Ser Leu Ala Cys Thr Gly |
| att gta aac cgc tgatgctcca ggaccctctg aaccacgacg t<br>Ile Val Asn Arg |

TABLE 121

| DNA Sequence (SEQ ID NO:377) and Protein Sequence (SEQ ID NO:378) of P1.8 |
|---|
| act gat ggc agg agt gct gca gcc ata gcg ttt gcc<br>Thr Asp Gly Arg Ser Ala Ala Ala Ile Ala Phe Ala |
| ctg atc gct ccg acc gtc tcc tgt act aat cct gcc<br>Leu Ile Ala Pro Thr Val Cys Cys Thr Asn Pro Ala |
| tgt ctc gtg aat aat ata cgc ttt tgt ggt gga aga<br>Cys Leu Val Asn Asn Ile Arg Phe Cys Gly Gly Arg |
| cgc tgatgcccca ggaccctctg aaccacgacg t<br>Arg |

TABLE 122

| DNA Sequence (SEQ ID NO:379) and Protein Sequence (SEQ ID NO:380) of Rg1.1 |
|---|
| tct gat gga aga aat gcc gca agc gac gcc aaa gcg<br>Ser Asp Gly Arg Asn Ala Ala Ser Asp Ala Lys Ala |
| ttt ccc cgg atc gct cca atc gtc agg gac gaa tgc<br>Phe Pro Arg Ile Ala Pro Ile Val Arg Asp Glu Cys |

TABLE 122-continued

| DNA Sequence (SEQ ID NO:379) and Protein Sequence (SEQ ID NO:380) of Rg1.1 |
|---|
| tgt agc gat cct agg tgt cac ggg aat aat cgg gac<br>Cys Ser Asp Pro Arg Cys His Gly Asn Asn Arg Asp |
| cac tgt gct tgaagacgct gctgctccag gaccctctga<br>His Cys Ala |
| accacgacgt |

TABLE 123

| DNA Sequence (SEQ ID NO:381) and Protein Sequence (SEQ ID NO:382) of Rg1.3 |
|---|
| tct gat ggc agg aat acc gag gcc gac gaa aaa gag<br>Ser Asp Gly Arg Asn Thr Ala Ala Asp Glu Lys Ala |
| tcc gac ctg atc tat caa act gtc aag aga gat tgc<br>Ser Asp Leu Ile Ser Gln Thr Val Lys Arg Asp Cys |
| tgt tcc cat cat cta tgt aga tta ttt gtt cca gga<br>Cys Ser His Pro Leu Cys Arg Leu Phe Val Pro Gly |
| ctt tgt att tgaagacgct gctgctccag gaccctctga<br>Leu Cys Ile |
| Accacgact |

TABLE 124

| DNA Sequence (SEQ ID NO:383) and Protein Sequence (SEQ ID NO:384) of Rg1.4 |
|---|
| tct gat ggc agg aat gcc gca gcc gac aac aaa gag<br>Ser Asp Gly Arg Asn Ala Ala Ala Asp Asn Lys Ala |
| tct gac cta atc gct caa atc gtc agg aga gga tgc<br>Ser Asp Leu Ile Ala Gln Ile Val Arg Arg Gly Cys |
| tgt tcc cat cat gtc tgt aaa gtg agg tat cca gac<br>Cys Ser His Pro Val Cys Lys Val Arg Tyr Pro Asp |
| ctg tgt cgt tgaagacgct gctgctccag gaccctctga<br>Leu Cys Arg |
| Accacgacgt |

TABLE 125

| DNA Sequence (SEQ ID NO:385) and Protein Sequence (SEQ ID NO:386) of Rg1.5 |
|---|
| tct gat ggc agg aat gcc gca gcc gac aac aga gag<br>Ser Asp Gly Arg Asn Ala Ala Ala Asp Asn Arg Ala |
| tct gac cta atc gct caa atc gtc agg aga gga tgc<br>Ser Asp Leu Ile Ala Gln Ile Val Arg Arg Gly Cys |
| tgt tcc cat cat gcc tgt aat gtg aat aat cca cac<br>Cys Ser His Pro Ala Cys Asn Val Asn Asn Pro His |
| att tgt ggt tgaagacgct gctgctccag gaccctctga<br>Ile Cys Gly |
| accacgacgt |

TABLE 126

| DNA Sequence (SEQ ID NO:387) and Protein Sequence (SEQ ID NO:388) of Rg1.8 |
|---|
| tct gat ggc agg aat gcc gca gcc gac aac aaa ccg<br>Ser Asp Gly Arg Asn Ala Ala Ala Asp Asn Lys Pro |
| tct gac cta atc gct caa atc gtc agg aga gga tgc<br>Ser Asp Leu Ile Ala Gln Ile Val Arg Arg Gly Cys |
| tgt tcg cat cct gtc tgt aaa gtg agg tat tca gac<br>Cys Ser His Pro Val Cys Lys Val Arg Tyr Ser Asp |
| atg tgt ggt tgaagacgct gctgctccag gaccctctga<br>Met Cys Gly |
| accacgacgt |

TABLE 127

| DNA Sequence (SEQ ID NO:389) and Protein Sequence (SEQ ID NO:390) of Sm1.4 |
|---|
| tct gat gga agg aat gaa gag aga aga aaa agc gtc<br>Ser Asp Gly Arg Asn Ala Glu Arg Arg Gln Ser Val |
| tgt cat ggt agc tct gga aaa agg gga gga tgt tgt<br>Cys Pro Gly Arg Ser Gly Pro Arg Gly Gly Cys Cys |
| taa aaa aat gaa tgt aag gtg aat ttt aaa aaa agt<br>Ser His Pro Ala Cys Lys Val His Phe Pro His Ser |
| tgt ggt tgaagaagat gatgataaag gaaaatatga<br>Cys Gly |
| aaaaagaagt |

TABLE 128

| DNA Sequence (SEQ ID NO:391) and Protein Sequence (SEQ ID NO:392) of Sm1.5 |
|---|
| tct gat ggc agg aat gcc gca gcc agc gac aga gag<br>Ser Asp Gly Arg Asn Ala Ala Ala Ser Asp Arg Ala |
| tct gac gag gcc cac cag gta tgc tgt tcc aac cat<br>Ser Asp Ala Ala His Gln Val Cys Cys Ser Asn Pro |
| gtc tgt cac gtg gat cat cca gaa ctt tgt cgt aga<br>Val Cys His Val Asp His Pro Glu Leu Cys Arg Arg |
| aga agc tgatgctcca ggaccctctg aaccacgacg t<br>Arg Arg |

TABLE 129

| DNA Sequence (SEQ ID NO:393) and Protein Sequence (SEQ ID NO:394) of S1.5 |
|---|
| tct gat ggc agg aat gcc gag gcc aac gac aaa gag<br>Ser Asp Gly Arg Asn Ala Ala Ala Asn Asp Lys Ala |
| tct gac ctg gtc gct cag gcc atc agg gga tgc tgt<br>Ser Asp Leu Val Ala Pro Ala Ile Arg Gly Cys Cys |
| tcc cac cat gtc tgt aac ttg agt aat cca caa att<br>Ser His Pro Val Cys Asn Leu Ser Asn Pro Gln Ile |
| tgt cgt gga aga agc tgatgctcca ggaccctctg<br>Cys Arg Gly Arg Arg |
| aaccacgacg t |

TABLE 130

| DNA Sequence (SEQ ID NO:395) and Protein Sequence (SEQ ID NO:396) of Tx1.5 |
|---|
| ttt cat ggc agg aat gcc gca gcc aaa gcg tct ggc<br>Phe His Gly Arg Asn Ala Ala Ala Lys Ala Ser Gly |
| ctg gtc ggt ctg acc gac aag agg caa gaa tgc tgt<br>Leu Val Gly Leu Thr Asp Lys Arg Gln Glu Cys Cys |
| tct cat cct gcc tgt aac gta gat cat cca gaa att<br>Ser His Pro Ala Cys Asn Val Asp His Pro Glu Ile |
| tgt cgt tga<br>Cys Arg |

TABLE 131

| DNA Sequence (SEQ ID NO:397) and Protein Sequence (SEQ ID NO:398) of T1.1 |
|---|
| act gat ggc agg agt gct gca gcc ata gcg ttt gcc<br>Thr Asp Gly Arg Ser Ala Ala Ala Ile Ala Phe Ala |
| ctg atc gct ccg acc gtc tgg gaa gga tgc tgt tct<br>Leu Ile Ala Pro Thr Val Trp Glu Gly Cys Cys Ser |
| aat cct gcc tgt ctc gtg aat cat ata cgc ttt tgt<br>Asn Pro Ala Cys Leu Val Asn His Ile Arg Phe Cys |
| ggt gga aga cgc tgatgcccca ggaccctctg aaccacgacg t<br>Gly Gly Arg Arg |

TABLE 132

| DNA Sequence (SEQ ID NO:399) and Protein Sequence (SEQ ID NO:400) of Vr1.3 |
|---|
| tct aat ggc atg aat gcc gca gcc atc agg aaa gcg<br>Ser Asn Gly Met Asn Ala Ala Ala Ile Arg Lys Ala |
| tct gcc ctg gtg gct cag atc gcc cat cga gac tgc<br>Ser Ala Leu Val Ala Gln Ile Ala His Arg Asp Cys |
| tgt gac gat cct gcc tgc acc gtg aat aat cca ggc<br>Cys Asp Asp Pro Ala Cys Thr Val Asn Asn Pro Gly |
| ctt tgc act tgaagatgct gctgccccag gaccctctga<br>Leu Cys Thr |
| accacgacgt |

TABLE 133

| DNA Sequence (SEQ ID NO:401) and Protein Sequence (SEQ ID NO:402) of G1.2 |
|---|
| tct gat ggc ggg aat gcc gca gca aaa gag tct gac<br>Ser Asp Gly Gly Asn Ala Ala Ala Lys Glu Ser Asp |
| gtg atc gct ctg acc gtc tgg aaa tgc tgt acc att<br>Val Ile Ala Leu Thr Val Trp Lys Cys Cys Thr Ile |
| cct tcc tgt tat gag aaa aaa aaa att aaa gca tgt<br>Pro Ser Cys Tyr Glu Lys Lys Lys Ile Lys Ala Cys |
| gtc ttt tgacgacgct gatgctccag gaccctctga<br>Val Phe |
| accacgacgt |

TABLE 134

| DNA Sequence (SEQ ID NO:403) and Protein Sequence (SEQ ID NO:404) of Rg1.12 |
|---|
| tct gat ggc gca gtc gac gac aaa gag ttg gat cga<br>Ser Asp Gly Ala Val Asp Asp Lys Ala Leu Asp Arg |
| atc gct gaa atc gtc agg aga gga tgc tgt ggc aat<br>Ile Ala Glu Ile Val Arg Arg Gly Cys Cys Gly Asn |
| cat gcc tgt agc ggc tcc tag aaa gat gca ccc tat<br>Pro Ala Cys Ser Gly Ser Ser Lys Asp Ala Pro Ser |
| tgt ggt tgaagacgct gctgctccag gaccctctga<br>Cys Gly |
| accacgacgt |

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

BIBLIOGRAPHY

Barnay, G. et al. (2000). *J. Med. Chem.*
Bitan, G. et al. (1997). *J. Peptide Res.* 49:421-426.
Blount, K. et al. (1992). *Toxicon* 30:835-842.
Bodansky et al. (1966). *Chem. Ind.* 38: 1597-98.
Cartier, G. E. et al. (1996). *J. Biol. Chem.* 271:7522-7528.
Cruz, L. J. at al. (1976). *Verliger* 18:302-308.
Cruz, L. J. et al. (1987). *J. Biol. Chem.* 260:9280-9288.
Fainzilber, M. et al. (1994). *Biochemistry* 33:9523-9529.
Gray, W. R. et al. (1981). *J. Biol. Chem.* 256:4734-4740.
Haack, J. A. et al. (1990). *J. Biol. Chem.* 265:6025-6029.
Horiki, K. et al. (1978). *Chemistry Letters* 165-68.
Hubry, V. et al. (1994). *Reactive Polymers* 22:231-241.
Jacobsen, R. et al. (1997). *J. Biol. Chem.* 272:22531-22537.
Johnson, D. S. et al. (1995). *Mol. Pharmacol.* 48:194-199.
Kapoor (1970). *J. Pharm. Sci.* 59:1-27.
Kornreich, W. D. et al. (1986). U.S. Pat. No. 4,569,967.
Luo, S. et al. (1998). *J. Neurosci.* 18:8571-8679.
Marshall, I. G. and Harvey, A. L. (1990). *Toxicon* 28:231-234.
Martinez, J. S. et al. (1995). *Biochem.* 34:14519-14526.
McIntosh, J. M. et al. (1982). *Arch. Biochem. Biophys.* 218: 329-334.
Mena, E. E. et al. (1990). *Neurosci. Lett.* 118:241-244.
*Methoden der Organischen Chemie* (*Houben-Weyl*): *Synthese von Peptiden*, E. Wunsch (Ed.), Georg Thieme Verlag, Stuttgart, Ger. (1974).
Myers, R. A. et al. (1991). *Biochemistry* 30:9370-9377.
Nishiuchi, Y. et al. (1993). *Int. J. Pept. Protein Res.* 42:533-538.
Nowak, L. et al. (1984). *Nature* 307:462-465.
Olivera, B. M. et al. (1984). U.S. Pat. No. 4,447,356.
Olivera, B. M. et al. (1985). *Science* 230:1338-1343.
Olivera, B. M. et al. (1996). U.S. Pat. No. 5,514,774.
Rivier, J. R. et al. (1978). *Biopolymers* 17:1927-38.
Rivier, J. R. et al. (1987). *Biochem.* 26:8508-8512.
Sambrook, J. et al. (1989). *Molecular Cloning: A Laboratory Manual,* 2nd Ed., Cold Spring Harbor Laboratory, Cold Spring Harbor, N.Y.
Schroder & Lubke (1965). *The Peptides* 1:72-75, Academic Press, NY.
Shon, K.-J. et al. (1994). *Biochemistry* 33:11420-11425.
Stewart and Young, *Solid-Phase Peptide Synthesis*, Freeman & Co., San Francisco, Calif. (1969).
Vale et al. (1978). U.S. Pat. No. 4,105,603.
Van de Steen, P. et al. (1998). *Critical Rev. in Biochem. and Mol. Biol.* 33:151-208.
Zafaralla, G. C. et al. (1988). *Biochemistry* 27:7102-7105.
Zhou L. M., et al. (1996). *J. Neurochem.* 66:620-628.
U.S. Pat. No. 3,972,859.
U.S. Pat. No. 3,842,067.
U.S. Pat. No. 3,862,925.
U.S. Pat. No. 5,550,050.
PCT Published Application WO 92/19195.
PCT Published Application WO 94/25503.
PCT Published Application WO 95/01203.
PCT Published Application WO 95/05452.
PCT Published Application WO 96/02286.
PCT Published Application WO 96/02646.
PCT Published Application WO 96/11698.
PCT Published Application WO 96/40871.
PCT Published Application WO 96/40959.
PCT Published Application WO 97/12635.

What is claimed is:

1. An isolated α-conotoxin polypeptide comprising the amino acid sequence of: Asp-Xaa1-Cys-Cys-Ser-Asn-Xaa5-Ala-Cys-Arg-Val-Asn-Asn-Xaa5-His-Val-Cys-Arg-Arg-Arg (SEQ ID NO:178); wherein Xaa1 is Glu or γ-carboxy-Glu; wherein Xaa5 is Pro or hydroxy-Pro; wherein the C-terminus contains a hydroxyl group or an amide group; wherein the His residue may be substituted with a halo-His residue; wherein an Arg residue may be substituted with homoarginine; and wherein the Cys residues may be in the D or L configuration or substituted with homocysteine in the D or L configuration.

2. The isolated α-conotoxin polypeptide of claim 1, wherein Xaa1 is Glu.

3. The isolated α-conotoxin peptide of claim 1, which is modified to contain an O-glycan, an S-glycan or an N-glycan.

4. An isolated α-conotoxin protein precursor comprising the amino acid sequence of SEQ ID NO:300.

5. The isolated α-conotoxin peptide of claim 1, wherein the halo-His is iodo-His.

* * * * *

SEQUENCE LISTING

```
<160> NUMBER OF SEQ ID NOS: 404

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence:
      Alpha-Conotoxin Peptide Generic Formula I
<220> FEATURE:
<221> NAME/KEY: SITE
<222> LOCATION: (1)..(3)
<223> OTHER INFORMATION: Xaa at residue 1 is des-Xaa, Ile, Leu or Val;
      Xaa at residue 2 is des-Xaa, Ala or Gly; Xaa at
      residue 3 is des-Xaa, Gly, Trp (D or L), neo-Trp,
      halo-Trp or any unnatural aromatic amino acid.
<220> FEATURE:
<221> NAME/KEY: SITE
<222> LOCATION: (4)..(5)
<223> OTHER INFORMATION: N-methyl-Lys, Xaa at residue 4 is des-Xaa, Gly,
```

-continued

```
      Trp (D or L), neo-Trp, halo-Trp or any unnatural
      aromatic amino acid; Xaa at residue 5 is Glu,
      gamma-carboxy-Glu (Gla), Asp, Ala, Thr, Ser, Gly,
<220> FEATURE:
<221> NAME/KEY: SITE
<222> LOCATION: (5)..(8)
<223> OTHER INFORMATION: Ile, Tyr, nor-Tyr, mono-halo-Tyr, di-halo-Tyr,
      O-sulpho-Tyr, O-phospho-Tyr, nitro-Tyr or any
      unnatural hydroxy containing amino acid; Xaa at
      residue 8 is Ser, Thr, Arg, ornithine,
<220> FEATURE:
<221> NAME/KEY: SITE
<222> LOCATION: (8)..(9)
<223> OTHER INFORMATION: homoarginine, Lys, N,N-dimethyl-Lys, N,N,N-
      trimethyl-Lys or any unnatural basic amino acid;
      Xaa at residue 9 is Asp, Glu, Gla, Arg, ornithine,
      homoarginine, Lys, N-methyl-Lys,N,N-dimethyl-
<220> FEATURE:
<221> NAME/KEY: SITE
<222> LOCATION: (9)..(10)
<223> OTHER INFORMATION: Lys, N,N,N-trimethyl-Lys or any unnatural basic
      amino acid; Xaa at residue 10 is Ser, Thr, Asn,
      Ala, Gly, Arg, Lys, ornithine, homoarginine,
      N-methyl-Lys, N,N-dimethyl-Lys, N,N,N-trimethyl-
<220> FEATURE:
<221> NAME/KEY: SITE
<222> LOCATION: (10)..(11)
<223> OTHER INFORMATION: Lys, any unnatural basic amino acid, His, halo-
      His, Pro or hydroxy-Pro; Xaa at residue 11 is
      Thr, Ser, Ala, Asp, Asn, Pro, hydroxy-Pro, Arg,
      ornithine, homoarginine, Lys, N-methyl-Lys,
<220> FEATURE:
<221> NAME/KEY: SITE
<222> LOCATION: (11)..(13)
<223> OTHER INFORMATION: N,N-dimethyl-Lys, N,N,N-trimethyl-Lys or any
      unnatural basic amino acid; Xaa at residue 13 is
      Gly, Ser, Thr, Ala, Asn, Arg, ornithine,
      homoarginine, Lys, N-methyl-Lys,
<220> FEATURE:
<221> NAME/KEY: SITE
<222> LOCATION: (13)..(14)
<223> OTHER INFORMATION: N,N-dimethyl-Lys, N,N,N-trimethyl-Lys or any
      unnatural basic amino acid; Xaa at residue 14 is
      Gln, Leu, His, halo-His, Trp (D or L), halo-Trp,
      neo-Trp, Tyr, nor-Tyr, mono-halo-Tyr, di-halo-
<220> FEATURE:
<221> NAME/KEY: SITE
<222> LOCATION: (14)
<223> OTHER INFORMATION: Tyr, O-sulpho-Tyr, O-phospho-Tyr, nitro-Tyr,
      Arg, ornithine, homoarginine, Lys, N-methyl-Lys, N,N-
      dimethyl-Lys, N,N,N-trimethyl-Lys, any unnatural
      basic amino acid or any unnatural aromatic amino
<220> FEATURE:
<221> NAME/KEY: SITE
<222> LOCATION: (14)..(15)
<223> OTHER INFORMATION: acid; Xaa at residue 15 is Asn, His, halo-His,
      Ile, Leu, Val, Gln, Arg, ornithine, homoarginine,
      Lys, N-methyl-Lys, N,N-dimethyl-Lys, N,N,N-
      trimethyl-Lys or any unnatural basic amino acid;
<220> FEATURE:
<221> NAME/KEY: SITE
<222> LOCATION: (17)
<223> OTHER INFORMATION: Xaa at residue 17 is des-Xaa, Val, Ile, Leu,
      Arg, ornithine, homoarginine, Lys, N-methyl-Lys, N,N-
      dimethyl-Lys, N,N,N-trimethyl-Lys or any
      unnatural basic amino acid.

<400> SEQUENCE: 1

Xaa Xaa Xaa Xaa Xaa Cys Cys Xaa Xaa Xaa Xaa Cys Xaa Xaa Xaa Cys
  1               5                  10                  15

Xaa


<210> SEQ ID NO 2
<211> LENGTH: 21
<212> TYPE: PRT
<213> ORGANISM: Artificial Sequence
```

-continued

```
<220> FEATURE:
<223> OTHER INFORMATION: Description of Artificial Sequence:
      Alpha-Conotoxin Peptide Generic Formula II.
<220> FEATURE:
<221> NAME/KEY: SITE
<222> LOCATION: (1)..(3)
<223> OTHER INFORMATION: Xaa at residue 1 is des-Xaa, Asp, Glu or gamma-
      carboxy-Glu (Gla); Xaa at residue 2 is des-Xaa,
      Gln, Ala, Asp, Glu, Gla; Xaa at residue 3 is des-
      Xaa, Gly, Ala, Asp, Glu, Gla, Pro or hydroxy-Pro.
<220> FEATURE:
<221> NAME/KEY: SITE
<222> LOCATION: (4)..(7)
<223> OTHER INFORMATION: Xaa at residue 4 is des-Xaa, Gly, Glu, Gla,
      Gln, Asp, Asn, Pro or hydroxy-Pro; Xaa at residue 7 is
      Ser, Thr, Gly, Glu, Gla, Asn, Trp (D or L),
      neo-Trp, halo-Trp, Arg, ornithine, homoarginine,
<220> FEATURE:
<221> NAME/KEY: SITE
<222> LOCATION: (7)
<223> OTHER INFORMATION: Lys, N-methyl-Lys, N,N-dimethyl-Lys, N,N,N-
      trimethyl-Lys, any unnatural basic amino acid,
      Tyr, nor-Tyr, mono-halo-Tyr, di-halo-Tyr,
      O-sulpho-Tyr, O-phospho-Tyr, nitro-Tyr or any
<220> FEATURE:
<221> NAME/KEY: SITE
<222> LOCATION: (7)..(8)
<223> OTHER INFORMATION: unnatural hydroxy containing amino acid; Xaa at
      residue 8 is Asp, Asn, His, halo-His, Thr, Ser,
      Tyr, nor-Tyr, mono-halo-Tyr, di-halo-Tyr,
      O-sulpho-Tyr, O-phospho-Tyr, nitro-Tyr or any
<220> FEATURE:
<221> NAME/KEY: SITE
<222> LOCATION: (8)..(10)
<223> OTHER INFORMATION: unnatural hydroxy containing amino acid; Xaa at
      residue 9 is Pro or hydroxy-Pro; Xaa at residue
      10 is Ala, Ser, Thr, Asp, Val, Ile, Pro, hydroxyl-
      Pro, Tyr, nor-Tyr, mono-halo-Tyr, di-halo-Tyr,
<220> FEATURE:
<221> NAME/KEY: SITE
<222> LOCATION: (10)..(12)
<223> OTHER INFORMATION: O-sulpho-Tyr, O-phospho-Tyr, nitro-Tyr or any
      unnatural hydroxy containing amino acid; Xaa at
      residue 12 is Gly, Ile, Leu, Val, Ala, Thr, Ser,
      Pro, hydroxy-Pro, Phe, Trp (D or L), neo-Trp,
<220> FEATURE:
<221> NAME/KEY: SITE
<222> LOCATION: (12)..(13)
<223> OTHER INFORMATION: halo-Trp, Arg, ornithine, homoarginine, Lys, N-
      methyl-Lys, N,N-dimethyl-Lys, N,N,N-trimethyl-
      Lys, any unnatural basic amino acid or any
      unnatural aromatic amino acid; Xaa at residue 13
<220> FEATURE:
<221> NAME/KEY: SITE
<222> LOCATION: (13)
<223> OTHER INFORMATION: is Ala, Asn, Phe, Pro, hydroxy-Pro, Glu, Gla,
      Gln, His, halo-His, Val, Ser, Thr, Arg,
      ornithine, homoarginine, Lys, N-methyl-Lys, N,N-
      dimethyl-Lys, N,N,N-trimethyl-Lys or any
<220> FEATURE:
<221> NAME/KEY: SITE
<222> LOCATION: (13)..(14)
<223> OTHER INFORMATION: unnatural basic amino acid; Xaa at residue 14
      is Thr, Ser, His, halo-His, Leu, Ile, Val, Asn, Met,
      Pro, hydroxy-Pro, Arg, ornithine, homoarginine,
      Lys, N-methyl-Lys, N,N-dimethyl-Lys, N,N,N-
<220> FEATURE:
<221> NAME/KEY: SITE
<222> LOCATION: (14)..(15)
<223> OTHER INFORMATION: trimethyl-Lys, any unnatural basic amino acid,
      Tyr, nor-Tyr, mono-halo-Tyr, di-halo-Tyr,
      O-sulpho-Tyr, O-phospho-Tyr, nitro-Tyr or any
      unnatural hydroxy containing amino acid; Xaa at
<220> FEATURE:
<221> NAME/KEY: SITE
<222> LOCATION: (15)
<223> OTHER INFORMATION: residue 15 is Asn, Pro, hydroxy-Pro, Gln, Ser,
      Thr, Arg, ornithine, homoarginine, Lys, N-methyl-
      Lys, N,N-dimethyl-Lys N,N,N-trimethyl-Lys, any
```

-continued

```
      unnatural basic amino acid, Tyr, nor-Tyr, mono-
<220> FEATURE:
<221> NAME/KEY: SITE
<222> LOCATION: (15)..(16)
<223> OTHER INFORMATION: halo-Tyr, di-halo-Tyr, O-sulpho-Tyr, O-phospho-
      Tyr, nitro-Tyr or any unnatural hydroxy contain-
      ing amino acid; Xaa at residue 16 is des-Xaa,
      Gly, Thr, Ser, Pro, hydroxy-Pro, Tyr, nor-Tyr,
<220> FEATURE:
<221> NAME/KEY: SITE
<222> LOCATION: (16)..(17)
<223> OTHER INFORMATION: mono-halo-Tyr, di-halo-Tyr, O-sulpho-Tyr,
      O-phospho-Tyr, nitro-Tyr or any unnatural hydroxy
      containing amino acid; Xaa at residue 17 is des-
      Xaa, Ile, Val, Asp, Leu, Phe, Arg, ornithine,
<220> FEATURE:
<221> NAME/KEY: SITE
<222> LOCATION: (17)
<223> OTHER INFORMATION: homoarginine, Lys, N-methyl-Lys, N,N-dimethyl-
      Lys, N,N,N-trimethyl-Lys, any unnatural basic
      amino acid, Tyr, nor-Tyr, mono-halo-Tyr, di-halo-
      Tyr, O-sulpho-Tyr, O-phospho-Tyr, nitro-Tyr or
<220> FEATURE:
<221> NAME/KEY: SITE
<222> LOCATION: (17)..(19)
<223> OTHER INFORMATION: any unnatural hydroxy containing amino acid;
      Xaa at residue 19 is des-Xaa, Gly, Ala, Met, Ser,
      Thr, Trp (D or L), neo-Trp, halo-Trp, any
      unnatural aromatic amino acid, Arg, ornithine,
<220> FEATURE:
<221> NAME/KEY: SITE
<222> LOCATION: (19)..(20)
<223> OTHER INFORMATION: homoarginine, Lys, N-methyl-Lys, N,N-dimethyl-
      Lys, N,N,N-trimethyl-Lys or any unnatural basic
      amino acid; Xaa at residue 20 is des-Xaa, Trp
      (D or L), neo-Trp, halo-Trp, any unnatural
<220> FEATURE:
<221> NAME/KEY: SITE
<222> LOCATION: (20)..(21)
<223> OTHER INFORMATION: aromatic amino acid, Arg, ornithine, homo-
      arginine, Lys, N-methyl-Lys, N,N-dimethyl-Lys,
      N,N,N-trimethyl-Lys or any unnatural basic amino
      acid; Xaa at residue 21 is des-Xaa, Arg,
<220> FEATURE:
<221> NAME/KEY: SITE
<222> LOCATION: (21)
<223> OTHER INFORMATION: ornithine, homoarginine, Lys, N-methyl-Lys,
      N,N-dimethyl-Lys, N,N,N-trimethyl-Lys or any
      unnatural basic amino acid.

<400> SEQUENCE: 2

Xaa Xaa Xaa Xaa Cys Cys Xaa Xaa Xaa Xaa Cys Xaa Xaa Xaa Xaa Xaa
  1               5                  10                  15

Xaa Cys Xaa Xaa Xaa
             20


<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence:
      Alpha-Conotoxin Peptide Generic Formula III.
<220> FEATURE:
<221> NAME/KEY: SITE
<222> LOCATION: (1)..(3)
<223> OTHER INFORMATION: Xaa at residue 1 is des-Xaa, Ser or Thr; Xaa at
      residue 2 is des-Xaa, Asp, Glu, gamma-carboxy-Glu
      (Gla), Asn, Ser or Thr; Xaa at residue 3 is des-
      Xaa, Ala, Gly, Asn, Ser, Thr, Pro, hydroxy-Pro,
<220> FEATURE:
<221> NAME/KEY: SITE
<222> LOCATION: (3)..(4)
<223> OTHER INFORMATION: Arg, ornithine, homoarginine, Lys,
      N-methyl-Lys, N,N-dimethyl-Lys, N,N,N-trimethyl-Lys or any
      unnatural basic amino acid; Xaa at residue 4 is
```

-continued

```
      des-Xaa, Ala, Val, Leu, Ile, Gly, Glu, Gla, Gln,
<220> FEATURE:
<221> NAME/KEY: SITE
<222> LOCATION: (4)..(5)
<223> OTHER INFORMATION: Asp, Asn, Phe, Pro, hydroxy-Pro or any
      unnatural aromatic amino acid; Xaa at residue 5 is des-Xaa,
      Thr, Ser, Asp, Glu, Gla, Gln, Gly, Val, Asp, Asn,
      Ala, Pro, hydroxy-Pro, Arg, ornithine, homo-
<220> FEATURE:
<221> NAME/KEY: SITE
<222> LOCATION: (5)..(8)
<223> OTHER INFORMATION: arginine, Lys, N-methyl-Lys, N,N-dimethyl-Lys,
      N,N,N-trimethyl-Lys or any unnatural basic amino
      acid; Xaa at residue 8 is Thr, Ser, Asp, Asn, Met,
      Val, Ala, Gly, Leu, Ile, Phe, any unnatural
<220> FEATURE:
<221> NAME/KEY: SITE
<222> LOCATION: (8)..(9)
<223> OTHER INFORMATION: aromatic amino acid, Pro, hydroxy-Pro, Tyr,
      nor-Tyr, mono-halo-Tyr, di-halo-Tyr, O-sulpho-Tyr,
      O-phospho-Tyr, nitro-Tyr or any unnatural hydroxy
      containing amino acid; Xaa at residue 9 is  Ile,
<220> FEATURE:
<221> NAME/KEY: SITE
<222> LOCATION: (9)
<223> OTHER INFORMATION: Leu, Val, Ser, Thr, Gln, Asn, Asp, Arg, His,
      halo-His, Phe,  any unnatural aromatic amino
      acid, homoarginine, ornithine, Lys, N-methyl-Lys,
      N,N-dimethyl-Lys, N,N,N-trimethyl-Lys, any
<220> FEATURE:
<221> NAME/KEY: SITE
<222> LOCATION: (9)..(10)
<223> OTHER INFORMATION: unnatural basic amino acid, Tyr, nor-Tyr, mono-
      halo-Tyr, di-halo-Tyr, O-sulpho-Tyr, O-phospho-
      Tyr, nitro-Tyr or any unnatural hydroxy contain-
      ing amino acid; Xaa at residue 10 is Pro, hyroxy-
<220> FEATURE:
<221> NAME/KEY: SITE
<222> LOCATION: (10)
<223> OTHER INFORMATION: Pro, Ser, Thr, Ile, Asp, Leu, Val, Gly, Ala,
      Phe, any unnatural aromatic amino acid, Arg, ornithine,
      homoarginine, Lys, N-methyl-Lys, N,N-dimethyl-Lys,
      N,N,N-trimethyl-Lys or any unnatural basic amino
<220> FEATURE:
<221> NAME/KEY: SITE
<222> LOCATION: (11)
<223> OTHER INFORMATION: acid; Xaa at residue 11 is Val, Ala, Gly, Ile,
      Leu, Asp, Ser, Thr, Pro, hydroxy-Pro, Arg,
      ornithine, homoarginine, Lys, N-methyl-Lys,
      N,N-dimethyl-Lys, N,N,N-trimethyl-Lys or any
<220> FEATURE:
<221> NAME/KEY: SITE
<222> LOCATION: (11)..(13)
<223> OTHER INFORMATION: unnatural basic amino acid; Xaa at residue 13
      is His, halo-His, Arg, homoarginine, ornithine, Lys,
      N-methyl-Lys, N,N-dimethyl-Lys, N,N,N-trimethyl-
      Lys, any unnatural basic amino acid, Asn, Ala,
<220> FEATURE:
<221> NAME/KEY: SITE
<222> LOCATION: (13)
<223> OTHER INFORMATION: Ser, Thr, Phe, Ile, Leu, Gly, Trp (D or L),
      neo-Trp, halo-Trp, any unnatural aromatic amino acid,
      Tyr, nor-Tyr, mono-halo-Tyr, di-halo-Tyr,
      O-sulpho-Tyr, O-phospho-Tyr, nitro-Tyr or any
<220> FEATURE:
<221> NAME/KEY: SITE
<222> LOCATION: (13)..(14)
<223> OTHER INFORMATION: unnatural hydroxy containing amino acid; Xaa at
      residue 14 is Leu, Gln, Val, Ile, Gly, Met, Ala,
      Lys, N-methyl-Lys, N,N-dimethyl-Lys, N,N,N-tri-
      Methyl-Lys, Ser, Thr, Arg, homoarginine, orni-
<220> FEATURE:
<221> NAME/KEY: SITE
<222> LOCATION: (14)..(15)
<223> OTHER INFORMATION: thine, any unnatural basic amino acid, Asn,
      Glu, Gla, Gln, Phe, Trp (D or L), neo-Trp, halo-Trp or
      any unnatural aromatic amino acid; Xaa at residue
      15 is Glu, Gla, Gln, Asn, Asp, Pro, hydroxy-Pro,
<220> FEATURE:
```

-continued

```
<221> NAME/KEY: SITE
<222> LOCATION: (15)
<223> OTHER INFORMATION: Ser, Gly, Thr, Lys, N-methyl-Lys, N,N-dimethyl-
      Lys, N,N,N-trimethyl-Lys, Arg, homoarginine,
      ornithine, any unnatural basic amino acid, Phe,
      His, halo-His, any unnatural aromatic acid, Leu,
<220> FEATURE:
<221> NAME/KEY: SITE
<222> LOCATION: (15)..(16)
<223> OTHER INFORMATION: Met, Gly, Ala, Tyr, nor-Tyr, mono-halo-Tyr, di-
      halo-Tyr, O-sulpho-Tyr, O-phospho-Tyr, nitro-Tyr
      or any unnatural hydroxy containing amino acid;
      Xaa at residue 16 is His, halo-His, Asn, Thr,
<220> FEATURE:
<221> NAME/KEY: SITE
<222> LOCATION: (16)
<223> OTHER INFORMATION: Ser, Ile, Val, Leu, Phe, any unnatural aromatic
      amino acid, Arg, homoarginine, ornithine, Lys, N-
      methyl-Lys, N,N-dimethyl-Lys, N,N,N-trimethyl-Lys,
      any unnatural basic amino acid, Tyr, nor-Tyr,
<220> FEATURE:
<221> NAME/KEY: SITE
<222> LOCATION: (16)..(17)
<223> OTHER INFORMATION: mono-halo-Tyr, di-halo-Tyr, O-sulpho-Tyr,
      O-phospho-Tyr, nitro-Tyr or any unnatural hydroxy
      containing amino acid; Xaa at residue 17 is Ser,
      Thr, Ala, Gln, Pro, hydroxy-Pro, Gly, Ile, Leu,
<220> FEATURE:
<221> NAME/KEY: SITE
<222> LOCATION: (17)..(18)
<223> OTHER INFORMATION: Arg, ornithine, homoarginine, Lys,
      N-methyl-Lys, N,N-dimethyl-Lys, N,N,N-trimethyl-Lys or any
      unnatural basic amino acid; Xaa at residue 18 is
      Asn, Glu, Gla, Asp, Gly, His, halo-His, Ala, Leu,
<220> FEATURE:
<221> NAME/KEY: SITE
<222> LOCATION: (18)
<223> OTHER INFORMATION: Gln, Arg,  ornithine, homoarginine, Lys,
      N-methyl-Lys, N,N-dimethyl-Lys, N,N,N-trimethyl-Lys, any
      unnatural basic amino acid, Tyr, nor-Tyr, mono-
      halo-Tyr, di-halo-Tyr, O-sulpho-Tyr, O-phospho-
<220> FEATURE:
<221> NAME/KEY: SITE
<222> LOCATION: (18)..(19)
<223> OTHER INFORMATION: Tyr, nitro-Tyr or any unnatural hydroxy
      containing amino acid; Xaa at residue 19 is Met, Ile, Thr,
      Ser, Val, Leu, Pro, hydroxy-Pro, Phe, any
      unnatural aromatic amino acid, Tyr, nor-Tyr, mono-
<220> FEATURE:
<221> NAME/KEY: SITE
<222> LOCATION: (19)
<223> OTHER INFORMATION: halo-Tyr, di-halo-Tyr, O-sulpho-Tyr, O-phospho-
      Tyr, nitro-Tyr, any unnatural hydroxy containing
      amino acid, Glu, Gla, Ala, His, halo-His, Arg,
      ornithine, homoarginine, Lys, N-methyl-Lys, N,N-
<220> FEATURE:
<221> NAME/KEY: SITE
<222> LOCATION: (21)
<223> OTHER INFORMATION: dimethyl-Lys, N,N,N-trimethyl-Lys or any
      unnatural basic amino acid; Xaa at residue 21 is des-Xaa,
      Gly, Asp, Asn, Ala, Ile, Leu, Ser, Thr, His, halo-
      His, Arg, ornithine, homoarginine, Lys, N-methyl-
<220> FEATURE:
<221> NAME/KEY: SITE
<222> LOCATION: (21)..(22)
<223> OTHER INFORMATION: Lys, N,N-dimethyl-Lys, N,N,N-trimethyl-Lys or
      any unnatural basic amino acid; Xaa at residue 22 is
      des-Xaa, Gly, Glu, Gla, Gln, Trp (D or L), neo-Trp,
      halo-Trp, any unnatural aromatic amino acid, Arg,
<220> FEATURE:
<221> NAME/KEY: SITE
<222> LOCATION: (22)..(23)
<223> OTHER INFORMATION: ornithine, homoarginine, Lys, N-methyl-Lys,
      N,N-dimethyl-Lys, N,N,N-trimethyl-Lys or any unnatural
      basic amino acid; Xaa at residue 23 is des-Xaa,
      Ser, Thr, Val, Ile, Ala, Arg, ornithine, homo-
<220> FEATURE:
<221> NAME/KEY: SITE
<222> LOCATION: (23)..(24)
```

-continued

```
<223> OTHER INFORMATION: arginine, Lys, N-methyl-Lys, N,N-dimethyl-Lys,
      N,N,N-trimethyl-Lys or any unnatural basic amino
      acid; Xaa at residue 24 is des-Xaa, Val, Asp, His,
      halo-His, Arg, ornithine, homoarginine, Lys, N-
<220> FEATURE:
<221> NAME/KEY: SITE
<222> LOCATION: (24)..(26)
<223> OTHER INFORMATION: methyl-Lys, N,N-dimethyl-Lys,
      N,N,N-trimethyl-Lys or any unnatural basic amino acid; Xaa at
      residue 25 is des-Xaa, Asn, Pro or hydroxy-Pro; Xaa at
      residue 26 is des-Xaa, Arg, ornithine, homo-
<220> FEATURE:
<221> NAME/KEY: SITE
<222> LOCATION: (26)..(28)
<223> OTHER INFORMATION: arginine, Lys, N-methyl-Lys, N,N-dimethyl-Lys,
      N,N,N-trimethyl-Lys or any unnatural basic amino
      acid; Xaa at residue 27 is des-Xaa, Ser or Thr;
      Xaa at residue 28 is des-Xaa, Leu, Ile or Val.

<400> SEQUENCE: 3

Xaa Xaa Xaa Xaa Xaa Cys Cys Xaa Xaa Xaa Xaa Cys Xaa Xaa Xaa Xaa
  1               5                  10                  15

Xaa Xaa Xaa Cys Xaa Xaa Xaa Xaa Xaa Xaa Xaa Xaa
             20                  25


<210> SEQ ID NO 4
<211> LENGTH: 14
<212> TYPE: PRT
<213> ORGANISM: Conus imperialis
<220> FEATURE:
<221> NAME/KEY: SITE
<222> LOCATION: (2)..(11)
<223> OTHER INFORMATION: Xaa at residue 2 is Glu or gamma-carboxy-Glu;
      Xaa at residue 11 is Lys, N-methyl-Lys,
      N,N-dimethyl-Lys or N,N,N-trimethyl-Lys.

<400> SEQUENCE: 4

Asp Xaa Cys Cys Ser Asp Ser Arg Cys Gly Xaa Asn Cys Leu
  1               5                  10


<210> SEQ ID NO 5
<211> LENGTH: 12
<212> TYPE: PRT
<213> ORGANISM: Conus imperialis
<220> FEATURE:
<221> NAME/KEY: SITE
<222> LOCATION: (10)
<223> OTHER INFORMATION: Xaa at residue 10 is Trp (D or L) or halo-Trp.

<400> SEQUENCE: 5

Ala Cys Cys Ser Asp Arg Arg Cys Arg Xaa Arg Cys
  1               5                  10


<210> SEQ ID NO 6
<211> LENGTH: 13
<212> TYPE: PRT
<213> ORGANISM: Conus regius

<400> SEQUENCE: 6

Phe Thr Cys Cys Arg Arg Gly Thr Cys Ser Gln His Cys
  1               5                  10


<210> SEQ ID NO 7
<211> LENGTH: 13
<212> TYPE: PRT
<213> ORGANISM: Conus regius
<220> FEATURE:
<221> NAME/KEY: SITE
<222> LOCATION: (2)
<223> OTHER INFORMATION: Xaa at residue 2 is Tyr, nor-Tyr,
```

-continued mono-halo-Tyr, di-halo-Tyr, O-sulpho-Tyr, O-phospho-Tyr or
nitro-Tyr.

<400> SEQUENCE: 7

Asp Xaa Cys Cys Arg Arg His Ala Cys Thr Leu Ile Cys
1 5 10

<210> SEQ ID NO 8
<211> LENGTH: 13
<212> TYPE: PRT
<213> ORGANISM: Conus regius
<220> FEATURE:
<221> NAME/KEY: SITE
<222> LOCATION: (2)..(8)
<223> OTHER INFORMATION: Xaa at residue 2 is Tyr, nor-Tyr,
mono-halo-Tyr, di-halo-Tyr, O-sulpho-Tyr, O-phospho-Tyr or
nitro-Tyr; Xaa at residues 7 and 8 is Pro or
hydroxy-Pro.

<400> SEQUENCE: 8

Asp Xaa Cys Cys Arg Arg Xaa Xaa Cys Thr Leu Ile Cys
1 5 10

<210> SEQ ID NO 9
<211> LENGTH: 13
<212> TYPE: PRT
<213> ORGANISM: Conus regius
<220> FEATURE:
<221> NAME/KEY: SITE
<222> LOCATION: (6)..(10)
<223> OTHER INFORMATION: Xaa at residue 6 is Pro or hydroxy-Pro; Xaa at
residue 10 is Tyr, nor-Tyr, mono-halo-Tyr,
di-halo-Tyr, O-sulpho-Tyr, O-phospho-Tyr or
nitro-Tyr.

<400> SEQUENCE: 9

Gly Cys Cys Ser Asp Xaa Arg Cys Arg Xaa Arg Cys Arg
1 5 10

<210> SEQ ID NO 10
<211> LENGTH: 13
<212> TYPE: PRT
<213> ORGANISM: Conus regius
<220> FEATURE:
<221> NAME/KEY: SITE
<222> LOCATION: (7)..(11)
<223> OTHER INFORMATION: Xaa at residue 7 is Pro or hydroxy-Pro; Xaa at
residue 11 is Trp (D or L) or halo-Trp.

<400> SEQUENCE: 10

Gly Gly Cys Cys Ser Asp Xaa Arg Cys Ala Xaa Arg Cys
1 5 10

<210> SEQ ID NO 11
<211> LENGTH: 17
<212> TYPE: PRT
<213> ORGANISM: Conus regius
<220> FEATURE:
<221> NAME/KEY: SITE
<222> LOCATION: (3)..(10)
<223> OTHER INFORMATION: Xaa at residue 3 is Trp (D or L) or halo-Trp;
Xaa at residue 9 is Glu or gamma-carboxy-Glu; Xaa at
residue 10 is Pro or hydroxy-Pro.
<220> FEATURE:
<221> NAME/KEY: SITE
<222> LOCATION: (15)
<223> OTHER INFORMATION: Xaa at residue 15 is Lys, N-methyl-Lys,
N,N-dimethyl-Lys or N,N,N-trimethyl-Lys.

<400> SEQUENCE: 11

-continued

```
Ile Ala Xaa Asp Ile Cys Cys Ser Xaa Xaa Asp Cys Asn His Xaa Cys
 1               5                  10                  15

Val


<210> SEQ ID NO 12
<211> LENGTH: 12
<212> TYPE: PRT
<213> ORGANISM: Conus regius
<220> FEATURE:
<221> NAME/KEY: SITE
<222> LOCATION: (6)..(9)
<223> OTHER INFORMATION: Xaa at residue 6 is Pro or hydroxy-Pro; Xaa at
      residue 9 is Lys, N-methyl-Lys, N,N-dimethyl-Lys
      or N,N,N-trimethyl-Lys.

<400> SEQUENCE: 12

Gly Cys Cys Ser Asp Xaa Arg Cys Xaa His Gln Cys
 1               5                  10


<210> SEQ ID NO 13
<211> LENGTH: 14
<212> TYPE: PRT
<213> ORGANISM: Conus sponsalis
<220> FEATURE:
<221> NAME/KEY: SITE
<222> LOCATION: (5)..(11)
<223> OTHER INFORMATION: Xaa at residues 5 and 11 is Pro or hydroxy-Pro;
      Xaa at residue 8 is Lys, N-methyl-Lys,
      N.N-dimethyl-Lys or N.N.N-trimethyl-Lys.

<400> SEQUENCE: 13

Cys Cys Ser Asp Xaa Ala Cys Xaa Gln Thr Xaa Gly Cys Arg
 1               5                  10


<210> SEQ ID NO 14
<211> LENGTH: 13
<212> TYPE: PRT
<213> ORGANISM: Conus sponsalis
<220> FEATURE:
<221> NAME/KEY: SITE
<222> LOCATION: (3)..(5)
<223> OTHER INFORMATION: Xaa at residue 3 is Glu or gamma-carboxy-Glu;
      Xaa at residue 5 is Pro or hydroxy-Pro.

<400> SEQUENCE: 14

Cys Cys Xaa Asn Xaa Ala Cys Arg His Thr Gln Gly Cys
 1               5                  10


<210> SEQ ID NO 15
<211> LENGTH: 13
<212> TYPE: PRT
<213> ORGANISM: Conus sulcatus
<220> FEATURE:
<221> NAME/KEY: SITE
<222> LOCATION: (4)..(12)
<223> OTHER INFORMATION: Xaa at residue 4 is Trp or halo-Trp; Xaa at
      residue 6 is Pro or hydroxy-Pro; Xaa at residue 12
      is Tyr, nor-Tyr, mono-halo-Tyr, di-halo-Tyr,
      O-sulpho-Tyr, O-phospho-Tyr or nitro-Tyr.

<400> SEQUENCE: 15

Gly Cys Cys Xaa His Xaa Ala Cys Gly Arg His Xaa Cys
 1               5                  10


<210> SEQ ID NO 16
<211> LENGTH: 14
<212> TYPE: PRT
<213> ORGANISM: Conus achatinus
<220> FEATURE:
```

-continued

<221> NAME/KEY: SITE
<222> LOCATION: (2)..(11)
<223> OTHER INFORMATION: Xaa at residues 2 and 7 is Pro or hydroxy-Pro; Xaa at residue 11 is Lys, N-methyl-Lys, N,N-dimethyl-Lys or N,N,N-trimethyl-Lys.

<400> SEQUENCE: 16

Ala Xaa Cys Cys Asn Asn Xaa Ala Cys Val Xaa His Arg Cys
1 5 10

<210> SEQ ID NO 17
<211> LENGTH: 15
<212> TYPE: PRT
<213> ORGANISM: Conus bullatus
<220> FEATURE:
<221> NAME/KEY: SITE
<222> LOCATION: (2)..(12)
<223> OTHER INFORMATION: Xaa at residues 2 and 8 is Pro or hydroxy-Pro; Xaa at residue 12 is Lys, N-methyl-Lys, N,N-dimethyl-Lys or N,N,N-trimethyl-Lys.

<400> SEQUENCE: 17

Ala Xaa Gly Cys Cys Asn Asn Xaa Ala Cys Val Xaa His Arg Cys
1 5 10 15

<210> SEQ ID NO 18
<211> LENGTH: 14
<212> TYPE: PRT
<213> ORGANISM: Conus bullatus
<220> FEATURE:
<221> NAME/KEY: SITE
<222> LOCATION: (1)..(11)
<223> OTHER INFORMATION: Xaa at residues 1, 2 and 7 is Pro or hydroxy-Pro; Xaa at residue 11 is Lys, N-methyl-Lys, N,N-dimethyl-Lys or N,N,N-trimethyl-Lys.

<400> SEQUENCE: 18

Xaa Xaa Cys Cys Asn Asn Xaa Ala Cys Val Xaa His Arg Cys
1 5 10

<210> SEQ ID NO 19
<211> LENGTH: 16
<212> TYPE: PRT
<213> ORGANISM: Conus bullatus
<220> FEATURE:
<221> NAME/KEY: SITE
<222> LOCATION: (2)..(13)
<223> OTHER INFORMATION: Xaa at residue 2 is Glu or gamma-carboxy-Glu; Xaa at residue 6 is Trp or halo-Trp; Xaa at residues 8 11 and 13 is Pro or hydroxy-Pro.

<400> SEQUENCE: 19

Asp Xaa Asn Cys Cys Xaa Asn Xaa Ser Cys Xaa Arg Xaa Arg Cys Thr
1 5 10 15

<210> SEQ ID NO 20
<211> LENGTH: 13
<212> TYPE: PRT
<213> ORGANISM: Conus bullatus
<220> FEATURE:
<221> NAME/KEY: SITE
<222> LOCATION: (6)..(12)
<223> OTHER INFORMATION: Xaa at residues 6 and 7 is Pro or hydroxy-Pro; Xaa at residue 12 is Tyr, nor-Tyr, mono-halo-Tyr, di-halo-Tyr, O-sulpho-Tyr, O-phospho-Tyr or nitro-Tyr.

<400> SEQUENCE: 20

Gly Cys Cys Ser Arg Xaa Xaa Cys Ala Val Leu Xaa Cys
1 5 10

-continued

<210> SEQ ID NO 21
<211> LENGTH: 13
<212> TYPE: PRT
<213> ORGANISM: Conus circumcisus
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 21

```
Gly Cys Cys Gly Asn Xaa Asp Cys Thr Ser His Ser Cys
  1               5                  10
```

<210> SEQ ID NO 22
<211> LENGTH: 16
<212> TYPE: PRT
<213> ORGANISM: Conus stercusmuscarum
<220> FEATURE:
<221> NAME/KEY: SITE
<222> LOCATION: (6)..(11)
<223> OTHER INFORMATION: Xaa at residue 6 is Pro or hydroxy-Pro; Xaa at residue 11 is Glu or gamma-carboxy-Glu.

<400> SEQUENCE: 22

```
Gly Cys Cys Ser Asn Xaa Val Cys His Leu Xaa His Ser Asn Met Cys
  1               5                  10                  15
```

<210> SEQ ID NO 23
<211> LENGTH: 17
<212> TYPE: PRT
<213> ORGANISM: Conus obscurus
<220> FEATURE:
<221> NAME/KEY: SITE
<222> LOCATION: (6)..(15)
<223> OTHER INFORMATION: Xaa at residue 6 is Pro or hydroxy-Pro; Xaa at residue 14 is Glu or gamma-carboxy-Glu; Xaa at residue 15 is Tyr, nor-Tyr, mono-halo-Tyr, di-halo-Tyr, O-sulpho-Tyr, O-phospho-Tyr or
<220> FEATURE:
<221> NAME/KEY: SITE
<222> LOCATION: (15)
<223> OTHER INFORMATION: nitro-Tyr.

<400> SEQUENCE: 23

```
Gly Cys Cys Ser Asn Xaa Val Cys Arg Gln Asn Asn Ala Xaa Xaa Cys
  1               5                  10                  15

Arg
```

<210> SEQ ID NO 24
<211> LENGTH: 18
<212> TYPE: PRT
<213> ORGANISM: Conus textile
<220> FEATURE:
<221> NAME/KEY: SITE
<222> LOCATION: (1)..(15)
<223> OTHER INFORMATION: Xaa at residues 1, 7 and 14 is Pro or hydroxy-Pro; Xaa at residue 15 is Glu or gamma-carboxy-Glu.

<400> SEQUENCE: 24

```
Xaa Gln Cys Cys Ser His Xaa Ala Cys Asn Val Asp His Xaa Xaa Ile
  1               5                  10                  15

Cys Arg
```

<210> SEQ ID NO 25
<211> LENGTH: 18
<212> TYPE: PRT
<213> ORGANISM: Conus radiatus

```
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residues 2 and 15 is Glu or
      gamma-carboxy-Glu.

<400> SEQUENCE: 25

Xaa Xaa Cys Cys Ser His Xaa Ala Cys Asn Val Asp His Xaa Xaa Ile
  1               5                  10                  15

Cys Arg


<210> SEQ ID NO 26
<211> LENGTH: 18
<212> TYPE: PRT
<213> ORGANISM: Conus radiatus
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 26

Xaa Gln Cys Cys Ser His Xaa Ala Cys Asn Val Asp His Xaa Xaa Ile
  1               5                  10                  15

Cys Asp


<210> SEQ ID NO 27
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.

<400> SEQUENCE: 27

Xaa Arg Cys Cys Ser His Xaa Ala Cys Asn Val Asp His Xaa Xaa Ile
  1               5                  10                  15

Cys Arg


<210> SEQ ID NO 28
<211> LENGTH: 18
<212> TYPE: PRT
<213> ORGANISM: Conus omaria
<220> FEATURE:
<221> NAME/KEY: SITE
<222> LOCATION: (1)..(14)
<223> OTHER INFORMATION: Xaa at residues 1, 7 and 14 is Pro or
      hydroxy-Pro.

<400> SEQUENCE: 28

Xaa Gln Cys Cys Ser His Xaa Ala Cys Asn Val Asp His Xaa Gly Ile
  1               5                  10                  15

Cys Arg


<210> SEQ ID NO 29
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or
      hydroxy-Pro; Xaa at residue 15 is Glu or gamma-carboxy-Glu.
```

-continued

<400> SEQUENCE: 29

Xaa Gln Cys Cys Ser His Xaa Ala Cys Asn Val Asp His Xaa Xaa Thr
1 5 10 15

Cys Arg

<210> SEQ ID NO 30
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or hydroxy-Pro; Xaa at residue 15 is Glu or gamma-carboxy-Glu.

<400> SEQUENCE: 30

Xaa Gln Cys Cys Ser His Xaa Ala Cys Asn Val Asp His Xaa Xaa Val
1 5 10 15

Cys Arg

<210> SEQ ID NO 31
<211> LENGTH: 18
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or hydroxy-Pro; Xaa at residue 15 is Glu or gamma-carboxy-Glu.

<400> SEQUENCE: 31

Xaa Gln Cys Cys Ser His Xaa Ala Cys Asn Ile Asp His Xaa Xaa Ile
1 5 10 15

Cys Arg

<210> SEQ ID NO 32
<211> LENGTH: 21
<212> TYPE: PRT
<213> ORGANISM: Conus omaria
<220> FEATURE:
<221> NAME/KEY: SITE
<222> LOCATION: (1)..(15)
<223> OTHER INFORMATION: Xaa at residues 1, 7 and 14 is Pro or hydroxy-Pro; Xaa at residue 15 is Glu or gamma-carboxy-Glu.

<400> SEQUENCE: 32

Xaa Gln Cys Cys Ser His Xaa Ala Cys Asn Val Asp His Xaa Xaa Ile
1 5 10 15

Cys Arg Arg Arg Arg
20

<210> SEQ ID NO 33
<211> LENGTH: 17
<212> TYPE: PRT
<213> ORGANISM: Conus betulinus
<220> FEATURE:
<221> NAME/KEY: SITE
<222> LOCATION: (7)..(15)
<223> OTHER INFORMATION: Xaa at residues 7 and 14 is Pro or hydroxy-Pro; Xaa at residue 15 is Glu or gamma-carboxy-Glu.

<400> SEQUENCE: 33

Gly Gly Cys Cys Ser His Xaa Ala Cys Ala Val Asn His Xaa Xaa Leu
1 5 10 15

Cys

-continued

<210> SEQ ID NO 34
<211> LENGTH: 16
<212> TYPE: PRT
<213> ORGANISM: Conus betulinus
<220> FEATURE:
<221> NAME/KEY: SITE
<222> LOCATION: (6)..(14)
<223> OTHER INFORMATION: Xaa at residues 6 and 13 is Pro or hydroxy-Pro; Xaa at residue 14 is Glu or gamma-carboxy-Glu.

<400> SEQUENCE: 34

Gly Cys Cys Ser His Xaa Ala Cys Ser Val Asn His Xaa Xaa Leu Cys
1 5 10 15

<210> SEQ ID NO 35
<211> LENGTH: 16
<212> TYPE: PRT
<213> ORGANISM: Conus dalli
<220> FEATURE:
<221> NAME/KEY: SITE
<222> LOCATION: (6)..(14)
<223> OTHER INFORMATION: Xaa at residues 6 and 13 is Pro or hydroxy-Pro; Xaa at residue 14 is Glu or gamma-carboxy-Glu.

<400> SEQUENCE: 35

Gly Cys Cys Ser His Xaa Ala Cys Asn Val Asp His Xaa Xaa Ile Cys
1 5 10 15

<210> SEQ ID NO 36
<211> LENGTH: 19
<212> TYPE: PRT
<213> ORGANISM: Conus obscurus
<220> FEATURE:
<221> NAME/KEY: SITE
<222> LOCATION: (6)..(18)
<223> OTHER INFORMATION: Xaa at residues 6 and 15 is Pro or hydroxy-Pro; Xaa at reside 11 is Lys, N-methyl-Lys, N,N-dimethyl-Lys or N,N,N-trimethyl-Lys; Xaa at residues 14 and 18 is Glu or gamma-carboxy-Glu.

<400> SEQUENCE: 36

Gly Cys Cys Ser His Xaa Ala Cys Ser Gly Xaa Thr Gln Xaa Xaa Cys
1 5 10 15

Arg Xaa Ser

<210> SEQ ID NO 37
<211> LENGTH: 18
<212> TYPE: PRT
<213> ORGANISM: Conus tulipa
<220> FEATURE:
<221> NAME/KEY: SITE
<222> LOCATION: (1)..(14)
<223> OTHER INFORMATION: Xaa at residues 1, 6 and 13 is Pro or hydroxy-Pro; Xaa at residue 14 is Glu or gamma-carboxy-Glu.

<400> SEQUENCE: 37

Xaa Cys Cys Ser His Xaa Ala Cys Ser Gly Asn Asn Xaa Xaa Phe Cys
1 5 10 15

Arg Gln

<210> SEQ ID NO 38
<211> LENGTH: 18
<212> TYPE: PRT
<213> ORGANISM: Conus tulipa
<220> FEATURE:
<221> NAME/KEY: SITE
<222> LOCATION: (6)..(14)

-continued

<223> OTHER INFORMATION: Xaa at residues 6 and 13 is Pro or hydroxy-Pro; Xaa at residue 14 is Glu or gamma-carboxy-Glu.

<400> SEQUENCE: 38

Gly Cys Cys Ser His Xaa Ala Cys Ser Gly Asn Asn Xaa Xaa Phe Cys
1 5 10 15

Arg Gln

<210> SEQ ID NO 39
<211> LENGTH: 16
<212> TYPE: PRT
<213> ORGANISM: Conus pennaceus
<220> FEATURE:
<221> NAME/KEY: SITE
<222> LOCATION: (6)..(15)
<223> OTHER INFORMATION: Xaa at residues 6, 7 and 13 is Pro or hydroxy-Pro; Xaa at residue 15 is Tyr, nor-Tyr, mono-halo-Tyr, di-halo-Tyr, O-sulpho-Tyr, O-phospho-Tyr or nitro-Tyr.

<400> SEQUENCE: 39

Gly Cys Cys Ser His Xaa Xaa Cys Ala Met Asn Asn Xaa Asp Xaa Cys
1 5 10 15

<210> SEQ ID NO 40
<211> LENGTH: 16
<212> TYPE: PRT
<213> ORGANISM: Conus pennaceus
<220> FEATURE:
<221> NAME/KEY: SITE
<222> LOCATION: (6)..(15)
<223> OTHER INFORMATION: Xaa at residuew 6, 7 and 13 is Pro or hydroxy-Pro; Xaa at residue 15 is Tyr, nor-Tyr, mono-halo-Tyr, di-halo-Tyr, O-sulpho-Tyr, O-phospho-Tyr or nitro-Tyr.

<400> SEQUENCE: 40

Gly Cys Cys Ser His Xaa Xaa Cys Phe Leu Asn Asn Xaa Asp Xaa Cys
1 5 10 15

<210> SEQ ID NO 41
<211> LENGTH: 17
<212> TYPE: PRT
<213> ORGANISM: Conus textile
<220> FEATURE:
<221> NAME/KEY: SITE
<222> LOCATION: (6)..(13)
<223> OTHER INFORMATION: Xaa at residues 6, 7 and 13 is Pro or hydroxy-Pro; Xaa at residue 11 is Lys, N-methyl-Lys, N,N-dimethyl-Lys or N.N.N-trimethyl-Lys.

<400> SEQUENCE: 41

Gly Cys Cys Ser Asn Xaa Xaa Cys Ile Ala Xaa Asn Xaa His Met Cys
1 5 10 15

Gly

<210> SEQ ID NO 42
<211> LENGTH: 16
<212> TYPE: PRT
<213> ORGANISM: Conus distans
<220> FEATURE:
<221> NAME/KEY: SITE
<222> LOCATION: (6)..(13)
<223> OTHER INFORMATION: Xaa at residues 6, 7 and 13 is Pro or hydroxy-Pro.

<400> SEQUENCE: 42

Gly Cys Cys Ser Asn Xaa Xaa Cys Ala His Asn Asn Xaa Asp Cys Arg

-continued

```
  1               5                   10                  15


<210> SEQ ID NO 43
<211> LENGTH: 17
<212> TYPE: PRT
<213> ORGANISM: Conus tulipa
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 43

Gly Cys Cys Ser Asn Xaa Ala Cys Ala Gly Asn Asn Xaa His Val Cys
  1               5                   10                  15

Arg


<210> SEQ ID NO 44
<211> LENGTH: 16
<212> TYPE: PRT
<213> ORGANISM: Conus dalli
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 44

Gly Cys Cys Ser Arg Xaa Ala Cys Ile Ala Asn Asn Xaa Asp Leu Cys
  1               5                   10                  15


<210> SEQ ID NO 45
<211> LENGTH: 20
<212> TYPE: PRT
<213> ORGANISM: Conus circumcisus
<220> FEATURE:
<221> NAME/KEY: SITE
<222> LOCATION: (6)..(14)
<223> OTHER INFORMATION: Xaa at residues 6 and 13 is Pro or hydroxy-Pro;
      Xaa at residues 11 and 14 is Glu or
      gamma-carboxy-Glu.

<400> SEQUENCE: 45

Gly Cys Cys Ser Asn Xaa Val Cys His Val Xaa His Xaa Xaa Leu Cys
  1               5                   10                  15

Arg Arg Arg Arg
            20


<210> SEQ ID NO 46
<211> LENGTH: 18
<212> TYPE: PRT
<213> ORGANISM: Conus sulcatus
<220> FEATURE:
<221> NAME/KEY: SITE
<222> LOCATION: (7)..(15)
<223> OTHER INFORMATION: Xaa at residues 7, 12 and 14 is Pro or
      hydroxy-Pro; Xaa at residue 11 is Lys,
      N-methyl-Lys, N,N-dimethyl-Lys or
      N,N,N-trimethyl-Lys; Xaa at residue 15 is Glu or
<220> FEATURE:
<221> NAME/KEY: SITE
<222> LOCATION: (7)..(15)
<223> OTHER INFORMATION: gamma-carboxy-Glu.

<400> SEQUENCE: 46

Gly Gly Cys Cys Ser Phe Xaa Ala Cys Arg Xaa Xaa Arg Xaa Xaa Met
  1               5                   10                  15

Cys Gly
```

-continued

<210> SEQ ID NO 47
<211> LENGTH: 18
<212> TYPE: PRT
<213> ORGANISM: Conus textile
<220> FEATURE:
<221> NAME/KEY: SITE
<222> LOCATION: (1)..(15)
<223> OTHER INFORMATION: Xaa at residues 1, 7 and 14 is Pro or hydroxy-Pro; Xaa at residues 2 and 15 is Glu or gamma-carboxy-Glu.

<400> SEQUENCE: 47

```
Xaa Xaa Cys Cys Ser Asp Xaa Arg Cys Asn Ser Ser His Xaa Xaa Leu
  1               5                  10                  15

Cys Arg
```

<210> SEQ ID NO 48
<211> LENGTH: 18
<212> TYPE: PRT
<213> ORGANISM: Conus dalli
<220> FEATURE:
<221> NAME/KEY: SITE
<222> LOCATION: (1)..(15)
<223> OTHER INFORMATION: Xaa at residues 1, 7 and 14 is Pro or hydroxy-Pro; Xaa at residue 15 is Glu or gamma-carboxy-Glu.

<400> SEQUENCE: 48

```
Xaa Gln Cys Cys Ser Asp Xaa Arg Cys Asn Val Gly His Xaa Xaa Leu
  1               5                  10                  15

Cys Gly
```

<210> SEQ ID NO 49
<211> LENGTH: 18
<212> TYPE: PRT
<213> ORGANISM: Conus dalli
<220> FEATURE:
<221> NAME/KEY: SITE
<222> LOCATION: (1)..(15)
<223> OTHER INFORMATION: Xaa at residue 1 is Gln or pyro-Glu; Xaa at residues 7 and 14 is Pro or hydroxy-Pro; Xaa at residue 15 is Glu or gamma-carboxy-Glu.

<400> SEQUENCE: 49

```
Xaa Val Cys Cys Ser Asp Xaa Arg Cys Asn Val Gly His Xaa Xaa Ile
  1               5                  10                  15

Cys Gly
```

<210> SEQ ID NO 50
<211> LENGTH: 16
<212> TYPE: PRT
<213> ORGANISM: Conus textile
<220> FEATURE:
<221> NAME/KEY: SITE
<222> LOCATION: (6)..(13)
<223> OTHER INFORMATION: Xaa at residues 6, 7 and 13 is Pro or hydroxy-Pro.

<400> SEQUENCE: 50

```
Gly Cys Cys Ser Arg Xaa Xaa Cys Ile Ala Asn Asn Xaa Asp Leu Cys
  1               5                  10                  15
```

<210> SEQ ID NO 51
<211> LENGTH: 18
<212> TYPE: PRT
<213> ORGANISM: Conus omaria
<220> FEATURE:
<221> NAME/KEY: SITE
<222> LOCATION: (1)..(15)

-continued

```
<223> OTHER INFORMATION: Xaa at residues 1 and 14 is Pro or hydroxy-Pro;
      Xaa at residue 15 is Glu or gamma-carboxy-Glu.

<400> SEQUENCE: 51

Xaa Gln Cys Cys Ser His Leu Ala Cys Asn Val Asp His Xaa Xaa Ile
  1               5                  10                  15

Cys Arg


<210> SEQ ID NO 52
<211> LENGTH: 19
<212> TYPE: PRT
<213> ORGANISM: Conus sulcatus
<220> FEATURE:
<221> NAME/KEY: SITE
<222> LOCATION: (5)..(14)
<223> OTHER INFORMATION: Xaa at residue 5 is Tyr, nor-Tyr,
      mono-halo-Tyr, di-halo-Tyr, O-sulpho-Tyr, O-phospho-Tyr or
      nitro-Tyr; Xaa at residue 13 is Pro or
      hydroxy-Pro; Xaa at residue 14 is Glu or
<220> FEATURE:
<221> NAME/KEY: SITE
<222> LOCATION: (14)..(18)
<223> OTHER INFORMATION: gamma-carboxy-Glu; Xaa at residue 18 is Trp or
      halo-Trp.

<400> SEQUENCE: 52

Gly Cys Cys Ser Xaa Phe Asp Cys Arg Met Met Phe Xaa Xaa Met Cys
  1               5                  10                  15

Gly Xaa Arg


<210> SEQ ID NO 53
<211> LENGTH: 18
<212> TYPE: PRT
<213> ORGANISM: Conus sulcatus
<220> FEATURE:
<221> NAME/KEY: SITE
<222> LOCATION: (11)..(12)
<223> OTHER INFORMATION: Xaa at residue 11 is Lys, N-methyl-Lys,
      N,N-dimethyl-Lys or N,N,N-trimethyl-Lys; Xaa at
      residue 12 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (12)..(15)
<223> OTHER INFORMATION: nitro-Tyr; Xaa at residue 14 is Pro or
      hydroxyl-Pro; Xaa at residue 15 is Glu or gamma-carboxy-
      Glu.

<400> SEQUENCE: 53

Gly Gly Cys Cys Ser Phe Ala Ala Cys Arg Xaa Xaa Arg Xaa Xaa Met
  1               5                  10                  15

Cys Gly


<210> SEQ ID NO 54
<211> LENGTH: 20
<212> TYPE: PRT
<213> ORGANISM: Conus sulcatus
<220> FEATURE:
<221> NAME/KEY: SITE
<222> LOCATION: (7)..(15)
<223> OTHER INFORMATION: Xaa at residue 7 is Pro or hydroxy-Pro; Xaa at
      residue 10 is Tyr, nor-Tyr, mono-halo-Tyr,
      di-halo-Tyr, O-sulpho-Tyr, O-phospho-Tyr or
      nitro-Tyr; Xaa at residue 15 is Glu or
<220> FEATURE:
<221> NAME/KEY: SITE
<222> LOCATION: (7)..(15)
<223> OTHER INFORMATION: gamma-carboxy-Glu.

<400> SEQUENCE: 54
```

-continued

```
Gly Gly Cys Cys Phe His Xaa Val Cys Xaa Ile Asn Leu Leu Xaa Met
  1               5                  10                  15

Cys Arg Gln Arg
            20


<210> SEQ ID NO 55
<211> LENGTH: 19
<212> TYPE: PRT
<213> ORGANISM: Conus betulinus
<220> FEATURE:
<221> NAME/KEY: SITE
<222> LOCATION: (7)..(15)
<223> OTHER INFORMATION: Xaa at residues 7, 11 and 14 is Tyr, nor-Tyr,
      mono-halo-Tyr, di-halo-Tyr, O-sulpho-Tyr,
      O-phospho-Tyr; Xaa at residues 8, 9 and 15 is Pro
      or hydroxy-Pro.
<220> FEATURE:
<221> NAME/KEY: SITE
<222> LOCATION: (12)..(16)
<223> OTHER INFORMATION: Xaa at residues 12 and 16 is Glu or
      gamma-carboxy-Glu.

<400> SEQUENCE: 55

Ser Ala Thr Cys Cys Asn Xaa Xaa Xaa Cys Xaa Xaa Thr Xaa Xaa Xaa
  1               5                  10                  15

Ser Cys Leu


<210> SEQ ID NO 56
<211> LENGTH: 17
<212> TYPE: PRT
<213> ORGANISM: Conus betulinus
<220> FEATURE:
<221> NAME/KEY: SITE
<222> LOCATION: (5)..(13)
<223> OTHER INFORMATION: Xaa at residues 5 and 12 is Tyr, nor-Tyr,
      mono-halo-Tyr, di-halo-Tyr, O-sulpho-Tyr,
      O-phospho-Tyr or nitro-Tyr; Xaa at residues 6, 7
      and 13 is Pro or hydroxy-Pro.
<220> FEATURE:
<221> NAME/KEY: SITE
<222> LOCATION: (10)..(14)
<223> OTHER INFORMATION: Xaa at residues 10 and 14 is Glu or
      gamma-carboxy-Glu.

<400> SEQUENCE: 56

Ala Cys Cys Ala Xaa Xaa Xaa Cys Phe Xaa Ala Xaa Xaa Xaa Arg Cys
  1               5                  10                  15

Leu


<210> SEQ ID NO 57
<211> LENGTH: 19
<212> TYPE: PRT
<213> ORGANISM: Conus betulinus
<220> FEATURE:
<221> NAME/KEY: SITE
<222> LOCATION: (3)..(16)
<223> OTHER INFORMATION: Xaa at residues 3, 12 and 16 is Glu or
      gamma-carboxy-Glu; Xaa at residues 6, 7, 11 and 14
      is Tyr, nor-Tyr, mono-halo-Tyr, di-halo-Tyr,
      O-sulpho-Tyr, O-phospho-Tyr or nitro-Tyr.
<220> FEATURE:
<221> NAME/KEY: SITE
<222> LOCATION: (8)..(15)
<223> OTHER INFORMATION: Xaa at residues 8, 9 and 15 is Pro or
      hydroxy-Pro.

<400> SEQUENCE: 57

Asn Ala Xaa Cys Cys Xaa Xaa Xaa Xaa Cys Xaa Xaa Ala Xaa Xaa Xaa
  1               5                  10                  15
```

-continued

```
Ile Cys Leu


<210> SEQ ID NO 58
<211> LENGTH: 227
<212> TYPE: DNA
<213> ORGANISM: Conus magus
<220> FEATURE:
<221> NAME/KEY: CDS
<222> LOCATION: (1)..(189)

<400> SEQUENCE: 58

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc cct tca gat cgt gca tct gat ggc agg aat gcc gca gcc aac gac       96
Phe Pro Ser Asp Arg Ala Ser Asp Gly Arg Asn Ala Ala Ala Asn Asp
             20                  25                  30

aaa gcg tct gac gtg atc acg ctg gcc ctc aag gga tgc tgt tcc aac      144
Lys Ala Ser Asp Val Ile Thr Leu Ala Leu Lys Gly Cys Cys Ser Asn
         35                  40                  45

cct gtc tgt cac ttg gag cat tca aac ctt tgt ggt aga aga cgc          189
Pro Val Cys His Leu Glu His Ser Asn Leu Cys Gly Arg Arg Arg
     50                  55                  60

tgatgctcca ggaccctctg aaccacgacg ttcgagca                            227


<210> SEQ ID NO 59
<211> LENGTH: 63
<212> TYPE: PRT
<213> ORGANISM: Conus magus

<400> SEQUENCE: 59

Met Phe Thr Val Phe Leu Leu Val Val Leu Ala Thr Thr Val Val Ser
  1               5                  10                  15

Phe Pro Ser Asp Arg Ala Ser Asp Gly Arg Asn Ala Ala Ala Asn Asp
             20                  25                  30

Lys Ala Ser Asp Val Ile Thr Leu Ala Leu Lys Gly Cys Cys Ser Asn
         35                  40                  45

Pro Val Cys His Leu Glu His Ser Asn Leu Cys Gly Arg Arg Arg
     50                  55                  60


<210> SEQ ID NO 60
<211> LENGTH: 208
<212> TYPE: DNA
<213> ORGANISM: Conus aulicus
<220> FEATURE:
<221> NAME/KEY: CDS
<222> LOCATION: (1)..(168)

<400> SEQUENCE: 60

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat cgt gca tct gat ggc agg aag gac gca gcg tct ggc       96
Phe Thr Ser Asp Arg Ala Ser Asp Gly Arg Lys Asp Ala Ala Ser Gly
             20                  25                  30

ctg atc gct ctg acc atc aag gga tgc tgt tct tat cct ccc tgt ttc      144
Leu Ile Ala Leu Thr Ile Lys Gly Cys Cys Ser Tyr Pro Pro Cys Phe
         35                  40                  45

gcg act aat tca gac tat tgt ggt tgacgacgct gatgctccag gaccctctga      198
Ala Thr Asn Ser Asp Tyr Cys Gly
     50                  55
```

-continued

```
accacgacgt                                                         208


<210> SEQ ID NO 61
<211> LENGTH: 56
<212> TYPE: PRT
<213> ORGANISM: Conus aulicus

<400> SEQUENCE: 61

Met Phe Thr Val Phe Leu Leu Val Val Leu Ala Thr Thr Val Val Ser
  1               5                  10                  15

Phe Thr Ser Asp Arg Ala Ser Asp Gly Arg Lys Asp Ala Ala Ser Gly
             20                  25                  30

Leu Ile Ala Leu Thr Ile Lys Gly Cys Cys Ser Tyr Pro Pro Cys Phe
         35                  40                  45

Ala Thr Asn Ser Asp Tyr Cys Gly
     50                  55


<210> SEQ ID NO 62
<211> LENGTH: 205
<212> TYPE: DNA
<213> ORGANISM: Conus aulicus
<220> FEATURE:
<221> NAME/KEY: CDS
<222> LOCATION: (1)..(174)

<400> SEQUENCE: 62

atg ttc acc gtg ttt ctg ttg gtc gtc ttg gca acc acc gtc gtt tcc       48
Met Phe Thr Val Phe Leu Leu Val Val Leu Ala Thr Thr Val Val Ser
  1               5                  10                  15

ttc act tca gat cgt gca tct gat ggc agg aag gac gca gcg tct ggc       96
Phe Thr Ser Asp Arg Ala Ser Asp Gly Arg Lys Asp Ala Ala Ser Gly
             20                  25                  30

ctg att gct ctg acc atg aag gga tgc tgt tct tat cct ccc tgt ttc      144
Leu Ile Ala Leu Thr Met Lys Gly Cys Cys Ser Tyr Pro Pro Cys Phe
         35                  40                  45

gcg act aat cca gac tgt ggt cga cga cgc tgatgctcca ggaccctctg        194
Ala Thr Asn Pro Asp Cys Gly Arg Arg Arg
     50                  55

aaccacgacg t                                                         205


<210> SEQ ID NO 63
<211> LENGTH: 58
<212> TYPE: PRT
<213> ORGANISM: Conus aulicus

<400> SEQUENCE: 63

Met Phe Thr Val Phe Leu Leu Val Val Leu Ala Thr Thr Val Val Ser
  1               5                  10                  15

Phe Thr Ser Asp Arg Ala Ser Asp Gly Arg Lys Asp Ala Ala Ser Gly
             20                  25                  30

Leu Ile Ala Leu Thr Met Lys Gly Cys Cys Ser Tyr Pro Pro Cys Phe
         35                  40                  45

Ala Thr Asn Pro Asp Cys Gly Arg Arg Arg
     50                  55


<210> SEQ ID NO 64
<211> LENGTH: 223
<212> TYPE: DNA
<213> ORGANISM: Conus textile
<220> FEATURE:
<221> NAME/KEY: CDS
<222> LOCATION: (1)..(192)
```

<400> SEQUENCE: 64

```
atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc tct tca ggt cgt agt aca ttt cgt ggc agg aat gcc gca gcc aaa       96
Phe Ser Ser Gly Arg Ser Thr Phe Arg Gly Arg Asn Ala Ala Ala Lys
             20                  25                  30

gcg tct ggc ctg gtc agt ctg act gac agg aga cca gaa tgc tgt agt      144
Ala Ser Gly Leu Val Ser Leu Thr Asp Arg Arg Pro Glu Cys Cys Ser
         35                  40                  45

gat cct cgc tgt aac tcg agt cat cca gaa ctt tgt ggt gga aga cgc      192
Asp Pro Arg Cys Asn Ser Ser His Pro Glu Leu Cys Gly Gly Arg Arg
     50                  55                  60

tgatgctcca ggaccctctg aaccacgacg t                                   223
```

<210> SEQ ID NO 65
<211> LENGTH: 64
<212> TYPE: PRT
<213> ORGANISM: Conus textile

<400> SEQUENCE: 65

```
Met Phe Thr Val Phe Leu Leu Val Val Leu Ala Thr Thr Val Val Ser
  1               5                  10                  15

Phe Ser Ser Gly Arg Ser Thr Phe Arg Gly Arg Asn Ala Ala Ala Lys
             20                  25                  30

Ala Ser Gly Leu Val Ser Leu Thr Asp Arg Arg Pro Glu Cys Cys Ser
         35                  40                  45

Asp Pro Arg Cys Asn Ser Ser His Pro Glu Leu Cys Gly Gly Arg Arg
     50                  55                  60
```

<210> SEQ ID NO 66
<211> LENGTH: 244
<212> TYPE: DNA
<213> ORGANISM: Conus textile
<220> FEATURE:
<221> NAME/KEY: CDS
<222> LOCATION: (1)..(168)

<400> SEQUENCE: 66

```
atg ttc acc gtg ttt ctg ttg gtt gtc ttg gca acc gcc gtc gtt tcc       48
Met Phe Thr Val Phe Leu Leu Val Val Leu Ala Thr Ala Val Val Ser
  1               5                  10                  15

ttc act tca gat cgt gca tct gat gac ggg aaa gcc gct gcg tct gac       96
Phe Thr Ser Asp Arg Ala Ser Asp Asp Gly Lys Ala Ala Ala Ser Asp
             20                  25                  30

ctg atc act ctg acc atc aag gga tgc tgt tct cgt cct ccc tgt atc      144
Leu Ile Thr Leu Thr Ile Lys Gly Cys Cys Ser Arg Pro Pro Cys Ile
         35                  40                  45

gcg aat aat cca gac ttg tgt ggt tgacgacgct gatgctccag aacggtctga     198
Ala Asn Asn Pro Asp Leu Cys Gly
     50                  55

accacgacgt tcgagcaatg ttcaccgtgt ttctgttggt tgtctt                   244
```

<210> SEQ ID NO 67
<211> LENGTH: 56
<212> TYPE: PRT
<213> ORGANISM: Conus textile

<400> SEQUENCE: 67

```
Met Phe Thr Val Phe Leu Leu Val Val Leu Ala Thr Ala Val Val Ser
```

-continued

```
  1               5                   10                  15

Phe Thr Ser Asp Arg Ala Ser Asp Asp Gly Lys Ala Ala Ala Ser Asp
            20                  25                  30

Leu Ile Thr Leu Thr Ile Lys Gly Cys Cys Ser Arg Pro Pro Cys Ile
        35                  40                  45

Ala Asn Asn Pro Asp Leu Cys Gly
    50                  55


<210> SEQ ID NO 68
<211> LENGTH: 223
<212> TYPE: DNA
<213> ORGANISM: Conus textile
<220> FEATURE:
<221> NAME/KEY: CDS
<222> LOCATION: (1)..(183)

<400> SEQUENCE: 68

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                   10                  15

ttc act tca ggt cgt agt aca ttt cgt ggc agg aat gcc gca gcc aaa       96
Phe Thr Ser Gly Arg Ser Thr Phe Arg Gly Arg Asn Ala Ala Ala Lys
            20                  25                  30

gcg tct ggc ctg gtc agt ctg act gac agg aga cca caa tgc tgt tct      144
Ala Ser Gly Leu Val Ser Leu Thr Asp Arg Arg Pro Gln Cys Cys Ser
        35                  40                  45

cat cct gcc tgt aac gta gat cat cca gaa att tgt cgt tgaagacgct      193
His Pro Ala Cys Asn Val Asp His Pro Glu Ile Cys Arg
    50                  55                  60

gatgctccag gaccctctga accacgacgt                                     223


<210> SEQ ID NO 69
<211> LENGTH: 61
<212> TYPE: PRT
<213> ORGANISM: Conus textile

<400> SEQUENCE: 69

Met Phe Thr Val Phe Leu Leu Val Val Leu Ala Thr Thr Val Val Ser
  1               5                   10                  15

Phe Thr Ser Gly Arg Ser Thr Phe Arg Gly Arg Asn Ala Ala Ala Lys
            20                  25                  30

Ala Ser Gly Leu Val Ser Leu Thr Asp Arg Arg Pro Gln Cys Cys Ser
        35                  40                  45

His Pro Ala Cys Asn Val Asp His Pro Glu Ile Cys Arg
    50                  55                  60


<210> SEQ ID NO 70
<211> LENGTH: 223
<212> TYPE: DNA
<213> ORGANISM: Conus radiatus
<220> FEATURE:
<221> NAME/KEY: CDS
<222> LOCATION: (1)..(183)

<400> SEQUENCE: 70

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                   10                  15

ttc act tca ggt cgt cgt aca ttt cat ggc agg aat gcc gca gcc aaa       96
Phe Thr Ser Gly Arg Arg Thr Phe His Gly Arg Asn Ala Ala Ala Lys
            20                  25                  30
```

-continued

```
gcg tct ggc ctg gtc agt ctg act gac agg aga cca gaa tgc tgt tct      144
Ala Ser Gly Leu Val Ser Leu Thr Asp Arg Arg Pro Glu Cys Cys Ser
        35                  40                  45

cat cct gcc tgt aac gta gat cat cca gaa att tgt cgt tgaagacgct       193
His Pro Ala Cys Asn Val Asp His Pro Glu Ile Cys Arg
    50                  55                  60

gatgctccag gaccctctga accacgacgt                                     223


<210> SEQ ID NO 71
<211> LENGTH: 61
<212> TYPE: PRT
<213> ORGANISM: Conus radiatus

<400> SEQUENCE: 71

Met Phe Thr Val Phe Leu Leu Val Val Leu Ala Thr Thr Val Val Ser
 1               5                  10                  15

Phe Thr Ser Gly Arg Arg Thr Phe His Gly Arg Asn Ala Ala Ala Lys
            20                  25                  30

Ala Ser Gly Leu Val Ser Leu Thr Asp Arg Arg Pro Glu Cys Cys Ser
        35                  40                  45

His Pro Ala Cys Asn Val Asp His Pro Glu Ile Cys Arg
    50                  55                  60


<210> SEQ ID NO 72
<211> LENGTH: 223
<212> TYPE: DNA
<213> ORGANISM: Conus radiatus
<220> FEATURE:
<221> NAME/KEY: CDS
<222> LOCATION: (1)..(183)

<400> SEQUENCE: 72

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
 1               5                  10                  15

ttc act tca ggt cgt agt aca ttt cgt ggc agg aat gcc gca gcc aaa       96
Phe Thr Ser Gly Arg Ser Thr Phe Arg Gly Arg Asn Ala Ala Ala Lys
            20                  25                  30

gcg tct ggc ctg gtc agt ctg act gac agg aga cca caa tgc tgt tct      144
Ala Ser Gly Leu Val Ser Leu Thr Asp Arg Arg Pro Gln Cys Cys Ser
        35                  40                  45

cat cct gcc tgt aac gta gat cat cca gaa att tgc gat tgaagacgct       193
His Pro Ala Cys Asn Val Asp His Pro Glu Ile Cys Asp
    50                  55                  60

gatgctccag gaccctctga accacgacgt                                     223


<210> SEQ ID NO 73
<211> LENGTH: 61
<212> TYPE: PRT
<213> ORGANISM: Conus radiatus

<400> SEQUENCE: 73

Met Phe Thr Val Phe Leu Leu Val Val Leu Ala Thr Thr Val Val Ser
 1               5                  10                  15

Phe Thr Ser Gly Arg Ser Thr Phe Arg Gly Arg Asn Ala Ala Ala Lys
            20                  25                  30

Ala Ser Gly Leu Val Ser Leu Thr Asp Arg Arg Pro Gln Cys Cys Ser
        35                  40                  45

His Pro Ala Cys Asn Val Asp His Pro Glu Ile Cys Asp
    50                  55                  60
```

-continued

```
<210> SEQ ID NO 74
<211> LENGTH: 218
<212> TYPE: DNA
<213> ORGANISM: Conus striatus
<220> FEATURE:
<221> NAME/KEY: CDS
<222> LOCATION: (1)..(171)

<400> SEQUENCE: 74

atg ttc act gtg ttt ctg ttg gtt gtc ttg gca atc act gtc gtt tcc       48
Met Phe Thr Val Phe Leu Leu Val Val Leu Ala Ile Thr Val Val Ser
  1               5                  10                  15

ttc cct tta gat cgt gaa tct gat ggc gcg aat gcc gaa gcc cgc acc       96
Phe Pro Leu Asp Arg Glu Ser Asp Gly Ala Asn Ala Glu Ala Arg Thr
             20                  25                  30

cac gat cat gag aag cac gca ctg gac cgg aat gga tgc tgt agg aat      144
His Asp His Glu Lys His Ala Leu Asp Arg Asn Gly Cys Cys Arg Asn
         35                  40                  45

cct gcc tgt gag agc cac aga tgt ggt tgacgacgct gatgctccag           191
Pro Ala Cys Glu Ser His Arg Cys Gly
     50                  55

gaccctctga accacgacgt tcgagca                                        218


<210> SEQ ID NO 75
<211> LENGTH: 57
<212> TYPE: PRT
<213> ORGANISM: Conus striatus

<400> SEQUENCE: 75

Met Phe Thr Val Phe Leu Leu Val Val Leu Ala Ile Thr Val Val Ser
  1               5                  10                  15

Phe Pro Leu Asp Arg Glu Ser Asp Gly Ala Asn Ala Glu Ala Arg Thr
             20                  25                  30

His Asp His Glu Lys His Ala Leu Asp Arg Asn Gly Cys Cys Arg Asn
         35                  40                  45

Pro Ala Cys Glu Ser His Arg Cys Gly
     50                  55


<210> SEQ ID NO 76
<211> LENGTH: 227
<212> TYPE: DNA
<213> ORGANISM: Conus bandanus
<220> FEATURE:
<221> NAME/KEY: CDS
<222> LOCATION: (1)..(180)

<400> SEQUENCE: 76

atg ttc acc atg ttt ctg ttg gtt gtc ttg gca acc act gtc gtt tcc       48
Met Phe Thr Met Phe Leu Leu Val Val Leu Ala Thr Thr Val Val Ser
  1               5                  10                  15

ttc gct tca gat cgt gca tct gat ggc agg aat gcc gca gcc aag gac       96
Phe Ala Ser Asp Arg Ala Ser Asp Gly Arg Asn Ala Ala Ala Lys Asp
             20                  25                  30

aaa gcg tct gac ctg gtc gct ctg acc gtc aag gga tgc tgt tct cat      144
Lys Ala Ser Asp Leu Val Ala Leu Thr Val Lys Gly Cys Cys Ser His
         35                  40                  45

cct gcc tgt agc gtg aat aat cca gac att tgt ggt tgaagacgct           190
Pro Ala Cys Ser Val Asn Asn Pro Asp Ile Cys Gly
     50                  55                  60

gatgctccag gaccctctga accacgacgt tcgagca                             227
```

-continued

```
<210> SEQ ID NO 77
<211> LENGTH: 60
<212> TYPE: PRT
<213> ORGANISM: Conus bandanus

<400> SEQUENCE: 77

Met Phe Thr Met Phe Leu Leu Val Val Leu Ala Thr Thr Val Val Ser
  1               5                  10                  15

Phe Ala Ser Asp Arg Ala Ser Asp Gly Arg Asn Ala Ala Ala Lys Asp
             20                  25                  30

Lys Ala Ser Asp Leu Val Ala Leu Thr Val Lys Gly Cys Cys Ser His
         35                  40                  45

Pro Ala Cys Ser Val Asn Asn Pro Asp Ile Cys Gly
     50                  55                  60


<210> SEQ ID NO 78
<211> LENGTH: 104
<212> TYPE: DNA
<213> ORGANISM: Conus bandanus
<220> FEATURE:
<221> NAME/KEY: CDS
<222> LOCATION: (1)..(54)

<400> SEQUENCE: 78

aaa gaa tgc tgt act cat cct gcc tgt cac gtg agt cat cca gaa ctc       48
Lys Glu Cys Cys Thr His Pro Ala Cys His Val Ser His Pro Glu Leu
  1               5                  10                  15

tgt ggt tgaaaagcga cgtgacgctc caggaccctc tgaaccacga cgttcgagca       104
Cys Gly


<210> SEQ ID NO 79
<211> LENGTH: 18
<212> TYPE: PRT
<213> ORGANISM: Conus bandanus

<400> SEQUENCE: 79

Lys Glu Cys Cys Thr His Pro Ala Cys His Val Ser His Pro Glu Leu
  1               5                  10                  15

Cys Gly


<210> SEQ ID NO 80
<211> LENGTH: 206
<212> TYPE: DNA
<213> ORGANISM: Conus bandanus
<220> FEATURE:
<221> NAME/KEY: CDS
<222> LOCATION: (1)..(171)

<400> SEQUENCE: 80

atg ttc acc gtg ttt ctg ttg gtt gtc ttg gca act gct gtt ctt cca       48
Met Phe Thr Val Phe Leu Leu Val Val Leu Ala Thr Ala Val Leu Pro
  1               5                  10                  15

gtc act tta gat cgt gca tct gat gga agg aat gca gca gcc aac gcc       96
Val Thr Leu Asp Arg Ala Ser Asp Gly Arg Asn Ala Ala Ala Asn Ala
             20                  25                  30

aaa acg cct cgc ctg atc gcg cca ttc atc agg gat tat tgc tgt cat      144
Lys Thr Pro Arg Leu Ile Ala Pro Phe Ile Arg Asp Tyr Cys Cys His
         35                  40                  45

aga ggt ccc tgt atg gta tgg tgt ggt tgaagccgct gctgctccag            191
Arg Gly Pro Cys Met Val Trp Cys Gly
     50                  55

gaccctctga accac                                                     206
```

-continued

<210> SEQ ID NO 81
<211> LENGTH: 57
<212> TYPE: PRT
<213> ORGANISM: Conus bandanus

<400> SEQUENCE: 81

```
Met Phe Thr Val Phe Leu Leu Val Val Leu Ala Thr Ala Val Leu Pro
  1               5                  10                  15

Val Thr Leu Asp Arg Ala Ser Asp Gly Arg Asn Ala Ala Ala Asn Ala
             20                  25                  30

Lys Thr Pro Arg Leu Ile Ala Pro Phe Ile Arg Asp Tyr Cys Cys His
         35                  40                  45

Arg Gly Pro Cys Met Val Trp Cys Gly
     50                  55
```

<210> SEQ ID NO 82
<211> LENGTH: 174
<212> TYPE: DNA
<213> ORGANISM: Conus caracteristicus
<220> FEATURE:
<221> NAME/KEY: CDS
<222> LOCATION: (1)..(171)

<400> SEQUENCE: 82

```
atg ttc acc gtg ttt ctg ttg gtt gtc ttg gca acc act gtg gtt tcc       48
Met Phe Thr Val Phe Leu Leu Val Val Leu Ala Thr Thr Val Val Ser
  1               5                  10                  15

ttc act tca gat cgt gct tct gat ggc agg aat gcc gca gcc aac gcg       96
Phe Thr Ser Asp Arg Ala Ser Asp Gly Arg Asn Ala Ala Ala Asn Ala
             20                  25                  30

ttt gac ctg atc gct ctg atc gcc agg caa aat tgc tgt agc att ccc      144
Phe Asp Leu Ile Ala Leu Ile Ala Arg Gln Asn Cys Cys Ser Ile Pro
         35                  40                  45

agc tgt tgg gag aaa tat aaa tgt agt taa                              174
Ser Cys Trp Glu Lys Tyr Lys Cys Ser
     50                  55
```

<210> SEQ ID NO 83
<211> LENGTH: 57
<212> TYPE: PRT
<213> ORGANISM: Conus caracteristicus

<400> SEQUENCE: 83

```
Met Phe Thr Val Phe Leu Leu Val Val Leu Ala Thr Thr Val Val Ser
  1               5                  10                  15

Phe Thr Ser Asp Arg Ala Ser Asp Gly Arg Asn Ala Ala Ala Asn Ala
             20                  25                  30

Phe Asp Leu Ile Ala Leu Ile Ala Arg Gln Asn Cys Cys Ser Ile Pro
         35                  40                  45

Ser Cys Trp Glu Lys Tyr Lys Cys Ser
     50                  55
```

<210> SEQ ID NO 84
<211> LENGTH: 219
<212> TYPE: DNA
<213> ORGANISM: Conus caracteristicus
<220> FEATURE:
<221> NAME/KEY: CDS
<222> LOCATION: (1)..(189)

<400> SEQUENCE: 84

```
atg ttc acc gtg ttt ctg ttg gtt gtc ttg gca acc act gtg gtt tcc       48
```

-continued

```
Met Phe Thr Val Phe Leu Leu Val Val Leu Ala Thr Thr Val Val Ser
  1               5                  10                  15

ttc act tca gat cgt gcg tct gaa ggc agg aat gct gca gcc aag gac       96
Phe Thr Ser Asp Arg Ala Ser Glu Gly Arg Asn Ala Ala Ala Lys Asp
             20                  25                  30

aaa gcg tct gac ctg gtg gct ctg aca gtc agg gga tgc tgt gcc att      144
Lys Ala Ser Asp Leu Val Ala Leu Thr Val Arg Gly Cys Cys Ala Ile
         35                  40                  45

cgt gaa tgt cgc ttg cag aat gca gcg tat tgt ggt gga ata tac          189
Arg Glu Cys Arg Leu Gln Asn Ala Ala Tyr Cys Gly Gly Ile Tyr
     50                  55                  60

tgatgctcca ggaccctctg aaccacgacg                                     219


<210> SEQ ID NO 85
<211> LENGTH: 63
<212> TYPE: PRT
<213> ORGANISM: Conus caracteristicus

<400> SEQUENCE: 85

Met Phe Thr Val Phe Leu Leu Val Val Leu Ala Thr Thr Val Val Ser
  1               5                  10                  15

Phe Thr Ser Asp Arg Ala Ser Glu Gly Arg Asn Ala Ala Ala Lys Asp
             20                  25                  30

Lys Ala Ser Asp Leu Val Ala Leu Thr Val Arg Gly Cys Cys Ala Ile
         35                  40                  45

Arg Glu Cys Arg Leu Gln Asn Ala Ala Tyr Cys Gly Gly Ile Tyr
     50                  55                  60


<210> SEQ ID NO 86
<211> LENGTH: 217
<212> TYPE: DNA
<213> ORGANISM: Conus tulipa
<220> FEATURE:
<221> NAME/KEY: CDS
<222> LOCATION: (1)..(186)

<400> SEQUENCE: 86

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc cct tca gat att gca act gag ggc agg aat gcc gca gcc aaa gcg       96
Phe Pro Ser Asp Ile Ala Thr Glu Gly Arg Asn Ala Ala Ala Lys Ala
             20                  25                  30

ttt gac ctg ata tct tcg atc gtc aag aaa gga tgc tgt tcc cat cct      144
Phe Asp Leu Ile Ser Ser Ile Val Lys Lys Gly Cys Cys Ser His Pro
         35                  40                  45

gcc tgt tcg ggg aat aat cca gaa ttt tgt cgt caa ggt cgc              186
Ala Cys Ser Gly Asn Asn Pro Glu Phe Cys Arg Gln Gly Arg
     50                  55                  60

tgatgctcca ggaccctctg aaccacgacg t                                   217


<210> SEQ ID NO 87
<211> LENGTH: 62
<212> TYPE: PRT
<213> ORGANISM: Conus tulipa

<400> SEQUENCE: 87

Met Phe Thr Val Phe Leu Leu Val Val Leu Ala Thr Thr Val Val Ser
  1               5                  10                  15

Phe Pro Ser Asp Ile Ala Thr Glu Gly Arg Asn Ala Ala Ala Lys Ala
             20                  25                  30
```

-continued

```
Phe Asp Leu Ile Ser Ser Ile Val Lys Lys Gly Cys Cys Ser His Pro
        35                  40                  45

Ala Cys Ser Gly Asn Asn Pro Glu Phe Cys Arg Gln Gly Arg
    50                  55                  60
```

<210> SEQ ID NO 88
<211> LENGTH: 217
<212> TYPE: DNA
<213> ORGANISM: Conus tulipa
<220> FEATURE:
<221> NAME/KEY: CDS
<222> LOCATION: (1)..(186)

<400> SEQUENCE: 88

```
atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc cct tca gat ata gca act gag ggc agg aat gcc gca gcc aaa gcg       96
Phe Pro Ser Asp Ile Ala Thr Glu Gly Arg Asn Ala Ala Ala Lys Ala
             20                  25                  30

ttt gac ctg ata tct tcg atc gtc agg aaa gga tgc tgt tcc aat ccc      144
Phe Asp Leu Ile Ser Ser Ile Val Arg Lys Gly Cys Cys Ser Asn Pro
         35                  40                  45

gcc tgt gcg ggg aat aat cca cat gtt tgt cgt caa ggt cgc              186
Ala Cys Ala Gly Asn Asn Pro His Val Cys Arg Gln Gly Arg
     50                  55                  60

tgatgctcca ggaccctctg aaccacgacg t                                   217
```

<210> SEQ ID NO 89
<211> LENGTH: 62
<212> TYPE: PRT
<213> ORGANISM: Conus tulipa

<400> SEQUENCE: 89

```
Met Phe Thr Val Phe Leu Leu Val Val Leu Ala Thr Thr Val Val Ser
  1               5                  10                  15

Phe Pro Ser Asp Ile Ala Thr Glu Gly Arg Asn Ala Ala Ala Lys Ala
             20                  25                  30

Phe Asp Leu Ile Ser Ser Ile Val Arg Lys Gly Cys Cys Ser Asn Pro
         35                  40                  45

Ala Cys Ala Gly Asn Asn Pro His Val Cys Arg Gln Gly Arg
     50                  55                  60
```

<210> SEQ ID NO 90
<211> LENGTH: 226
<212> TYPE: DNA
<213> ORGANISM: Conus sulcatus
<220> FEATURE:
<221> NAME/KEY: CDS
<222> LOCATION: (1)..(195)

<400> SEQUENCE: 90

```
atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc aat tca gat cgt gat cca gca tta ggt ggc agg aat gct gca gcc       96
Phe Asn Ser Asp Arg Asp Pro Ala Leu Gly Gly Arg Asn Ala Ala Ala
             20                  25                  30

aaa gcg tct gac aag atc gct tcg acc ctc aag aga aga gga tgc tgt      144
Lys Ala Ser Asp Lys Ile Ala Ser Thr Leu Lys Arg Arg Gly Cys Cys
         35                  40                  45
```

-continued

```
tcg tat ttt gac tgt aga atg atg ttt cca gaa atg tgt ggt tgg cga      192
Ser Tyr Phe Asp Cys Arg Met Met Phe Pro Glu Met Cys Gly Trp Arg
     50                  55                  60

ggc tgatgctcca ggaccctctg aaccacgacg t                               226
Gly
 65


<210> SEQ ID NO 91
<211> LENGTH: 65
<212> TYPE: PRT
<213> ORGANISM: Conus sulcatus

<400> SEQUENCE: 91

Met Phe Thr Val Phe Leu Leu Val Val Leu Ala Thr Thr Val Val Ser
  1               5                  10                  15

Phe Asn Ser Asp Arg Asp Pro Ala Leu Gly Gly Arg Asn Ala Ala Ala
             20                  25                  30

Lys Ala Ser Asp Lys Ile Ala Ser Thr Leu Lys Arg Arg Gly Cys Cys
         35                  40                  45

Ser Tyr Phe Asp Cys Arg Met Met Phe Pro Glu Met Cys Gly Trp Arg
     50                  55                  60

Gly
 65


<210> SEQ ID NO 92
<211> LENGTH: 226
<212> TYPE: DNA
<213> ORGANISM: Conus sulcatus
<220> FEATURE:
<221> NAME/KEY: CDS
<222> LOCATION: (1)..(195)

<400> SEQUENCE: 92

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc aat tca gat cgt gat cca gca tta ggt ggc agg aat gct gca gcc       96
Phe Asn Ser Asp Arg Asp Pro Ala Leu Gly Gly Arg Asn Ala Ala Ala
             20                  25                  30

ata gcg tct gac aag atc gct tcg acc ctc agg aga gga gga tgc tgt      144
Ile Ala Ser Asp Lys Ile Ala Ser Thr Leu Arg Arg Gly Gly Cys Cys
         35                  40                  45

tct ttt cct gcc tgt aga aag tat cgt cca gaa atg tgt ggt gga cga      192
Ser Phe Pro Ala Cys Arg Lys Tyr Arg Pro Glu Met Cys Gly Gly Arg
     50                  55                  60

cgc tgatgctcca ggaccctctg aaccacgacg t                               226
Arg
 65


<210> SEQ ID NO 93
<211> LENGTH: 65
<212> TYPE: PRT
<213> ORGANISM: Conus sulcatus

<400> SEQUENCE: 93

Met Phe Thr Val Phe Leu Leu Val Val Leu Ala Thr Thr Val Val Ser
  1               5                  10                  15

Phe Asn Ser Asp Arg Asp Pro Ala Leu Gly Gly Arg Asn Ala Ala Ala
             20                  25                  30

Ile Ala Ser Asp Lys Ile Ala Ser Thr Leu Arg Arg Gly Gly Cys Cys
         35                  40                  45
```

-continued

```
Ser Phe Pro Ala Cys Arg Lys Tyr Arg Pro Glu Met Cys Gly Gly Arg
     50                  55                  60

Arg
 65


<210> SEQ ID NO 94
<211> LENGTH: 211
<212> TYPE: DNA
<213> ORGANISM: Conus sulcatus
<220> FEATURE:
<221> NAME/KEY: CDS
<222> LOCATION: (1)..(180)

<400> SEQUENCE: 94

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat cat gaa tct gat cgc ggt gat gcc caa acc atc caa       96
Phe Thr Ser Asp His Glu Ser Asp Arg Gly Asp Ala Gln Thr Ile Gln
             20                  25                  30

gaa gtg ttt gag atg ttc gct ctg gac agc gat gga tgc tgt tgg cat      144
Glu Val Phe Glu Met Phe Ala Leu Asp Ser Asp Gly Cys Cys Trp His
         35                  40                  45

cct gct tgt ggc aga cac tat tgt ggt cga aga cgc tgatgctcca           190
Pro Ala Cys Gly Arg His Tyr Cys Gly Arg Arg Arg
     50                  55                  60

ggaccctctg aaccacgacg t                                              211


<210> SEQ ID NO 95
<211> LENGTH: 60
<212> TYPE: PRT
<213> ORGANISM: Conus sulcatus

<400> SEQUENCE: 95

Met Phe Thr Val Phe Leu Leu Val Val Leu Ala Thr Thr Val Val Ser
  1               5                  10                  15

Phe Thr Ser Asp His Glu Ser Asp Arg Gly Asp Ala Gln Thr Ile Gln
             20                  25                  30

Glu Val Phe Glu Met Phe Ala Leu Asp Ser Asp Gly Cys Cys Trp His
         35                  40                  45

Pro Ala Cys Gly Arg His Tyr Cys Gly Arg Arg Arg
     50                  55                  60


<210> SEQ ID NO 96
<211> LENGTH: 202
<212> TYPE: DNA
<213> ORGANISM: Conus sulcatus
<220> FEATURE:
<221> NAME/KEY: CDS
<222> LOCATION: (1)..(195)

<400> SEQUENCE: 96

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc aat tca gat cgt gat cca gca tta ggt ggc agg aat gct gca gcc       96
Phe Asn Ser Asp Arg Asp Pro Ala Leu Gly Gly Arg Asn Ala Ala Ala
             20                  25                  30

ata gcg tct gac aag atc gct tcg acc ctc agg aga gga gga tgc tgt      144
Ile Ala Ser Asp Lys Ile Ala Ser Thr Leu Arg Arg Gly Gly Cys Cys
         35                  40                  45

tct ttt gct gcc tgt aga aag tat cgt cca gaa atg tgt ggt gga cga      192
```

-continued

```
Ser Phe Ala Ala Cys Arg Lys Tyr Arg Pro Glu Met Cys Gly Gly Arg
     50                  55                  60

cgc tgatgct                                                       202
Arg
 65


<210> SEQ ID NO 97
<211> LENGTH: 65
<212> TYPE: PRT
<213> ORGANISM: Conus sulcatus

<400> SEQUENCE: 97

Met Phe Thr Val Phe Leu Leu Val Val Leu Ala Thr Thr Val Val Ser
  1               5                  10                  15

Phe Asn Ser Asp Arg Asp Pro Ala Leu Gly Gly Arg Asn Ala Ala Ala
             20                  25                  30

Ile Ala Ser Asp Lys Ile Ala Ser Thr Leu Arg Arg Gly Gly Cys Cys
         35                  40                  45

Ser Phe Ala Ala Cys Arg Lys Tyr Arg Pro Glu Met Cys Gly Gly Arg
     50                  55                  60

Arg
 65


<210> SEQ ID NO 98
<211> LENGTH: 220
<212> TYPE: DNA
<213> ORGANISM: Conus sulcatus
<220> FEATURE:
<221> NAME/KEY: CDS
<222> LOCATION: (1)..(189)

<400> SEQUENCE: 98

atg ttc acc gtg ttt ctg ttg gtt ctc ttg gca acc acc gtc gtt tcc       48
Met Phe Thr Val Phe Leu Leu Val Leu Leu Ala Thr Thr Val Val Ser
  1               5                  10                  15

ttc aat tca gat cgt gca tta ggt ggc agg aat gct gca gcc aaa gcg       96
Phe Asn Ser Asp Arg Ala Leu Gly Gly Arg Asn Ala Ala Ala Lys Ala
             20                  25                  30

tct gac aag atc ctt tcg aac ctc agg aga gga gga tgc tgt ttt cat      144
Ser Asp Lys Ile Leu Ser Asn Leu Arg Arg Gly Gly Cys Cys Phe His
         35                  40                  45

cct gtc tgt tac atc aat ctt cta gaa atg tgt cgt caa cga ggc          189
Pro Val Cys Tyr Ile Asn Leu Leu Glu Met Cys Arg Gln Arg Gly
     50                  55                  60

tgatcgtcca ggaccctctg aaccacgacg t                                   220


<210> SEQ ID NO 99
<211> LENGTH: 63
<212> TYPE: PRT
<213> ORGANISM: Conus sulcatus

<400> SEQUENCE: 99

Met Phe Thr Val Phe Leu Leu Val Leu Leu Ala Thr Thr Val Val Ser
  1               5                  10                  15

Phe Asn Ser Asp Arg Ala Leu Gly Gly Arg Asn Ala Ala Ala Lys Ala
             20                  25                  30

Ser Asp Lys Ile Leu Ser Asn Leu Arg Arg Gly Gly Cys Cys Phe His
         35                  40                  45

Pro Val Cys Tyr Ile Asn Leu Leu Glu Met Cys Arg Gln Arg Gly
     50                  55                  60
```

-continued

<210> SEQ ID NO 100
<211> LENGTH: 208
<212> TYPE: DNA
<213> ORGANISM: Conus consors
<220> FEATURE:
<221> NAME/KEY: CDS
<222> LOCATION: (1)..(177)

<400> SEQUENCE: 100

```
atg ttc acc gtg ttt ctg ttg gtt gtc ttg aca acc act gtc gtt tcc       48
Met Phe Thr Val Phe Leu Leu Val Val Leu Thr Thr Thr Val Val Ser
  1               5                  10                  15

ttc cct tca gat agt gca tct gat gtc agg gat gac gaa gcc aaa gac       96
Phe Pro Ser Asp Ser Ala Ser Asp Val Arg Asp Asp Glu Ala Lys Asp
             20                  25                  30

gaa agg tct gac atg tac aaa tcg aaa cgg aat gga cgc tgt tgc cat      144
Glu Arg Ser Asp Met Tyr Lys Ser Lys Arg Asn Gly Arg Cys Cys His
         35                  40                  45

cct gcc tgt ggc aaa cac ttt agt tgt gga cgc tgatgctcca ggaccctctg    197
Pro Ala Cys Gly Lys His Phe Ser Cys Gly Arg
     50                  55

aaccacgacg t                                                         208
```

<210> SEQ ID NO 101
<211> LENGTH: 59
<212> TYPE: PRT
<213> ORGANISM: Conus consors

<400> SEQUENCE: 101

```
Met Phe Thr Val Phe Leu Leu Val Val Leu Thr Thr Thr Val Val Ser
  1               5                  10                  15

Phe Pro Ser Asp Ser Ala Ser Asp Val Arg Asp Asp Glu Ala Lys Asp
             20                  25                  30

Glu Arg Ser Asp Met Tyr Lys Ser Lys Arg Asn Gly Arg Cys Cys His
         35                  40                  45

Pro Ala Cys Gly Lys His Phe Ser Cys Gly Arg
     50                  55
```

<210> SEQ ID NO 102
<211> LENGTH: 219
<212> TYPE: DNA
<213> ORGANISM: Conus stercusmuscarum
<220> FEATURE:
<221> NAME/KEY: CDS
<222> LOCATION: (1)..(189)

<400> SEQUENCE: 102

```
atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

tcc cct tca gat cgt gca tct gat ggc agg aat gcc gca gcc aac gag       96
Ser Pro Ser Asp Arg Ala Ser Asp Gly Arg Asn Ala Ala Ala Asn Glu
             20                  25                  30

aaa gcg tct gac gtg atc gcg ctg gcc ctc aag gga tgc tgt tcc aac      144
Lys Ala Ser Asp Val Ile Ala Leu Ala Leu Lys Gly Cys Cys Ser Asn
         35                  40                  45

cct gtc tgt cac ctg gag cat tca aac atg tgt ggt aga aga cgc          189
Pro Val Cys His Leu Glu His Ser Asn Met Cys Gly Arg Arg Arg
     50                  55                  60

tgatgctcca ggaccctctg aaccacgacg                                     219
```

-continued

<210> SEQ ID NO 103
<211> LENGTH: 63
<212> TYPE: PRT
<213> ORGANISM: Conus stercusmuscarum

<400> SEQUENCE: 103

Met Phe Thr Val Phe Leu Leu Val Val Leu Ala Thr Thr Val Val Ser
1 5 10 15

Ser Pro Ser Asp Arg Ala Ser Asp Gly Arg Asn Ala Ala Ala Asn Glu
20 25 30

Lys Ala Ser Asp Val Ile Ala Leu Ala Leu Lys Gly Cys Cys Ser Asn
35 40 45

Pro Val Cys His Leu Glu His Ser Asn Met Cys Gly Arg Arg Arg
50 55 60

<210> SEQ ID NO 104
<211> LENGTH: 248
<212> TYPE: DNA
<213> ORGANISM: Conus betulinus
<220> FEATURE:
<221> NAME/KEY: CDS
<222> LOCATION: (1)..(180)

<400> SEQUENCE: 104 atg ttc tcc gtg ttt ctg ttg gtt gtc ttg gca acc act gtc gtt tcc 48
Met Phe Ser Val Phe Leu Leu Val Val Leu Ala Thr Thr Val Val Ser
1 5 10 15 tcc act tca ggt ggt gca tct ggt ggc agg aag gct gca gcc aaa gcg 96
Ser Thr Ser Gly Gly Ala Ser Gly Gly Arg Lys Ala Ala Ala Lys Ala
20 25 30 tct aac cgg atc gct ctg acc gtc agg agt gca aca tgc tgt aat tat 144
Ser Asn Arg Ile Ala Leu Thr Val Arg Ser Ala Thr Cys Cys Asn Tyr
35 40 45 cct ccc tgt tac gag act tat cca gaa agt tgt ctg taacgtgaat 190
Pro Pro Cys Tyr Glu Thr Tyr Pro Glu Ser Cys Leu
50 55 60 catccagagc tttgtggctg aagacactga tgctccagga ccctctgaac cacgacgt 248

<210> SEQ ID NO 105
<211> LENGTH: 60
<212> TYPE: PRT
<213> ORGANISM: Conus betulinus

<400> SEQUENCE: 105

Met Phe Ser Val Phe Leu Leu Val Val Leu Ala Thr Thr Val Val Ser
1 5 10 15

Ser Thr Ser Gly Gly Ala Ser Gly Gly Arg Lys Ala Ala Ala Lys Ala
20 25 30

Ser Asn Arg Ile Ala Leu Thr Val Arg Ser Ala Thr Cys Cys Asn Tyr
35 40 45

Pro Pro Cys Tyr Glu Thr Tyr Pro Glu Ser Cys Leu
50 55 60

<210> SEQ ID NO 106
<211> LENGTH: 223
<212> TYPE: DNA
<213> ORGANISM: Conus betulinus
<220> FEATURE:
<221> NAME/KEY: CDS
<222> LOCATION: (1)..(183)

<400> SEQUENCE: 106

-continued

```
atg ttc acc gtg ttt ctg ttg gtt gtc ttg gca acc act gtg gtt tcc       48
Met Phe Thr Val Phe Leu Leu Val Val Leu Ala Thr Thr Val Val Ser
  1               5                  10                  15

ttc act tca ggt cgt gca ttt cgt ggc agg aat cgc gca gcc gac gac       96
Phe Thr Ser Gly Arg Ala Phe Arg Gly Arg Asn Arg Ala Ala Asp Asp
             20                  25                  30

aaa agg tct gac ctg gcc gct ctg agc gtc agg gga gga tgc tgt tcc      144
Lys Arg Ser Asp Leu Ala Ala Leu Ser Val Arg Gly Gly Cys Cys Ser
         35                  40                  45

cat cct gcc tgt gcg gtg aat cat cca gag ctt tgt ggc tgaagacgct      193
His Pro Ala Cys Ala Val Asn His Pro Glu Leu Cys Gly
     50                  55                  60

gatgccccag gaccctctga accacgacgt                                     223


<210> SEQ ID NO 107
<211> LENGTH: 61
<212> TYPE: PRT
<213> ORGANISM: Conus betulinus

<400> SEQUENCE: 107

Met Phe Thr Val Phe Leu Leu Val Val Leu Ala Thr Thr Val Val Ser
  1               5                  10                  15

Phe Thr Ser Gly Arg Ala Phe Arg Gly Arg Asn Arg Ala Ala Asp Asp
             20                  25                  30

Lys Arg Ser Asp Leu Ala Ala Leu Ser Val Arg Gly Gly Cys Cys Ser
         35                  40                  45

His Pro Ala Cys Ala Val Asn His Pro Glu Leu Cys Gly
     50                  55                  60


<210> SEQ ID NO 108
<211> LENGTH: 248
<212> TYPE: DNA
<213> ORGANISM: Conus betulinus
<220> FEATURE:
<221> NAME/KEY: CDS
<222> LOCATION: (1)..(180)

<400> SEQUENCE: 108

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc act tca ggt cgt gca tct ggt ggc agg aat gct gca gcc aaa gcg       96
Phe Thr Ser Gly Arg Ala Ser Gly Gly Arg Asn Ala Ala Ala Lys Ala
             20                  25                  30

tct aac cgg atc gct atg gcc atc agc agt gga gca tgc tgt gca tat      144
Ser Asn Arg Ile Ala Met Ala Ile Ser Ser Gly Ala Cys Cys Ala Tyr
         35                  40                  45

cct ccc tgt ttc gag gct tat cca gaa aga tgt ctg taacgtgaat          190
Pro Pro Cys Phe Glu Ala Tyr Pro Glu Arg Cys Leu
     50                  55                  60

catccagacc tttgtggctg aagacgctga tgccccagga ccctctgaac cacgacgt      248


<210> SEQ ID NO 109
<211> LENGTH: 60
<212> TYPE: PRT
<213> ORGANISM: Conus betulinus

<400> SEQUENCE: 109

Met Phe Thr Val Phe Leu Leu Val Val Leu Ala Thr Thr Val Val Ser
  1               5                  10                  15

Phe Thr Ser Gly Arg Ala Ser Gly Gly Arg Asn Ala Ala Ala Lys Ala
```

-continued

```
            20                  25                  30

Ser Asn Arg Ile Ala Met Ala Ile Ser Ser Gly Ala Cys Cys Ala Tyr
        35                  40                  45

Pro Pro Cys Phe Glu Ala Tyr Pro Glu Arg Cys Leu
    50                  55                  60


<210> SEQ ID NO 110
<211> LENGTH: 223
<212> TYPE: DNA
<213> ORGANISM: Conus betulinus
<220> FEATURE:
<221> NAME/KEY: CDS
<222> LOCATION: (1)..(192)

<400> SEQUENCE: 110

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc act tca gat cgt gca ttt cgt ggc agg aat tcc gca gcc aac gac       96
Phe Thr Ser Asp Arg Ala Phe Arg Gly Arg Asn Ser Ala Ala Asn Asp
            20                  25                  30

aaa agg tct gac ctg gcc gct ctg agc gtc agg aga gga tgc tgc tcc      144
Lys Arg Ser Asp Leu Ala Ala Leu Ser Val Arg Arg Gly Cys Cys Ser
        35                  40                  45

cat ccc gcc tgt agc gtg aat cat cca gag ctt tgt ggt aga aga cgc      192
His Pro Ala Cys Ser Val Asn His Pro Glu Leu Cys Gly Arg Arg Arg
    50                  55                  60

tgatgcccca ggaccctctg aaccacgacg t                                   223


<210> SEQ ID NO 111
<211> LENGTH: 64
<212> TYPE: PRT
<213> ORGANISM: Conus betulinus

<400> SEQUENCE: 111

Met Phe Thr Val Phe Leu Leu Val Val Leu Ala Thr Thr Val Val Ser
  1               5                  10                  15

Phe Thr Ser Asp Arg Ala Phe Arg Gly Arg Asn Ser Ala Ala Asn Asp
            20                  25                  30

Lys Arg Ser Asp Leu Ala Ala Leu Ser Val Arg Arg Gly Cys Cys Ser
        35                  40                  45

His Pro Ala Cys Ser Val Asn His Pro Glu Leu Cys Gly Arg Arg Arg
    50                  55                  60


<210> SEQ ID NO 112
<211> LENGTH: 248
<212> TYPE: DNA
<213> ORGANISM: Conus betulinus
<220> FEATURE:
<221> NAME/KEY: CDS
<222> LOCATION: (1)..(180)

<400> SEQUENCE: 112

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc act tca ggt cgt gca tct ggt ggc agg aat gct gca gcc aaa gcg       96
Phe Thr Ser Gly Arg Ala Ser Gly Gly Arg Asn Ala Ala Ala Lys Ala
            20                  25                  30

tct aac cgg atc gct ctg atc gtc agg aat gca gaa tgc tgt tat tat      144
Ser Asn Arg Ile Ala Leu Ile Val Arg Asn Ala Glu Cys Cys Tyr Tyr
        35                  40                  45
```

```
cct ccc tgt tac gag gct tat cca gaa att tgt ctg taacgtgaat          190
Pro Pro Cys Tyr Glu Ala Tyr Pro Glu Ile Cys Leu
     50                  55                  60

catccagacc tttgtggctg aagaccctga tgctccagga ccctctgaac cacgacgt      248


<210> SEQ ID NO 113
<211> LENGTH: 60
<212> TYPE: PRT
<213> ORGANISM: Conus betulinus

<400> SEQUENCE: 113

Met Phe Thr Val Phe Leu Leu Val Val Leu Ala Thr Thr Val Val Ser
  1               5                  10                  15

Phe Thr Ser Gly Arg Ala Ser Gly Gly Arg Asn Ala Ala Ala Lys Ala
             20                  25                  30

Ser Asn Arg Ile Ala Leu Ile Val Arg Asn Ala Glu Cys Cys Tyr Tyr
         35                  40                  45

Pro Pro Cys Tyr Glu Ala Tyr Pro Glu Ile Cys Leu
     50                  55                  60


<210> SEQ ID NO 114
<211> LENGTH: 207
<212> TYPE: DNA
<213> ORGANISM: Conus pennaceus
<220> FEATURE:
<221> NAME/KEY: CDS
<222> LOCATION: (1)..(168)

<400> SEQUENCE: 114

atg ttc acc gtg ttt ctg ttg gtt gtc ttg gca acc acc gtc att tcc       48
Met Phe Thr Val Phe Leu Leu Val Val Leu Ala Thr Thr Val Ile Ser
  1               5                  10                  15

ttc act tca gat cgt gca tct gat ggc ggg aat gcc gca gcg tct gac       96
Phe Thr Ser Asp Arg Ala Ser Asp Gly Gly Asn Ala Ala Ala Ser Asp
             20                  25                  30

ctg atc gct ctg acc atc aag gga tgc tgt tct cat cct ccc tgt gcc      144
Leu Ile Ala Leu Thr Ile Lys Gly Cys Cys Ser His Pro Pro Cys Ala
         35                  40                  45

atg aat aat cca gac tat tgt ggt tgacgacgct gatgctccag gaccctctga     198
Met Asn Asn Pro Asp Tyr Cys Gly
     50                  55

accacgacg                                                            207


<210> SEQ ID NO 115
<211> LENGTH: 56
<212> TYPE: PRT
<213> ORGANISM: Conus pennaceus

<400> SEQUENCE: 115

Met Phe Thr Val Phe Leu Leu Val Val Leu Ala Thr Thr Val Ile Ser
  1               5                  10                  15

Phe Thr Ser Asp Arg Ala Ser Asp Gly Gly Asn Ala Ala Ala Ser Asp
             20                  25                  30

Leu Ile Ala Leu Thr Ile Lys Gly Cys Cys Ser His Pro Pro Cys Ala
         35                  40                  45

Met Asn Asn Pro Asp Tyr Cys Gly
     50                  55


<210> SEQ ID NO 116
<211> LENGTH: 207
```

-continued

```
<212> TYPE: DNA
<213> ORGANISM: Conus pennaceus
<220> FEATURE:
<221> NAME/KEY: CDS
<222> LOCATION: (1)..(168)

<400> SEQUENCE: 116

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat cgt gca tct gat ggc ggg aat gcc gca atg tct gac       96
Phe Thr Ser Asp Arg Ala Ser Asp Gly Gly Asn Ala Ala Met Ser Asp
             20                  25                  30

ctg atc gct ctg acc atc aag gga tgc tgt tct cat cct ccc tgt ttc      144
Leu Ile Ala Leu Thr Ile Lys Gly Cys Cys Ser His Pro Pro Cys Phe
         35                  40                  45

ctg aat aat cca gac tat tgt ggt tgacgacgct gatgctccag gaccctctga     198
Leu Asn Asn Pro Asp Tyr Cys Gly
     50                  55

accacgacg                                                            207


<210> SEQ ID NO 117
<211> LENGTH: 56
<212> TYPE: PRT
<213> ORGANISM: Conus pennaceus

<400> SEQUENCE: 117

Met Phe Thr Val Phe Leu Leu Val Val Leu Ala Thr Thr Val Val Ser
  1               5                  10                  15

Phe Thr Ser Asp Arg Ala Ser Asp Gly Gly Asn Ala Ala Met Ser Asp
             20                  25                  30

Leu Ile Ala Leu Thr Ile Lys Gly Cys Cys Ser His Pro Pro Cys Phe
         35                  40                  45

Leu Asn Asn Pro Asp Tyr Cys Gly
     50                  55


<210> SEQ ID NO 118
<211> LENGTH: 210
<212> TYPE: DNA
<213> ORGANISM: Conus stercusmuscarum
<220> FEATURE:
<221> NAME/KEY: CDS
<222> LOCATION: (1)..(171)

<400> SEQUENCE: 118

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc cct tca gat cgt gaa tct gat ggc gcg aat gac gaa gcc cgc acc       96
Phe Pro Ser Asp Arg Glu Ser Asp Gly Ala Asn Asp Glu Ala Arg Thr
             20                  25                  30

gac gag cct gag gag cac gga ccg gac agg aat gga tgc tgt agg aat      144
Asp Glu Pro Glu Glu His Gly Pro Asp Arg Asn Gly Cys Cys Arg Asn
         35                  40                  45

cct gcc tgt gag agc cac aga tgt ggt tgacgacgct gatgctccag            191
Pro Ala Cys Glu Ser His Arg Cys Gly
     50                  55

gaccctctga accacgacg                                                 210


<210> SEQ ID NO 119
<211> LENGTH: 57
<212> TYPE: PRT
```

-continued

<213> ORGANISM: Conus stercusmuscarum

<400> SEQUENCE: 119

```
Met Phe Thr Val Phe Leu Leu Val Val Leu Ala Thr Thr Val Val Ser
  1               5                  10                  15

Phe Pro Ser Asp Arg Glu Ser Asp Gly Ala Asn Asp Glu Ala Arg Thr
             20                  25                  30

Asp Glu Pro Glu Glu His Gly Pro Asp Arg Asn Gly Cys Cys Arg Asn
         35                  40                  45

Pro Ala Cys Glu Ser His Arg Cys Gly
     50                  55
```

<210> SEQ ID NO 120
<211> LENGTH: 210
<212> TYPE: DNA
<213> ORGANISM: Conus circumcisus
<220> FEATURE:
<221> NAME/KEY: CDS
<222> LOCATION: (1)..(180)

<400> SEQUENCE: 120

```
atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc cct tca gat cgt gca tct gat ggc agg aat gcc gca gcc agc gac       96
Phe Pro Ser Asp Arg Ala Ser Asp Gly Arg Asn Ala Ala Ala Ser Asp
             20                  25                  30

aga gcg tct gac gcg gcc cac cag gga tgc tgt tcc aac cct gtc tgt      144
Arg Ala Ser Asp Ala Ala His Gln Gly Cys Cys Ser Asn Pro Val Cys
         35                  40                  45

cac gtg gaa cat cca gaa ctt tgt cgt aga aga cgc tgatgctcca           190
His Val Glu His Pro Glu Leu Cys Arg Arg Arg Arg
     50                  55                  60

ggaccctctg aaccacgacg                                                210
```

<210> SEQ ID NO 121
<211> LENGTH: 60
<212> TYPE: PRT
<213> ORGANISM: Conus circumcisus

<400> SEQUENCE: 121

```
Met Phe Thr Val Phe Leu Leu Val Val Leu Ala Thr Thr Val Val Ser
  1               5                  10                  15

Phe Pro Ser Asp Arg Ala Ser Asp Gly Arg Asn Ala Ala Ala Ser Asp
             20                  25                  30

Arg Ala Ser Asp Ala Ala His Gln Gly Cys Cys Ser Asn Pro Val Cys
         35                  40                  45

His Val Glu His Pro Glu Leu Cys Arg Arg Arg Arg
     50                  55                  60
```

<210> SEQ ID NO 122
<211> LENGTH: 213
<212> TYPE: DNA
<213> ORGANISM: Conus circumcisus
<220> FEATURE:
<221> NAME/KEY: CDS
<222> LOCATION: (1)..(174)

<400> SEQUENCE: 122

```
atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15
```

-continued

```
ttc cct tca aat cgt gaa tct gat ggc gcg aat gcc gaa gtc cgc acc       96
Phe Pro Ser Asn Arg Glu Ser Asp Gly Ala Asn Ala Glu Val Arg Thr
            20                  25                  30

gac gag cct gag gag cac gac gaa ctg ggc ggg aat gga tgc tgt ggg      144
Asp Glu Pro Glu Glu His Asp Glu Leu Gly Gly Asn Gly Cys Cys Gly
        35                  40                  45

aat cct gac tgt acg agc cac agt tgt gat tgacgacgct gatgctccag        194
Asn Pro Asp Cys Thr Ser His Ser Cys Asp
    50                  55

gaccctctga accacgacg                                                 213


<210> SEQ ID NO 123
<211> LENGTH: 58
<212> TYPE: PRT
<213> ORGANISM: Conus circumcisus

<400> SEQUENCE: 123

Met Phe Thr Val Phe Leu Leu Val Val Leu Ala Thr Thr Val Val Ser
  1               5                  10                  15

Phe Pro Ser Asn Arg Glu Ser Asp Gly Ala Asn Ala Glu Val Arg Thr
            20                  25                  30

Asp Glu Pro Glu Glu His Asp Glu Leu Gly Gly Asn Gly Cys Cys Gly
        35                  40                  45

Asn Pro Asp Cys Thr Ser His Ser Cys Asp
    50                  55


<210> SEQ ID NO 124
<211> LENGTH: 207
<212> TYPE: DNA
<213> ORGANISM: Conus episcopatus
<220> FEATURE:
<221> NAME/KEY: CDS
<222> LOCATION: (1)..(168)

<400> SEQUENCE: 124

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat cgt gca tct gat agc agg aag gac gca gcg tct ggc       96
Phe Thr Ser Asp Arg Ala Ser Asp Ser Arg Lys Asp Ala Ala Ser Gly
            20                  25                  30

ctg atc gct ctg acc atc aag gga tgc tgt tct gat cct cgc tgt aac      144
Leu Ile Ala Leu Thr Ile Lys Gly Cys Cys Ser Asp Pro Arg Cys Asn
        35                  40                  45

atg aat aat cca gac tat tgt ggt tgacgacgct gatgctccag gaccctctga     198
Met Asn Asn Pro Asp Tyr Cys Gly
    50                  55

accacgacg                                                            207


<210> SEQ ID NO 125
<211> LENGTH: 56
<212> TYPE: PRT
<213> ORGANISM: Conus episcopatus

<400> SEQUENCE: 125

Met Phe Thr Val Phe Leu Leu Val Val Leu Ala Thr Thr Val Val Ser
  1               5                  10                  15

Phe Thr Ser Asp Arg Ala Ser Asp Ser Arg Lys Asp Ala Ala Ser Gly
            20                  25                  30

Leu Ile Ala Leu Thr Ile Lys Gly Cys Cys Ser Asp Pro Arg Cys Asn
```

-continued

```
        35                  40                  45

Met Asn Asn Pro Asp Tyr Cys Gly
     50                  55


<210> SEQ ID NO 126
<211> LENGTH: 213
<212> TYPE: DNA
<213> ORGANISM: Conus sponsalis
<220> FEATURE:
<221> NAME/KEY: CDS
<222> LOCATION: (1)..(174)

<400> SEQUENCE: 126

atg tcc acc gtg ttt ctg ttg gtt gtc ctc gca acc acc gtc gtt tcc       48
Met Ser Thr Val Phe Leu Leu Val Val Leu Ala Thr Thr Val Val Ser
  1               5                  10                  15

ttc act gta gat cgt gca tct gat ggc agg gat gtc gca atc gac gac       96
Phe Thr Val Asp Arg Ala Ser Asp Gly Arg Asp Val Ala Ile Asp Asp
             20                  25                  30

aga ttg gtg tct ctc cct cag atc gcc cat gct gac tgt tgt tcc gat      144
Arg Leu Val Ser Leu Pro Gln Ile Ala His Ala Asp Cys Cys Ser Asp
        35                  40                  45

cct gcc tgc aag cag acg ccc ggt tgt cgt taaagacgct gctgctccag        194
Pro Ala Cys Lys Gln Thr Pro Gly Cys Arg
     50                  55

gaccctctga accacgacg                                                 213


<210> SEQ ID NO 127
<211> LENGTH: 58
<212> TYPE: PRT
<213> ORGANISM: Conus sponsalis

<400> SEQUENCE: 127

Met Ser Thr Val Phe Leu Leu Val Val Leu Ala Thr Thr Val Val Ser
  1               5                  10                  15

Phe Thr Val Asp Arg Ala Ser Asp Gly Arg Asp Val Ala Ile Asp Asp
             20                  25                  30

Arg Leu Val Ser Leu Pro Gln Ile Ala His Ala Asp Cys Cys Ser Asp
        35                  40                  45

Pro Ala Cys Lys Gln Thr Pro Gly Cys Arg
     50                  55


<210> SEQ ID NO 128
<211> LENGTH: 221
<212> TYPE: DNA
<213> ORGANISM: Conus sponsalis
<220> FEATURE:
<221> NAME/KEY: CDS
<222> LOCATION: (1)..(168)

<400> SEQUENCE: 128

atg ttc acc gtg ttt ctg ttg gtt gtc ttg gca acc acc gtc gct tcc       48
Met Phe Thr Val Phe Leu Leu Val Val Leu Ala Thr Thr Val Ala Ser
  1               5                  10                  15

ttc att atc gat gat cca tct gat ggc agg aat att gca gtc gac gac       96
Phe Ile Ile Asp Asp Pro Ser Asp Gly Arg Asn Ile Ala Val Asp Asp
             20                  25                  30

aga ggg ctt ttc tct acg ctc ttc cat gct gat tgc tgt gaa aat cct      144
Arg Gly Leu Phe Ser Thr Leu Phe His Ala Asp Cys Cys Glu Asn Pro
        35                  40                  45

gcc tgt aga cac acg cag ggt tgt tgatctttgt tcttcaaaga cactgctggc     198
Ala Cys Arg His Thr Gln Gly Cys
```

-continued

```
     50                  55

ccaggaccct ctgaaccacg acg                                           221


<210> SEQ ID NO 129
<211> LENGTH: 56
<212> TYPE: PRT
<213> ORGANISM: Conus sponsalis

<400> SEQUENCE: 129

Met Phe Thr Val Phe Leu Leu Val Val Leu Ala Thr Thr Val Ala Ser
  1               5                  10                  15

Phe Ile Ile Asp Asp Pro Ser Asp Gly Arg Asn Ile Ala Val Asp Asp
             20                  25                  30

Arg Gly Leu Phe Ser Thr Leu Phe His Ala Asp Cys Cys Glu Asn Pro
         35                  40                  45

Ala Cys Arg His Thr Gln Gly Cys
     50                  55


<210> SEQ ID NO 130
<211> LENGTH: 220
<212> TYPE: DNA
<213> ORGANISM: Conus dalli
<220> FEATURE:
<221> NAME/KEY: CDS
<222> LOCATION: (1)..(180)

<400> SEQUENCE: 130

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat cgt gca ttt cgt ggc agg aat gcc gca gcc aaa gag       96
Phe Thr Ser Asp Arg Ala Phe Arg Gly Arg Asn Ala Ala Ala Lys Glu
             20                  25                  30

tct ggc ctg gtc ggt ctg acc gac aag acg cga gga tgc tgt tct cat      144
Ser Gly Leu Val Gly Leu Thr Asp Lys Thr Arg Gly Cys Cys Ser His
         35                  40                  45

cct gcc tgt aac gta gat cat cca gaa att tgt ggt tgaagacgct           190
Pro Ala Cys Asn Val Asp His Pro Glu Ile Cys Gly
     50                  55                  60

gatgctccag gaccctctga accacgacgt                                     220


<210> SEQ ID NO 131
<211> LENGTH: 60
<212> TYPE: PRT
<213> ORGANISM: Conus dalli

<400> SEQUENCE: 131

Met Phe Thr Val Phe Leu Leu Val Val Leu Ala Thr Thr Val Val Ser
  1               5                  10                  15

Phe Thr Ser Asp Arg Ala Phe Arg Gly Arg Asn Ala Ala Ala Lys Glu
             20                  25                  30

Ser Gly Leu Val Gly Leu Thr Asp Lys Thr Arg Gly Cys Cys Ser His
         35                  40                  45

Pro Ala Cys Asn Val Asp His Pro Glu Ile Cys Gly
     50                  55                  60


<210> SEQ ID NO 132
<211> LENGTH: 208
<212> TYPE: DNA
<213> ORGANISM: Conus dalli
<220> FEATURE:
```

-continued

```
<221> NAME/KEY: CDS
<222> LOCATION: (1)..(177)

<400> SEQUENCE: 132

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat ggt gca tct gat gac agg aaa gcc gct gcg tct gac       96
Phe Thr Ser Asp Gly Ala Ser Asp Asp Arg Lys Ala Ala Ala Ser Asp
             20                  25                  30

ctg atc act ctg acc atc aag gga tgc tgt tct cgt cct ccc tgt atc      144
Leu Ile Thr Leu Thr Ile Lys Gly Cys Cys Ser Arg Pro Pro Cys Ile
         35                  40                  45

gcg aat aat cca gac ttg tgt ggt cga cga cgc tgatgctcca ggaccctctg    197
Ala Asn Asn Pro Asp Leu Cys Gly Arg Arg Arg
     50                  55

aaccacgacg t                                                         208


<210> SEQ ID NO 133
<211> LENGTH: 59
<212> TYPE: PRT
<213> ORGANISM: Conus dalli

<400> SEQUENCE: 133

Met Phe Thr Val Phe Leu Leu Val Val Leu Ala Thr Thr Val Val Ser
  1               5                  10                  15

Phe Thr Ser Asp Gly Ala Ser Asp Asp Arg Lys Ala Ala Ala Ser Asp
             20                  25                  30

Leu Ile Thr Leu Thr Ile Lys Gly Cys Cys Ser Arg Pro Pro Cys Ile
         35                  40                  45

Ala Asn Asn Pro Asp Leu Cys Gly Arg Arg Arg
     50                  55


<210> SEQ ID NO 134
<211> LENGTH: 223
<212> TYPE: DNA
<213> ORGANISM: Conus dalli
<220> FEATURE:
<221> NAME/KEY: CDS
<222> LOCATION: (1)..(192)

<400> SEQUENCE: 134

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

tcc act tca ggt cgt cgt gca ttt cat ggc agg aat gcc gca gcc aaa       96
Ser Thr Ser Gly Arg Arg Ala Phe His Gly Arg Asn Ala Ala Ala Lys
             20                  25                  30

gcg tct gga ctg gtc ggt ctg act gac agg aga cca caa tgc tgt agt      144
Ala Ser Gly Leu Val Gly Leu Thr Asp Arg Arg Pro Gln Cys Cys Ser
         35                  40                  45

gat cct cgc tgt aac gta ggt cat cca gaa ctt tgt ggt gga aga cgc      192
Asp Pro Arg Cys Asn Val Gly His Pro Glu Leu Cys Gly Gly Arg Arg
     50                  55                  60

tgatgctcca ggaccctctg aaccacaacg t                                   223


<210> SEQ ID NO 135
<211> LENGTH: 64
<212> TYPE: PRT
<213> ORGANISM: Conus dalli

<400> SEQUENCE: 135
```

-continued

```
Met Phe Thr Val Phe Leu Leu Val Val Leu Ala Thr Thr Val Val Ser
  1               5                  10                  15

Ser Thr Ser Gly Arg Arg Ala Phe His Gly Arg Asn Ala Ala Ala Lys
             20                  25                  30

Ala Ser Gly Leu Val Gly Leu Thr Asp Arg Arg Pro Gln Cys Cys Ser
         35                  40                  45

Asp Pro Arg Cys Asn Val Gly His Pro Glu Leu Cys Gly Gly Arg Arg
     50                  55                  60


<210> SEQ ID NO 136
<211> LENGTH: 220
<212> TYPE: DNA
<213> ORGANISM: Conus dalli
<220> FEATURE:
<221> NAME/KEY: CDS
<222> LOCATION: (1)..(189)

<400> SEQUENCE: 136

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

tcc act tca ggt cgt gca ttt cat ggc agg aat gcc gca gcc aaa gcg       96
Ser Thr Ser Gly Arg Ala Phe His Gly Arg Asn Ala Ala Ala Lys Ala
             20                  25                  30

tct ggc ctg gtc ggt ctg acc gac aag agg caa gta tgc tgt agt gat      144
Ser Gly Leu Val Gly Leu Thr Asp Lys Arg Gln Val Cys Cys Ser Asp
         35                  40                  45

cct cgc tgt aac gta ggt cat cca gaa att tgt ggt gga aga cgc          189
Pro Arg Cys Asn Val Gly His Pro Glu Ile Cys Gly Gly Arg Arg
     50                  55                  60

tgatgctcca ggaccctctg aaccacgacg t                                   220


<210> SEQ ID NO 137
<211> LENGTH: 63
<212> TYPE: PRT
<213> ORGANISM: Conus dalli

<400> SEQUENCE: 137

Met Phe Thr Val Phe Leu Leu Val Val Leu Ala Thr Thr Val Val Ser
  1               5                  10                  15

Ser Thr Ser Gly Arg Ala Phe His Gly Arg Asn Ala Ala Ala Lys Ala
             20                  25                  30

Ser Gly Leu Val Gly Leu Thr Asp Lys Arg Gln Val Cys Cys Ser Asp
         35                  40                  45

Pro Arg Cys Asn Val Gly His Pro Glu Ile Cys Gly Gly Arg Arg
     50                  55                  60


<210> SEQ ID NO 138
<211> LENGTH: 208
<212> TYPE: DNA
<213> ORGANISM: Conus achatinus
<220> FEATURE:
<221> NAME/KEY: CDS
<222> LOCATION: (1)..(180)

<400> SEQUENCE: 138

atg ttc acc gtg ttt ctg ttg gtt gtc ttg aca acc act gtc gtt tcc       48
Met Phe Thr Val Phe Leu Leu Val Val Leu Thr Thr Thr Val Val Ser
  1               5                  10                  15

ttc cct tca gat agt gca tct ggt ggc agg gat gac gag gcc aaa gac       96
Phe Pro Ser Asp Ser Ala Ser Gly Gly Arg Asp Asp Glu Ala Lys Asp
```

-continued

```
             20                  25                  30

gaa agg tct gac atg tac gaa ttg aaa cgg aat gga cgc tgt tgc cat      144
Glu Arg Ser Asp Met Tyr Glu Leu Lys Arg Asn Gly Arg Cys Cys His
         35                  40                  45

cct gcc tgt ggt ggc aaa tac gtt aaa tgt gga cgc tgatgctcca           190
Pro Ala Cys Gly Gly Lys Tyr Val Lys Cys Gly Arg
     50                  55                  60

ggaccctctc gaaccacg                                                  208


<210> SEQ ID NO 139
<211> LENGTH: 60
<212> TYPE: PRT
<213> ORGANISM: Conus achatinus

<400> SEQUENCE: 139

Met Phe Thr Val Phe Leu Leu Val Val Leu Thr Thr Thr Val Val Ser
  1               5                  10                  15

Phe Pro Ser Asp Ser Ala Ser Gly Gly Arg Asp Asp Glu Ala Lys Asp
             20                  25                  30

Glu Arg Ser Asp Met Tyr Glu Leu Lys Arg Asn Gly Arg Cys Cys His
         35                  40                  45

Pro Ala Cys Gly Gly Lys Tyr Val Lys Cys Gly Arg
     50                  55                  60


<210> SEQ ID NO 140
<211> LENGTH: 211
<212> TYPE: DNA
<213> ORGANISM: Conus bullatus
<220> FEATURE:
<221> NAME/KEY: CDS
<222> LOCATION: (1)..(174)

<400> SEQUENCE: 140

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc tct aca gat gat gaa tct gat ggc tcg aat gaa gaa ccc agc gcc       96
Phe Ser Thr Asp Asp Glu Ser Asp Gly Ser Asn Glu Glu Pro Ser Ala
             20                  25                  30

gac cag act gcc agg tcc tca atg aac agg gcg cct gga tgc tgt aac      144
Asp Gln Thr Ala Arg Ser Ser Met Asn Arg Ala Pro Gly Cys Cys Asn
         35                  40                  45

aat cct gcc tgt gtg aag cac aga tgt gga tgacgctgat gctccaggac        194
Asn Pro Ala Cys Val Lys His Arg Cys Gly
     50                  55

cctctgaacc acgacgt                                                   211


<210> SEQ ID NO 141
<211> LENGTH: 58
<212> TYPE: PRT
<213> ORGANISM: Conus bullatus

<400> SEQUENCE: 141

Met Phe Thr Val Phe Leu Leu Val Val Leu Ala Thr Thr Val Val Ser
  1               5                  10                  15

Phe Ser Thr Asp Asp Glu Ser Asp Gly Ser Asn Glu Glu Pro Ser Ala
             20                  25                  30

Asp Gln Thr Ala Arg Ser Ser Met Asn Arg Ala Pro Gly Cys Cys Asn
         35                  40                  45

Asn Pro Ala Cys Val Lys His Arg Cys Gly
```

-continued

```
     50                  55


<210> SEQ ID NO 142
<211> LENGTH: 214
<212> TYPE: DNA
<213> ORGANISM: Conus bullatus
<220> FEATURE:
<221> NAME/KEY: CDS
<222> LOCATION: (1)..(177)

<400> SEQUENCE: 142

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc tct aca gat gat gaa tct gat ggc tcg aat gaa gaa ccc agc gcc       96
Phe Ser Thr Asp Asp Glu Ser Asp Gly Ser Asn Glu Glu Pro Ser Ala
             20                  25                  30

gac cag gct gcc agg tcc gca atg aac agg ccg cct gga tgc tgt aac      144
Asp Gln Ala Ala Arg Ser Ala Met Asn Arg Pro Pro Gly Cys Cys Asn
         35                  40                  45

aat cct gcc tgt gtg aag cac aga tgt ggt gga tgacgctgat gctccaggac    197
Asn Pro Ala Cys Val Lys His Arg Cys Gly Gly
     50                  55

cctctgaacc acgacgt                                                   214


<210> SEQ ID NO 143
<211> LENGTH: 59
<212> TYPE: PRT
<213> ORGANISM: Conus bullatus

<400> SEQUENCE: 143

Met Phe Thr Val Phe Leu Leu Val Val Leu Ala Thr Thr Val Val Ser
  1               5                  10                  15

Phe Ser Thr Asp Asp Glu Ser Asp Gly Ser Asn Glu Glu Pro Ser Ala
             20                  25                  30

Asp Gln Ala Ala Arg Ser Ala Met Asn Arg Pro Pro Gly Cys Cys Asn
         35                  40                  45

Asn Pro Ala Cys Val Lys His Arg Cys Gly Gly
     50                  55


<210> SEQ ID NO 144
<211> LENGTH: 208
<212> TYPE: DNA
<213> ORGANISM: Conus bullatus
<220> FEATURE:
<221> NAME/KEY: CDS
<222> LOCATION: (1)..(177)

<400> SEQUENCE: 144

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc cct tca gat cgt gac tct gat ggc gcg gat gcc gaa gcc agt gac       96
Phe Pro Ser Asp Arg Asp Ser Asp Gly Ala Asp Ala Glu Ala Ser Asp
             20                  25                  30

gag cct gtt gag ttc gaa agg gac gag aat gga tgc tgt tgg aat cct      144
Glu Pro Val Glu Phe Glu Arg Asp Glu Asn Gly Cys Cys Trp Asn Pro
         35                  40                  45

tcc tgt ccg agg ccc aga tgt aca gga cga cgc taatgctcca ggaccctctg    197
Ser Cys Pro Arg Pro Arg Cys Thr Gly Arg Arg
     50                  55

aaccacgacg t                                                         208
```

-continued

```
<210> SEQ ID NO 145
<211> LENGTH: 59
<212> TYPE: PRT
<213> ORGANISM: Conus bullatus

<400> SEQUENCE: 145

Met Phe Thr Val Phe Leu Leu Val Val Leu Ala Thr Thr Val Val Ser
  1               5                  10                  15

Phe Pro Ser Asp Arg Asp Ser Asp Gly Ala Asp Ala Glu Ala Ser Asp
             20                  25                  30

Glu Pro Val Glu Phe Glu Arg Asp Glu Asn Gly Cys Cys Trp Asn Pro
         35                  40                  45

Ser Cys Pro Arg Pro Arg Cys Thr Gly Arg Arg
     50                  55


<210> SEQ ID NO 146
<211> LENGTH: 211
<212> TYPE: DNA
<213> ORGANISM: Conus bullatus
<220> FEATURE:
<221> NAME/KEY: CDS
<222> LOCATION: (1)..(180)

<400> SEQUENCE: 146

atg ttc acc gtg ttt ctg ttg gtt gtc ttg aca acc act gtc gtt tcc       48
Met Phe Thr Val Phe Leu Leu Val Val Leu Thr Thr Thr Val Val Ser
  1               5                  10                  15

ttc cct tca gat cgt gca tct gat ggc agg aat gcc gca gcc aac gac       96
Phe Pro Ser Asp Arg Ala Ser Asp Gly Arg Asn Ala Ala Ala Asn Asp
             20                  25                  30

aaa gcg tct gac gtg gtc acg ctg gtc ctc aag gga tgc tgt tcc acc      144
Lys Ala Ser Asp Val Val Thr Leu Val Leu Lys Gly Cys Cys Ser Thr
         35                  40                  45

cct ccc tgt gct gtg ctg tat tgt ggt aga aga cgc tgatgctcca           190
Pro Pro Cys Ala Val Leu Tyr Cys Gly Arg Arg Arg
     50                  55                  60

ggaccctctg aaccacgacg t                                              211


<210> SEQ ID NO 147
<211> LENGTH: 60
<212> TYPE: PRT
<213> ORGANISM: Conus bullatus

<400> SEQUENCE: 147

Met Phe Thr Val Phe Leu Leu Val Val Leu Thr Thr Thr Val Val Ser
  1               5                  10                  15

Phe Pro Ser Asp Arg Ala Ser Asp Gly Arg Asn Ala Ala Ala Asn Asp
             20                  25                  30

Lys Ala Ser Asp Val Val Thr Leu Val Leu Lys Gly Cys Cys Ser Thr
         35                  40                  45

Pro Pro Cys Ala Val Leu Tyr Cys Gly Arg Arg Arg
     50                  55                  60


<210> SEQ ID NO 148
<211> LENGTH: 212
<212> TYPE: DNA
<213> ORGANISM: Conus distans
<220> FEATURE:
<221> NAME/KEY: CDS
<222> LOCATION: (1)..(171)
```

-continued

<400> SEQUENCE: 148

```
atg ttc acc gtg ttt ctg ttg gtt gtc ttc gca tcc tct gtc acc tta       48
Met Phe Thr Val Phe Leu Leu Val Val Phe Ala Ser Ser Val Thr Leu
  1               5                  10                  15

gat cgt gca tct tat ggc agg tat gcc tca ccc gtc gac aga gcg tct       96
Asp Arg Ala Ser Tyr Gly Arg Tyr Ala Ser Pro Val Asp Arg Ala Ser
             20                  25                  30

gcc ctg atc gct cag gcc atc ctt cga gat tgc tgc tcc aat cct cct      144
Ala Leu Ile Ala Gln Ala Ile Leu Arg Asp Cys Cys Ser Asn Pro Pro
         35                  40                  45

tgt gcc cat aat aat cca gac tgt cgt taaagacgct gcttgctcca            191
Cys Ala His Asn Asn Pro Asp Cys Arg
     50                  55

ggaccctctg aaccacgacg t                                              212
```

<210> SEQ ID NO 149
<211> LENGTH: 57
<212> TYPE: PRT
<213> ORGANISM: Conus distans

<400> SEQUENCE: 149

```
Met Phe Thr Val Phe Leu Leu Val Val Phe Ala Ser Ser Val Thr Leu
  1               5                  10                  15

Asp Arg Ala Ser Tyr Gly Arg Tyr Ala Ser Pro Val Asp Arg Ala Ser
             20                  25                  30

Ala Leu Ile Ala Gln Ala Ile Leu Arg Asp Cys Cys Ser Asn Pro Pro
         35                  40                  45

Cys Ala His Asn Asn Pro Asp Cys Arg
     50                  55
```

<210> SEQ ID NO 150
<211> LENGTH: 63
<212> TYPE: DNA
<213> ORGANISM: Conus textile
<220> FEATURE:
<221> NAME/KEY: CDS
<222> LOCATION: (1)..(60)

<400> SEQUENCE: 150

```
gga tgc tgt tct aat cct ccc tgt atc gcg aag aat cca cac atg tgt       48
Gly Cys Cys Ser Asn Pro Pro Cys Ile Ala Lys Asn Pro His Met Cys
  1               5                  10                  15

ggt gga aga cgc tga                                                   63
Gly Gly Arg Arg
             20
```

<210> SEQ ID NO 151
<211> LENGTH: 20
<212> TYPE: PRT
<213> ORGANISM: Conus textile

<400> SEQUENCE: 151

```
Gly Cys Cys Ser Asn Pro Pro Cys Ile Ala Lys Asn Pro His Met Cys
  1               5                  10                  15

Gly Gly Arg Arg
             20
```

<210> SEQ ID NO 152
<211> LENGTH: 220
<212> TYPE: DNA
<213> ORGANISM: Conus consors
<220> FEATURE:

-continued

```
<221> NAME/KEY: CDS
<222> LOCATION: (1)..(189)

<400> SEQUENCE: 152

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

ttc cct tca gat cgt gca tct gat ggc agg aat gcc gca gcc aac gac       96
Phe Pro Ser Asp Arg Ala Ser Asp Gly Arg Asn Ala Ala Ala Asn Asp
             20                  25                  30

aaa gcg tct gac gtg atc acg ctg gcc ctc aag gga tgc tgt tcc aac      144
Lys Ala Ser Asp Val Ile Thr Leu Ala Leu Lys Gly Cys Cys Ser Asn
         35                  40                  45

cct gtc tgt cac ttg gag cat tca aac ctt tgt ggt aga aga cgc          189
Pro Val Cys His Leu Glu His Ser Asn Leu Cys Gly Arg Arg Arg
     50                  55                  60

tgatgctcca ggaccctctg aaccacgacg t                                   220


<210> SEQ ID NO 153
<211> LENGTH: 63
<212> TYPE: PRT
<213> ORGANISM: Conus consors

<400> SEQUENCE: 153

Met Phe Thr Val Phe Leu Leu Val Val Leu Ala Thr Thr Val Val Ser
  1               5                  10                  15

Phe Pro Ser Asp Arg Ala Ser Asp Gly Arg Asn Ala Ala Ala Asn Asp
             20                  25                  30

Lys Ala Ser Asp Val Ile Thr Leu Ala Leu Lys Gly Cys Cys Ser Asn
         35                  40                  45

Pro Val Cys His Leu Glu His Ser Asn Leu Cys Gly Arg Arg Arg
     50                  55                  60


<210> SEQ ID NO 154
<211> LENGTH: 15
<212> TYPE: PRT
<213> ORGANISM: Conus musicus
<220> FEATURE:
<221> NAME/KEY: SITE
<222> LOCATION: (4)..(12)
<223> OTHER INFORMATION: Xaa at residues 4, 11 and 12 is Tyr, nor-Tyr,
      mono-halo-Tyr, di-halo-Tyr, O-sulpho-Tyr,
      O-phospho-Tyr or nitro-Tyr. Xaa at residue 6 is
      Pro or hydroxy-Pro.
<220> FEATURE:
<221> NAME/KEY: SITE
<222> LOCATION: (9)..(15)
<223> OTHER INFORMATION: Xaa at residues 9, 10 and 15 is Lys,
      N-methyl-Lys, N,N-dimethyl-Lys or N,N,N-trimethyl-Lys; Xaa at
      residue 14 is Trp (D or L) or halo-Trp.

<400> SEQUENCE: 154

Gly Cys Cys Xaa Asn Xaa Val Cys Xaa Xaa Xaa Xaa Cys Xaa Xaa
  1               5                  10                  15


<210> SEQ ID NO 155
<211> LENGTH: 16
<212> TYPE: PRT
<213> ORGANISM: Conus purpurascens
<220> FEATURE:
<221> NAME/KEY: SITE
<222> LOCATION: (1)..(3)
<223> OTHER INFORMATION: Xaa at residue 1 is Gln or pyro-Glu; Xaa at
      residue 2 is Glu or gamma-carboxy-Glu; Xaa at
      residues 3 and 9 is Pro or hydroxy-Pro.
<220> FEATURE:
```

-continued

<221> NAME/KEY: SITE
<222> LOCATION: (13)
<223> OTHER INFORMATION: Xaa at residue 13 is Lys, N-methyl-Lys, N,N-dimethyl-Lys or N,N,N-trimethyl-Lys.

<400> SEQUENCE: 155

Xaa Xaa Xaa Gly Cys Cys Arg His Xaa Ala Cys Gly Xaa Asn Arg Cys
1 5 10 15

<210> SEQ ID NO 156
<211> LENGTH: 13
<212> TYPE: PRT
<213> ORGANISM: Conus musicus
<220> FEATURE:
<221> NAME/KEY: SITE
<222> LOCATION: (5)..(11)
<223> OTHER INFORMATION: Xaa at residues 5 and 11 is Pro or hydroxy-Pro.

<400> SEQUENCE: 156

Cys Cys Ala Asp Xaa Asp Cys Arg Phe Arg Xaa Gly Cys
1 5 10

<210> SEQ ID NO 157
<211> LENGTH: 17
<212> TYPE: PRT
<213> ORGANISM: Conus musicus
<220> FEATURE:
<221> NAME/KEY: SITE
<222> LOCATION: (4)..(13)
<223> OTHER INFORMATION: Xaa at residues 4 and 13 is Tyr, nor-Tyr, mono-halo-Tyr, di-halo-Tyr, O-sulpho-Tyr, O-phospho-Tyr or nitro-Tyr; Xaa at residues 6 and 10 is Pro or hydroxy-Pro.
<220> FEATURE:
<221> NAME/KEY: SITE
<222> LOCATION: (9)..(17)
<223> OTHER INFORMATION: Xaa at residues 9 and 16 is Trp (D or L) or halo-Trp; Xaa at residues 11 and 17 is Lys, N-methyl-Lys, N,N-dimethyl-Lys or N,N,N-trimethyl-Lys.

<400> SEQUENCE: 157

Gly Cys Cys Xaa Asn Xaa Ser Cys Xaa Xaa Xaa Thr Xaa Cys Ser Xaa
1 5 10 15

Xaa

<210> SEQ ID NO 158
<211> LENGTH: 13
<212> TYPE: PRT
<213> ORGANISM: Conus musicus
<220> FEATURE:
<221> NAME/KEY: SITE
<222> LOCATION: (5)..(8)
<223> OTHER INFORMATION: Xaa at residue 5 is Pro or hydroxy-Pro; Xaa at residue 8 is Lys, N-methyl-Lys, N,N-dimethyl-Lys or N,N,N-trimethyl-Lys.
<220> FEATURE:
<221> NAME/KEY: SITE
<222> LOCATION: (9)..(11)
<223> OTHER INFORMATION: Xaa at residue 9 is Glu or gamma-carboxy-Glu; Xaa at residue 11 is Tyr, nor-Tyr, mono-halo-Tyr, di-halo-Tyr, O-sulpho-Tyr, O-phospho-Tyr or nitro-Tyr.

<400> SEQUENCE: 158

Cys Cys Ser Asn Xaa Thr Cys Xaa Xaa Thr Xaa Gly Cys
1 5 10

<210> SEQ ID NO 159
<211> LENGTH: 13

-continued

<212> TYPE: PRT
<213> ORGANISM: Conus musicus
<220> FEATURE:
<221> NAME/KEY: SITE
<222> LOCATION: (5)..(11)
<223> OTHER INFORMATION: Xaa at residues 5 and 11 is Pro or hydroxy-Pro; Xaa at residue 8 is Lys, N-methyl-Lys, N,N-dimethyl-Lys or N,N,N-trimethyl-Lys.

<400> SEQUENCE: 159

Cys Cys Ala Asn Xaa Ile Cys Xaa Asn Thr Xaa Gly Cys
1 5 10

<210> SEQ ID NO 160
<211> LENGTH: 13
<212> TYPE: PRT
<213> ORGANISM: Conus musicus
<220> FEATURE:
<221> NAME/KEY: SITE
<222> LOCATION: (5)..(8)
<223> OTHER INFORMATION: Xaa at residue 5 is Pro or hydroxy-Pro; Xaa at residue 8 is Lys, N-methyl-Lys, N,N-dimethyl-Lys or N,N,N-trimethyl-Lys.
<220> FEATURE:
<221> NAME/KEY: SITE
<222> LOCATION: (9)..(11)
<223> OTHER INFORMATION: Xaa at residue 9 is Glu or gamma-carboxy-Glu; Xaa at residue 11 is Tyr, mono-halo-Tyr, di-halo-Tyr, O-sulpho-Tyr, O-phospho-Tyr or nitro-Tyr.

<400> SEQUENCE: 160

Cys Cys Asn Asn Xaa Thr Cys Xaa Xaa Thr Xaa Gly Cys
1 5 10

<210> SEQ ID NO 161
<211> LENGTH: 13
<212> TYPE: PRT
<213> ORGANISM: Conus musicus
<220> FEATURE:
<221> NAME/KEY: SITE
<222> LOCATION: (5)..(8)
<223> OTHER INFORMATION: Xaa at residue 5 is Pro or hydroxy-Pro; Xaa at residue 8 is Lys, N-methyl-Lys, N,N-dimethyl-Lys or N,N,N-trimethyl-Lys.
<220> FEATURE:
<221> NAME/KEY: SITE
<222> LOCATION: (9)..(11)
<223> OTHER INFORMATION: Xaa at residue 9 is Glu or gamma-carboxy-Glu; Xaa at residue 11 is Tyr, nor-Tyr, mono-halo-Tyr, di-halo-Tyr, O-sulpho-Tyr, O-phospho-Tyr or nitro-Tyr.

<400> SEQUENCE: 161

Cys Cys Ser Asn Xaa Val Cys Xaa Xaa Thr Xaa Gly Cys
1 5 10

<210> SEQ ID NO 162
<211> LENGTH: 17
<212> TYPE: PRT
<213> ORGANISM: Conus betulinus
<220> FEATURE:
<221> NAME/KEY: SITE
<222> LOCATION: (6)..(14)
<223> OTHER INFORMATION: Xaa at residue 6 is Tyr, nor-Tyr, mono-halo-Tyr, di-halo-Tyr, O-sulpho-Tyr, O-phospho-Tyr or nitro-Tyr; Xaa at residues 7, 8 and 14 is Pro or hydroxy-Pro.
<220> FEATURE:
<221> NAME/KEY: SITE
<222> LOCATION: (15)
<223> OTHER INFORMATION: Xaa at residue 15 is Lys, N-methyl-Lys, N,N-dimethyl-Lys or N,N,N-trimethyl-Lys.

-continued

<400> SEQUENCE: 162

Gly Gly Cys Cys Ser Xaa Xaa Xaa Cys Ile Ala Ser Asn Xaa Xaa Cys
1 5 10 15

Gly

<210> SEQ ID NO 163
<211> LENGTH: 15
<212> TYPE: PRT
<213> ORGANISM: Conus lividus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 163

Gly Cys Cys Ser His Xaa Val Cys Ser Ala Met Ser Xaa Ile Cys
1 5 10 15

<210> SEQ ID NO 164
<211> LENGTH: 15
<212> TYPE: PRT
<213> ORGANISM: Conus musicus
<220> FEATURE:
<221> NAME/KEY: SITE
<222> LOCATION: (4)..(12)
<223> OTHER INFORMATION: Xaa at residues 4 and 12 is Lys, N-methyl-Lys, N,N-dimethyl-Lys or N,N,N-trimethyl-Lys; Xaa at residue 6 is Pro or hydroxy-Pro.
<220> FEATURE:
<221> NAME/KEY: SITE
<222> LOCATION: (7)..(14)
<223> OTHER INFORMATION: Xaa at residues 7 and 14 is Tyr, mono-halo-Tyr, di-halo-Tyr, O-sulpho-Tyr, O-phospho-Tyr or nitro-Tyr.

<400> SEQUENCE: 164

Gly Cys Cys Xaa Asn Xaa Xaa Cys Gly Ala Ser Xaa Thr Xaa Cys
1 5 10 15

<210> SEQ ID NO 165
<211> LENGTH: 15
<212> TYPE: PRT
<213> ORGANISM: Conus omaria
<220> FEATURE:
<221> NAME/KEY: SITE
<222> LOCATION: (5)..(13)
<223> OTHER INFORMATION: Xaa at residue 5 is Tyr, nor-Tyr, mono-halo-Tyr, di-halo-Tyr, O-sulpho-Tyr, O-phospho-Tyr or nitro-Tyr; Xaa at residues 6, 7 and 13 is Pro or hydroxy-Pro.

<400> SEQUENCE: 165

Gly Cys Cys Ser Xaa Xaa Xaa Cys Phe Ala Thr Asn Xaa Asp Cys
1 5 10 15

<210> SEQ ID NO 166
<211> LENGTH: 17
<212> TYPE: PRT
<213> ORGANISM: Conus radiatus
<220> FEATURE:
<221> NAME/KEY: SITE
<222> LOCATION: (6)..(14)
<223> OTHER INFORMATION: Xaa at residue 6 is Tyr, nor-Tyr, mono-halo-Tyr, di-halo-Tyr, O-sulpho-Tyr, O-phospho-Tyr or nitro-Tyr; Xaa at residues 7, 8 and 14 is Pro or hydroxy-Pro.

<400> SEQUENCE: 166

Gly Gly Cys Cys Ser Xaa Xaa Xaa Cys Ile Ala Asn Asn Xaa Leu Cys

-continued

```
  1               5                   10                  15

Ala


<210> SEQ ID NO 167
<211> LENGTH: 17
<212> TYPE: PRT
<213> ORGANISM: Conus radiatus
<220> FEATURE:
<221> NAME/KEY: SITE
<222> LOCATION: (6)..(14)
<223> OTHER INFORMATION: Xaa at residue 6 is Tyr, nor-Tyr,
      mono-halo-Tyr, di-halo-Tyr, O-sulpho-Tyr, O-phospho-Tyr or
      nitro-Tyr; Xaa at residues 7, 8 and 14 is Pro or
      hydroxy-Pro.

<400> SEQUENCE: 167

Gly Gly Cys Cys Ser Xaa Xaa Xaa Cys Ile Ala Asn Asn Xaa Phe Cys
  1               5                   10                  15

Ala


<210> SEQ ID NO 168
<211> LENGTH: 16
<212> TYPE: PRT
<213> ORGANISM: Conus virgo
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro.

<400> SEQUENCE: 168

Asp Cys Cys Ser Asn Xaa Xaa Cys Ser Gln Asn Asn Xaa Asp Cys Met
  1               5                   10                  15


<210> SEQ ID NO 169
<211> LENGTH: 16
<212> TYPE: PRT
<213> ORGANISM: Conus virgo
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro.

<400> SEQUENCE: 169

Asp Cys Cys Ser Asn Xaa Xaa Cys Ala His Asn Asn Xaa Asp Cys Arg
  1               5                   10                  15


<210> SEQ ID NO 170
<211> LENGTH: 20
<212> TYPE: PRT
<213> ORGANISM: Conus achatinus
<220> FEATURE:
<221> NAME/KEY: SITE
<222> LOCATION: (1)..(14)
<223> OTHER INFORMATION: Xaa at residues 1, 11 and 14 is Glu or
      gamma-carboxy-Glu; Xaa at residue 6 is Pro or
      hydroxy-Pro.

<400> SEQUENCE: 170

Xaa Cys Cys Thr Asn Xaa Val Cys His Ala Xaa His Gln Xaa Leu Cys
  1               5                   10                  15

Ala Arg Arg Arg
            20


<210> SEQ ID NO 171
<211> LENGTH: 16
```

-continued

<212> TYPE: PRT
<213> ORGANISM: Conus achatinus
<220> FEATURE:
<221> NAME/KEY: SITE
<222> LOCATION: (6)..(10)
<223> OTHER INFORMATION: Xaa at residue 6 is Pro or hydroxy-Pro; Xaa at residue 11 is Glu or gamma-carboxy-Glu.

<400> SEQUENCE: 171

Gly Cys Cys Ser Asn Xaa Val Cys His Leu Xaa His Ser Asn Leu Cys
1 5 10 15

<210> SEQ ID NO 172
<211> LENGTH: 20
<212> TYPE: PRT
<213> ORGANISM: Conus achatinus
<220> FEATURE:
<221> NAME/KEY: SITE
<222> LOCATION: (1)..(14)
<223> OTHER INFORMATION: Xaa at residues 1, 11 and 14 is Glu or gamma-carboxy-Glu; Xaa at residue 6 is Pro or hydroxy-Pro.

<400> SEQUENCE: 172

Xaa Cys Cys Thr Asn Xaa Val Cys His Val Xaa His Gln Xaa Leu Cys
1 5 10 15

Ala Arg Arg Arg
20

<210> SEQ ID NO 173
<211> LENGTH: 17
<212> TYPE: PRT
<213> ORGANISM: Conus ammiralis
<220> FEATURE:
<221> NAME/KEY: SITE
<222> LOCATION: (1)..(15)
<223> OTHER INFORMATION: Xaa at residue 1 is Gln or pyro-Glu; Xaa at residues 2 and 15 is Glu or gamma-carboxy-Glu; Xaa at residue 6 is Tyr, nor-Tyr, mono-halo-Tyr, di-halo-Tyr, O-sulpho-Tyr, O-phospho-Tyr or
<220> FEATURE:
<221> NAME/KEY: SITE
<222> LOCATION: (6)..(14)
<223> OTHER INFORMATION: nitro-Tyr; Xaa at residues 7 and 14 is Pro or hydroxy-Pro.

<400> SEQUENCE: 173

Xaa Xaa Cys Cys Ser Xaa Xaa Ala Cys Asn Leu Asp His Xaa Xaa Leu
1 5 10 15

Cys

<210> SEQ ID NO 174
<211> LENGTH: 18
<212> TYPE: PRT
<213> ORGANISM: Conus ammiralis
<220> FEATURE:
<221> NAME/KEY: SITE
<222> LOCATION: (1)..(15)
<223> OTHER INFORMATION: Xaa at residues 1, 7 and 14 is Pro or hydroxy-Pro; Xaa at residues 2 and 15 is Glu or gamma-carboxy-Glu.

<400> SEQUENCE: 174

Xaa Xaa Cys Cys Ser Asp Xaa Arg Cys Asn Ser Thr His Xaa Xaa Leu
1 5 10 15

Cys Gly

<210> SEQ ID NO 175

-continued

<211> LENGTH: 21
<212> TYPE: PRT
<213> ORGANISM: Conus arenatus
<220> FEATURE:
<221> NAME/KEY: SITE
<222> LOCATION: (7)..(12)
<223> OTHER INFORMATION: Xaa at residues 7 and 8 is Pro or hydroxy-Pro; Xaa at residue 10 is Trp (D or L) or halo-Trp; Xaa at residues 11 and 12 is Lys, N-methyl-Lys, N,N-dimethyl-Lys or N,N,N-trimethyl-Lys.
<220> FEATURE:
<221> NAME/KEY: SITE
<222> LOCATION: (13)..(19)
<223> OTHER INFORMATION: Xaa at residue 13 is Tyr, nor-Tyr, mono-halo-Tyr, di-halo-Tyr, O-sulpho-Tyr, O-phospho-Tyr or nitro-Tyr ; Xaa at residue 19 is Glu or gamma-carboxy-Glu.

<400> SEQUENCE: 175

```
Leu Asn Cys Cys Met Ile Xaa Xaa Cys Xaa Xaa Xaa Xaa Gly Asp Arg
  1               5                  10                  15

Cys Ser Xaa Val Arg
             20
```

<210> SEQ ID NO 176
<211> LENGTH: 22
<212> TYPE: PRT
<213> ORGANISM: Conus arenatus
<220> FEATURE:
<221> NAME/KEY: SITE
<222> LOCATION: (9)..(20)
<223> OTHER INFORMATION: Xaa at residue 9 is Pro or hydroxy-Pro; Xaa at residues 12 and 20 is Glu or gamma-carboxy-Glu; Xaa at residue 14 is Tyr, nor-Tyr, mono-halo-Tyr, di-halo-Tyr, O-sulpho-Tyr, O-phospho-Tyr or
<220> FEATURE:
<221> NAME/KEY: SITE
<222> LOCATION: (9)..(20)
<223> OTHER INFORMATION: nitro-Tyr.

<400> SEQUENCE: 176

```
Ala Phe Gly Cys Cys Asp Leu Ile Xaa Cys Leu Xaa Arg Xaa Gly Asn
  1               5                  10                  15

Arg Cys Asn Xaa Val His
             20
```

<210> SEQ ID NO 177
<211> LENGTH: 21
<212> TYPE: PRT
<213> ORGANISM: Conus arenatus
<220> FEATURE:
<221> NAME/KEY: SITE
<222> LOCATION: (8)..(16)
<223> OTHER INFORMATION: Xaa at residue 8 is Pro or hydroxy-Pro; Xaa at residue 10 is Trp (D or L) or halo-Trp; Xaa at residues 12 and 16 is Lys, N-methyl-Lys, N,N-dimethyl-Lys or N,N,N-trimethyl-Lys.
<220> FEATURE:
<221> NAME/KEY: SITE
<222> LOCATION: (11)..(19)
<223> OTHER INFORMATION: Xaa at residues 11 and 19 is Glu or gamma-carboxy-Glu; Xaa at residue 13 is Tyr, mono-halo-Tyr, di-halo-Tyr, O-sulpho-Tyr, O-phospho-Tyr or nitro-Tyr.

<400> SEQUENCE: 177

```
Leu Gly Cys Cys Asn Val Thr Xaa Cys Xaa Xaa Xaa Xaa Gly Asp Xaa
  1               5                  10                  15

Cys Asn Xaa Val Arg
             20
```

-continued

<210> SEQ ID NO 178
<211> LENGTH: 20
<212> TYPE: PRT
<213> ORGANISM: Conus arenatus
<220> FEATURE:
<221> NAME/KEY: SITE
<222> LOCATION: (2)..(14)
<223> OTHER INFORMATION: Xaa at residue 2 is Glu or gamma-carboxy-Glu; Xaa at residues 7 and 14 is Pro or hydroxy-Pro.

<400> SEQUENCE: 178

Asp Xaa Cys Cys Ser Asn Xaa Ala Cys Arg Val Asn Asn Xaa His Val
1 5 10 15

Cys Arg Arg Arg
20

<210> SEQ ID NO 179
<211> LENGTH: 21
<212> TYPE: PRT
<213> ORGANISM: Conus arenatus
<220> FEATURE:
<221> NAME/KEY: SITE
<222> LOCATION: (7)..(13)
<223> OTHER INFORMATION: Xaa at residue 7 is Pro or hydroxy-Pro; Xaa at residue 10 is Trp (D or L) or halo-Trp; Xaa at residue 12 is Glu or gamma-carboxy-Glu; Xaa at residue 13 is Tyr, nor-Tyr, mono-halo-Tyr,
<220> FEATURE:
<221> NAME/KEY: SITE
<222> LOCATION: (13)..(19)
<223> OTHER INFORMATION: di-halo-Tyr, O-sulpho-Tyr, O-phospho-Tyr or nitro-Tyr; Xaa at residues 14 and 19 is Lys, N-methyl-Lys, N,N-dimethyl-Lys or N,N,N-trimethyl-Lys.

<400> SEQUENCE: 179

Leu Asn Cys Cys Ser Ile Xaa Gly Cys Xaa Asn Xaa Xaa Xaa Asp Arg
1 5 10 15

Cys Ser Xaa Val Arg
20

<210> SEQ ID NO 180
<211> LENGTH: 18
<212> TYPE: PRT
<213> ORGANISM: Conus aurisiacus
<220> FEATURE:
<221> NAME/KEY: SITE
<222> LOCATION: (7)..(14)
<223> OTHER INFORMATION: Xaa at residues 7 and 14 is Pro or hydroxy-Pro; Xaa at residue 10 is Tyr, mono-halo-Tyr, di-halo-Tyr, O-sulpho-Tyr, O-phospho-Tyr or nitro-Tyr.

<400> SEQUENCE: 180

Gly Gly Cys Cys Ser His Xaa Val Cys Xaa Phe Asn Asn Xaa Gln Met
1 5 10 15

Cys Arg

<210> SEQ ID NO 181
<211> LENGTH: 18
<212> TYPE: PRT
<213> ORGANISM: Conus aurisiacus
<220> FEATURE:
<221> NAME/KEY: SITE
<222> LOCATION: (7)..(14)
<223> OTHER INFORMATION: Xaa at residues 7 and 14 is Pro or hydroxy-Pro.

<400> SEQUENCE: 181

-continued

```
Gly Gly Cys Cys Ser His Xaa Val Cys Asn Leu Asn Asn Xaa Gln Met
  1               5                  10                  15

Cys Arg


<210> SEQ ID NO 182
<211> LENGTH: 17
<212> TYPE: PRT
<213> ORGANISM: Conus bandanus
<220> FEATURE:
<221> NAME/KEY: SITE
<222> LOCATION: (6)..(15)
<223> OTHER INFORMATION: Xaa at residues 6 and 7 is Pro or hydroxy-Pro;
      Xaa at residues 9 and 15 is Tyr, mono-halo-Tyr,
      di-halo-Tyr, O-sulpho-Tyr, O-phospho-Tyr or
      nitro-Tyr.

<400> SEQUENCE: 182

Gly Cys Cys Ser His Xaa Xaa Cys Xaa Ala Asn Asn Gln Ala Xaa Cys
  1               5                  10                  15

Asn


<210> SEQ ID NO 183
<211> LENGTH: 17
<212> TYPE: PRT
<213> ORGANISM: Conus betulinus
<220> FEATURE:
<221> NAME/KEY: SITE
<222> LOCATION: (7)..(15)
<223> OTHER INFORMATION: Xaa at residues 7 and 14 is Pro and
      hydroxy-Pro; Xaa at residue 15 is Glu or gamma-carboxy-Glu.

<400> SEQUENCE: 183

Gly Gly Cys Cys Ser His Xaa Ala Cys Ser Val Thr His Xaa Xaa Leu
  1               5                  10                  15

Cys


<210> SEQ ID NO 184
<211> LENGTH: 18
<212> TYPE: PRT
<213> ORGANISM: Conus betulinus
<220> FEATURE:
<221> NAME/KEY: SITE
<222> LOCATION: (6)..(12)
<223> OTHER INFORMATION: Xaa at residue 6 is Tyr, nor-Tyr,
      mono-halo-Tyr, di-halo-Tyr, O-sulpho-Tyr, O-phospho-Tyr or
      nitro-Tyr; Xaa at residue 7 is Pro and
      hydroxy-Pro; Xaa at residue 12 is Glu or
<220> FEATURE:
<221> NAME/KEY: SITE
<222> LOCATION: (6)..(12)
<223> OTHER INFORMATION: gamma-carboxy-Glu.

<400> SEQUENCE: 184

Gly Gly Cys Cys Ser Xaa Xaa Ala Cys Ser Val Xaa His Gln Asp Leu
  1               5                  10                  15

Cys Asp


<210> SEQ ID NO 185
<211> LENGTH: 25
<212> TYPE: PRT
<213> ORGANISM: Conus caracteristicus
<220> FEATURE:
<221> NAME/KEY: SITE
<222> LOCATION: (8)..(22)
<223> OTHER INFORMATION: Xaa at residues 8 and 22 is Pro or hydroxy-Pro;
      Xaa at residue 10 is Trp (D or L) or halo-Trp; Xaa
      at residue 13 is Tyr, nor-Tyr, mono-halo-Tyr,
      di-halo-Tyr, O-sulpho-Tyr, O-phospho-Tyr or
```

-continued

```
<220> FEATURE:
<221> NAME/KEY: SITE
<222> LOCATION: (8)..(22)
<223> OTHER INFORMATION: nitro-Tyr; Xaa at residues 15, 16 and 19 is Glu
      or gamma-carboxy-Glu.

<400> SEQUENCE: 185

Val Ser Cys Cys Val Val Arg Xaa Cys Xaa Ile Arg Xaa Gln Xaa Xaa
  1               5                  10                  15

Cys Leu Xaa Ala Asp Xaa Arg Thr Leu
             20                  25


<210> SEQ ID NO 186
<211> LENGTH: 21
<212> TYPE: PRT
<213> ORGANISM: Conus caracteristicus
<220> FEATURE:
<221> NAME/KEY: SITE
<222> LOCATION: (1)..(19)
<223> OTHER INFORMATION: Xaa at residue 1 is Gln or pyro-Glu; Xaa at
      residue 7 is Pro or hydroxy-Pro; Xaa at residue 10
      is Trp (D or L) or halo-Trp; Xaa at residues 11
      and 19 is Glu or gamma-carboxy-Glu.
<220> FEATURE:
<221> NAME/KEY: SITE
<222> LOCATION: (12)..(16)
<223> OTHER INFORMATION: Xaa at residues 12 and 16 is Lys, N-methyl-Lys,
      N,N-dimethyl-Lys or N,N,N-trimethyl-Lys; Xaa at
      residue 13 is Tyr, mono-halo-Tyr, di-halo-Tyr,
      O-sulpho-Tyr, O-phospho-Tyr or nitro-Tyr.

<400> SEQUENCE: 186

Xaa Asn Cys Cys Ser Ile Xaa Gly Cys Xaa Xaa Xaa Xaa Gly Asp Xaa
  1               5                  10                  15

Cys Ser Xaa Val Arg
             20


<210> SEQ ID NO 187
<211> LENGTH: 16
<212> TYPE: PRT
<213> ORGANISM: Conus catus
<220> FEATURE:
<221> NAME/KEY: SITE
<222> LOCATION: (6)..(13)
<223> OTHER INFORMATION: Xaa at residues 6 and 13 is Pro or hydroxy-Pro;
      Xaa at residue 11 is Glu or gamma-carboxy-Glu.

<400> SEQUENCE: 187

Gly Cys Cys Ser Asn Xaa Val Cys His Leu Xaa His Xaa Asn Ala Cys
  1               5                  10                  15


<210> SEQ ID NO 188
<211> LENGTH: 17
<212> TYPE: PRT
<213> ORGANISM: Conus catus
<220> FEATURE:
<221> NAME/KEY: SITE
<222> LOCATION: (6)..(13)
<223> OTHER INFORMATION: Xaa at residues 6 and 13 is Pro or hydroxy-Pro;
      Xaa at residue 9 is Tyr, nor-Tyr, mono-halo-Tyr,
      di-halo-Tyr, O-sulpho-Tyr, O-phospho-Tyr or
      nitro-Tyr.

<400> SEQUENCE: 188

Gly Cys Cys Ser Asn Xaa Ile Cys Xaa Phe Asn Asn Xaa Arg Ile Cys
  1               5                  10                  15

Arg
```

-continued

<210> SEQ ID NO 189
<211> LENGTH: 17
<212> TYPE: PRT
<213> ORGANISM: Conus episcopatus
<220> FEATURE:
<221> NAME/KEY: SITE
<222> LOCATION: (1)..(14)
<223> OTHER INFORMATION: Xaa at residues 1 and 14 is Glu or gamma-carboxy-Glu; Xaa at residues 6, 7 and 13 is Pro or hydroxy-Pro; Xaa at residue 10 is Trp (D or L) or halo-Trp.
<220> FEATURE:
<221> NAME/KEY: SITE
<222> LOCATION: (11)
<223> OTHER INFORMATION: Xaa at residue 11 is Lys, N-methyl-Lys, N,N-dimethyl-Lys or N,N,N-trimethyl-Lys.

<400> SEQUENCE: 189

```
Xaa Cys Cys Ser Gln Xaa Xaa Cys Arg Xaa Xaa His Xaa Xaa Leu Cys
  1               5                  10                  15

Ser
```

<210> SEQ ID NO 190
<211> LENGTH: 16
<212> TYPE: PRT
<213> ORGANISM: Conus geographus
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 190

```
Gly Cys Cys Ser His Xaa Ala Cys Ala Gly Asn Asn Gln His Ile Cys
  1               5                  10                  15
```

<210> SEQ ID NO 191
<211> LENGTH: 18
<212> TYPE: PRT
<213> ORGANISM: Conus geographus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 191

```
Gly Cys Cys Ala Val Xaa Ser Cys Arg Leu Arg Asn Xaa Asp Leu Cys
  1               5                  10                  15

Gly Gly
```

<210> SEQ ID NO 192
<211> LENGTH: 16
<212> TYPE: PRT
<213> ORGANISM: Conus imperialis
<220> FEATURE:
<221> NAME/KEY: NP_BIND
<222> LOCATION: (6)..(13)
<223> OTHER INFORMATION: Xaa at residues 6 and 13 is Pro or hydroxy-Pro.

<400> SEQUENCE: 192

```
Gly Cys Cys Ser His Xaa Ala Cys Asn Val Asn Asn Xaa His Ile Cys
  1               5                  10                  15
```

<210> SEQ ID NO 193
<211> LENGTH: 20
<212> TYPE: PRT
<213> ORGANISM: Conus lividus
<220> FEATURE:
<221> NAME/KEY: SITE
<222> LOCATION: (2)..(10)

-continued

<223> OTHER INFORMATION: Xaa at residues 2, 7, 9 and 10 is Pro or hydroxy-Pro; Xaa at residues 3 and 4 is Glu or gamma-carboxy-Glu.

<400> SEQUENCE: 193

Thr Xaa Xaa Xaa Cys Cys Xaa Asn Xaa Xaa Cys Phe Ala Thr Asn Ser
1 5 10 15

Asp Ile Cys Gly
20

<210> SEQ ID NO 194
<211> LENGTH: 17
<212> TYPE: PRT
<213> ORGANISM: Conus lividus
<220> FEATURE:
<221> NAME/KEY: SITE
<222> LOCATION: (7)..(12)
<223> OTHER INFORMATION: Xaa at residue 7 is Pro or hydroxy-Pro; Xaa at residue 12 is Lys, N-methyl-Lys, N,N-dimethyl-Lys or N,N,N-trimethyl-Lys.

<400> SEQUENCE: 194

Asp Ala Cys Cys Ser Asp Xaa Arg Cys Ser Gly Xaa His Gln Asp Leu
1 5 10 15

Cys

<210> SEQ ID NO 195
<211> LENGTH: 17
<212> TYPE: PRT
<213> ORGANISM: Conus lividus
<220> FEATURE:
<221> NAME/KEY: SITE
<222> LOCATION: (1)..(7)
<223> OTHER INFORMATION: Xaa at residue 1 is Glu or gamma-carboxy-Glu; Xaa at residue 7 is Pro or hydroxy-Pro.

<400> SEQUENCE: 195

Xaa Asp Cys Cys Ser Asp Xaa Arg Cys Ser Val Gly His Gln Asp Leu
1 5 10 15

Cys

<210> SEQ ID NO 196
<211> LENGTH: 16
<212> TYPE: PRT
<213> ORGANISM: Conus lividus
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 196

Gly Cys Cys Ser His Xaa Ala Cys Ala Gly Ser Asn Ala His Ile Cys
1 5 10 15

<210> SEQ ID NO 197
<211> LENGTH: 17
<212> TYPE: PRT
<213> ORGANISM: Conus lividus
<220> FEATURE:
<221> NAME/KEY: SITE
<222> LOCATION: (1)..(7)
<223> OTHER INFORMATION: Xaa at residue 1 is Glu or gamma-carboxy-Glu; Xaa at residue 7 is Pro or hydroxy-Pro.

<400> SEQUENCE: 197

Xaa Asp Cys Cys Ser Asp Xaa Arg Cys Ser Val Gly His Gln Asp Met
1 5 10 15

-continued

Cys

<210> SEQ ID NO 198
<211> LENGTH: 16
<212> TYPE: PRT
<213> ORGANISM: Conus lividus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 198

```
Gly Cys Cys Ser His Xaa Ala Cys Ala Gly Asn Asn Xaa His Ile Cys
  1               5                  10                  15
```

<210> SEQ ID NO 199
<211> LENGTH: 17
<212> TYPE: PRT
<213> ORGANISM: Conus lividus
<220> FEATURE:
<221> NAME/KEY: SITE
<222> LOCATION: (6)..(14)
<223> OTHER INFORMATION: Xaa at residues 6 and 13 is Pro or hydroxy-Pro; Xaa at residue 14 is Tyr, mono-halo-Tyr, di-halo-Tyr, O-sulpho-Tyr, O-phospho-Tyr or nitro-Tyr.

<400> SEQUENCE: 199

```
Gly Cys Cys Gly Asn Xaa Ser Cys Ser Ile His Ile Xaa Xaa Val Cys
  1               5                  10                  15

Asn
```

<210> SEQ ID NO 200
<211> LENGTH: 21
<212> TYPE: PRT
<213> ORGANISM: Conus lividus
<220> FEATURE:
<221> NAME/KEY: SITE
<222> LOCATION: (4)..(5)
<223> OTHER INFORMATION: Xaa at residues 4 and 5 is Glu or gamma-carboxy-Glu.

<400> SEQUENCE: 200

```
Thr Asp Ser Xaa Xaa Cys Cys Leu Asp Ser Arg Cys Ala Gly Gln His
  1               5                  10                  15

Gln Asp Leu Cys Gly
             20
```

<210> SEQ ID NO 201
<211> LENGTH: 17
<212> TYPE: PRT
<213> ORGANISM: Conus marmoreus
<220> FEATURE:
<221> NAME/KEY: SITE
<222> LOCATION: (6)..(15)
<223> OTHER INFORMATION: Xaa at residues 6 and 7 is Pro or hydroxy-Pro; Xaa at residues 9 and 15 is Tyr, mono-halo-Tyr, di-halo-Tyr, O-sulpho-Tyr, O-phospho-Tyr or nitro-Tyr.

<400> SEQUENCE: 201

```
Gly Cys Cys Ser Asn Xaa Xaa Cys Xaa Ala Asn Asn Gln Ala Xaa Cys
  1               5                  10                  15

Asn
```

<210> SEQ ID NO 202

-continued

<211> LENGTH: 16
<212> TYPE: PRT
<213> ORGANISM: Conus marmoreus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 202

```
Gly Cys Cys Ser His Xaa Ala Cys Ser Val Asn Asn Xaa Asp Ile Cys
  1               5                  10                  15
```

<210> SEQ ID NO 203
<211> LENGTH: 18
<212> TYPE: PRT
<213> ORGANISM: Conus musicus
<220> FEATURE:
<221> NAME/KEY: SITE
<222> LOCATION: (2)..(15)
<223> OTHER INFORMATION: Xaa at residues 2 and 12 is Lys, N-methyl-Lys, N,N-dimethyl-Lys or N,N,N-trimethyl-Lys; Xaa at residue 14 is Pro or hydroxy-Pro.
<220> FEATURE:
<221> NAME/KEY: SITE
<222> LOCATION: (16)
<223> OTHER INFORMATION: Xaa at residue 16 is Tyr, mono-halo-Tyr, di-halo-Tyr, O-sulpho-Tyr, O-phospho-Tyr or nitro-Tyr.

<400> SEQUENCE: 203

```
Gly Xaa Cys Cys Ile Asn Asp Ala Cys Arg Ser Xaa His Xaa Gln Xaa
  1               5                  10                  15

Cys Ser
```

<210> SEQ ID NO 204
<211> LENGTH: 17
<212> TYPE: PRT
<213> ORGANISM: Conus musicus
<220> FEATURE:
<221> NAME/KEY: SITE
<222> LOCATION: (4)..(15)
<223> OTHER INFORMATION: Xaa at residues 4 and 15 is Tyr, nor-Tyr, mono-halo-Tyr, di-halo-Tyr, O-sulpho-Tyr, O-phospho-Tyr or nitro-Tyr; Xaa at residue 13 is Pro or hydroxy-Pro.

<400> SEQUENCE: 204

```
Gly Cys Cys Xaa Asn Ile Ala Cys Arg Ile Asn Asn Xaa Arg Xaa Cys
  1               5                  10                  15

Arg
```

<210> SEQ ID NO 205
<211> LENGTH: 17
<212> TYPE: PRT
<213> ORGANISM: Conus obscurus
<220> FEATURE:
<221> NAME/KEY: SITE
<222> LOCATION: (6)..(15)
<223> OTHER INFORMATION: Xaa at residues 6 and 13 is Pro or hydroxy-Pro; Xaa at residues 12 and 15 is Tyr, nor-Tyr, mono-halo-Tyr, di-halo-Tyr, O-sulpho-Tyr, O-phospho-Tyr or nitro-Tyr.
<220> FEATURE:
<221> NAME/KEY: SITE
<222> LOCATION: (14)
<223> OTHER INFORMATION: Xaa at residue 14 is Lys, N-methyl-Lys, N,N-dimethyl-Lys or N,N,N-trimethyl-Lys.

<400> SEQUENCE: 205

```
Gly Cys Cys Ser His Xaa Val Cys Arg Phe Asn Xaa Xaa Xaa Xaa Cys
```

-continued

```
  1               5                   10                  15

Gly


<210> SEQ ID NO 206
<211> LENGTH: 18
<212> TYPE: PRT
<213> ORGANISM: Conus obscurus
<220> FEATURE:
<221> NAME/KEY: SITE
<222> LOCATION: (2)..(15)
<223> OTHER INFORMATION: Xaa at residue 2 is Glu or gamma-carboxy-Glu;
      Xaa at residues 7, 8 and 14 is Pro or hydroxy-Pro; Xaa
      at residue 15 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (2)..(15)
<223> OTHER INFORMATION: nitro-Tyr

<400> SEQUENCE: 206

Asp Xaa Cys Cys Ala Ser Xaa Xaa Cys Arg Leu Asn Asn Xaa Xaa Val
  1               5                   10                  15

Cys His


<210> SEQ ID NO 207
<211> LENGTH: 19
<212> TYPE: PRT
<213> ORGANISM: Conus obscurus
<220> FEATURE:
<221> NAME/KEY: SITE
<222> LOCATION: (6)..(18)
<223> OTHER INFORMATION: Xaa at residue 6 is Pro or hydroxy-Pro; Xaa at
      residue 9 is Trp (D or L) or halo-Trp; Xaa at
      residues 14 and 18 is Glu or gamma-carboxy-Glu.
<220> FEATURE:
<221> NAME/KEY: SITE
<222> LOCATION: (15)
<223> OTHER INFORMATION: Xaa at residue 15 is Tyr, nor-Tyr,
      mono-halo-Tyr, di-halo-Tyr, O-sulpho-Tyr, O-phospho-Tyr or
      nitro-Tyr.

<400> SEQUENCE: 207

Gly Cys Cys Ser Asn Xaa Val Cys Xaa Gln Asn Asn Ala Xaa Xaa Cys
  1               5                   10                  15

Arg Xaa Ser


<210> SEQ ID NO 208
<211> LENGTH: 16
<212> TYPE: PRT
<213> ORGANISM: Conus obscurus
<220> FEATURE:
<221> NAME/KEY: SITE
<222> LOCATION: (6)..(15)
<223> OTHER INFORMATION: Xaa at residues 6 and 7 is Pro or hydroxy-Pro;
      Xaa at residue 15 is Tyr, nor-Tyr, mono-halo-Tyr,
      di-halo-Tyr, O-sulpho-Tyr, O-phospho-Tyr or
      nitro-Tyr.

<400> SEQUENCE: 208

Gly Cys Cys Ser His Xaa Xaa Cys Ala Gln Asn Asn Gln Asp Xaa Cys
  1               5                   10                  15


<210> SEQ ID NO 209
<211> LENGTH: 19
<212> TYPE: PRT
<213> ORGANISM: Conus obscurus
<220> FEATURE:
<221> NAME/KEY: SITE
<222> LOCATION: (6)..(15)
```

-continued

```
<223> OTHER INFORMATION: Xaa at residue 6 is Pro or hydroxy-Pro; Xaa at
      residues 14 and 18 is Glu or gamma-carboxy-Glu;
      Xaa at residue 15 is Tyr, nor-Tyr, mono-halo-Tyr,
      di-halo-Tyr, O-sulpho-Tyr, O-phospho-Tyr or
<220> FEATURE:
<221> NAME/KEY: SITE
<222> LOCATION: (6)..(15)
<223> OTHER INFORMATION: nitro-Tyr.

<400> SEQUENCE: 209

Gly Cys Cys Ser His Xaa Ala Cys Ser Gly Asn Asn Arg Xaa Xaa Cys
  1               5                  10                  15

Arg Xaa Ser


<210> SEQ ID NO 210
<211> LENGTH: 18
<212> TYPE: PRT
<213> ORGANISM: Conus omaria
<220> FEATURE:
<221> NAME/KEY: SITE
<222> LOCATION: (2)..(15)
<223> OTHER INFORMATION: Xaa at residues 2, 7 and 14 is Pro or
      hydroxy-Pro; Xaa at residue 6 is Tyr, nor-Tyr, mono-halo-Tyr,
      di-halo-Tyr, O-sulpho-Tyr, O-phospho-Tyr or
      nitro-Tyr; Xaa at residue 15 is Glu or
<220> FEATURE:
<221> NAME/KEY: SITE
<222> LOCATION: (2)..(15)
<223> OTHER INFORMATION: gamma-carboxy-Glu

<400> SEQUENCE: 210

Asp Xaa Cys Cys Ser Xaa Xaa Asp Cys Gly Ala Asn His Xaa Xaa Ile
  1               5                  10                  15

Cys Gly


<210> SEQ ID NO 211
<211> LENGTH: 17
<212> TYPE: PRT
<213> ORGANISM: Conus omaria
<220> FEATURE:
<221> NAME/KEY: SITE
<222> LOCATION: (1)..(14)
<223> OTHER INFORMATION: Xaa at residues 1 and 14 is Glu or
      gamma-carboxy-Glu; Xaa at residues 6, 7 and 13 is
      Pro or hydroxy-Pro; Xaa at residue 10 is Trp (D or
      L) or halo-Trp.
<220> FEATURE:
<221> NAME/KEY: SITE
<222> LOCATION: (11)
<223> OTHER INFORMATION: Xaa at residue 11 is Lys, N-methyl-Lys,
      N,N-dimethyl-Lys or N,N,N-trimethyl-Lys.

<400> SEQUENCE: 211

Xaa Cys Cys Ser Gln Xaa Xaa Cys Arg Xaa Xaa His Xaa Xaa Leu Cys
  1               5                  10                  15

Ser


<210> SEQ ID NO 212
<211> LENGTH: 16
<212> TYPE: PRT
<213> ORGANISM: Conus omaria
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 212

Gly Cys Cys Ser His Xaa Ala Cys Ala Gly Asn Asn Xaa His Ile Cys
  1               5                  10                  15
```

-continued

<210> SEQ ID NO 213
<211> LENGTH: 16
<212> TYPE: PRT
<213> ORGANISM: Conus omaria
<220> FEATURE:
<221> NAME/KEY: SITE
<222> LOCATION: (6)..(15)
<223> OTHER INFORMATION: Xaa at residues 6 and 13 is Pro or hydroxy-Pro; Xaa at residue 15 is Tyr, nor-Tyr, mono-halo-Tyr, di-halo-Tyr, O-sulpho-Tyr, O-phospho-Tyr or nitro-Tyr.

<400> SEQUENCE: 213

Gly Cys Cys Ser Asp Xaa Ser Cys Asn Val Asn Asn Xaa Asp Xaa Cys
1 5 10 15

<210> SEQ ID NO 214
<211> LENGTH: 18
<212> TYPE: PRT
<213> ORGANISM: Conus omaria
<220> FEATURE:
<221> NAME/KEY: SITE
<222> LOCATION: (1)..(7)
<223> OTHER INFORMATION: Xaa at residues 1 and 2 is Glu or gamma-carboxy-Glu; Xaa at residue 7 is Pro or hydroxy-Pro.

<400> SEQUENCE: 214

Xaa Xaa Cys Cys Ser Asp Xaa Arg Cys Ser Val Gly His Gln Asp Met
1 5 10 15

Cys Arg

<210> SEQ ID NO 215
<211> LENGTH: 17
<212> TYPE: PRT
<213> ORGANISM: Conus purpurascens
<220> FEATURE:
<221> NAME/KEY: SITE
<222> LOCATION: (7)..(15)
<223> OTHER INFORMATION: Xaa at residue 7 is Pro or hydroxy-Pro; Xaa at residue 15 is Glu or gamma-carboxy-Glu.

<400> SEQUENCE: 215

Gly Gly Cys Cys Ser Asn Xaa Ala Cys Leu Val Asn His Leu Xaa Met
1 5 10 15

Cys

<210> SEQ ID NO 216
<211> LENGTH: 18
<212> TYPE: PRT
<213> ORGANISM: Conus purpurascens
<220> FEATURE:
<221> NAME/KEY: SITE
<222> LOCATION: (3)..(15)
<223> OTHER INFORMATION: Xaa at residues 3, 8 and 15 is Pro or hydroxy-Pro.

<400> SEQUENCE: 216

Arg Asp Xaa Cys Cys Phe Asn Xaa Ala Cys Asn Val Asn Asn Xaa Gln
1 5 10 15

Ile Cys

<210> SEQ ID NO 217
<211> LENGTH: 21
<212> TYPE: PRT
<213> ORGANISM: Conus purpurascens -continued
<220> FEATURE:
<221> NAME/KEY: SITE
<222> LOCATION: (5)..(8)
<223> OTHER INFORMATION: Xaa at residue 5 is Pro or hydroxy-Pro; Xaa at residue 8 is Trp (D or L) or halo-Trp.

<400> SEQUENCE: 217

Cys Cys Ser Asp Xaa Ser Cys Xaa Arg Leu His Ser Leu Ala Cys Thr
1 5 10 15

Gly Ile Val Asn Arg
20

<210> SEQ ID NO 218
<211> LENGTH: 16
<212> TYPE: PRT
<213> ORGANISM: Conus purpurascens
<220> FEATURE:
<221> NAME/KEY: SITE
<222> LOCATION: (5)
<223> OTHER INFORMATION: Xaa at residue 5 is Pro or hydroxy-Pro.

<400> SEQUENCE: 218

Cys Cys Thr Asn Xaa Ala Cys Leu Val Asn Asn Ile Arg Phe Cys Gly
1 5 10 15

<210> SEQ ID NO 219
<211> LENGTH: 18
<212> TYPE: PRT
<213> ORGANISM: Conus regius
<220> FEATURE:
<221> NAME/KEY: SITE
<222> LOCATION: (2)..(7)
<223> OTHER INFORMATION: Xaa at residue 2 is Glu or gamma-carboxy-Glu; Xaa at residue 7 is Pro or hydroxy-Pro.

<400> SEQUENCE: 219

Asp Xaa Cys Cys Ser Asp Xaa Arg Cys His Gly Asn Asn Arg Asp His
1 5 10 15

Cys Ala

<210> SEQ ID NO 220
<211> LENGTH: 17
<212> TYPE: PRT
<213> ORGANISM: Conus regius
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 220

Asp Cys Cys Ser His Xaa Leu Cys Arg Leu Phe Val Xaa Gly Leu Cys
1 5 10 15

Ile

<210> SEQ ID NO 221
<211> LENGTH: 17
<212> TYPE: PRT
<213> ORGANISM: Conus regius
<220> FEATURE:
<221> NAME/KEY: SITE
<222> LOCATION: (6)..(13)
<223> OTHER INFORMATION: Xaa at residues 6 and 13 is Pro or hydroxy-Pro; Xaa at residue 9 is Lys, N-methyl-Lys, N,N-dimethyl-Lys or N,N,N-trimethyl-Lys.
<220> FEATURE:
<221> NAME/KEY: SITE
<222> LOCATION: (12)
<223> OTHER INFORMATION: Xaa at residue 12 is Tyr, nor-Tyr, -continued mono-halo-Tyr, di-halo-Tyr, O-sulpho-Tyr, O-phospho-Tyr or nitro-Tyr.

<400> SEQUENCE: 221

Gly Cys Cys Ser His Xaa Val Cys Xaa Val Arg Xaa Xaa Asp Leu Cys
1 5 10 15

Arg

<210> SEQ ID NO 222
<211> LENGTH: 16
<212> TYPE: PRT
<213> ORGANISM: Conus regius
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 222

Gly Cys Cys Ser His Xaa Ala Cys Asn Val Asn Asn Xaa His Ile Cys
1 5 10 15

<210> SEQ ID NO 223
<211> LENGTH: 16
<212> TYPE: PRT
<213> ORGANISM: Conus regius
<220> FEATURE:
<221> NAME/KEY: SITE
<222> LOCATION: (6)..(12)
<223> OTHER INFORMATION: Xaa at residue 6 is Pro or hydroxy-Pro; Xaa at residue 12 is Tyr, nor-Tyr, nor-Tyr, mono-halo-Tyr, di-halo-Tyr, O-sulpho-Tyr, O-phospho-Tyr or nitro-Tyr.
<220> FEATURE:
<221> NAME/KEY: SITE
<222> LOCATION: (9)
<223> OTHER INFORMATION: Xaa at residue 9 is Lys, N-methyl-Lys, N,N-dimethyl-Lys or N,N,N-trimethyl-Lys.

<400> SEQUENCE: 223

Gly Cys Cys Ser His Xaa Val Cys Xaa Val Arg Xaa Ser Asp Met Cys
1 5 10 15

<210> SEQ ID NO 224
<211> LENGTH: 17
<212> TYPE: PRT
<213> ORGANISM: Conus stercusmuscarum
<220> FEATURE:
<221> NAME/KEY: SITE
<222> LOCATION: (7)..(14)
<223> OTHER INFORMATION: Xaa at residues 7 and 14 is Pro or hydroxy-Pro; Xaa at residue 10 is Lys, N-methyl-Lys, N,N-dimethyl-Lys or N,N,N-trimethyl-Lys.

<400> SEQUENCE: 224

Gly Gly Cys Cys Ser His Xaa Ala Cys Xaa Val His Phe Xaa His Ser
1 5 10 15

Cys

<210> SEQ ID NO 225
<211> LENGTH: 20
<212> TYPE: PRT
<213> ORGANISM: Conus stercusmuscarum
<220> FEATURE:
<221> NAME/KEY: SITE
<222> LOCATION: (6)..(14)
<223> OTHER INFORMATION: Xaa at residues 6 and 13 is Pro or hydroxy-Pro; Xaa at residue 14 is Glu or gamma-carboxy-Glu.

<400> SEQUENCE: 225

Val Cys Cys Ser Asn Xaa Val Cys His Val Asp His Xaa Xaa Leu Cys
1 5 10 15

Arg Arg Arg Arg
20

<210> SEQ ID NO 226
<211> LENGTH: 17
<212> TYPE: PRT
<213> ORGANISM: Conus striatus
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 226

Gly Cys Cys Ser His Xaa Val Cys Asn Leu Ser Asn Xaa Gln Ile Cys
1 5 10 15

Arg

<210> SEQ ID NO 227
<211> LENGTH: 18
<212> TYPE: PRT
<213> ORGANISM: Conus textile
<220> FEATURE:
<221> NAME/KEY: SITE
<222> LOCATION: (1)..(15)
<223> OTHER INFORMATION: Xaa at residue 1 is Gln or pyro-Glu; Xaa at residues 2 and 15 is Glu or gamma-carboxy-Glu; Xaa at residues 7 and 14 is Pro or hydroxy-Pro.

<400> SEQUENCE: 227

Xaa Xaa Cys Cys Ser His Xaa Ala Cys Asn Val Asp His Xaa Xaa Ile
1 5 10 15

Cys Arg

<210> SEQ ID NO 228
<211> LENGTH: 17
<212> TYPE: PRT
<213> ORGANISM: Conus tulipa
<220> FEATURE:
<221> NAME/KEY: SITE
<222> LOCATION: (6)
<223> OTHER INFORMATION: Xaa at residue 6 is Pro or hydroxy-Pro.

<400> SEQUENCE: 228

Gly Cys Cys Ser Asn Xaa Ala Cys Leu Val Asn His Ile Arg Phe Cys
1 5 10 15

Gly

<210> SEQ ID NO 229
<211> LENGTH: 17
<212> TYPE: PRT
<213> ORGANISM: Conus virgo
<220> FEATURE:
<221> NAME/KEY: SITE
<222> LOCATION: (6)..(13)
<223> OTHER INFORMATION: Xaa at residues 6 and 13 is Pro or hydroxy-Pro.

<400> SEQUENCE: 229

Asp Cys Cys Asp Asp Xaa Ala Cys Thr Val Asn Asn Xaa Gly Leu Cys
1 5 10 15

Thr

<210> SEQ ID NO 230

-continued

```
<211> LENGTH: 20
<212> TYPE: PRT
<213> ORGANISM: Conus textile
<220> FEATURE:
<221> NAME/KEY: SITE
<222> LOCATION: (6)..(13)
<223> OTHER INFORMATION: Xaa at residues 6, 7 and 13 is Pro or
      hydroxy-Pro; Xaa at residue 11 is Lys, N-methyl-Lys,
      N,N-dimethyl-Lys or N,N,N-trimethyl-Lys.

<400> SEQUENCE: 230

Gly Cys Cys Ser Asn Xaa Xaa Cys Ile Ala Xaa Asn Xaa His Met Cys
  1               5                  10                  15

Gly Gly Arg Arg
             20


<210> SEQ ID NO 231
<211> LENGTH: 18
<212> TYPE: PRT
<213> ORGANISM: Conus geographus
<220> FEATURE:
<221> NAME/KEY: SITE
<222> LOCATION: (5)..(9)
<223> OTHER INFORMATION: Xaa at residue 5 is Pro or hydroxy-Pro; Xaa at
      residue 8 is Tyr, nor-Tyr, mono-halo-Tyr,
      di-halo-Tyr, O-sulpho-Tyr, O-phospho-Tyr or
      nitro-Tyr; Xaa at residue 9 is Glu or
<220> FEATURE:
<221> NAME/KEY: SITE
<222> LOCATION: (9)..(14)
<223> OTHER INFORMATION: gamma-carboxy-Glu; Xaa at residues 10, 11, 12
      and 14 is Lys, N-methyl-Lys, N,N-dimethyl-Lys or
      N,N,N-trimethyl-Lys.

<400> SEQUENCE: 231

Cys Cys Thr Ile Xaa Ser Cys Xaa Xaa Xaa Xaa Xaa Ile Xaa Ala Cys
  1               5                  10                  15

Val Phe


<210> SEQ ID NO 232
<211> LENGTH: 18
<212> TYPE: PRT
<213> ORGANISM: Conus regius
<220> FEATURE:
<221> NAME/KEY: SITE
<222> LOCATION: (6)..(16)
<223> OTHER INFORMATION: Xaa at residues 6 and 16 is Pro or hydroxy-Pro;
      Xaa at residue 13 is Lys, N-methyl-Lys,
      N,N-dimethyl-Lys or N,N,N-trimethyl-Lys.

<400> SEQUENCE: 232

Gly Cys Cys Gly Asn Xaa Ala Cys Ser Gly Ser Ser Xaa Asp Ala Xaa
  1               5                  10                  15

Ser Cys


<210> SEQ ID NO 233
<211> LENGTH: 108
<212> TYPE: DNA
<213> ORGANISM: Conus imperialis
<220> FEATURE:
<221> NAME/KEY: CDS
<222> LOCATION: (1)..(105)

<400> SEQUENCE: 233

tct gat gga aag agt gcc gcg gcc aaa gcc aaa ccg tct cac ctg acg       48
Ser Asp Gly Lys Ser Ala Ala Ala Lys Ala Lys Pro Ser His Leu Thr
  1               5                  10                  15

gct cca ttc atc agg gac gaa tgc tgt tcc gat tct cgc tgt ggc aag       96
```

-continued

```
Ala Pro Phe Ile Arg Asp Glu Cys Cys Ser Asp Ser Arg Cys Gly Lys
            20                  25                  30

aac tgt ctt tga                                                  108
Asn Cys Leu
        35


<210> SEQ ID NO 234
<211> LENGTH: 35
<212> TYPE: PRT
<213> ORGANISM: Conus imperialis

<400> SEQUENCE: 234

Ser Asp Gly Lys Ser Ala Ala Ala Lys Ala Lys Pro Ser His Leu Thr
  1               5                  10                  15

Ala Pro Phe Ile Arg Asp Glu Cys Cys Ser Asp Ser Arg Cys Gly Lys
            20                  25                  30

Asn Cys Leu
        35


<210> SEQ ID NO 235
<211> LENGTH: 108
<212> TYPE: DNA
<213> ORGANISM: Conus imperialis
<220> FEATURE:
<221> NAME/KEY: CDS
<222> LOCATION: (1)..(105)

<400> SEQUENCE: 235

ttt gat gga agg aat gcc cca gcc gac gac aaa gcg tct gac ctg atc       48
Phe Asp Gly Arg Asn Ala Pro Ala Asp Asp Lys Ala Ser Asp Leu Ile
  1               5                  10                  15

gct caa atc gtc agg aga gca tgc tgt tcc gat cgt cgc tgt aga tgg       96
Ala Gln Ile Val Arg Arg Ala Cys Cys Ser Asp Arg Arg Cys Arg Trp
            20                  25                  30

agg tgt ggt tga                                                  108
Arg Cys Gly
        35


<210> SEQ ID NO 236
<211> LENGTH: 35
<212> TYPE: PRT
<213> ORGANISM: Conus imperialis

<400> SEQUENCE: 236

Phe Asp Gly Arg Asn Ala Pro Ala Asp Asp Lys Ala Ser Asp Leu Ile
  1               5                  10                  15

Ala Gln Ile Val Arg Arg Ala Cys Cys Ser Asp Arg Arg Cys Arg Trp
            20                  25                  30

Arg Cys Gly
        35


<210> SEQ ID NO 237
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 237

tct gat gga agg aat gcc gca gcc gac gcc aga gcg tct ccc cgg atc       48
Ser Asp Gly Arg Asn Ala Ala Ala Asp Ala Arg Ala Ser Pro Arg Ile
  1               5                  10                  15
```

-continued

```
gct ctt ttc ctc agg ttc aca tgc tgt agg aga ggt acc tgt tcc cag       96
Ala Leu Phe Leu Arg Phe Thr Cys Cys Arg Arg Gly Thr Cys Ser Gln
             20                  25                  30

cac tgt ggt tgaagacact gctgctccag gaccctctga accacgacgt              145
His Cys Gly
         35


<210> SEQ ID NO 238
<211> LENGTH: 35
<212> TYPE: PRT
<213> ORGANISM: Conus regius

<400> SEQUENCE: 238

Ser Asp Gly Arg Asn Ala Ala Ala Asp Ala Arg Ala Ser Pro Arg Ile
  1               5                  10                  15

Ala Leu Phe Leu Arg Phe Thr Cys Cys Arg Arg Gly Thr Cys Ser Gln
             20                  25                  30

His Cys Gly
         35


<210> SEQ ID NO 239
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 239

tct aat gga agg aat gcc gca gcc gac gcc aaa gcg tct caa cgg atc       48
Ser Asn Gly Arg Asn Ala Ala Ala Asp Ala Lys Ala Ser Gln Arg Ile
  1               5                  10                  15

gct cca ttc ctc agg gac tat tgc tgt agg aga cat gcc tgt acg ttg       96
Ala Pro Phe Leu Arg Asp Tyr Cys Cys Arg Arg His Ala Cys Thr Leu
             20                  25                  30

att tgt ggt tgaagacgct gctgctccag gaccctctga accacgacgt              145
Ile Cys Gly
         35


<210> SEQ ID NO 240
<211> LENGTH: 35
<212> TYPE: PRT
<213> ORGANISM: Conus regius

<400> SEQUENCE: 240

Ser Asn Gly Arg Asn Ala Ala Ala Asp Ala Lys Ala Ser Gln Arg Ile
  1               5                  10                  15

Ala Pro Phe Leu Arg Asp Tyr Cys Cys Arg Arg His Ala Cys Thr Leu
             20                  25                  30

Ile Cys Gly
         35


<210> SEQ ID NO 241
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 241

tct aat gga agg aat gcc gca gcc gac gcc aaa gcg tct caa cgg atc       48
Ser Asn Gly Arg Asn Ala Ala Ala Asp Ala Lys Ala Ser Gln Arg Ile
  1               5                  10                  15
```

-continued

```
gct cca ttc ctc agg gac tat tgc tgt agg aga cct ccc tgt acg ttg       96
Ala Pro Phe Leu Arg Asp Tyr Cys Cys Arg Arg Pro Pro Cys Thr Leu
             20                  25                  30

att tgt ggt tgaagacgct gctgctccag gaccctctga accacgacgt              145
Ile Cys Gly
        35


<210> SEQ ID NO 242
<211> LENGTH: 35
<212> TYPE: PRT
<213> ORGANISM: Conus regius

<400> SEQUENCE: 242

Ser Asn Gly Arg Asn Ala Ala Ala Asp Ala Lys Ala Ser Gln Arg Ile
  1               5                  10                  15

Ala Pro Phe Leu Arg Asp Tyr Cys Cys Arg Arg Pro Pro Cys Thr Leu
             20                  25                  30

Ile Cys Gly
        35


<210> SEQ ID NO 243
<211> LENGTH: 136
<212> TYPE: DNA
<213> ORGANISM: Conus regius
<220> FEATURE:
<221> NAME/KEY: CDS
<222> LOCATION: (1)..(96)

<400> SEQUENCE: 243

tct aat aaa agg aag aat gcc gca atg ctt gac atg atc gct caa cac       48
Ser Asn Lys Arg Lys Asn Ala Ala Met Leu Asp Met Ile Ala Gln His
  1               5                  10                  15

gcc ata agg ggt tgc tgt tcc gat cct cgc tgt aga tat aga tgt cgt       96
Ala Ile Arg Gly Cys Cys Ser Asp Pro Arg Cys Arg Tyr Arg Cys Arg
             20                  25                  30

tgaagacgct gctgctccag gaccctctga accacgacgt                          136


<210> SEQ ID NO 244
<211> LENGTH: 32
<212> TYPE: PRT
<213> ORGANISM: Conus regius

<400> SEQUENCE: 244

Ser Asn Lys Arg Lys Asn Ala Ala Met Leu Asp Met Ile Ala Gln His
  1               5                  10                  15

Ala Ile Arg Gly Cys Cys Ser Asp Pro Arg Cys Arg Tyr Arg Cys Arg
             20                  25                  30


<210> SEQ ID NO 245
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 245

ttt aat gga agg agt gcc gca gcc gac caa aat gcg cct ggc ctg atc       48
Phe Asn Gly Arg Ser Ala Ala Ala Asp Gln Asn Ala Pro Gly Leu Ile
  1               5                  10                  15

gct caa gtc gtc aga gga ggg tgc tgt tcc gat ccc cgc tgc gcc tgg       96
Ala Gln Val Val Arg Gly Gly Cys Cys Ser Asp Pro Arg Cys Ala Trp
             20                  25                  30
```

-continued

```
aga tgt ggt tgaagacgtt gctgctccag gaccctctga accacgacgt             145
Arg Cys Gly
        35


<210> SEQ ID NO 246
<211> LENGTH: 35
<212> TYPE: PRT
<213> ORGANISM: Conus regius

<400> SEQUENCE: 246

Phe Asn Gly Arg Ser Ala Ala Ala Asp Gln Asn Ala Pro Gly Leu Ile
  1               5                  10                  15

Ala Gln Val Val Arg Gly Gly Cys Cys Ser Asp Pro Arg Cys Ala Trp
            20                  25                  30

Arg Cys Gly
        35


<210> SEQ ID NO 247
<211> LENGTH: 145
<212> TYPE: DNA
<213> ORGANISM: Conus regius
<220> FEATURE:
<221> NAME/KEY: CDS
<222> LOCATION: (1)..(105)

<400> SEQUENCE: 247

ttt gat gga agg aat gcc gca gcc gac gcc aaa gtg att aac acg gtc       48
Phe Asp Gly Arg Asn Ala Ala Ala Asp Ala Lys Val Ile Asn Thr Val
  1               5                  10                  15

gct cga atc gcc tgg gat ata tgc tgt tcc gaa cct gac tgt aac cat       96
Ala Arg Ile Ala Trp Asp Ile Cys Cys Ser Glu Pro Asp Cys Asn His
            20                  25                  30

aaa tgt gtt tgaagacgct tctgctccag gaccctctga accacgacgt             145
Lys Cys Val
        35


<210> SEQ ID NO 248
<211> LENGTH: 35
<212> TYPE: PRT
<213> ORGANISM: Conus regius

<400> SEQUENCE: 248

Phe Asp Gly Arg Asn Ala Ala Ala Asp Ala Lys Val Ile Asn Thr Val
  1               5                  10                  15

Ala Arg Ile Ala Trp Asp Ile Cys Cys Ser Glu Pro Asp Cys Asn His
            20                  25                  30

Lys Cys Val
        35


<210> SEQ ID NO 249
<211> LENGTH: 136
<212> TYPE: DNA
<213> ORGANISM: Conus regius
<220> FEATURE:
<221> NAME/KEY: CDS
<222> LOCATION: (1)..(96)

<400> SEQUENCE: 249

tct aat aaa agg aag aat gcc gca atg ctt gac atg atc gct caa cac       48
Ser Asn Lys Arg Lys Asn Ala Ala Met Leu Asp Met Ile Ala Gln His
  1               5                  10                  15

gcc ata agg ggt tgc tgt tcc gat cct cgc tgt aaa cat cag tgt ggt       96
Ala Ile Arg Gly Cys Cys Ser Asp Pro Arg Cys Lys His Gln Cys Gly
```

-continued

```
            20                  25                  30

tgaagacgct gctgctccag gaccctctga accacgacgt                          136


<210> SEQ ID NO 250
<211> LENGTH: 32
<212> TYPE: PRT
<213> ORGANISM: Conus regius

<400> SEQUENCE: 250

Ser Asn Lys Arg Lys Asn Ala Ala Met Leu Asp Met Ile Ala Gln His
  1               5                  10                  15

Ala Ile Arg Gly Cys Cys Ser Asp Pro Arg Cys Lys His Gln Cys Gly
            20                  25                  30


<210> SEQ ID NO 251
<211> LENGTH: 136
<212> TYPE: DNA
<213> ORGANISM: Conus musicus
<220> FEATURE:
<221> NAME/KEY: CDS
<222> LOCATION: (1)..(105)

<400> SEQUENCE: 251

atc aag aat aca gca gcc agc aac aaa gcg tct agc ctg gtg gct ctt       48
Ile Lys Asn Thr Ala Ala Ser Asn Lys Ala Ser Ser Leu Val Ala Leu
  1               5                  10                  15

gtt gtc agg gga tgc tgt tac aat cct gtc tgc aag aaa tat tat tgt       96
Val Val Arg Gly Cys Cys Tyr Asn Pro Val Cys Lys Lys Tyr Tyr Cys
            20                  25                  30

tgg aaa ggc tgatgctcca ggaccctctg aaccacgacg t                       136
Trp Lys Gly
        35


<210> SEQ ID NO 252
<211> LENGTH: 35
<212> TYPE: PRT
<213> ORGANISM: Conus musicus

<400> SEQUENCE: 252

Ile Lys Asn Thr Ala Ala Ser Asn Lys Ala Ser Ser Leu Val Ala Leu
  1               5                  10                  15

Val Val Arg Gly Cys Cys Tyr Asn Pro Val Cys Lys Lys Tyr Tyr Cys
            20                  25                  30

Trp Lys Gly
        35


<210> SEQ ID NO 253
<211> LENGTH: 148
<212> TYPE: DNA
<213> ORGANISM: Conus purpurascens
<220> FEATURE:
<221> NAME/KEY: CDS
<222> LOCATION: (1)..(117)

<400> SEQUENCE: 253

tct gaa ggc agg aat gct gaa gcc atc gac aac gcc tta gac cag agg       48
Ser Glu Gly Arg Asn Ala Glu Ala Ile Asp Asn Ala Leu Asp Gln Arg
  1               5                  10                  15

gat cca aag cga cag gag ccg ggg tgc tgt agg cat cct gcc tgt ggg       96
Asp Pro Lys Arg Gln Glu Pro Gly Cys Cys Arg His Pro Ala Cys Gly
            20                  25                  30

aag aac aga tgt gga aga cgc tgatgctcca ggaccctctg aaccacgacg t      148
Lys Asn Arg Cys Gly Arg Arg
```

-continued

```
        35


<210> SEQ ID NO 254
<211> LENGTH: 39
<212> TYPE: PRT
<213> ORGANISM: Conus purpurascens

<400> SEQUENCE: 254

Ser Glu Gly Arg Asn Ala Glu Ala Ile Asp Asn Ala Leu Asp Gln Arg
  1               5                  10                  15

Asp Pro Lys Arg Gln Glu Pro Gly Cys Cys Arg His Pro Ala Cys Gly
             20                  25                  30

Lys Asn Arg Cys Gly Arg Arg
        35


<210> SEQ ID NO 255
<211> LENGTH: 156
<212> TYPE: DNA
<213> ORGANISM: Conus musicus
<220> FEATURE:
<221> NAME/KEY: CDS
<222> LOCATION: (1)..(102)

<400> SEQUENCE: 255

tct gat ggc agg aat att gca gtc gac gac aga tgg tct ttc tat acg       48
Ser Asp Gly Arg Asn Ile Ala Val Asp Asp Arg Trp Ser Phe Tyr Thr
  1               5                  10                  15

ctc ttc cat gct act tgc tgt gcc gat cct gac tgt aga ttc cgg ccc       96
Leu Phe His Ala Thr Cys Cys Ala Asp Pro Asp Cys Arg Phe Arg Pro
             20                  25                  30

ggt tgt tgatctttgt tcttcaaaga cgctgctggc ccaggaccct ctgaaccacg       152
Gly Cys

acgt                                                                  156


<210> SEQ ID NO 256
<211> LENGTH: 34
<212> TYPE: PRT
<213> ORGANISM: Conus musicus

<400> SEQUENCE: 256

Ser Asp Gly Arg Asn Ile Ala Val Asp Asp Arg Trp Ser Phe Tyr Thr
  1               5                  10                  15

Leu Phe His Ala Thr Cys Cys Ala Asp Pro Asp Cys Arg Phe Arg Pro
             20                  25                  30

Gly Cys


<210> SEQ ID NO 257
<211> LENGTH: 142
<212> TYPE: DNA
<213> ORGANISM: Conus musicus
<220> FEATURE:
<221> NAME/KEY: CDS
<222> LOCATION: (1)..(102)

<400> SEQUENCE: 257

atc aag aat act gca gcc agc aac aaa gcg cct agc ctg gtg gct att       48
Ile Lys Asn Thr Ala Ala Ser Asn Lys Ala Pro Ser Leu Val Ala Ile
  1               5                  10                  15

gcc gtc agg gga tgc tgt tac aat cct tcc tgt tgg ccg aaa aca tat       96
Ala Val Arg Gly Cys Cys Tyr Asn Pro Ser Cys Trp Pro Lys Thr Tyr
             20                  25                  30

tgt agt tggaaaggct gatgctccag gaccctctga accacgacgt                  142
```

-continued

Cys Ser

<210> SEQ ID NO 258
<211> LENGTH: 34
<212> TYPE: PRT
<213> ORGANISM: Conus musicus

<400> SEQUENCE: 258

```
Ile Lys Asn Thr Ala Ala Ser Asn Lys Ala Pro Ser Leu Val Ala Ile
  1               5                  10                  15

Ala Val Arg Gly Cys Cys Tyr Asn Pro Ser Cys Trp Pro Lys Thr Tyr
             20                  25                  30

Cys Ser
```

<210> SEQ ID NO 259
<211> LENGTH: 161
<212> TYPE: DNA
<213> ORGANISM: Conus musicus
<220> FEATURE:
<221> NAME/KEY: CDS
<222> LOCATION: (1)..(108)

<400> SEQUENCE: 259

```
tct gat agc agg aat gtc gca atc gag gac aga gtg tct gac ctg cac       48
Ser Asp Ser Arg Asn Val Ala Ile Glu Asp Arg Val Ser Asp Leu His
  1               5                  10                  15

tct atg ttc ttc gat gtt tct tgc tgt agc aat cct acc tgt aaa gaa       96
Ser Met Phe Phe Asp Val Ser Cys Cys Ser Asn Pro Thr Cys Lys Glu
             20                  25                  30

acg tat ggt tgt tgatcgttgg ttttgaagac gctgatgctc caggaccctc          148
Thr Tyr Gly Cys
         35

tgaaccacga cgt                                                        161
```

<210> SEQ ID NO 260
<211> LENGTH: 36
<212> TYPE: PRT
<213> ORGANISM: Conus musicus

<400> SEQUENCE: 260

```
Ser Asp Ser Arg Asn Val Ala Ile Glu Asp Arg Val Ser Asp Leu His
  1               5                  10                  15

Ser Met Phe Phe Asp Val Ser Cys Cys Ser Asn Pro Thr Cys Lys Glu
             20                  25                  30

Thr Tyr Gly Cys
         35
```

<210> SEQ ID NO 261
<211> LENGTH: 156
<212> TYPE: DNA
<213> ORGANISM: Conus musicus
<220> FEATURE:
<221> NAME/KEY: CDS
<222> LOCATION: (1)..(102)

<400> SEQUENCE: 261

```
tct gtt ggc agg aat att gca gtc gac gac aga ggg att ttc tct acg       48
Ser Val Gly Arg Asn Ile Ala Val Asp Asp Arg Gly Ile Phe Ser Thr
  1               5                  10                  15

ctc ttc cat gct cat tgc tgt gcc aat ccc atc tgt aaa aac acg ccc       96
Leu Phe His Ala His Cys Cys Ala Asn Pro Ile Cys Lys Asn Thr Pro
             20                  25                  30
```

-continued

```
ggt tgt tgatctttgt tcttcaaaga cgctgctggc ccaggaccct ctgaaccacg       152
Gly Cys

acgt                                                                 156


<210> SEQ ID NO 262
<211> LENGTH: 34
<212> TYPE: PRT
<213> ORGANISM: Conus musicus

<400> SEQUENCE: 262

Ser Val Gly Arg Asn Ile Ala Val Asp Asp Arg Gly Ile Phe Ser Thr
  1               5                  10                  15

Leu Phe His Ala His Cys Cys Ala Asn Pro Ile Cys Lys Asn Thr Pro
             20                  25                  30

Gly Cys


<210> SEQ ID NO 263
<211> LENGTH: 161
<212> TYPE: DNA
<213> ORGANISM: Conus musicus
<220> FEATURE:
<221> NAME/KEY: CDS
<222> LOCATION: (1)..(108)

<400> SEQUENCE: 263

tcc gat ggc agg aat gtc gca atc gac gac aga gtg tct gac ctg cac       48
Ser Asp Gly Arg Asn Val Ala Ile Asp Asp Arg Val Ser Asp Leu His
  1               5                  10                  15

tct atg ttc ttc gat att gct tgc tgt aac aat cct acc tgt aaa gaa       96
Ser Met Phe Phe Asp Ile Ala Cys Cys Asn Asn Pro Thr Cys Lys Glu
             20                  25                  30

acg tat ggt tgt tgatcgttgg ttttgaagac gctgatgctc caggaccctc          148
Thr Tyr Gly Cys
         35

tgaaccacga cgt                                                       161


<210> SEQ ID NO 264
<211> LENGTH: 36
<212> TYPE: PRT
<213> ORGANISM: Conus musicus

<400> SEQUENCE: 264

Ser Asp Gly Arg Asn Val Ala Ile Asp Asp Arg Val Ser Asp Leu His
  1               5                  10                  15

Ser Met Phe Phe Asp Ile Ala Cys Cys Asn Asn Pro Thr Cys Lys Glu
             20                  25                  30

Thr Tyr Gly Cys
         35


<210> SEQ ID NO 265
<211> LENGTH: 161
<212> TYPE: DNA
<213> ORGANISM: Conus musicus
<220> FEATURE:
<221> NAME/KEY: CDS
<222> LOCATION: (1)..(108)

<400> SEQUENCE: 265

tct gat ggc agg aat gtc gca atc gag gac aga gtg tct gac ctg ctc       48
Ser Asp Gly Arg Asn Val Ala Ile Glu Asp Arg Val Ser Asp Leu Leu
  1               5                  10                  15

tct atg ctc ttc gat gtt gct tgc tgt agc aat cct gtc tgt aaa gaa       96
```

-continued

```
Ser Met Leu Phe Asp Val Ala Cys Cys Ser Asn Pro Val Cys Lys Glu
            20                  25                  30

acg tat ggt tgt tgatcgttgg ttttgaagac gctgatgctc caggaccctc          148
Thr Tyr Gly Cys
        35

tgaaccacga cgt                                                        161


<210> SEQ ID NO 266
<211> LENGTH: 36
<212> TYPE: PRT
<213> ORGANISM: Conus musicus

<400> SEQUENCE: 266

Ser Asp Gly Arg Asn Val Ala Ile Glu Asp Arg Val Ser Asp Leu Leu
  1               5                  10                  15

Ser Met Leu Phe Asp Val Ala Cys Cys Ser Asn Pro Val Cys Lys Glu
            20                  25                  30

Thr Tyr Gly Cys
        35


<210> SEQ ID NO 267
<211> LENGTH: 154
<212> TYPE: DNA
<213> ORGANISM: Conus betulinus
<220> FEATURE:
<221> NAME/KEY: CDS
<222> LOCATION: (1)..(123)

<400> SEQUENCE: 267

tat gat ggc agg aat gct gcc gcc gac gac aaa gct ttt gac ctg ctg       48
Tyr Asp Gly Arg Asn Ala Ala Ala Asp Asp Lys Ala Phe Asp Leu Leu
  1               5                  10                  15

gct atg acc ata agg gga gga tgc tgt tcc tat cct ccc tgt atc gcg       96
Ala Met Thr Ile Arg Gly Gly Cys Cys Ser Tyr Pro Pro Cys Ile Ala
            20                  25                  30

agt aat cct aaa tgt ggt gga aga cgc tgatgctcca ggaccctctg            143
Ser Asn Pro Lys Cys Gly Gly Arg Arg
        35                  40

aaccacaacg t                                                          154


<210> SEQ ID NO 268
<211> LENGTH: 41
<212> TYPE: PRT
<213> ORGANISM: Conus betulinus

<400> SEQUENCE: 268

Tyr Asp Gly Arg Asn Ala Ala Ala Asp Asp Lys Ala Phe Asp Leu Leu
  1               5                  10                  15

Ala Met Thr Ile Arg Gly Gly Cys Cys Ser Tyr Pro Pro Cys Ile Ala
            20                  25                  30

Ser Asn Pro Lys Cys Gly Gly Arg Arg
        35                  40


<210> SEQ ID NO 269
<211> LENGTH: 151
<212> TYPE: DNA
<213> ORGANISM: Conus lividus
<220> FEATURE:
<221> NAME/KEY: CDS
<222> LOCATION: (1)..(111)

<400> SEQUENCE: 269
```

-continued

```
ttt gat ggc agg aat gct gca ggc aac gcc aaa atg tcc gcc ctg atg       48
Phe Asp Gly Arg Asn Ala Ala Gly Asn Ala Lys Met Ser Ala Leu Met
  1               5                  10                  15

gcc ctg acc atc agg gga tgc tgt tcc cat cct gtc tgt agc gcg atg       96
Ala Leu Thr Ile Arg Gly Cys Cys Ser His Pro Val Cys Ser Ala Met
             20                  25                  30

agt cca atc tgt ggc tgaagacgct gatgccccag gaccctctga accacgacgt      151
Ser Pro Ile Cys Gly
         35
```

<210> SEQ ID NO 270
<211> LENGTH: 37
<212> TYPE: PRT
<213> ORGANISM: Conus lividus

<400> SEQUENCE: 270

```
Phe Asp Gly Arg Asn Ala Ala Gly Asn Ala Lys Met Ser Ala Leu Met
  1               5                  10                  15

Ala Leu Thr Ile Arg Gly Cys Cys Ser His Pro Val Cys Ser Ala Met
             20                  25                  30

Ser Pro Ile Cys Gly
         35
```

<210> SEQ ID NO 271
<211> LENGTH: 196
<212> TYPE: DNA
<213> ORGANISM: Conus musicus
<220> FEATURE:
<221> NAME/KEY: CDS
<222> LOCATION: (1)..(165)

<400> SEQUENCE: 271

```
atc aag aat gct gca gct gac gac aaa gca tct gac ctg ctc tct cag       48
Ile Lys Asn Ala Ala Ala Asp Asp Lys Ala Ser Asp Leu Leu Ser Gln
  1               5                  10                  15

atc gtc agg aat gct gca tcc aat gac aaa ggg tct gac ctg atg act       96
Ile Val Arg Asn Ala Ala Ser Asn Asp Lys Gly Ser Asp Leu Met Thr
             20                  25                  30

ctt gcc ctc agg gga tgc tgt aaa aat cct tac tgt ggt gcg tcg aaa      144
Leu Ala Leu Arg Gly Cys Cys Lys Asn Pro Tyr Cys Gly Ala Ser Lys
         35                  40                  45

aca tat tgt ggt aga aga cgc tgatgctcca ggaccctctg aaccacgacg t       196
Thr Tyr Cys Gly Arg Arg Arg
     50                  55
```

<210> SEQ ID NO 272
<211> LENGTH: 55
<212> TYPE: PRT
<213> ORGANISM: Conus musicus

<400> SEQUENCE: 272

```
Ile Lys Asn Ala Ala Ala Asp Asp Lys Ala Ser Asp Leu Leu Ser Gln
  1               5                  10                  15

Ile Val Arg Asn Ala Ala Ser Asn Asp Lys Gly Ser Asp Leu Met Thr
             20                  25                  30

Leu Ala Leu Arg Gly Cys Cys Lys Asn Pro Tyr Cys Gly Ala Ser Lys
         35                  40                  45

Thr Tyr Cys Gly Arg Arg Arg
     50                  55
```

<210> SEQ ID NO 273
<211> LENGTH: 139

-continued

```
<212> TYPE: DNA
<213> ORGANISM: Conus omaria
<220> FEATURE:
<221> NAME/KEY: CDS
<222> LOCATION: (40)..(108)

<400> SEQUENCE: 273

tctgatggca ggaatgccgc agcgtctgac ctgatggat ctg acc atc aag gga        54
                                           Leu Thr Ile Lys Gly
                                             1               5

tgc tgt tct tat cct ccc tgt ttc gcg act aat cca gac tgt ggt cga      102
Cys Cys Ser Tyr Pro Pro Cys Phe Ala Thr Asn Pro Asp Cys Gly Arg
                10                  15                  20

cga cgc tgatgctcca ggaccctctg aaccacgacg t                           139
Arg Arg


<210> SEQ ID NO 274
<211> LENGTH: 23
<212> TYPE: PRT
<213> ORGANISM: Conus omaria

<400> SEQUENCE: 274

Leu Thr Ile Lys Gly Cys Cys Ser Tyr Pro Pro Cys Phe Ala Thr Asn
  1               5                  10                  15

Pro Asp Cys Gly Arg Arg Arg
             20


<210> SEQ ID NO 275
<211> LENGTH: 126
<212> TYPE: DNA
<213> ORGANISM: Conus radiatus
<220> FEATURE:
<221> NAME/KEY: CDS
<222> LOCATION: (1)..(123)

<400> SEQUENCE: 275

ttt gat ggc agg aat gcc gca gcc gac tac aaa ggg tct gaa ttg ctc       48
Phe Asp Gly Arg Asn Ala Ala Ala Asp Tyr Lys Gly Ser Glu Leu Leu
  1               5                  10                  15

gct atg acc gtc agg gga gga tgc tgt tcc tat cct ccc tgt atc gca       96
Ala Met Thr Val Arg Gly Gly Cys Cys Ser Tyr Pro Pro Cys Ile Ala
             20                  25                  30

aat aat cct ctt tgt gct gga aga cgc tga                              126
Asn Asn Pro Leu Cys Ala Gly Arg Arg
         35                  40


<210> SEQ ID NO 276
<211> LENGTH: 41
<212> TYPE: PRT
<213> ORGANISM: Conus radiatus

<400> SEQUENCE: 276

Phe Asp Gly Arg Asn Ala Ala Ala Asp Tyr Lys Gly Ser Glu Leu Leu
  1               5                  10                  15

Ala Met Thr Val Arg Gly Gly Cys Cys Ser Tyr Pro Pro Cys Ile Ala
             20                  25                  30

Asn Asn Pro Leu Cys Ala Gly Arg Arg
         35                  40


<210> SEQ ID NO 277
<211> LENGTH: 126
<212> TYPE: DNA
<213> ORGANISM: Conus radiatus
<220> FEATURE:
```

-continued

<221> NAME/KEY: CDS
<222> LOCATION: (1)..(123)

<400> SEQUENCE: 277

```
ttt gat ggc agg aat gcc gca gcc gac tac aaa ggg tct gaa ttg ctc       48
Phe Asp Gly Arg Asn Ala Ala Ala Asp Tyr Lys Gly Ser Glu Leu Leu
  1               5                  10                  15

gct atg acc gtc agg gga gga tgc tgt tcc tat cct ccc tgt atc gca       96
Ala Met Thr Val Arg Gly Gly Cys Cys Ser Tyr Pro Pro Cys Ile Ala
             20                  25                  30

aat aat cct ttt tgt gct gga aga cgc tga                              126
Asn Asn Pro Phe Cys Ala Gly Arg Arg
         35                  40
```

<210> SEQ ID NO 278
<211> LENGTH: 41
<212> TYPE: PRT
<213> ORGANISM: Conus radiatus

<400> SEQUENCE: 278

```
Phe Asp Gly Arg Asn Ala Ala Ala Asp Tyr Lys Gly Ser Glu Leu Leu
  1               5                  10                  15

Ala Met Thr Val Arg Gly Gly Cys Cys Ser Tyr Pro Pro Cys Ile Ala
             20                  25                  30

Asn Asn Pro Phe Cys Ala Gly Arg Arg
         35                  40
```

<210> SEQ ID NO 279
<211> LENGTH: 155
<212> TYPE: DNA
<213> ORGANISM: Conus virgo
<220> FEATURE:
<221> NAME/KEY: CDS
<222> LOCATION: (1)..(114)

<400> SEQUENCE: 279

```
tct tat gac agg tat gcc tcg ccc gtc gac aga gcg tct gcc ctg atc       48
Ser Tyr Asp Arg Tyr Ala Ser Pro Val Asp Arg Ala Ser Ala Leu Ile
  1               5                  10                  15

gct cag gcc atc ctt cga gat tgc tgt tcc aat cct ccc tgt tcc caa       96
Ala Gln Ala Ile Leu Arg Asp Cys Cys Ser Asn Pro Pro Cys Ser Gln
             20                  25                  30

aat aat cca gac tgt atg taaagacgct gcttgctcca ggaccctctg             144
Asn Asn Pro Asp Cys Met
         35

aaccacgacg t                                                         155
```

<210> SEQ ID NO 280
<211> LENGTH: 38
<212> TYPE: PRT
<213> ORGANISM: Conus virgo

<400> SEQUENCE: 280

```
Ser Tyr Asp Arg Tyr Ala Ser Pro Val Asp Arg Ala Ser Ala Leu Ile
  1               5                  10                  15

Ala Gln Ala Ile Leu Arg Asp Cys Cys Ser Asn Pro Pro Cys Ser Gln
             20                  25                  30

Asn Asn Pro Asp Cys Met
         35
```

<210> SEQ ID NO 281
<211> LENGTH: 155

-continued

```
<212> TYPE: DNA
<213> ORGANISM: Conus virgo
<220> FEATURE:
<221> NAME/KEY: CDS
<222> LOCATION: (1)..(114)

<400> SEQUENCE: 281

tct tat ggc agg tat gcc tca ccc gtc gac aga gcg tct gcc ctg atc       48
Ser Tyr Gly Arg Tyr Ala Ser Pro Val Asp Arg Ala Ser Ala Leu Ile
  1               5                  10                  15

gct cag gcc atc ctt cga gat tgc tgc tcc aat cct cct tgt gcc cat       96
Ala Gln Ala Ile Leu Arg Asp Cys Cys Ser Asn Pro Pro Cys Ala His
             20                  25                  30

aat aat cca gac tgt cgt taaagacgct gcttgctcca ggaccctctg             144
Asn Asn Pro Asp Cys Arg
         35

aaccacgacg t                                                          155


<210> SEQ ID NO 282
<211> LENGTH: 38
<212> TYPE: PRT
<213> ORGANISM: Conus virgo

<400> SEQUENCE: 282

Ser Tyr Gly Arg Tyr Ala Ser Pro Val Asp Arg Ala Ser Ala Leu Ile
  1               5                  10                  15

Ala Gln Ala Ile Leu Arg Asp Cys Cys Ser Asn Pro Pro Cys Ala His
             20                  25                  30

Asn Asn Pro Asp Cys Arg
         35


<210> SEQ ID NO 283
<211> LENGTH: 126
<212> TYPE: DNA
<213> ORGANISM: Conus achatinus
<220> FEATURE:
<221> NAME/KEY: CDS
<222> LOCATION: (1)..(123)

<400> SEQUENCE: 283

tct gat ggc agg aat gcc gca gcc aac gac aaa gcg tct ggc atg agc       48
Ser Asp Gly Arg Asn Ala Ala Ala Asn Asp Lys Ala Ser Gly Met Ser
  1               5                  10                  15

gcg ctg gcc gtc aat gaa tgc tgt acc aac cct gtc tgt cac gcg gaa       96
Ala Leu Ala Val Asn Glu Cys Cys Thr Asn Pro Val Cys His Ala Glu
             20                  25                  30

cat caa gaa ctt tgt gct aga aga cgc tga                              126
His Gln Glu Leu Cys Ala Arg Arg Arg
         35                  40


<210> SEQ ID NO 284
<211> LENGTH: 41
<212> TYPE: PRT
<213> ORGANISM: Conus achatinus

<400> SEQUENCE: 284

Ser Asp Gly Arg Asn Ala Ala Ala Asn Asp Lys Ala Ser Gly Met Ser
  1               5                  10                  15

Ala Leu Ala Val Asn Glu Cys Cys Thr Asn Pro Val Cys His Ala Glu
             20                  25                  30

His Gln Glu Leu Cys Ala Arg Arg Arg
         35                  40
```

-continued

<210> SEQ ID NO 285
<211> LENGTH: 126
<212> TYPE: DNA
<213> ORGANISM: Conus achatinus
<220> FEATURE:
<221> NAME/KEY: CDS
<222> LOCATION: (1)..(123)

<400> SEQUENCE: 285

```
tct gat ggc agg aat gcc gca gcc aac gac aaa gcg tct gac gtg atc       48
Ser Asp Gly Arg Asn Ala Ala Ala Asn Asp Lys Ala Ser Asp Val Ile
  1               5                  10                  15

acg ctg gcc ctc aag gga tgc tgt tcc aac cct gtc tgt cac ttg gag       96
Thr Leu Ala Leu Lys Gly Cys Cys Ser Asn Pro Val Cys His Leu Glu
             20                  25                  30

cat tca aac ctt tgt ggt aga aga cgc tga                              126
His Ser Asn Leu Cys Gly Arg Arg Arg
         35                  40
```

<210> SEQ ID NO 286
<211> LENGTH: 41
<212> TYPE: PRT
<213> ORGANISM: Conus achatinus

<400> SEQUENCE: 286

```
Ser Asp Gly Arg Asn Ala Ala Ala Asn Asp Lys Ala Ser Asp Val Ile
  1               5                  10                  15

Thr Leu Ala Leu Lys Gly Cys Cys Ser Asn Pro Val Cys His Leu Glu
             20                  25                  30

His Ser Asn Leu Cys Gly Arg Arg Arg
         35                  40
```

<210> SEQ ID NO 287
<211> LENGTH: 126
<212> TYPE: DNA
<213> ORGANISM: Conus achatinus
<220> FEATURE:
<221> NAME/KEY: CDS
<222> LOCATION: (1)..(123)

<400> SEQUENCE: 287

```
tct gat ggc agg aat gcc gca gcc aac gac aaa gcg tct ggc atg agc       48
Ser Asp Gly Arg Asn Ala Ala Ala Asn Asp Lys Ala Ser Gly Met Ser
  1               5                  10                  15

gcg ctg gcc gtc aat gaa tgc tgt acc aac cct gtc tgt cac gtg gaa       96
Ala Leu Ala Val Asn Glu Cys Cys Thr Asn Pro Val Cys His Val Glu
             20                  25                  30

cat caa gaa ctt tgt gct aga aga cgc tga                              126
His Gln Glu Leu Cys Ala Arg Arg Arg
         35                  40
```

<210> SEQ ID NO 288
<211> LENGTH: 41
<212> TYPE: PRT
<213> ORGANISM: Conus achatinus

<400> SEQUENCE: 288

```
Ser Asp Gly Arg Asn Ala Ala Ala Asn Asp Lys Ala Ser Gly Met Ser
  1               5                  10                  15

Ala Leu Ala Val Asn Glu Cys Cys Thr Asn Pro Val Cys His Val Glu
             20                  25                  30

His Gln Glu Leu Cys Ala Arg Arg Arg
         35                  40
```

-continued

```
<210> SEQ ID NO 289
<211> LENGTH: 220
<212> TYPE: DNA
<213> ORGANISM: Conus ammiralis
<220> FEATURE:
<221> NAME/KEY: CDS
<222> LOCATION: (1)..(180)

<400> SEQUENCE: 289

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat cgt gca ttt cgt ggc agg aat gcc gca gcc aaa gcg       96
Phe Thr Ser Asp Arg Ala Phe Arg Gly Arg Asn Ala Ala Ala Lys Ala
             20                  25                  30

tct ggc ctg gtc ggt ctg acc gac aag agg caa gaa tgc tgt tct tat      144
Ser Gly Leu Val Gly Leu Thr Asp Lys Arg Gln Glu Cys Cys Ser Tyr
         35                  40                  45

cct gcc tgt aac cta gat cat cca gaa ctt tgt ggt tgaagacgct           190
Pro Ala Cys Asn Leu Asp His Pro Glu Leu Cys Gly
     50                  55                  60

gatgctccag gaccctctga accacgacgt                                     220


<210> SEQ ID NO 290
<211> LENGTH: 60
<212> TYPE: PRT
<213> ORGANISM: Conus ammiralis

<400> SEQUENCE: 290

Met Phe Thr Val Phe Leu Leu Val Val Leu Ala Thr Thr Val Val Ser
  1               5                  10                  15

Phe Thr Ser Asp Arg Ala Phe Arg Gly Arg Asn Ala Ala Ala Lys Ala
             20                  25                  30

Ser Gly Leu Val Gly Leu Thr Asp Lys Arg Gln Glu Cys Cys Ser Tyr
         35                  40                  45

Pro Ala Cys Asn Leu Asp His Pro Glu Leu Cys Gly
     50                  55                  60


<210> SEQ ID NO 291
<211> LENGTH: 223
<212> TYPE: DNA
<213> ORGANISM: Conus ammiralis
<220> FEATURE:
<221> NAME/KEY: CDS
<222> LOCATION: (1)..(192)

<400> SEQUENCE: 291

atg ttc acc gtg ttt ctg ttg gtt gtc ttg gca acc act gtc gtt tcc       48
Met Phe Thr Val Phe Leu Leu Val Val Leu Ala Thr Thr Val Val Ser
  1               5                  10                  15

tcc act tca ggt cgt cgt gca ttt cgt ggc agg aat gcc gca gcc aaa       96
Ser Thr Ser Gly Arg Arg Ala Phe Arg Gly Arg Asn Ala Ala Ala Lys
             20                  25                  30

gcg tct gga ctg gtc ggt ctg act gac agg aga cca gaa tgc tgt agt      144
Ala Ser Gly Leu Val Gly Leu Thr Asp Arg Arg Pro Glu Cys Cys Ser
         35                  40                  45

gat cct cgc tgt aac tcg act cat cca gaa ctt tgt ggt gga aga cgc      192
Asp Pro Arg Cys Asn Ser Thr His Pro Glu Leu Cys Gly Gly Arg Arg
     50                  55                  60

tgatgctcca ggaccctctg aaccacgacg t                                   223
```

-continued

<210> SEQ ID NO 292
<211> LENGTH: 64
<212> TYPE: PRT
<213> ORGANISM: Conus ammiralis

<400> SEQUENCE: 292

```
Met Phe Thr Val Phe Leu Leu Val Val Leu Ala Thr Thr Val Val Ser
  1               5                  10                  15

Ser Thr Ser Gly Arg Arg Ala Phe Arg Gly Arg Asn Ala Ala Ala Lys
             20                  25                  30

Ala Ser Gly Leu Val Gly Leu Thr Asp Arg Arg Pro Glu Cys Cys Ser
         35                  40                  45

Asp Pro Arg Cys Asn Ser Thr His Pro Glu Leu Cys Gly Gly Arg Arg
     50                  55                  60
```

<210> SEQ ID NO 293
<211> LENGTH: 151
<212> TYPE: DNA
<213> ORGANISM: Conus arenatus
<220> FEATURE:
<221> NAME/KEY: CDS
<222> LOCATION: (1)..(120)

<400> SEQUENCE: 293

```
tct gat ggc agg aat gcc gca gcc aac gcg ttt gac ctg atc gat ctg       48
Ser Asp Gly Arg Asn Ala Ala Ala Asn Ala Phe Asp Leu Ile Asp Leu
  1               5                  10                  15

acc gcc agg cta aat tgc tgt atg att ccc ccc tgt tgg aag aaa tat       96
Thr Ala Arg Leu Asn Cys Cys Met Ile Pro Pro Cys Trp Lys Lys Tyr
             20                  25                  30

gga gac aga tgt agt gaa gta cgc tgatgctcca ggaccctctg aaccacgacg     150
Gly Asp Arg Cys Ser Glu Val Arg
         35                  40

t                                                                    151
```

<210> SEQ ID NO 294
<211> LENGTH: 40
<212> TYPE: PRT
<213> ORGANISM: Conus arenatus

<400> SEQUENCE: 294

```
Ser Asp Gly Arg Asn Ala Ala Ala Asn Ala Phe Asp Leu Ile Asp Leu
  1               5                  10                  15

Thr Ala Arg Leu Asn Cys Cys Met Ile Pro Pro Cys Trp Lys Lys Tyr
             20                  25                  30

Gly Asp Arg Cys Ser Glu Val Arg
         35                  40
```

<210> SEQ ID NO 295
<211> LENGTH: 126
<212> TYPE: DNA
<213> ORGANISM: Conus arenatus
<220> FEATURE:
<221> NAME/KEY: CDS
<222> LOCATION: (1)..(93)

<400> SEQUENCE: 295

```
tct gat ggc agg aat gcc gca cgc aaa gcg ttt ggc tgc tgc gac tta       48
Ser Asp Gly Arg Asn Ala Ala Arg Lys Ala Phe Gly Cys Cys Asp Leu
  1               5                  10                  15

ata ccc tgt ttg gag aga tat ggt aac aga tgt aat gaa gtg cac          93
Ile Pro Cys Leu Glu Arg Tyr Gly Asn Arg Cys Asn Glu Val His
```

-continued

```
            20                  25                  30

tgatgctcca ggaccctctg aaccacgcga cgt                                126


<210> SEQ ID NO 296
<211> LENGTH: 31
<212> TYPE: PRT
<213> ORGANISM: Conus arenatus

<400> SEQUENCE: 296

Ser Asp Gly Arg Asn Ala Ala Arg Lys Ala Phe Gly Cys Cys Asp Leu
  1               5                  10                  15

Ile Pro Cys Leu Glu Arg Tyr Gly Asn Arg Cys Asn Glu Val His
            20                  25                  30


<210> SEQ ID NO 297
<211> LENGTH: 151
<212> TYPE: DNA
<213> ORGANISM: Conus arenatus
<220> FEATURE:
<221> NAME/KEY: CDS
<222> LOCATION: (1)..(120)

<400> SEQUENCE: 297

tct gat ggc agc aat gcc gca gcc aac gag ttt gac ctg atc gct ctg       48
Ser Asp Gly Ser Asn Ala Ala Ala Asn Glu Phe Asp Leu Ile Ala Leu
  1               5                  10                  15

acc gcc agg cta ggt tgc tgt aac gtt aca ccc tgt tgg gag aaa tat       96
Thr Ala Arg Leu Gly Cys Cys Asn Val Thr Pro Cys Trp Glu Lys Tyr
            20                  25                  30

gga gac aaa tgt aat gaa gta cgc tgatgcttca ggaccctctg aaccacgacg     150
Gly Asp Lys Cys Asn Glu Val Arg
        35                  40

t                                                                    151


<210> SEQ ID NO 298
<211> LENGTH: 40
<212> TYPE: PRT
<213> ORGANISM: Conus arenatus

<400> SEQUENCE: 298

Ser Asp Gly Ser Asn Ala Ala Ala Asn Glu Phe Asp Leu Ile Ala Leu
  1               5                  10                  15

Thr Ala Arg Leu Gly Cys Cys Asn Val Thr Pro Cys Trp Glu Lys Tyr
            20                  25                  30

Gly Asp Lys Cys Asn Glu Val Arg
        35                  40


<210> SEQ ID NO 299
<211> LENGTH: 148
<212> TYPE: DNA
<213> ORGANISM: Conus arenatus
<220> FEATURE:
<221> NAME/KEY: CDS
<222> LOCATION: (1)..(117)

<400> SEQUENCE: 299

tct gat ggc agg aat gtc gca gca aaa gcg ttt cac cgg atc ggc cgg       48
Ser Asp Gly Arg Asn Val Ala Ala Lys Ala Phe His Arg Ile Gly Arg
  1               5                  10                  15

acc atc agg gat gaa tgc tgt tcc aat cct gcc tgt agg gtg aat aat       96
Thr Ile Arg Asp Glu Cys Cys Ser Asn Pro Ala Cys Arg Val Asn Asn
            20                  25                  30
```

-continued

```
cca cac gtt tgt aga cga cgc tgatgctcca ggaccctctg aaccacgacg t       148
Pro His Val Cys Arg Arg Arg
        35


<210> SEQ ID NO 300
<211> LENGTH: 39
<212> TYPE: PRT
<213> ORGANISM: Conus arenatus

<400> SEQUENCE: 300

Ser Asp Gly Arg Asn Val Ala Ala Lys Ala Phe His Arg Ile Gly Arg
  1               5                  10                  15

Thr Ile Arg Asp Glu Cys Cys Ser Asn Pro Ala Cys Arg Val Asn Asn
             20                  25                  30

Pro His Val Cys Arg Arg Arg
        35


<210> SEQ ID NO 301
<211> LENGTH: 151
<212> TYPE: DNA
<213> ORGANISM: Conus arenatus
<220> FEATURE:
<221> NAME/KEY: CDS
<222> LOCATION: (1)..(120)

<400> SEQUENCE: 301

tct gat ggc agg aat gcc gca gcc aac gcg ttt gac ctg atg cct ctg       48
Ser Asp Gly Arg Asn Ala Ala Ala Asn Ala Phe Asp Leu Met Pro Leu
  1               5                  10                  15

acc gcc agg cta aat tgc tgt agc att ccc ggc tgt tgg aac gaa tat       96
Thr Ala Arg Leu Asn Cys Cys Ser Ile Pro Gly Cys Trp Asn Glu Tyr
             20                  25                  30

aaa gac aga tgt agt aaa gta cgc tgatgctcca ggaccctctg aaccacgacg     150
Lys Asp Arg Cys Ser Lys Val Arg
        35                  40

t                                                                     151


<210> SEQ ID NO 302
<211> LENGTH: 40
<212> TYPE: PRT
<213> ORGANISM: Conus arenatus

<400> SEQUENCE: 302

Ser Asp Gly Arg Asn Ala Ala Ala Asn Ala Phe Asp Leu Met Pro Leu
  1               5                  10                  15

Thr Ala Arg Leu Asn Cys Cys Ser Ile Pro Gly Cys Trp Asn Glu Tyr
             20                  25                  30

Lys Asp Arg Cys Ser Lys Val Arg
        35                  40


<210> SEQ ID NO 303
<211> LENGTH: 157
<212> TYPE: DNA
<213> ORGANISM: Conus aurisiacus
<220> FEATURE:
<221> NAME/KEY: CDS
<222> LOCATION: (52)..(126)

<400> SEQUENCE: 303

tctgatggca ggaatgccgc agccgacgac aaagcgtctg acctggtcgc t ctg gtc      57
                                                         Leu Val
                                                           1

gtc agg gga gga tgc tgt tcc cac cct gtc tgt tac ttt aat aat cca      105
```

-continued

```
Val Arg Gly Gly Cys Cys Ser His Pro Val Cys Tyr Phe Asn Asn Pro
         5                  10                  15

caa atg tgt cgt gga aga cgc tgatgctcca ggaccctctg aaccacgacg t       157
Gln Met Cys Arg Gly Arg Arg
     20                  25


<210> SEQ ID NO 304
<211> LENGTH: 25
<212> TYPE: PRT
<213> ORGANISM: Conus aurisiacus

<400> SEQUENCE: 304

Leu Val Val Arg Gly Gly Cys Cys Ser His Pro Val Cys Tyr Phe Asn
  1               5                  10                  15

Asn Pro Gln Met Cys Arg Gly Arg Arg
             20                  25


<210> SEQ ID NO 305
<211> LENGTH: 157
<212> TYPE: DNA
<213> ORGANISM: Conus aurisiacus
<220> FEATURE:
<221> NAME/KEY: CDS
<222> LOCATION: (52)..(126)

<400> SEQUENCE: 305

tctgatggca ggaatgccgc agccgacgac aaagcgtctg acctggtcgc t ctg gcc      57
                                                         Leu Ala
                                                           1

gtc agg gga gga tgc tgt tcc cac cct gtc tgt aac ttg aat aat cca      105
Val Arg Gly Gly Cys Cys Ser His Pro Val Cys Asn Leu Asn Asn Pro
         5                  10                  15

caa atg tgt cgt gga aga cgc tgatgctcca ggaccctctg aaccacgacg t       157
Gln Met Cys Arg Gly Arg Arg
     20                  25


<210> SEQ ID NO 306
<211> LENGTH: 25
<212> TYPE: PRT
<213> ORGANISM: Conus aurisiacus

<400> SEQUENCE: 306

Leu Ala Val Arg Gly Gly Cys Cys Ser His Pro Val Cys Asn Leu Asn
  1               5                  10                  15

Asn Pro Gln Met Cys Arg Gly Arg Arg
             20                  25


<210> SEQ ID NO 307
<211> LENGTH: 157
<212> TYPE: DNA
<213> ORGANISM: Conus betulinus
<220> FEATURE:
<221> NAME/KEY: CDS
<222> LOCATION: (1)..(117)

<400> SEQUENCE: 307

ttt cgt ggc agg aat ccc gca gcc aac gac aaa agg tct gac ctg gcc       48
Phe Arg Gly Arg Asn Pro Ala Ala Asn Asp Lys Arg Ser Asp Leu Ala
  1               5                  10                  15

gct ctg agc gtc agg gga gga tgc tgt tcc cat cct gcc tgt agc gtg       96
Ala Leu Ser Val Arg Gly Gly Cys Cys Ser His Pro Ala Cys Ser Val
             20                  25                  30

act cat cca gag ctt tgt ggc tgaagacgct gatgccccag gaccctctga         147
Thr His Pro Glu Leu Cys Gly
```

-continued

```
        35

accacgacgt                                                        157


<210> SEQ ID NO 308
<211> LENGTH: 39
<212> TYPE: PRT
<213> ORGANISM: Conus betulinus

<400> SEQUENCE: 308

Phe Arg Gly Arg Asn Pro Ala Ala Asn Asp Lys Arg Ser Asp Leu Ala
  1               5                  10                  15

Ala Leu Ser Val Arg Gly Gly Cys Cys Ser His Pro Ala Cys Ser Val
             20                  25                  30

Thr His Pro Glu Leu Cys Gly
        35


<210> SEQ ID NO 309
<211> LENGTH: 151
<212> TYPE: DNA
<213> ORGANISM: Conus betulinus
<220> FEATURE:
<221> NAME/KEY: CDS
<222> LOCATION: (1)..(120)

<400> SEQUENCE: 309

tct gat ggc ggg aat gcc gca gcc aaa gcg tct gac ctg atc gct cag       48
Ser Asp Gly Gly Asn Ala Ala Ala Lys Ala Ser Asp Leu Ile Ala Gln
  1               5                  10                  15

acc atc agg gga gga tgc tgt tcc tat cct gcc tgt agc gtg gaa cat       96
Thr Ile Arg Gly Gly Cys Cys Ser Tyr Pro Ala Cys Ser Val Glu His
             20                  25                  30

caa gac ctt tgt gat gga aga cgc tgatgctcca ggaccctctg aaccacgacg     150
Gln Asp Leu Cys Asp Gly Arg Arg
        35                  40

t                                                                 151


<210> SEQ ID NO 310
<211> LENGTH: 40
<212> TYPE: PRT
<213> ORGANISM: Conus betulinus

<400> SEQUENCE: 310

Ser Asp Gly Gly Asn Ala Ala Ala Lys Ala Ser Asp Leu Ile Ala Gln
  1               5                  10                  15

Thr Ile Arg Gly Gly Cys Cys Ser Tyr Pro Ala Cys Ser Val Glu His
             20                  25                  30

Gln Asp Leu Cys Asp Gly Arg Arg
        35                  40


<210> SEQ ID NO 311
<211> LENGTH: 114
<212> TYPE: DNA
<213> ORGANISM: Conus caracteristicus
<220> FEATURE:
<221> NAME/KEY: CDS
<222> LOCATION: (1)..(111)

<400> SEQUENCE: 311

tct tat ggc agg aat gcc gca gcc aaa gcg ttt gaa gtg agt tgc tgt       48
Ser Tyr Gly Arg Asn Ala Ala Ala Lys Ala Phe Glu Val Ser Cys Cys
  1               5                  10                  15

gtc gtt cgc ccc tgt tgg att cgc tat caa gag gaa tgt ctt gaa gca       96
```

-continued

```
Val Val Arg Pro Cys Trp Ile Arg Tyr Gln Glu Glu Cys Leu Glu Ala
            20                  25                  30

gat ccc agg acc ctc tga                                          114
Asp Pro Arg Thr Leu
        35


<210> SEQ ID NO 312
<211> LENGTH: 37
<212> TYPE: PRT
<213> ORGANISM: Conus caracteristicus

<400> SEQUENCE: 312

Ser Tyr Gly Arg Asn Ala Ala Ala Lys Ala Phe Glu Val Ser Cys Cys
  1               5                  10                  15

Val Val Arg Pro Cys Trp Ile Arg Tyr Gln Glu Glu Cys Leu Glu Ala
            20                  25                  30

Asp Pro Arg Thr Leu
        35


<210> SEQ ID NO 313
<211> LENGTH: 123
<212> TYPE: DNA
<213> ORGANISM: Conus caracteristicus
<220> FEATURE:
<221> NAME/KEY: CDS
<222> LOCATION: (1)..(120)

<400> SEQUENCE: 313

tct gat ggc agg aat gcc gca gcc aac gcc ctt gac ctg atc act ctg       48
Ser Asp Gly Arg Asn Ala Ala Ala Asn Ala Leu Asp Leu Ile Thr Leu
  1               5                  10                  15

atc gcc agg caa aat tgc tgt agc att ccc ggc tgt tgg gag aaa tat       96
Ile Ala Arg Gln Asn Cys Cys Ser Ile Pro Gly Cys Trp Glu Lys Tyr
            20                  25                  30

gga gac aaa tgt agt gaa gta cgc tga                              123
Gly Asp Lys Cys Ser Glu Val Arg
        35                  40


<210> SEQ ID NO 314
<211> LENGTH: 40
<212> TYPE: PRT
<213> ORGANISM: Conus caracteristicus

<400> SEQUENCE: 314

Ser Asp Gly Arg Asn Ala Ala Ala Asn Ala Leu Asp Leu Ile Thr Leu
  1               5                  10                  15

Ile Ala Arg Gln Asn Cys Cys Ser Ile Pro Gly Cys Trp Glu Lys Tyr
            20                  25                  30

Gly Asp Lys Cys Ser Glu Val Arg
        35                  40


<210> SEQ ID NO 315
<211> LENGTH: 154
<212> TYPE: DNA
<213> ORGANISM: Conus catus
<220> FEATURE:
<221> NAME/KEY: CDS
<222> LOCATION: (1)..(123)

<400> SEQUENCE: 315

tct gat ggc agg aat gaa gca gcc aac gac gaa gcg tct gac gtg atc       48
Ser Asp Gly Arg Asn Glu Ala Ala Asn Asp Glu Ala Ser Asp Val Ile
  1               5                  10                  15
```

-continued

```
gag ctg gcc ctc aag gga tgc tgt tcc aac cct gtc tgt cac ttg gag       96
Glu Leu Ala Leu Lys Gly Cys Cys Ser Asn Pro Val Cys His Leu Glu
            20                  25                  30

cat cca aac gct tgt ggt aga aga cgc tgatgctcca ggaccctctg            143
His Pro Asn Ala Cys Gly Arg Arg Arg
        35                  40

aaccacgacg t                                                         154
```

<210> SEQ ID NO 316
<211> LENGTH: 41
<212> TYPE: PRT
<213> ORGANISM: Conus catus

<400> SEQUENCE: 316

```
Ser Asp Gly Arg Asn Glu Ala Ala Asn Asp Glu Ala Ser Asp Val Ile
  1               5                  10                  15

Glu Leu Ala Leu Lys Gly Cys Cys Ser Asn Pro Val Cys His Leu Glu
            20                  25                  30

His Pro Asn Ala Cys Gly Arg Arg Arg
        35                  40
```

<210> SEQ ID NO 317
<211> LENGTH: 154
<212> TYPE: DNA
<213> ORGANISM: Conus catus
<220> FEATURE:
<221> NAME/KEY: CDS
<222> LOCATION: (1)..(123)

<400> SEQUENCE: 317

```
tct gat ggc agg aat gcc gca gcc aac gac aaa gcg tct gac ctg gtc       48
Ser Asp Gly Arg Asn Ala Ala Ala Asn Asp Lys Ala Ser Asp Leu Val
  1               5                  10                  15

gct ctg gcc gtc agg gga tgc tgt tcc aac cct atc tgt tac ttt aat       96
Ala Leu Ala Val Arg Gly Cys Cys Ser Asn Pro Ile Cys Tyr Phe Asn
            20                  25                  30

aat cca cga att tgt cgt gga aga cgc tgatgctcca ggaccctctg            143
Asn Pro Arg Ile Cys Arg Gly Arg Arg
        35                  40

aaccacgacg t                                                         154
```

<210> SEQ ID NO 318
<211> LENGTH: 41
<212> TYPE: PRT
<213> ORGANISM: Conus catus

<400> SEQUENCE: 318

```
Ser Asp Gly Arg Asn Ala Ala Ala Asn Asp Lys Ala Ser Asp Leu Val
  1               5                  10                  15

Ala Leu Ala Val Arg Gly Cys Cys Ser Asn Pro Ile Cys Tyr Phe Asn
            20                  25                  30

Asn Pro Arg Ile Cys Arg Gly Arg Arg
        35                  40
```

<210> SEQ ID NO 319
<211> LENGTH: 111
<212> TYPE: DNA
<213> ORGANISM: Conus episcopatus
<220> FEATURE:
<221> NAME/KEY: CDS
<222> LOCATION: (1)..(108)

<400> SEQUENCE: 319

-continued

```
tct cat ggc agg aat gcc gca cgc aaa gcg tct gac ctg atc gct ctg       48
Ser His Gly Arg Asn Ala Ala Arg Lys Ala Ser Asp Leu Ile Ala Leu
  1               5                  10                  15

acc gtc agg gaa tgc tgt tct cag cct ccc tgt cgc tgg aaa cat cca       96
Thr Val Arg Glu Cys Cys Ser Gln Pro Pro Cys Arg Trp Lys His Pro
             20                  25                  30

gaa ctt tgt agt tga                                                  111
Glu Leu Cys Ser
         35


<210> SEQ ID NO 320
<211> LENGTH: 36
<212> TYPE: PRT
<213> ORGANISM: Conus episcopatus

<400> SEQUENCE: 320

Ser His Gly Arg Asn Ala Ala Arg Lys Ala Ser Asp Leu Ile Ala Leu
  1               5                  10                  15

Thr Val Arg Glu Cys Cys Ser Gln Pro Pro Cys Arg Trp Lys His Pro
             20                  25                  30

Glu Leu Cys Ser
         35


<210> SEQ ID NO 321
<211> LENGTH: 151
<212> TYPE: DNA
<213> ORGANISM: Conus geographus
<220> FEATURE:
<221> NAME/KEY: CDS
<222> LOCATION: (1)..(120)

<400> SEQUENCE: 321

tct gat ggc agg aat gac gca gcc aaa gcg ttt gac ctg ata tct tcg       48
Ser Asp Gly Arg Asn Asp Ala Ala Lys Ala Phe Asp Leu Ile Ser Ser
  1               5                  10                  15

acc gtc aag aaa gga tgc tgt tcc cat cct gcc tgt gcg ggg aat aat       96
Thr Val Lys Lys Gly Cys Cys Ser His Pro Ala Cys Ala Gly Asn Asn
             20                  25                  30

caa cat att tgt ggc cga aga cgc tgatgctcca ggaccctctg aaccacgacg     150
Gln His Ile Cys Gly Arg Arg Arg
         35                  40

t                                                                    151


<210> SEQ ID NO 322
<211> LENGTH: 40
<212> TYPE: PRT
<213> ORGANISM: Conus geographus

<400> SEQUENCE: 322

Ser Asp Gly Arg Asn Asp Ala Ala Lys Ala Phe Asp Leu Ile Ser Ser
  1               5                  10                  15

Thr Val Lys Lys Gly Cys Cys Ser His Pro Ala Cys Ala Gly Asn Asn
             20                  25                  30

Gln His Ile Cys Gly Arg Arg Arg
         35                  40


<210> SEQ ID NO 323
<211> LENGTH: 154
<212> TYPE: DNA
<213> ORGANISM: Conus geographus
<220> FEATURE:
<221> NAME/KEY: CDS
```

-continued

<222> LOCATION: (1)..(123)

<400> SEQUENCE: 323

```
tct gat ggc agg aat gcc gca gcc aac gac caa gcg tct gac ctg atg       48
Ser Asp Gly Arg Asn Ala Ala Ala Asn Asp Gln Ala Ser Asp Leu Met
  1               5                  10                  15

gct gcg acc gtc agg gga tgc tgt gcc gtt cct tcc tgt cgc ctc cgt       96
Ala Ala Thr Val Arg Gly Cys Cys Ala Val Pro Ser Cys Arg Leu Arg
             20                  25                  30

aat cca gac ctt tgt ggt gga gga cgc tgatgctcca ggaccctctg           143
Asn Pro Asp Leu Cys Gly Gly Gly Arg
         35                  40

aaccacgacg t                                                         154
```

<210> SEQ ID NO 324
<211> LENGTH: 41
<212> TYPE: PRT
<213> ORGANISM: Conus geographus

<400> SEQUENCE: 324

```
Ser Asp Gly Arg Asn Ala Ala Ala Asn Asp Gln Ala Ser Asp Leu Met
  1               5                  10                  15

Ala Ala Thr Val Arg Gly Cys Cys Ala Val Pro Ser Cys Arg Leu Arg
             20                  25                  30

Asn Pro Asp Leu Cys Gly Gly Gly Arg
         35                  40
```

<210> SEQ ID NO 325
<211> LENGTH: 120
<212> TYPE: DNA
<213> ORGANISM: Conus imperialis
<220> FEATURE:
<221> NAME/KEY: CDS
<222> LOCATION: (1)..(117)

<400> SEQUENCE: 325

```
ctt gat gaa agg aat gcc gca gcc gac gac aaa gcg tct gac ctg atc       48
Leu Asp Glu Arg Asn Ala Ala Ala Asp Asp Lys Ala Ser Asp Leu Ile
  1               5                  10                  15

gct caa atc gtc agg aga gga tgc tgt tcc cat cct gcc tgt aac gtg       96
Ala Gln Ile Val Arg Arg Gly Cys Cys Ser His Pro Ala Cys Asn Val
             20                  25                  30

aat aat cca cac att tgt ggt tga                                      120
Asn Asn Pro His Ile Cys Gly
         35
```

<210> SEQ ID NO 326
<211> LENGTH: 39
<212> TYPE: PRT
<213> ORGANISM: Conus imperialis

<400> SEQUENCE: 326

```
Leu Asp Glu Arg Asn Ala Ala Ala Asp Asp Lys Ala Ser Asp Leu Ile
  1               5                  10                  15

Ala Gln Ile Val Arg Arg Gly Cys Cys Ser His Pro Ala Cys Asn Val
             20                  25                  30

Asn Asn Pro His Ile Cys Gly
         35
```

<210> SEQ ID NO 327
<211> LENGTH: 142
<212> TYPE: DNA

-continued

```
<213> ORGANISM: Conus lividus
<220> FEATURE:
<221> NAME/KEY: CDS
<222> LOCATION: (1)..(111)

<400> SEQUENCE: 327

tct gat ggc agg aat act gca gcc aaa gtc aaa tat tct aag acg ccg       48
Ser Asp Gly Arg Asn Thr Ala Ala Lys Val Lys Tyr Ser Lys Thr Pro
  1               5                  10                  15

gag gaa tgc tgt ccc aat cct ccc tgt ttc gcg aca aat tcg gat att       96
Glu Glu Cys Cys Pro Asn Pro Pro Cys Phe Ala Thr Asn Ser Asp Ile
             20                  25                  30

tgt ggc gga aga cgc tgatgctcca ggaccctctg aaccacgacg t               142
Cys Gly Gly Arg Arg
         35


<210> SEQ ID NO 328
<211> LENGTH: 37
<212> TYPE: PRT
<213> ORGANISM: Conus lividus

<400> SEQUENCE: 328

Ser Asp Gly Arg Asn Thr Ala Ala Lys Val Lys Tyr Ser Lys Thr Pro
  1               5                  10                  15

Glu Glu Cys Cys Pro Asn Pro Pro Cys Phe Ala Thr Asn Ser Asp Ile
             20                  25                  30

Cys Gly Gly Arg Arg
         35


<210> SEQ ID NO 329
<211> LENGTH: 157
<212> TYPE: DNA
<213> ORGANISM: Conus lividus
<220> FEATURE:
<221> NAME/KEY: CDS
<222> LOCATION: (1)..(117)

<400> SEQUENCE: 329

tct aat ggc agg aat gcc gca gcc aaa ttc aaa gcg cct gcc ctg atg       48
Ser Asn Gly Arg Asn Ala Ala Ala Lys Phe Lys Ala Pro Ala Leu Met
  1               5                  10                  15

aag cgg acc gtc agg gat gct tgc tgt tca gac cct cgc tgt tcc ggg       96
Lys Arg Thr Val Arg Asp Ala Cys Cys Ser Asp Pro Arg Cys Ser Gly
             20                  25                  30

aaa cat caa gac ctg tgt ggc tgaagacgct gatgctccag gaccctctga         147
Lys His Gln Asp Leu Cys Gly
         35

accacgacgt                                                           157


<210> SEQ ID NO 330
<211> LENGTH: 39
<212> TYPE: PRT
<213> ORGANISM: Conus lividus

<400> SEQUENCE: 330

Ser Asn Gly Arg Asn Ala Ala Ala Lys Phe Lys Ala Pro Ala Leu Met
  1               5                  10                  15

Lys Arg Thr Val Arg Asp Ala Cys Cys Ser Asp Pro Arg Cys Ser Gly
             20                  25                  30

Lys His Gln Asp Leu Cys Gly
         35
```

-continued

```
<210> SEQ ID NO 331
<211> LENGTH: 157
<212> TYPE: DNA
<213> ORGANISM: Conus lividus
<220> FEATURE:
<221> NAME/KEY: CDS
<222> LOCATION: (1)..(117)

<400> SEQUENCE: 331

tct aat ggc agg aat gcc gca gcc aaa ttc aaa gcg cct gcc ctg atg       48
Ser Asn Gly Arg Asn Ala Ala Ala Lys Phe Lys Ala Pro Ala Leu Met
  1               5                  10                  15

gag ctg acc gtc agg gaa gat tgc tgt tca gac cct cgc tgt tcc gtg       96
Glu Leu Thr Val Arg Glu Asp Cys Cys Ser Asp Pro Arg Cys Ser Val
             20                  25                  30

gga cat caa gac ctg tgt ggc tgaagacgct gatgctccag gaccctctga         147
Gly His Gln Asp Leu Cys Gly
         35

accacgacgt                                                           157


<210> SEQ ID NO 332
<211> LENGTH: 39
<212> TYPE: PRT
<213> ORGANISM: Conus lividus

<400> SEQUENCE: 332

Ser Asn Gly Arg Asn Ala Ala Ala Lys Phe Lys Ala Pro Ala Leu Met
  1               5                  10                  15

Glu Leu Thr Val Arg Glu Asp Cys Cys Ser Asp Pro Arg Cys Ser Val
             20                  25                  30

Gly His Gln Asp Leu Cys Gly
         35


<210> SEQ ID NO 333
<211> LENGTH: 157
<212> TYPE: DNA
<213> ORGANISM: Conus lividus
<220> FEATURE:
<221> NAME/KEY: CDS
<222> LOCATION: (1)..(126)

<400> SEQUENCE: 333

gca ttt gat ggc agg aat gct gca gcc agc gac aaa gcg tcc gag ctg       48
Ala Phe Asp Gly Arg Asn Ala Ala Ala Ser Asp Lys Ala Ser Glu Leu
  1               5                  10                  15

atg gct ctg gcc gtc agg gga tgc tgt tcc cat cct gcc tgt gct ggg       96
Met Ala Leu Ala Val Arg Gly Cys Cys Ser His Pro Ala Cys Ala Gly
             20                  25                  30

agt aat gca cat atc tgt ggc aga aga cgc tgatgctcca ggaccctctg        146
Ser Asn Ala His Ile Cys Gly Arg Arg Arg
         35                  40

aaccacgacg t                                                         157


<210> SEQ ID NO 334
<211> LENGTH: 42
<212> TYPE: PRT
<213> ORGANISM: Conus lividus

<400> SEQUENCE: 334

Ala Phe Asp Gly Arg Asn Ala Ala Ala Ser Asp Lys Ala Ser Glu Leu
  1               5                  10                  15

Met Ala Leu Ala Val Arg Gly Cys Cys Ser His Pro Ala Cys Ala Gly
             20                  25                  30
```

```
Ser Asn Ala His Ile Cys Gly Arg Arg Arg
        35                  40


<210> SEQ ID NO 335
<211> LENGTH: 157
<212> TYPE: DNA
<213> ORGANISM: Conus lividus
<220> FEATURE:
<221> NAME/KEY: CDS
<222> LOCATION: (1)..(117)

<400> SEQUENCE: 335

tct aat ggc agg aat gcc gca gcc aaa ttc aaa gcg cct gcc ctg atg       48
Ser Asn Gly Arg Asn Ala Ala Ala Lys Phe Lys Ala Pro Ala Leu Met
  1               5                  10                  15

aag ctg acc gtc agg gag gat tgc tgt tca gac cct cgc tgt tcc gtg       96
Lys Leu Thr Val Arg Glu Asp Cys Cys Ser Asp Pro Arg Cys Ser Val
             20                  25                  30

gga cat caa gac atg tgt ggc tgaagacgct gatgctccag gaccctctga         147
Gly His Gln Asp Met Cys Gly
        35

atcacgacgt                                                           157


<210> SEQ ID NO 336
<211> LENGTH: 39
<212> TYPE: PRT
<213> ORGANISM: Conus lividus

<400> SEQUENCE: 336

Ser Asn Gly Arg Asn Ala Ala Ala Lys Phe Lys Ala Pro Ala Leu Met
  1               5                  10                  15

Lys Leu Thr Val Arg Glu Asp Cys Cys Ser Asp Pro Arg Cys Ser Val
             20                  25                  30

Gly His Gln Asp Met Cys Gly
        35


<210> SEQ ID NO 337
<211> LENGTH: 154
<212> TYPE: DNA
<213> ORGANISM: Conus lividus
<220> FEATURE:
<221> NAME/KEY: CDS
<222> LOCATION: (1)..(114)

<400> SEQUENCE: 337

ttt gaa tgc agg aat gct gca ggc aac gac aaa gcg act gac ctg atg       48
Phe Glu Cys Arg Asn Ala Ala Gly Asn Asp Lys Ala Thr Asp Leu Met
  1               5                  10                  15

gct ctg act gtc agg gga tgc tgt tcc cat cct gcc tgt gct ggg aat       96
Ala Leu Thr Val Arg Gly Cys Cys Ser His Pro Ala Cys Ala Gly Asn
             20                  25                  30

aat cca cat atc tgc ggc tgaagacgct gatgctccag gaccctctga             144
Asn Pro His Ile Cys Gly
        35

accacgacgt                                                           154


<210> SEQ ID NO 338
<211> LENGTH: 38
<212> TYPE: PRT
<213> ORGANISM: Conus lividus

<400> SEQUENCE: 338
```

-continued

```
Phe Glu Cys Arg Asn Ala Ala Gly Asn Asp Lys Ala Thr Asp Leu Met
  1               5                  10                  15

Ala Leu Thr Val Arg Gly Cys Cys Ser His Pro Ala Cys Ala Gly Asn
             20                  25                  30

Asn Pro His Ile Cys Gly
         35


<210> SEQ ID NO 339
<211> LENGTH: 154
<212> TYPE: DNA
<213> ORGANISM: Conus lividus
<220> FEATURE:
<221> NAME/KEY: CDS
<222> LOCATION: (1)..(114)

<400> SEQUENCE: 339

ttt gat ggc agg aac gcc gca gcc aac aac aaa gcg act gat ctg atg       48
Phe Asp Gly Arg Asn Ala Ala Ala Asn Asn Lys Ala Thr Asp Leu Met
  1               5                  10                  15

gct ctg act gtc aga gga tgc tgt ggc aat cct tca tgt agc atc cat       96
Ala Leu Thr Val Arg Gly Cys Cys Gly Asn Pro Ser Cys Ser Ile His
             20                  25                  30

att cct tac gtt tgt aat tagagacact gatgctccag gaccctctga             144
Ile Pro Tyr Val Cys Asn
         35

accacgacgt                                                           154


<210> SEQ ID NO 340
<211> LENGTH: 38
<212> TYPE: PRT
<213> ORGANISM: Conus lividus

<400> SEQUENCE: 340

Phe Asp Gly Arg Asn Ala Ala Ala Asn Asn Lys Ala Thr Asp Leu Met
  1               5                  10                  15

Ala Leu Thr Val Arg Gly Cys Cys Gly Asn Pro Ser Cys Ser Ile His
             20                  25                  30

Ile Pro Tyr Val Cys Asn
         35


<210> SEQ ID NO 341
<211> LENGTH: 157
<212> TYPE: DNA
<213> ORGANISM: Conus lividus
<220> FEATURE:
<221> NAME/KEY: CDS
<222> LOCATION: (1)..(126)

<400> SEQUENCE: 341

tct aat ggc agg aat gcc gca gcc aaa ttc aaa gcg cct gcc ctg atg       48
Ser Asn Gly Arg Asn Ala Ala Ala Lys Phe Lys Ala Pro Ala Leu Met
  1               5                  10                  15

aag cgg acc gac agc gaa gaa tgc tgt tta gac tct cgc tgt gcc ggg       96
Lys Arg Thr Asp Ser Glu Glu Cys Cys Leu Asp Ser Arg Cys Ala Gly
             20                  25                  30

caa cat caa gac ctg tgt ggc gga aga cgc tgatgctcca ggaccctctg        146
Gln His Gln Asp Leu Cys Gly Gly Arg Arg
         35                  40

aaccacgacg t                                                         157


<210> SEQ ID NO 342
<211> LENGTH: 42
```

-continued

<212> TYPE: PRT
<213> ORGANISM: Conus lividus

<400> SEQUENCE: 342

```
Ser Asn Gly Arg Asn Ala Ala Ala Lys Phe Lys Ala Pro Ala Leu Met
  1               5                  10                  15

Lys Arg Thr Asp Ser Glu Glu Cys Cys Leu Asp Ser Arg Cys Ala Gly
             20                  25                  30

Gln His Gln Asp Leu Cys Gly Gly Arg Arg
         35                  40
```

<210> SEQ ID NO 343
<211> LENGTH: 126
<212> TYPE: DNA
<213> ORGANISM: Conus marmoreus
<220> FEATURE:
<221> NAME/KEY: CDS
<222> LOCATION: (1)..(123)

<400> SEQUENCE: 343

```
tct gat ggc agg aat gcc gca gcc aag gac aaa gcg tct gac ctg gtc       48
Ser Asp Gly Arg Asn Ala Ala Ala Lys Asp Lys Ala Ser Asp Leu Val
  1               5                  10                  15

gct ctg acc gtc aag gga tgc tgt tct aat cct ccc tgt tac gcg aat       96
Ala Leu Thr Val Lys Gly Cys Cys Ser Asn Pro Pro Cys Tyr Ala Asn
             20                  25                  30

aat caa gcc tat tgt aat gga aga cgc tga                              126
Asn Gln Ala Tyr Cys Asn Gly Arg Arg
         35                  40
```

<210> SEQ ID NO 344
<211> LENGTH: 41
<212> TYPE: PRT
<213> ORGANISM: Conus marmoreus

<400> SEQUENCE: 344

```
Ser Asp Gly Arg Asn Ala Ala Ala Lys Asp Lys Ala Ser Asp Leu Val
  1               5                  10                  15

Ala Leu Thr Val Lys Gly Cys Cys Ser Asn Pro Pro Cys Tyr Ala Asn
             20                  25                  30

Asn Gln Ala Tyr Cys Asn Gly Arg Arg
         35                  40
```

<210> SEQ ID NO 345
<211> LENGTH: 117
<212> TYPE: DNA
<213> ORGANISM: Conus marmoreus
<220> FEATURE:
<221> NAME/KEY: CDS
<222> LOCATION: (1)..(114)

<400> SEQUENCE: 345

```
tct gat ggc agg aat gcc gca gcc aag gac aaa gcg tct gac ctg gtc       48
Ser Asp Gly Arg Asn Ala Ala Ala Lys Asp Lys Ala Ser Asp Leu Val
  1               5                  10                  15

gct ctg acc gtc aag gga tgc tgt tct cat cct gcc tgt agc gtg aat       96
Ala Leu Thr Val Lys Gly Cys Cys Ser His Pro Ala Cys Ser Val Asn
             20                  25                  30

aat cca gac att tgt ggt tga                                          117
Asn Pro Asp Ile Cys Gly
         35
```

<210> SEQ ID NO 346

-continued

<211> LENGTH: 38
<212> TYPE: PRT
<213> ORGANISM: Conus marmoreus

<400> SEQUENCE: 346

```
Ser Asp Gly Arg Asn Ala Ala Ala Lys Asp Lys Ala Ser Asp Leu Val
  1               5                  10                  15

Ala Leu Thr Val Lys Gly Cys Cys Ser His Pro Ala Cys Ser Val Asn
             20                  25                  30

Asn Pro Asp Ile Cys Gly
         35
```

<210> SEQ ID NO 347
<211> LENGTH: 145
<212> TYPE: DNA
<213> ORGANISM: Conus musicus
<220> FEATURE:
<221> NAME/KEY: CDS
<222> LOCATION: (1)..(114)

<400> SEQUENCE: 347

```
tct gat ggc agg aat gct gca gcc aac aac aaa gtg gct ttg acc atg       48
Ser Asp Gly Arg Asn Ala Ala Ala Asn Asn Lys Val Ala Leu Thr Met
  1               5                  10                  15

agg gga aaa tgc tgt atc aat gat gcg tgt cgc tcg aaa cat cca cag       96
Arg Gly Lys Cys Cys Ile Asn Asp Ala Cys Arg Ser Lys His Pro Gln
             20                  25                  30

tac tgt tct gga aga cgc tgatactcca ggaccctctg aaccacgacg t          145
Tyr Cys Ser Gly Arg Arg
         35
```

<210> SEQ ID NO 348
<211> LENGTH: 38
<212> TYPE: PRT
<213> ORGANISM: Conus musicus

<400> SEQUENCE: 348

```
Ser Asp Gly Arg Asn Ala Ala Ala Asn Asn Lys Val Ala Leu Thr Met
  1               5                  10                  15

Arg Gly Lys Cys Cys Ile Asn Asp Ala Cys Arg Ser Lys His Pro Gln
             20                  25                  30

Tyr Cys Ser Gly Arg Arg
         35
```

<210> SEQ ID NO 349
<211> LENGTH: 154
<212> TYPE: DNA
<213> ORGANISM: Conus musicus
<220> FEATURE:
<221> NAME/KEY: CDS
<222> LOCATION: (1)..(123)

<400> SEQUENCE: 349

```
tct gat ggc agg aat gct gca gcc aac gac aaa gtg tct gac cag atg       48
Ser Asp Gly Arg Asn Ala Ala Ala Asn Asp Lys Val Ser Asp Gln Met
  1               5                  10                  15

gct ctg gtt gtc agg gga tgc tgt tac aat att gcc tgt aga att aat       96
Ala Leu Val Val Arg Gly Cys Cys Tyr Asn Ile Ala Cys Arg Ile Asn
             20                  25                  30

aat cca cgg tac tgt cgt gga aaa cgc tgatgttcca ggaccctctg            143
Asn Pro Arg Tyr Cys Arg Gly Lys Arg
         35                  40

aaccacgacg t                                                         154
```

-continued

```
<210> SEQ ID NO 350
<211> LENGTH: 41
<212> TYPE: PRT
<213> ORGANISM: Conus musicus

<400> SEQUENCE: 350

Ser Asp Gly Arg Asn Ala Ala Ala Asn Asp Lys Val Ser Asp Gln Met
  1               5                  10                  15

Ala Leu Val Val Arg Gly Cys Cys Tyr Asn Ile Ala Cys Arg Ile Asn
             20                  25                  30

Asn Pro Arg Tyr Cys Arg Gly Lys Arg
         35                  40


<210> SEQ ID NO 351
<211> LENGTH: 154
<212> TYPE: DNA
<213> ORGANISM: Conus obscurus
<220> FEATURE:
<221> NAME/KEY: CDS
<222> LOCATION: (52)..(123)

<400> SEQUENCE: 351

tctgaaggca ggaatgccgc agccaacgac aaagcgtctg acctgatggc t ctg aac       57
                                                          Leu Asn
                                                            1

gtc agg gga tgc tgt tcc cat cct gtc tgt cgc ttc aat tat cca aaa      105
Val Arg Gly Cys Cys Ser His Pro Val Cys Arg Phe Asn Tyr Pro Lys
          5                  10                  15

tat tgt ggt gga aga cgc tgatggtcca ggaccctctg aaccacgacg t           154
Tyr Cys Gly Gly Arg Arg
     20


<210> SEQ ID NO 352
<211> LENGTH: 24
<212> TYPE: PRT
<213> ORGANISM: Conus obscurus

<400> SEQUENCE: 352

Leu Asn Val Arg Gly Cys Cys Ser His Pro Val Cys Arg Phe Asn Tyr
  1               5                  10                  15

Pro Lys Tyr Cys Gly Gly Arg Arg
             20


<210> SEQ ID NO 353
<211> LENGTH: 151
<212> TYPE: DNA
<213> ORGANISM: Conus obscurus
<220> FEATURE:
<221> NAME/KEY: CDS
<222> LOCATION: (46)..(111)

<400> SEQUENCE: 353

tctgatggcg ggaatgccgc agcaaaagcg tttgatctaa tcact ctg gcc ctc agg     57
                                                  Leu Ala Leu Arg
                                                    1

gat gaa tgc tgt gcc agt cct ccc tgt cgt ttg aat aat cca tac gta      105
Asp Glu Cys Cys Ala Ser Pro Pro Cys Arg Leu Asn Asn Pro Tyr Val
  5                  10                  15                  20

tgt cat tgacgacgct gatgctccag gaccctctga accacgacgt                  151
Cys His


<210> SEQ ID NO 354
```

-continued

```
<211> LENGTH: 22
<212> TYPE: PRT
<213> ORGANISM: Conus obscurus

<400> SEQUENCE: 354

Leu Ala Leu Arg Asp Glu Cys Cys Ala Ser Pro Pro Cys Arg Leu Asn
  1               5                  10                  15

Asn Pro Tyr Val Cys His
             20


<210> SEQ ID NO 355
<211> LENGTH: 217
<212> TYPE: DNA
<213> ORGANISM: Conus obscurus
<220> FEATURE:
<221> NAME/KEY: CDS
<222> LOCATION: (1)..(186)

<400> SEQUENCE: 355

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ccc act tca gat cgt gca tct gat agg agg aat gcc gca gcc aaa gcg       96
Pro Thr Ser Asp Arg Ala Ser Asp Arg Arg Asn Ala Ala Ala Lys Ala
             20                  25                  30

ttt gac ctg aga tat tcg acc gcc aag aga gga tgc tgt tcc aat cct      144
Phe Asp Leu Arg Tyr Ser Thr Ala Lys Arg Gly Cys Cys Ser Asn Pro
         35                  40                  45

gtc tgt tgg cag aat aat gca gaa tac tgt cgt gaa agt ggc              186
Val Cys Trp Gln Asn Asn Ala Glu Tyr Cys Arg Glu Ser Gly
     50                  55                  60

taatgctcca ggaccctctg aaccacgacg t                                   217


<210> SEQ ID NO 356
<211> LENGTH: 62
<212> TYPE: PRT
<213> ORGANISM: Conus obscurus

<400> SEQUENCE: 356

Met Phe Thr Val Phe Leu Leu Val Val Leu Ala Thr Thr Val Val Ser
  1               5                  10                  15

Pro Thr Ser Asp Arg Ala Ser Asp Arg Arg Asn Ala Ala Ala Lys Ala
             20                  25                  30

Phe Asp Leu Arg Tyr Ser Thr Ala Lys Arg Gly Cys Cys Ser Asn Pro
         35                  40                  45

Val Cys Trp Gln Asn Asn Ala Glu Tyr Cys Arg Glu Ser Gly
     50                  55                  60


<210> SEQ ID NO 357
<211> LENGTH: 208
<212> TYPE: DNA
<213> ORGANISM: Conus obscurus
<220> FEATURE:
<221> NAME/KEY: CDS
<222> LOCATION: (1)..(168)

<400> SEQUENCE: 357

atg ttc acc gtg ttt ctg ttg gtt gtc ttg gca acc acc gtc gtt tcc       48
Met Phe Thr Val Phe Leu Leu Val Val Leu Ala Thr Thr Val Val Ser
  1               5                  10                  15

ttc act tca gat cgt gca tct gat ggc ggg aat gtc gca gcg tct cac       96
Phe Thr Ser Asp Arg Ala Ser Asp Gly Gly Asn Val Ala Ala Ser His
             20                  25                  30
```

-continued

```
ctg atc gct ctg acc atc aag gga tgc tgt tct cac cct ccc tgt gcc      144
Leu Ile Ala Leu Thr Ile Lys Gly Cys Cys Ser His Pro Pro Cys Ala
        35                  40                  45

cag aat aat caa gac tat tgt ggt tgacgacgct gatgctccag gaccctctga     198
Gln Asn Asn Gln Asp Tyr Cys Gly
    50                  55

accacgacgt                                                           208


<210> SEQ ID NO 358
<211> LENGTH: 56
<212> TYPE: PRT
<213> ORGANISM: Conus obscurus

<400> SEQUENCE: 358

Met Phe Thr Val Phe Leu Leu Val Val Leu Ala Thr Thr Val Val Ser
  1               5                  10                  15

Phe Thr Ser Asp Arg Ala Ser Asp Gly Gly Asn Val Ala Ala Ser His
             20                  25                  30

Leu Ile Ala Leu Thr Ile Lys Gly Cys Cys Ser His Pro Pro Cys Ala
        35                  40                  45

Gln Asn Asn Gln Asp Tyr Cys Gly
    50                  55


<210> SEQ ID NO 359
<211> LENGTH: 217
<212> TYPE: DNA
<213> ORGANISM: Conus obscurus
<220> FEATURE:
<221> NAME/KEY: CDS
<222> LOCATION: (1)..(186)

<400> SEQUENCE: 359

atg ttc acc gtg ttt ctg ttg gtt gtc tta tca acc acc gtc gtt tcc       48
Met Phe Thr Val Phe Leu Leu Val Val Leu Ser Thr Thr Val Val Ser
  1               5                  10                  15

tcc act tca gat cgt gca tct gat agg agg aat gcc gca gcc aaa gcg       96
Ser Thr Ser Asp Arg Ala Ser Asp Arg Arg Asn Ala Ala Ala Lys Ala
             20                  25                  30

tct gac ctg atg tat tcg acc gtc aag aaa gga tgt tgt tcc cat cct      144
Ser Asp Leu Met Tyr Ser Thr Val Lys Lys Gly Cys Cys Ser His Pro
        35                  40                  45

gcc tgt tcg ggg aat aat cga gaa tat tgt cgt gaa agt ggc              186
Ala Cys Ser Gly Asn Asn Arg Glu Tyr Cys Arg Glu Ser Gly
    50                  55                  60

taatgctcca ggaccctctg aaccacgacg t                                   217


<210> SEQ ID NO 360
<211> LENGTH: 62
<212> TYPE: PRT
<213> ORGANISM: Conus obscurus

<400> SEQUENCE: 360

Met Phe Thr Val Phe Leu Leu Val Val Leu Ser Thr Thr Val Val Ser
  1               5                  10                  15

Ser Thr Ser Asp Arg Ala Ser Asp Arg Arg Asn Ala Ala Ala Lys Ala
             20                  25                  30

Ser Asp Leu Met Tyr Ser Thr Val Lys Lys Gly Cys Cys Ser His Pro
        35                  40                  45

Ala Cys Ser Gly Asn Asn Arg Glu Tyr Cys Arg Glu Ser Gly
    50                  55                  60
```

-continued

```
<210> SEQ ID NO 361
<211> LENGTH: 157
<212> TYPE: DNA
<213> ORGANISM: Conus omaria
<220> FEATURE:
<221> NAME/KEY: CDS
<222> LOCATION: (52)..(126)

<400> SEQUENCE: 361

tttgatggca ggaatgcctc agccgacagc aaagtggctg cccggatcgc t cag atc      57
                                                         Gln Ile
                                                           1

gac agg gat cca tgc tgt tcc tat cct gac tgt ggc gcg aat cat cca      105
Asp Arg Asp Pro Cys Cys Ser Tyr Pro Asp Cys Gly Ala Asn His Pro
          5                  10                  15

gag att tgt ggt gga aaa cgc tgatgctcca ggaccctctg aaccacgacg t       157
Glu Ile Cys Gly Gly Lys Arg
     20                  25


<210> SEQ ID NO 362
<211> LENGTH: 25
<212> TYPE: PRT
<213> ORGANISM: Conus omaria

<400> SEQUENCE: 362

Gln Ile Asp Arg Asp Pro Cys Cys Ser Tyr Pro Asp Cys Gly Ala Asn
  1               5                  10                  15

His Pro Glu Ile Cys Gly Gly Lys Arg
             20                  25


<210> SEQ ID NO 363
<211> LENGTH: 128
<212> TYPE: DNA
<213> ORGANISM: Conus omaria
<220> FEATURE:
<221> NAME/KEY: CDS
<222> LOCATION: (26)..(88)

<400> SEQUENCE: 363

tctcatggca ggaatgccgc acgct ctg acc gtc agg gaa tgc tgt tct cag       52
                            Leu Thr Val Arg Glu Cys Cys Ser Gln
                              1               5

cct cct tgt cgc tgg aaa cat cca gaa ctt tgt agt tgaagacgct            98
Pro Pro Cys Arg Trp Lys His Pro Glu Leu Cys Ser
 10                  15                  20

gatgctccag gaccctctga accacgacgt                                     128


<210> SEQ ID NO 364
<211> LENGTH: 21
<212> TYPE: PRT
<213> ORGANISM: Conus omaria

<400> SEQUENCE: 364

Leu Thr Val Arg Glu Cys Cys Ser Gln Pro Pro Cys Arg Trp Lys His
  1               5                  10                  15

Pro Glu Leu Cys Ser
             20


<210> SEQ ID NO 365
<211> LENGTH: 154
<212> TYPE: DNA
<213> ORGANISM: Conus omaria
<220> FEATURE:
```

-continued

```
<221> NAME/KEY: CDS
<222> LOCATION: (52)..(123)

<400> SEQUENCE: 365

tttgatggca ggaatgctgc agccagcgac aaagcgtctg agctgatggc t ctg gcc      57
                                                         Leu Ala
                                                           1

gtc agg gga tgc tgt tcc cat cct gcc tgt gct ggg aat aat cca cat      105
Val Arg Gly Cys Cys Ser His Pro Ala Cys Ala Gly Asn Asn Pro His
          5                  10                  15

atc tgt ggc aga aga cgc tgatgctcca ggaccctctg aaccacgacg t           154
Ile Cys Gly Arg Arg Arg
     20


<210> SEQ ID NO 366
<211> LENGTH: 24
<212> TYPE: PRT
<213> ORGANISM: Conus omaria

<400> SEQUENCE: 366

Leu Ala Val Arg Gly Cys Cys Ser His Pro Ala Cys Ala Gly Asn Asn
  1               5                  10                  15

Pro His Ile Cys Gly Arg Arg Arg
             20


<210> SEQ ID NO 367
<211> LENGTH: 142
<212> TYPE: DNA
<213> ORGANISM: Conus omaria
<220> FEATURE:
<221> NAME/KEY: CDS
<222> LOCATION: (40)..(102)

<400> SEQUENCE: 367

tctggtgtca ggaaagacgc agcgcctggc ctgatcgct ctg acc atc aag gga        54
                                           Leu Thr Ile Lys Gly
                                             1               5

tgc tgt tct gat cct agc tgt aac gtg aat aat cca gac tat tgt ggt      102
Cys Cys Ser Asp Pro Ser Cys Asn Val Asn Asn Pro Asp Tyr Cys Gly
                10                  15                  20

tgacgacgct gatgctccag gaccctctga accacgacgt                          142


<210> SEQ ID NO 368
<211> LENGTH: 21
<212> TYPE: PRT
<213> ORGANISM: Conus omaria

<400> SEQUENCE: 368

Leu Thr Ile Lys Gly Cys Cys Ser Asp Pro Ser Cys Asn Val Asn Asn
  1               5                  10                  15

Pro Asp Tyr Cys Gly
             20


<210> SEQ ID NO 369
<211> LENGTH: 157
<212> TYPE: DNA
<213> ORGANISM: Conus omaria
<220> FEATURE:
<221> NAME/KEY: CDS
<222> LOCATION: (52)..(117)

<400> SEQUENCE: 369

tctaatggca ggaatgccgc agccaaattc aaagcgcctg ccctgatgga g ctg acc      57
                                                         Leu Thr
```

-continued

```
                                                   1

gtc agg gaa gaa tgc tgt tca gac cct cgc tgt tcc gtg gga cat caa      105
Val Arg Glu Glu Cys Cys Ser Asp Pro Arg Cys Ser Val Gly His Gln
          5                  10                  15

gat atg tgt cgg tgaagcacgt gatgctccag gaccctctga accacgacgt          157
Asp Met Cys Arg
     20


<210> SEQ ID NO 370
<211> LENGTH: 22
<212> TYPE: PRT
<213> ORGANISM: Conus omaria

<400> SEQUENCE: 370

Leu Thr Val Arg Glu Glu Cys Cys Ser Asp Pro Arg Cys Ser Val Gly
  1               5                  10                  15

His Gln Asp Met Cys Arg
             20


<210> SEQ ID NO 371
<211> LENGTH: 151
<212> TYPE: DNA
<213> ORGANISM: Conus purpurascens
<220> FEATURE:
<221> NAME/KEY: CDS
<222> LOCATION: (1)..(120)

<400> SEQUENCE: 371

act gat ggc agg aat gct gca gcc ata gcg ctt gac ctg atc gct ccg       48
Thr Asp Gly Arg Asn Ala Ala Ala Ile Ala Leu Asp Leu Ile Ala Pro
  1               5                  10                  15

gcc gtc agg gga gga tgc tgt tcc aat cct gcc tgt tta gtg aat cat       96
Ala Val Arg Gly Gly Cys Cys Ser Asn Pro Ala Cys Leu Val Asn His
             20                  25                  30

cta gaa atg tgt ggt aaa aga cgc tgatgcccca ggaccctctg aaccacgacg     150
Leu Glu Met Cys Gly Lys Arg Arg
         35                  40

t                                                                    151


<210> SEQ ID NO 372
<211> LENGTH: 40
<212> TYPE: PRT
<213> ORGANISM: Conus purpurascens

<400> SEQUENCE: 372

Thr Asp Gly Arg Asn Ala Ala Ala Ile Ala Leu Asp Leu Ile Ala Pro
  1               5                  10                  15

Ala Val Arg Gly Gly Cys Cys Ser Asn Pro Ala Cys Leu Val Asn His
             20                  25                  30

Leu Glu Met Cys Gly Lys Arg Arg
         35                  40


<210> SEQ ID NO 373
<211> LENGTH: 160
<212> TYPE: DNA
<213> ORGANISM: Conus purpurascens
<220> FEATURE:
<221> NAME/KEY: CDS
<222> LOCATION: (1)..(120)

<400> SEQUENCE: 373

tct gat ggc agg gat gcc gca gcc aac gac aaa gcg tct gac ctg atc       48
Ser Asp Gly Arg Asp Ala Ala Ala Asn Asp Lys Ala Ser Asp Leu Ile
```

-continued

```
  1               5                   10                  15

gct ctg acc gcc agg aga gat cca tgc tgt ttc aat cct gcc tgt aac       96
Ala Leu Thr Ala Arg Arg Asp Pro Cys Cys Phe Asn Pro Ala Cys Asn
             20                  25                  30

gtg aat aat cca cag att tgt ggt tgaagacgct gatgctccag gaccctctga     150
Val Asn Asn Pro Gln Ile Cys Gly
         35                  40

accacgacgt                                                            160


<210> SEQ ID NO 374
<211> LENGTH: 40
<212> TYPE: PRT
<213> ORGANISM: Conus purpurascens

<400> SEQUENCE: 374

Ser Asp Gly Arg Asp Ala Ala Ala Asn Asp Lys Ala Ser Asp Leu Ile
  1               5                   10                  15

Ala Leu Thr Ala Arg Arg Asp Pro Cys Cys Phe Asn Pro Ala Cys Asn
             20                  25                  30

Val Asn Asn Pro Gln Ile Cys Gly
         35                  40


<210> SEQ ID NO 375
<211> LENGTH: 151
<212> TYPE: DNA
<213> ORGANISM: Conus purpurascens
<220> FEATURE:
<221> NAME/KEY: CDS
<222> LOCATION: (1)..(120)

<400> SEQUENCE: 375

tct gat ggc agg gat gct gag aaa aca ggc ttt gac acg acc att gtg       48
Ser Asp Gly Arg Asp Ala Glu Lys Thr Gly Phe Asp Thr Thr Ile Val
  1               5                   10                  15

ccg gaa gac tgc tgt tcg gat cct tcc tgt tgg agg ctg cat agt tta       96
Pro Glu Asp Cys Cys Ser Asp Pro Ser Cys Trp Arg Leu His Ser Leu
             20                  25                  30

gct tgt act gga att gta aac cgc tgatgctcca ggaccctctg aaccacgacg     150
Ala Cys Thr Gly Ile Val Asn Arg
         35                  40

t                                                                     151


<210> SEQ ID NO 376
<211> LENGTH: 40
<212> TYPE: PRT
<213> ORGANISM: Conus purpurascens

<400> SEQUENCE: 376

Ser Asp Gly Arg Asp Ala Glu Lys Thr Gly Phe Asp Thr Thr Ile Val
  1               5                   10                  15

Pro Glu Asp Cys Cys Ser Asp Pro Ser Cys Trp Arg Leu His Ser Leu
             20                  25                  30

Ala Cys Thr Gly Ile Val Asn Arg
         35                  40


<210> SEQ ID NO 377
<211> LENGTH: 142
<212> TYPE: DNA
<213> ORGANISM: Conus purpurascens
<220> FEATURE:
<221> NAME/KEY: CDS
<222> LOCATION: (1)..(111)
```

-continued

<400> SEQUENCE: 377

```
act gat ggc agg agt gct gca gcc ata gcg ttt gcc ctg atc gct ccg       48
Thr Asp Gly Arg Ser Ala Ala Ala Ile Ala Phe Ala Leu Ile Ala Pro
  1               5                  10                  15

acc gtc tgc tgt act aat cct gcc tgt ctc gtg aat aat ata cgc ttt       96
Thr Val Cys Cys Thr Asn Pro Ala Cys Leu Val Asn Asn Ile Arg Phe
             20                  25                  30

tgt ggt gga aga cgc tgatgcccca ggaccctctg aaccacgacg t              142
Cys Gly Gly Arg Arg
         35
```

<210> SEQ ID NO 378
<211> LENGTH: 37
<212> TYPE: PRT
<213> ORGANISM: Conus purpurascens

<400> SEQUENCE: 378

```
Thr Asp Gly Arg Ser Ala Ala Ala Ile Ala Phe Ala Leu Ile Ala Pro
  1               5                  10                  15

Thr Val Cys Cys Thr Asn Pro Ala Cys Leu Val Asn Asn Ile Arg Phe
             20                  25                  30

Cys Gly Gly Arg Arg
         35
```

<210> SEQ ID NO 379
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 379

```
tct gat gga aga aat gcc gca agc gac gcc aaa gcg ttt ccc cgg atc       48
Ser Asp Gly Arg Asn Ala Ala Ser Asp Ala Lys Ala Phe Pro Arg Ile
  1               5                  10                  15

gct cca atc gtc agg gac gaa tgc tgt agc gat cct agg tgt cac ggg       96
Ala Pro Ile Val Arg Asp Glu Cys Cys Ser Asp Pro Arg Cys His Gly
             20                  25                  30

aat aat cgg gac cac tgt gct tgaagacgct gctgctccag gaccctctga        147
Asn Asn Arg Asp His Cys Ala
         35

accacgacgt                                                           157
```

<210> SEQ ID NO 380
<211> LENGTH: 39
<212> TYPE: PRT
<213> ORGANISM: Conus regius

<400> SEQUENCE: 380

```
Ser Asp Gly Arg Asn Ala Ala Ser Asp Ala Lys Ala Phe Pro Arg Ile
  1               5                  10                  15

Ala Pro Ile Val Arg Asp Glu Cys Cys Ser Asp Pro Arg Cys His Gly
             20                  25                  30

Asn Asn Arg Asp His Cys Ala
         35
```

<210> SEQ ID NO 381
<211> LENGTH: 156
<212> TYPE: DNA
<213> ORGANISM: Conus regius -continued

<220> FEATURE:
<221> NAME/KEY: CDS
<222> LOCATION: (1)..(117)

<400> SEQUENCE: 381

```
tct gat ggc agg aat acc gcg gcc gac gaa aaa gcg tcc gac ctg atc       48
Ser Asp Gly Arg Asn Thr Ala Ala Asp Glu Lys Ala Ser Asp Leu Ile
  1               5                  10                  15

tct caa act gtc aag aga gat tgc tgt tcc cat cct ctc tgt aga tta       96
Ser Gln Thr Val Lys Arg Asp Cys Cys Ser His Pro Leu Cys Arg Leu
             20                  25                  30

ttt gtt cca gga ctt tgt att tgaagacgct gctgctccag gaccctctga         147
Phe Val Pro Gly Leu Cys Ile
         35

accacgact                                                             156
```

<210> SEQ ID NO 382
<211> LENGTH: 39
<212> TYPE: PRT
<213> ORGANISM: Conus regius

<400> SEQUENCE: 382

```
Ser Asp Gly Arg Asn Thr Ala Ala Asp Glu Lys Ala Ser Asp Leu Ile
  1               5                  10                  15

Ser Gln Thr Val Lys Arg Asp Cys Cys Ser His Pro Leu Cys Arg Leu
             20                  25                  30

Phe Val Pro Gly Leu Cys Ile
         35
```

<210> SEQ ID NO 383
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 383

```
tct gat ggc agg aat gcc gca gcc gac aac aaa gcg tct gac cta atc       48
Ser Asp Gly Arg Asn Ala Ala Ala Asp Asn Lys Ala Ser Asp Leu Ile
  1               5                  10                  15

gct caa atc gtc agg aga gga tgc tgt tcc cat cct gtc tgt aaa gtg       96
Ala Gln Ile Val Arg Arg Gly Cys Cys Ser His Pro Val Cys Lys Val
             20                  25                  30

agg tat cca gac ctg tgt cgt tgaagacgct gctgctccag gaccctctga         147
Arg Tyr Pro Asp Leu Cys Arg
         35

accacgacgt                                                            157
```

<210> SEQ ID NO 384
<211> LENGTH: 39
<212> TYPE: PRT
<213> ORGANISM: Conus regius

<400> SEQUENCE: 384

```
Ser Asp Gly Arg Asn Ala Ala Ala Asp Asn Lys Ala Ser Asp Leu Ile
  1               5                  10                  15

Ala Gln Ile Val Arg Arg Gly Cys Cys Ser His Pro Val Cys Lys Val
             20                  25                  30

Arg Tyr Pro Asp Leu Cys Arg
         35
```

```
<210> SEQ ID NO 385
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 385

tct gat ggc agg aat gcc gca gcc gac aac aga gcg tct gac cta atc       48
Ser Asp Gly Arg Asn Ala Ala Ala Asp Asn Arg Ala Ser Asp Leu Ile
  1               5                  10                  15

gct caa atc gtc agg aga gga tgc tgt tcc cat cct gcc tgt aat gtg       96
Ala Gln Ile Val Arg Arg Gly Cys Cys Ser His Pro Ala Cys Asn Val
             20                  25                  30

aat aat cca cac att tgt ggt tgaagacgct gctgctccag gaccctctga         147
Asn Asn Pro His Ile Cys Gly
         35

accacgacgt                                                           157


<210> SEQ ID NO 386
<211> LENGTH: 39
<212> TYPE: PRT
<213> ORGANISM: Conus regius

<400> SEQUENCE: 386

Ser Asp Gly Arg Asn Ala Ala Ala Asp Asn Arg Ala Ser Asp Leu Ile
  1               5                  10                  15

Ala Gln Ile Val Arg Arg Gly Cys Cys Ser His Pro Ala Cys Asn Val
             20                  25                  30

Asn Asn Pro His Ile Cys Gly
         35


<210> SEQ ID NO 387
<211> LENGTH: 157
<212> TYPE: DNA
<213> ORGANISM: Conus regius
<220> FEATURE:
<221> NAME/KEY: CDS
<222> LOCATION: (1)..(117)

<400> SEQUENCE: 387

tct gat ggc agg aat gcc gca gcc gac aac aaa ccg tct gac cta atc       48
Ser Asp Gly Arg Asn Ala Ala Ala Asp Asn Lys Pro Ser Asp Leu Ile
  1               5                  10                  15

gct caa atc gtc agg aga gga tgc tgt tcg cat cct gtc tgt aaa gtg       96
Ala Gln Ile Val Arg Arg Gly Cys Cys Ser His Pro Val Cys Lys Val
             20                  25                  30

agg tat tca gac atg tgt ggt tgaagacgct gctgctccag gaccctctga         147
Arg Tyr Ser Asp Met Cys Gly
         35

accacgacgt                                                           157


<210> SEQ ID NO 388
<211> LENGTH: 39
<212> TYPE: PRT
<213> ORGANISM: Conus regius

<400> SEQUENCE: 388

Ser Asp Gly Arg Asn Ala Ala Ala Asp Asn Lys Pro Ser Asp Leu Ile
  1               5                  10                  15

Ala Gln Ile Val Arg Arg Gly Cys Cys Ser His Pro Val Cys Lys Val
```

-continued

```
            20                  25                  30

Arg Tyr Ser Asp Met Cys Gly
        35


<210> SEQ ID NO 389
<211> LENGTH: 154
<212> TYPE: DNA
<213> ORGANISM: Conus stercusmuscarum
<220> FEATURE:
<221> NAME/KEY: CDS
<222> LOCATION: (1)..(114)

<400> SEQUENCE: 389

tct gat ggc agg aat gca gag cga cga caa agc gtc tgt cct ggt cgc       48
Ser Asp Gly Arg Asn Ala Glu Arg Arg Gln Ser Val Cys Pro Gly Arg
  1               5                  10                  15

tct ggc ccc agg gga gga tgt tgt tcc cac cct gcc tgt aag gtg cat       96
Ser Gly Pro Arg Gly Gly Cys Cys Ser His Pro Ala Cys Lys Val His
            20                  25                  30

ttt cca cac agt tgt ggt tgacgacgct gatgctccag gaccctctga             144
Phe Pro His Ser Cys Gly
        35

accacgacgt                                                           154


<210> SEQ ID NO 390
<211> LENGTH: 38
<212> TYPE: PRT
<213> ORGANISM: Conus stercusmuscarum

<400> SEQUENCE: 390

Ser Asp Gly Arg Asn Ala Glu Arg Arg Gln Ser Val Cys Pro Gly Arg
  1               5                  10                  15

Ser Gly Pro Arg Gly Gly Cys Cys Ser His Pro Ala Cys Lys Val His
            20                  25                  30

Phe Pro His Ser Cys Gly
        35


<210> SEQ ID NO 391
<211> LENGTH: 145
<212> TYPE: DNA
<213> ORGANISM: Conus stercusmuscarum
<220> FEATURE:
<221> NAME/KEY: CDS
<222> LOCATION: (1)..(114)

<400> SEQUENCE: 391

tct gat ggc agg aat gcc gca gcc agc gac aga gcg tct gac gcg gcc       48
Ser Asp Gly Arg Asn Ala Ala Ala Ser Asp Arg Ala Ser Asp Ala Ala
  1               5                  10                  15

cac cag gta tgc tgt tcc aac cct gtc tgt cac gtg gat cat cca gaa       96
His Gln Val Cys Cys Ser Asn Pro Val Cys His Val Asp His Pro Glu
            20                  25                  30

ctt tgt cgt aga aga cgc tgatgctcca ggaccctctg aaccacgacg t           145
Leu Cys Arg Arg Arg Arg
        35


<210> SEQ ID NO 392
<211> LENGTH: 38
<212> TYPE: PRT
<213> ORGANISM: Conus stercusmuscarum

<400> SEQUENCE: 392

Ser Asp Gly Arg Asn Ala Ala Ala Ser Asp Arg Ala Ser Asp Ala Ala
```

-continued

```
 1               5                  10                  15

His Gln Val Cys Cys Ser Asn Pro Val Cys His Val Asp His Pro Glu
            20                  25                  30

Leu Cys Arg Arg Arg Arg
        35


<210> SEQ ID NO 393
<211> LENGTH: 154
<212> TYPE: DNA
<213> ORGANISM: Conus striatus
<220> FEATURE:
<221> NAME/KEY: CDS
<222> LOCATION: (1)..(123)

<400> SEQUENCE: 393

tct gat ggc agg aat gcc gcg gcc aac gac aaa gcg tct gac ctg gtc       48
Ser Asp Gly Arg Asn Ala Ala Ala Asn Asp Lys Ala Ser Asp Leu Val
 1               5                  10                  15

gct ccg gcc atc agg gga tgc tgt tcc cac cct gtc tgt aac ttg agt       96
Ala Pro Ala Ile Arg Gly Cys Cys Ser His Pro Val Cys Asn Leu Ser
            20                  25                  30

aat cca caa att tgt cgt gga aga cgc tgatgctcca ggaccctctg            143
Asn Pro Gln Ile Cys Arg Gly Arg Arg
        35                  40

aaccacgacg t                                                         154


<210> SEQ ID NO 394
<211> LENGTH: 41
<212> TYPE: PRT
<213> ORGANISM: Conus striatus

<400> SEQUENCE: 394

Ser Asp Gly Arg Asn Ala Ala Ala Asn Asp Lys Ala Ser Asp Leu Val
 1               5                  10                  15

Ala Pro Ala Ile Arg Gly Cys Cys Ser His Pro Val Cys Asn Leu Ser
            20                  25                  30

Asn Pro Gln Ile Cys Arg Gly Arg Arg
        35                  40


<210> SEQ ID NO 395
<211> LENGTH: 117
<212> TYPE: DNA
<213> ORGANISM: Conus textile
<220> FEATURE:
<221> NAME/KEY: CDS
<222> LOCATION: (1)..(114)

<400> SEQUENCE: 395

ttt cat ggc agg aat gcc gca gcc aaa gcg tct ggc ctg gtc ggt ctg       48
Phe His Gly Arg Asn Ala Ala Ala Lys Ala Ser Gly Leu Val Gly Leu
 1               5                  10                  15

acc gac aag agg caa gaa tgc tgt tct cat cct gcc tgt aac gta gat       96
Thr Asp Lys Arg Gln Glu Cys Cys Ser His Pro Ala Cys Asn Val Asp
            20                  25                  30

cat cca gaa att tgt cgt tga                                          117
His Pro Glu Ile Cys Arg
        35


<210> SEQ ID NO 396
<211> LENGTH: 38
<212> TYPE: PRT
<213> ORGANISM: Conus textile
```

-continued

<400> SEQUENCE: 396

Phe His Gly Arg Asn Ala Ala Ala Lys Ala Ser Gly Leu Val Gly Leu
1 5 10 15

Thr Asp Lys Arg Gln Glu Cys Cys Ser His Pro Ala Cys Asn Val Asp
20 25 30

His Pro Glu Ile Cys Arg
35

<210> SEQ ID NO 397
<211> LENGTH: 151
<212> TYPE: DNA
<213> ORGANISM: Conus tulipa
<220> FEATURE:
<221> NAME/KEY: CDS
<222> LOCATION: (1)..(120)

<400> SEQUENCE: 397 act gat ggc agg agt gct gca gcc ata gcg ttt gcc ctg atc gct ccg 48
Thr Asp Gly Arg Ser Ala Ala Ala Ile Ala Phe Ala Leu Ile Ala Pro
1 5 10 15 acc gtc tgg gaa gga tgc tgt tct aat cct gcc tgt ctc gtg aat cat 96
Thr Val Trp Glu Gly Cys Cys Ser Asn Pro Ala Cys Leu Val Asn His
20 25 30 ata cgc ttt tgt ggt gga aga cgc tgatgcccca ggaccctctg aaccacgacg 150
Ile Arg Phe Cys Gly Gly Arg Arg
35 40 t 151

<210> SEQ ID NO 398
<211> LENGTH: 40
<212> TYPE: PRT
<213> ORGANISM: Conus tulipa

<400> SEQUENCE: 398

Thr Asp Gly Arg Ser Ala Ala Ala Ile Ala Phe Ala Leu Ile Ala Pro
1 5 10 15

Thr Val Trp Glu Gly Cys Cys Ser Asn Pro Ala Cys Leu Val Asn His
20 25 30

Ile Arg Phe Cys Gly Gly Arg Arg
35 40

<210> SEQ ID NO 399
<211> LENGTH: 157
<212> TYPE: DNA
<213> ORGANISM: Conus virgo
<220> FEATURE:
<221> NAME/KEY: CDS
<222> LOCATION: (1)..(117)

<400> SEQUENCE: 399 tct aat ggc atg aat gcc gca gcc atc agg aaa gcg tct gcc ctg gtg 48
Ser Asn Gly Met Asn Ala Ala Ala Ile Arg Lys Ala Ser Ala Leu Val
1 5 10 15 gct cag atc gcc cat cga gac tgc tgt gac gat cct gcc tgc acc gtg 96
Ala Gln Ile Ala His Arg Asp Cys Cys Asp Asp Pro Ala Cys Thr Val
20 25 30 aat aat cca ggc ctt tgc act tgaagatgct gctgccccag gaccctctga 147
Asn Asn Pro Gly Leu Cys Thr
35 accacgacgt 157

```
<210> SEQ ID NO 400
<211> LENGTH: 39
<212> TYPE: PRT
<213> ORGANISM: Conus virgo

<400> SEQUENCE: 400

Ser Asn Gly Met Asn Ala Ala Ala Ile Arg Lys Ala Ser Ala Leu Val
  1               5                  10                  15

Ala Gln Ile Ala His Arg Asp Cys Cys Asp Asp Pro Ala Cys Thr Val
             20                  25                  30

Asn Asn Pro Gly Leu Cys Thr
         35


<210> SEQ ID NO 401
<211> LENGTH: 154
<212> TYPE: DNA
<213> ORGANISM: Conus geographus
<220> FEATURE:
<221> NAME/KEY: CDS
<222> LOCATION: (1)..(114)

<400> SEQUENCE: 401

tct gat ggc ggg aat gcc gca gca aaa gag tct gac gtg atc gct ctg       48
Ser Asp Gly Gly Asn Ala Ala Ala Lys Glu Ser Asp Val Ile Ala Leu
  1               5                  10                  15

acc gtc tgg aaa tgc tgt acc att cct tcc tgt tat gag aaa aaa aaa       96
Thr Val Trp Lys Cys Cys Thr Ile Pro Ser Cys Tyr Glu Lys Lys Lys
             20                  25                  30

att aaa gca tgt gtc ttt tgacgacgct gatgctccag gaccctctga             144
Ile Lys Ala Cys Val Phe
         35

accacgacgt                                                           154


<210> SEQ ID NO 402
<211> LENGTH: 38
<212> TYPE: PRT
<213> ORGANISM: Conus geographus

<400> SEQUENCE: 402

Ser Asp Gly Gly Asn Ala Ala Ala Lys Glu Ser Asp Val Ile Ala Leu
  1               5                  10                  15

Thr Val Trp Lys Cys Cys Thr Ile Pro Ser Cys Tyr Glu Lys Lys Lys
             20                  25                  30

Ile Lys Ala Cys Val Phe
         35


<210> SEQ ID NO 403
<211> LENGTH: 154
<212> TYPE: DNA
<213> ORGANISM: Conus regius
<220> FEATURE:
<221> NAME/KEY: CDS
<222> LOCATION: (1)..(114)

<400> SEQUENCE: 403

tct gat ggc gca gtc gac gac aaa gcg ttg gat cga atc gct gaa atc       48
Ser Asp Gly Ala Val Asp Asp Lys Ala Leu Asp Arg Ile Ala Glu Ile
  1               5                  10                  15

gtc agg aga gga tgc tgt ggc aat cct gcc tgt agc ggc tcc tcg aaa       96
Val Arg Arg Gly Cys Cys Gly Asn Pro Ala Cys Ser Gly Ser Ser Lys
             20                  25                  30

gat gca ccc tct tgt ggt tgaagacgct gctgctccag gaccctctga             144
Asp Ala Pro Ser Cys Gly
```

-continued

```
        35

accacgacgt                                                            154


<210> SEQ ID NO 404
<211> LENGTH: 38
<212> TYPE: PRT
<213> ORGANISM: Conus regius

<400> SEQUENCE: 404

Ser Asp Gly Ala Val Asp Asp Lys Ala Leu Asp Arg Ile Ala Glu Ile
  1               5                  10                  15

Val Arg Arg Gly Cys Cys Gly Asn Pro Ala Cys Ser Gly Ser Ser Lys
             20                  25                  30

Asp Ala Pro Ser Cys Gly
        35
```